United States Patent
Subkowski et al.

(10) Patent No.: US 10,398,159 B2
(45) Date of Patent: Sep. 3, 2019

(54) LOW MOLECULAR WEIGHT MODULATORS OF THE COLD MENTHOL RECEPTOR TRPM8 AND USE THEREOF

(71) Applicant: BASF SE, Ludwigshafen (DE)

(72) Inventors: Thomas Subkowski, Schriesheim (DE); Claus Bollschweiler, Heidelberg (DE); Jens Wittenberg, Limburgerhof (DE); Wolfgang Siegel, Limburgerhof (DE); Ralf Pelzer, Fürstenberg (DE)

(73) Assignee: BASF SE, Ludwigshafen am Rhein (DE)

( * ) Notice: Subject to any disclaimer, the term of this patent is extended or adjusted under 35 U.S.C. 154(b) by 12 days.

(21) Appl. No.: 15/610,958

(22) Filed: Jun. 1, 2017

(65) Prior Publication Data

US 2017/0265510 A1    Sep. 21, 2017

Related U.S. Application Data

(63) Continuation of application No. 13/623,378, filed on Sep. 20, 2012, now abandoned.

(60) Provisional application No. 61/536,621, filed on Sep. 20, 2011.

(51) Int. Cl.
| | | |
|---|---|---|
| A23L 27/00 | (2016.01) | |
| A61K 8/35 | (2006.01) | |
| A61K 8/49 | (2006.01) | |
| A61K 8/55 | (2006.01) | |
| A61Q 19/00 | (2006.01) | |
| C07C 49/665 | (2006.01) | |
| C07D 209/48 | (2006.01) | |
| C07D 311/78 | (2006.01) | |
| C07D 311/94 | (2006.01) | |
| C07D 339/06 | (2006.01) | |
| C07D 339/08 | (2006.01) | |
| C07D 405/06 | (2006.01) | |
| C07D 471/04 | (2006.01) | |
| C07D 491/20 | (2006.01) | |
| C07D 493/10 | (2006.01) | |
| C07D 495/10 | (2006.01) | |
| C07D 495/20 | (2006.01) | |
| C07F 9/572 | (2006.01) | |
| A23L 27/20 | (2016.01) | |
| C07J 63/00 | (2006.01) | |
| C07C 49/675 | (2006.01) | |
| C07J 33/00 | (2006.01) | |
| C07J 73/00 | (2006.01) | |
| C07J 11/00 | (2006.01) | |

(52) U.S. Cl.
CPC ........... *A23L 27/2056* (2016.08); *A23L 27/88* (2016.08); *A61K 8/35* (2013.01); *A61K 8/49* (2013.01); *A61K 8/492* (2013.01); *A61K 8/498* (2013.01); *A61K 8/4926* (2013.01); *A61K 8/4986* (2013.01); *A61K 8/55* (2013.01); *A61Q 19/00* (2013.01); *C07C 49/675* (2013.01); *C07D 209/48* (2013.01); *C07D 311/78* (2013.01); *C07D 311/94* (2013.01); *C07D 339/06* (2013.01); *C07D 339/08* (2013.01); *C07D 405/06* (2013.01); *C07D 471/04* (2013.01); *C07D 491/20* (2013.01); *C07D 493/10* (2013.01); *C07D 495/10* (2013.01); *C07D 495/20* (2013.01); *C07F 9/5728* (2013.01); *C07J 33/007* (2013.01); *C07J 63/008* (2013.01); *C07J 73/003* (2013.01); *A61K 2800/244* (2013.01); *C07C 2603/26* (2017.05); *C07J 11/00* (2013.01)

(58) Field of Classification Search
None
See application file for complete search history.

(56) References Cited

U.S. PATENT DOCUMENTS

| | | |
|---|---|---|
| 8,710,096 B2 | 4/2014 | Subkowski |
| 9,346,823 B2 | 5/2016 | Subkowski |
| 2011/0145970 A1* | 6/2011 | Subkowski ............... A61K 8/42 2/69 |
| 2012/0263659 A1 | 10/2012 | Subkowski |

FOREIGN PATENT DOCUMENTS

| | | | |
|---|---|---|---|
| WO | WO 2008/154243 A1 | 12/2008 | |
| WO | WO 2010/026094 A1 | 3/2010 | |
| WO | WO-2010026094 A1 * | 3/2010 | ............... A61K 8/42 |
| WO | WO 2011/061330 A2 | 3/2011 | |

OTHER PUBLICATIONS

D.A. Peak and R. Robinson, Experiments on the synthesis of substances related to the sterols. Part XVIII. J Chem Soc 1937, 1581-1591.
D.A. Peak and R. Robinson, Experiments on the synthesis of substances related to the sterols. Part XVII. J Chem Soc 1936, 759-763.
Ricard, M., Jacob, G, and de Maack F. The mass spectra of octahydro 12-oxo-cyclopentaphenanthrene and its sulfur and oxygen analogues. Organic Mass Spectrometry, vol. 17, No. 3, 1982, pp. 153-154.
W.E. Bachmannann, D.G. Dana Johnson, 3-Ketohydrophenanthrenes and 2-Ketohydro-1,2-cyclopentenonaphthalenes,m J. Am. Chem. Soc. 71, 3463-3468 (1949).
Translation of the International Preliminary Report on Patentability for PCT/EP2012/068538 dated Mar. 25, 2014.

(Continued)

*Primary Examiner* — Michael P Cohen
(74) *Attorney, Agent, or Firm* — Drinker Biddle & Reath LLP

(57) ABSTRACT

The invention relates to new types of modulators of the cold menthol receptor TRPM8, to methods of modulating the TRPM8 receptor using these modulators; and in particular the use of the modulators for inducing a sensation of coldness; and also the articles and compositions produced using these modulators.

8 Claims, No Drawings

(56) References Cited

OTHER PUBLICATIONS

Szántay, C., et al., "Azaberbene Derivatives as $\alpha_{2A}$-Adrenoceptor Antagonists", Arch. Pharm, (2002), vol. 335, No. 1, pp. 22-26.
Rubiralta, M., et al., "New Synthesis of Benzo [α] Quinolizidin-2-ones via Protected 2-aryl-4-piperidones", Tetrahedron, (1987), vol. 43, No. 13, pp. 3021-3030.
Fahrenholtz, K.E., et al., "Octahydrophenanthrene Analogs of Tetrabenazine", J. Med. Chem., (1966), vol. 9, No. 3, pp. 304-310.
Menéndez, J.C., et al., "The Reactivity of 2-Iminobenzo [α]Quinolizidines Towards 2-Mercaptoacetic Acid", Heterocycles, (1990), vol. 31, No. 11, pp. 2065-2071.
Popp, F.D., et al., "Synthesis of Potential Antineoplastic Agents XXVI: 1,3,4,6,7,11b-Hexahydro-9,10-dimethoxy-2H-benzo[α]2-quinolizinone Derivatives", J. Pharm Sci., (1978), vol. 67, No. 6, pp. 871-873.
Carosati, E., et al., "Discovery of Novel and Cardioselective Diltiazem-like Calcium Channel Blockers via Virtual Screening", J. Med. Chem., (2008), vol. 51, No. 18, pp. 5552-5565.
Yu, Q-S, et al., "Preparation and Characterization of Tetrabenazine Enantiomers against Vesicular Monoamine Transporter 2", ACS Medicinal Chemistry Letters, (2010), vol. 1, No. 3, pp. 105-109.
Database Chemabs, Itoh, N., et al., Database Accession No. 1960-56497, 1959.
Database Chemabs, King et al., Database Accession No. 1959-99863, dated 1958.
Database Chemabs, Itoh, N., et al., Database Accession No. 1959-99862, dated 1959.

\* cited by examiner

LOW MOLECULAR WEIGHT MODULATORS OF THE COLD MENTHOL RECEPTOR TRPM8 AND USE THEREOF

CROSS-REFERENCE TO RELATED APPLICATIONS

This application is a continuation application of U.S. patent application Ser. No. 13/623,378, filed Sep. 20, 2012, which is incorporated by reference herein in its entirety, and which claims the benefit of U.S. Provisional Application 61/536,621, filed Sep. 20, 2011.

The invention relates to new types of modulators of the cold menthol receptor TRPM8, methods for modulating the TRPM8 receptor using these modulators; in particular the use of the modulators for inducing a sensation of coldness; and also the articles and compositions produced using these modulators.

BACKGROUND OF THE INVENTION

The cold menthol receptor TRPM8 (also referred to as Cold Membrane Receptor (CMR)1) belongs to the family of the "Transient Receptor Potential Ion Channels", is specifically expressed in a special group of neurons and, in the cell membrane, forms pores (in each case 4 units combine to give a tetramer), which selectively allow $Ca^{2+}$ ions to pass. The protein has 6 transmembrane domains and a cytoplasmatic C and N terminus. Low temperatures (preferably 10-25° C.) stimulate this receptor, resulting in a signal transduction which is interpreted by the nervous system as a sensation of coldness. The receptor was described for the first time in 2002 as cold receptor in a number of publications (Peier A M et al., A TRP channel that senses cold stimuli and menthol. Cell. 2002 Mar. 8; 108(5):705-15; McKemy D D et al. Identification of a cold receptor reveals a general role for TRP channels in thermosensation Nature 2002 Mar. 7; 416 (6876): 52-8; Zuker C S. Neurobiology: A cool ion channel Nature 2002 Mar. 7; 416 (6876): 27-8).

Cooling compounds, such as e.g. menthol, have for a long time played an important role in the flavorings and fragrance industry in order to produce an association with freshness and cleanliness. For the compound menthol, it has been shown that it acts as a natural modulator of the receptor TRPM8 (McKemy D. D., *Molecular Pain* 1, 2005, 16; McKemy D. D., *Nature* 416, 2002, 52-58; Peier A. M., *Cell* 108, 2002, 705-715; Dhaka A., *Annu. Rev. Neurosci.* 29, 2006, 135-161). By applying menthol, TRPM8 is activated, which brings about a $Ca^{2+}$ influx into the cold-sensitive neurons. The electrical signal produced as a result is ultimately perceived as a sensation of coldness. Elevated menthol concentrations lead to irritation and an anesthetic effect. Moreover, various publications have described menthol derivatives with a similar effect (British Patent 1971 #1315761 Watson H. R., *J. Soc. Cosmet. Chem.* 29, 1978, 185-200; Furrer S. M., *Chem. Percept.* 1, 2008, 119-126). There are also individual compounds, structurally unrelated to menthol, which bring about a significant TRPM8 modulation, such as e.g. Icilin (Wei E. T., *J. Pharm. Pharmacol.* 35, 1983, 110-112; WO 2004/026840), WS-23 or compounds listed in the patent application WO 2007/019719.

Further effects of substances which modulate the TRPM8 receptor and/or its insect analogs are a repellent effect on insects (WO 2002/015692; WO 2004/000023, US 2004/0028714), and also activity in antitumor therapy (e.g. an influencing of prostate tumors), activity in the treatment of inflammatory pain/hyperalgesia and an effect as TRPM8 antagonists in the treatment of bladder syndrome or overactive bladder (Beck B. Cell Calcium, 41, 2007, 285-294; Levine J. D. *Biochim. Biophys. Acta, Mol. Basis Dis.* 1772, 2007, 989-1003; Mukerji G., *BMC Urology* 6, 2006, 6; US 2003/0207904; US 2005/6893626, Dissertation Behrendt H. J. 2004, Universität Bochum; Lashinger E. S. R. *Am. J. Physiol. Renal Physiol.* Am J Physiol Renal Physiol. 2008 Jun. 18. [Epub ahead of print]; PMID: 18562636).

However, many of the TRPM8 modulators found hitherto have deficiencies with regard to strength of effect, duration of effect, skin/mucosa irritation, odor, taste, solubility and/or volatility.

The international patent application WO 2010/026094 by the applicant proposes individual specific compounds for modulating the TRPM8 receptor. These comprise the following specifically disclosed compounds:

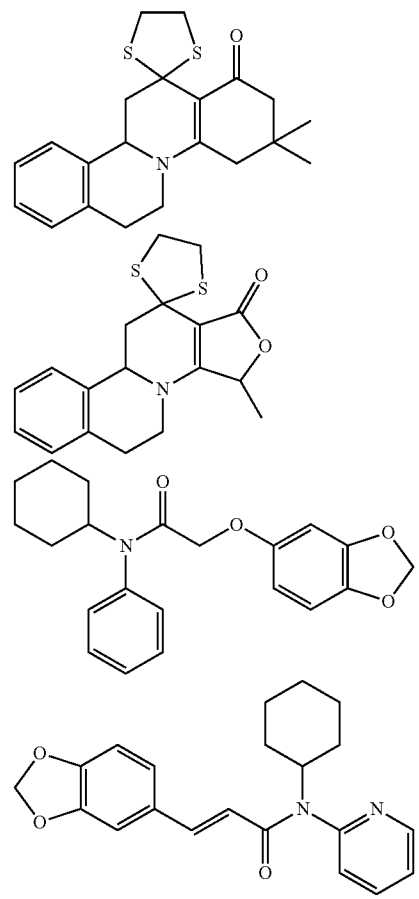

where the compound may be present in chemically pure or enriched form, as individual stereoisomer or in the form of stereoisomer mixtures.

Moreover, WO 2011/061330 from the applicant describes three new types of substance classes of generic TRPM-8 modulators.

There continues to be a need for further substances for modulating the TRPM8 receptor; in particular substances for inducing a sensation of coldness on skin and mucosa.

SUMMARY OF THE INVENTION

It was therefore an object of the present invention to identify novel substances, which lead to a modulation of the TRPM8 receptor, which can be used as alternatives to the modulators known hitherto. Such compounds should in particular also be suitable for applications in the field of cosmetics (e.g. hair care, skin care, oral care), nutrition (feed/food), textiles, OTC products (e.g. burn ointment), pharmaceuticals (e.g. tumor treatment, bladder weakness) or packagings.

DETAILED DESCRIPTION OF THE INVENTION

1. Definitions 1.1 General Terms

In the literature there are various synonyms for "TRPM8": TRPP8, LTRPC6, CMR1, MGC2849, transient receptor potential cation channel subfamily M member 8. Within the context of the present invention, all names are encompassed. Also encompassed are all functional modifications of the receptor, such as, in particular, splice variants, isoforms, such as e.g. TRPM8 CRA_a, TRPM8 CRA_b and all analogous receptors from various organisms, such as human, mouse, rat. The nucleotide and amino acid sequences of the various receptors are known per se and listed in sequence databases. Thus, e.g. the sequence information for hTRPM8 is entered under the number NM_024080.

Within the context of the invention, a "modulator" is a compound which can act as agonist and/or antagonist of the TRPM8 receptor in vivo and/or in vitro, in particular in vivo.

Suitable modulators here can act either only as antagonist or agonist, in particular only as agonist, or both as antagonist and also as agonist. Here, in particular an agonistic or an antagonistic effect can be established depending on the particular modulator concentration selected.

Here, an "agonist" is a compound which mediates an activation of the TRPM8 receptor, thus induces a $Ca^{2+}$ ingress into the cold-sensitive neurons and thereby mediates a sensation of coldness. By contrast, an "antagonist" is a compound which can counteract this activation of the TRPM8 receptor.

The mediators according to the invention can exert their effect by binding reversibly or irreversibly, specifically or nonspecifically to a TRPM8 receptor molecule. Usually, the binding takes place noncovalently via ionic and/or nonionic, such as e.g. hydrophobic, interactions with the receptor molecule. Here, "specific" encompasses both exclusive interaction with one or more different TRPM8 receptor molecules (such as e.g. TRPM8 molecules of different origin or various isoforms). By contrast, "nonspecific" is an interaction of the modulator with a plurality of various receptor molecules of different function and/or sequence but where, as a consequence, a desired agonistic and/or antagonistic modulation (as described above) of the TRPM8 receptor can be established.

In this connection, "standard conditions" in a cellular activity test for modulators according to the invention is understood as meaning an activity test carried out with HEK293 cells which have been transformed with human TRPM8 and loaded with calcium-sensitive dye (such as e.g. Fluo-4AM, i.e. fluo-4-acetoxymethyl ester), subsequent addition of the test compound and detection of the color change, the experimental procedure taking place at 37° C.; as described e.g. in reference example 3 below, or in Behrendt et al (2004) loc. cit.).

A "modified form" or "derivative" of a modulator according to the invention is also referred to as "functional analog" or "functionally equivalent compound", particularly if they furthermore exhibit the desired biological activity (receptor-TRPM8 modulation).

Within the context of the invention, "derivatives" are also compounds which permit a coupling of the specifically disclosed substances to solid carriers; a large selection of corresponding linker/spacer groups is known to the person skilled in the art. The derivatization can take place here prior to the coupling to a solid phase or only as a result of the coupling.

A modulator according to the invention serves in particular to induce a sensation of coldness in humans and/or animals. An "induction of a sensation of coldness" is present when the compound in the cellular activity test described above exhibits an agonistic effect on hTRPM8.

Besides the customary constituents for the particular composition, compositions according to the invention comprise an "effective amount" of at least one modulator according to the invention. In this connection, "effective" means a concentration of the modulator which suffices to bring about the desired effect, such as e.g. pharmacological effect, or sensory effect, such as the olfactory effect of coldness, upon application of the composition (e.g. application to the skin).

A "topical" application encompasses in particular cutaneous or oral application forms.

Unless specified otherwise, according to the invention, all compounds mentioned herein in all of their isomeric or stereoisomeric forms, as pure substance or as a mixture of isomeric and/or stereoisomeric forms are encompassed.

1.2 Chemical Terms

Unless details to the contrary are given, then the following general meanings apply within the context of the present invention:

Halogen: F, Cl, Br or I

Alkyl and also all alkyl moieties in radicals derived therefrom, such as e.g. alkoxy, alkylthio, alkoxyalkyl, alkoxyalkoxy, alkylamino and dialkylamino: saturated, straight-chain or branched hydrocarbon radicals having 1 to 4, 1 to 6, 1 to 8, 1 to 10 or 1 to 10 carbon atoms, e.g.

$C_1$-$C_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl.

$C_1$-$C_6$-alkoxy comprising $C_1$-$C_4$-alkoxy, such as e.g. methoxy, ethoxy, n-propoxy, 1-methylethoxy, butoxy, 1-methylpropoxy, 2-methylpropoxy or 1,1-dimethylethoxy; and also e.g. pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy;

Alkenyl: mono- or poly-, in particular monounsaturated, straight-chain or branched hydrocarbon radicals having 2 to 4, 2 to 6, 2 to 8, 2 to 10 or 2 to 20 carbon atoms and a double bond in any desired position, e.g. $C_2$-$C_6$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

Alkynyl: mono- or polyunsaturated, in particular monounsaturated, straight-chain or branched hydrocarbon radicals having 2 to 4, 2 to 6 or 2 to 8 carbon atoms and a triple bond in any desired position, in particular the radicals with C—C triple bond analogous to the alkenyl radicals explicitly specified above; e.g. $C_2$-$C_6$-alkynyl, such as ethynyl, 1-propynyl, 2-propynyl, 1-butynyl, 2-butynyl, 3-butynyl, 1-pentynyl, 2-pentynyl, 3-pentynyl, 4-pentynyl, 3-methyl-1-butynyl, 1-methyl-2-butynyl, 1-methyl-2-butynyl, 1-methyl-3-butynyl, 2-methyl-3-butynyl, 1,1-dimethyl-2-propynyl, 1-ethyl-2-propynyl, 1-hexynyl and isomeric forms thereof.

Haloalkyl: straight-chain or branched alkyl groups having 1 to 4, 1 to 6, 1 to 8, 1 to 10 or 1 to 20 carbon atoms (as specified above), where, within these groups, some or all of the hydrogen atoms can be replaced by halogen atoms as specified above, e.g. $C_1$-$C_2$-haloalkyl such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and 1,1,1-trifluoroprop-2-yl.

Haloalkoxy: is an alkoxy radical having 1 to 8, in particular 1 to 6 and specifically 1 to 4 carbon atoms as specified above which is partially or completely substituted by fluorine, chlorine, bromine and/or iodine, preferably by fluorine, thus e.g. $OCH_2F$, $OCHF_2$, $OCF_3$, $OCH_2Cl$, $OCHCl_2$, $OCCl_3$, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, $OC_2F_5$, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, $OCH_2$—$C_2F_5$, $OCF_2$—$C_2F_5$, 1-($CH_2F$)-2-fluoroethoxy, 1-($CH_2Cl$)-2-chloroethoxy, 1-($CH_2Br$)-2-bromoethoxy, 4-fluorobutoxy, 4-chlorobutoxy, 4-bromobutoxy or nonafluorobutoxy;

Cycloalkyl: carbocyclic radicals having 3 to 20 carbon atoms, such as e.g. $C_3$-$C_{12}$-cycloalkyl, such as cyclopropyl, cyclobutyl, cyclopentyl, cyclohexyl, cycloheptyl, cyclooctyl, cyclononyl, cyclodecyl, cycloundecyl and cyclododecyl; preference is given to cyclopentyl, cyclohexyl, cycloheptyl, and also cyclopropylmethyl, cyclopropylethyl, cyclobutylmethyl, cyclobutylethyl, cyclopentylmethyl, cyclopentylethyl, cyclohexylmethyl or $C_3$-$C_7$-cycloalkyl, such as cyclopropyl, cyclobutyl, cyclopentyl, cyclohexyl, cycloheptyl, cyclopropylmethyl, cyclopropylethyl, cyclobutylmethyl, cyclopentylethyl, cyclohexylmethyl, where the bond to the radical of the molecule can be via any suitable carbon atom.

Cycloalkenyl: monocyclic, monounsaturated hydrocarbon groups having 5 to 8, preferably up to 6, carbon ring members, such as cyclopenten-1-yl, cyclopenten-3-yl, cyclohexen-1-yl, cyclohexen-3-yl and cyclohexen-4-yl;

Alkylene: straight-chain or mono- or polybranched hydrocarbon bridging groups having 1 to 20 carbon atoms, such as e.g. $C_1$-$C_8$-alkylene groups or $C_1$-$C_7$-alkylene groups selected from —$CH_2$—, —$(CH_2)_2$—, —$(CH_2)_3$—, —$(CH_2)_4$—, —$(CH_2)_2$—$CH(CH_3)$—, —$CH_2$—$CH(CH_3)$—$CH_2$—, —$(CH_2)_4$—, —$(CH_2)_5$—, —$(CH_2)_6$—, —$(CH_2)_7$—, —$(CH_2)_8$—, —$CH(CH_3)$—$CH_2$—$CH_2$—$CH(CH_3)$—, —$CH(CH_3)$—$CH_2$—$CH_2$—$CH_2$—$CH(CH_3)$— or —$CH(CH_3)$—$CH_2$—$CH_2$—$CH_2$—$CH_2$—$CH(CH_3)$— or $C_1$-$C_4$-alkylene groups selected from —$CH_2$—, —$(CH_2)_2$—, —$(CH_2)_3$—, —$(CH_2)_4$—, —$(CH_2)_2$—$CH(CH_3)$—, —$CH_2$—$CH(CH_3)$—$CH_2$—.

Alkenylene: the mono- or poly-, in particular monounsaturated, analogs of the above alkylene groups having 2 to 20 carbon atoms, in particular $C_2$-$C_7$-alkenylenes or $C_2$-$C_4$-alkenylene, such as —CH═CH—, —CH═CH—$CH_2$—, —$CH_2$—CH═CH—, —CH═CH—$CH_2$—$CH_2$—, —$CH_2$—CH═CH—$CH_2$—, —$CH_2$—$CH_2$—CH═CH—, —$CH(CH_3)$—CH═CH—, —$CH_2$—$C(CH_3)$═CH—.

Aryl: mono- or polynuclear, preferably mono- or dinuclear, optionally substituted aromatic radicals having 6 to 20, such as e.g. 6 to 10, ring carbon atoms, such as e.g. phenyl, biphenyl, naphthyl such as 1- or 2-naphthyl, tetrahydronaphthyl, fluorenyl, indenyl and phenanthrenyl. The aryl radicals can optionally carry 1, 2, 3, 4, 5 or 6 identical or different substituents. In the case of a polynuclear aryl radical, at least one of the rings has aromatic character; however, it is also possible for several or all of the rings to have aromatic character.

Arylalkyl: the aryl-substituted analogs of the above alkyl radicals, where aryl likewise has the aforementioned meanings, such as e.g. phenyl-$C_1$-$C_4$-alkyl radicals selected from phenylmethyl or phenylethyl.

Aryloxy: the oxygen-linked analogs of the above optionally substituted aryl radicals.

Heterocyclyl: five- to seven-membered saturated, partially unsaturated or aromatic heterocyclene or heterocyclyl radicals comprising one, two, three or four heteroatoms from the group O, N or S. For example, the following subgroups may be mentioned 5- or 6-membered saturated or monounsaturated heterocyclyl, comprising one to two nitrogen atoms and/or one oxygen or sulfur atom or one or two oxygen and/or sulfur atoms as ring members, e.g. 2-tetrahydrofuranyl, 3-tetrahydrofuranyl, 2-tetrahydrothienyl, 3-tetrahydrothienyl, 1-pyrrolidinyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 2-pyrrolin-2-yl, 2-pyrrolin-3-yl, 3-pyrrolin-2-yl, 3-pyrrolin-3-yl, 1-piperidinyl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-hexahydropyridazinyl, 4-hexahydropyridazinyl, 2-hexahydropyrimidinyl, 4-hexahydropyrimidinyl, 5-hexahydropyrimidinyl and 2-piperazinyl;

5-membered aromatic heterocyclyl (=heteroaryl or hetaryl), comprising, besides carbon atoms, one, two or three nitrogen atoms or one or two nitrogen atoms and one sulfur or oxygen atom as ring members, e.g. 2-furyl, 3-furyl, 2-thienyl, 3-thienyl, 2-pyrrolyl, 3-pyrrolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, and 1,3,4-triazol-2-yl;

5-membered aromatic heterocyclyl (=heteroaryl or hetaryl) which has 1, 2, 3 or 4 nitrogen atoms as ring members, such as 1-, 2- or 3-pyrrolyl, 1-, 3- or 4-pyrazolyl, 1-, 2- or 4-imidazolyl, 1,2,3-[1H]-triazol-1-yl, 1,2,3-[2H]-triazol-2-yl, 1,2,3-[1H]-triazol-4-yl, 1,2,3-[1H]-triazol-5-yl, 1,2,3-[2H]-triazol-4-yl, 1,2,4-[1H]-triazol-1-yl, 1,2,4-[1H]-triazol-3-yl, 1,2,4-[1H]-triazol-5-yl, 1,2,4-[4H]-triazol-4-yl, 1,2,4-[4H]-triazol-3-yl, [1H]-tetrazol-1-yl, [1H]-tetrazol-5-yl, [2H]-tetrazol-2-yl and [2H]-tetrazol-5-yl;

5-membered aromatic heterocyclyl (=heteroaryl or hetaryl) which has 1 heteroatom selected from oxygen and sulfur and optionally 1, 2 or 3 nitrogen atoms as ring members, for example 2-furyl, 3-furyl, 2-thienyl, 3-thienyl, 3- or 4-isoxazolyl, 3- or 4-isothiazolyl, 2-, 4- or 5-oxazolyl, 2-, 4 or 5-thiazolyl, 1,2,4-thiadiazol-3-yl, 1,2,4-thiadiazol-5-yl, 1,3,4-thiadiazol-2-yl, 1,2,4-oxadiazol-3-yl, 1,2,4-oxadiazol-5-yl and 1,3,4-oxadiazol-2-yl;

6-membered heterocyclyl (=heteroaryl or hetaryl) comprising, besides carbon atoms, one or two or one, two or three nitrogen atoms as ring members, e.g. 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,2,4-triazin-3-yl; 1,2,4-triazin-5-yl, 1,2,4-triazin-6-yl and 1,3,5-triazin-2-yl;

"heterocyclyl" also comprises "polynuclear", such as e.g. di- or trinuclear, cyclic ring systems in which one of the aforementioned mononuclear heterocyclyl radicals is condensed with at least one further, identical or different heterocycle, at least one aryl ring and/or at least one cycloalkyl or cycloalkenyl ring in each case in accordance with the above definition.

"Heteroaryl" also comprises "polynuclear", such as e.g. di- or trinuclear, cyclic ring systems in which one of the aforementioned polynuclear heteroaryl radicals is condensed with at least one further identical or different heteroaryl ring, at least one aryl ring and/or at least one cycloalkyl or cycloalkenyl ring, in each case in accordance with the above definition.

Heterocyclyloxy or Heteroaryloxy stands for the oxygen-linked analogs of the above heterocyclyl or heteroaryl radicals.

Substituents, as in particular for the above radicals, are in particular selected from keto groups, —COOH, —COO-alkyl, —OH, —SH, —CN, amino, —NO$_2$, alkyl, or alkenyl groups, where, in the alkyl or alkenyl groups, one or more H atoms can be replaced by halogen; or two adjacent alkyl or alkenyl substituents, together with the carbon atom to which they are bonded, can form a 4 to 7-membered, in particular 5- or 6-membered ring, and where this ring can also carry one or more identical or different heteroatoms, such as O, S, N or NH, in the ring.

The definitions listed in this section also apply to specific aspects of the invention, unless stated otherwise.

2. Particular Embodiments of the Invention

The invention relates especially to the following specific embodiments:
1. Method for the in-vitro or in-vivo modulation of the cold menthol receptor TRMP8, where the receptor is brought into contact with at least one modulator which is selected from compounds of the following structure type I:

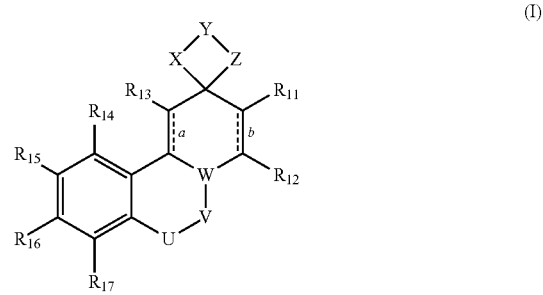

(I)

in which
the bonds a and b, independently of one another, are a C—C single bond or a C—C double bond, or a and b are simultaneously in each case a C—C double bond or simultaneously in each case a C—C single bond;
U is —CH$_2$—, —O— or a chemical single bond;
V is —CH$_2$— or carbonyl;
W is N or CH;
X and Z, independently of one another, are selected from —O—, —S—, —NR$_{18}$—, —S(=O)—, or —S(=O)$_2$— groups;
Y is selected from
straight-chain or branched C$_1$-C$_8$-alkylene groups which optionally carry 1, 2, 3 or 4 identical or different substituents which are selected from NH$_2$, OH, SH, halogen or straight-chain or branched C$_1$-C$_6$-alkoxy groups; or
X—Y—Z, together with the carbon atom to which they are bonded, form a keto group,
R$_{11}$ to R$_{18}$, independently of one another, are selected from: H; aryl;
straight-chain or branched C$_1$-C$_6$-alkyl groups which are optionally mono- or poly- (such as, e.g., mono- or bi-) unsaturated (by C—C double and/or triple bonds, in particular double bonds) and which optionally carry 1, 2, 3 or 4 identical or different substituents which are selected from oxo groups (=O), NH$_2$, OH, SH, halogen or straight-chain or branched C$_1$-C$_6$-alkoxy groups; and
straight-chain or branched C$_1$-C$_6$-alkyloxy groups which optionally carry 1, 2, 3 or 4 identical or different substituents which are selected from NH$_2$, OH, SH, halogen or straight-chain or branched C$_1$-C$_6$-alkoxy groups; or R$_{11}$ and R$_{12}$, together with the carbon atoms to which they are bonded, form a 4-, 5-, 6- or 7-membered, saturated or mono- or polyunsaturated, carbo- or heterocyclic ring which optionally carries 1, 2, 3, 4 or 5 identical or different substituents which are selected from straight-chain or branched $C_1$-$C_6$-alkyl groups, and oxo groups (=O), and the ring heteroatoms are identical or different and are selected from O, N and S;

and also salts of these compounds, in particular acid addition salts with inorganic or in particular organic, mono- or in particular polybasic carboxylic acids;

and optionally in stereoisomerically pure form or as a mixture of stereoisomers.

2. The method according to embodiment 1, in which the compound is selected from:
a) compounds of the general formula IA:

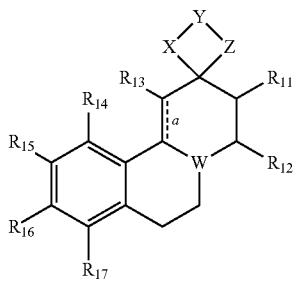

(IA)

in which:
a, W, X, Y, Z and $R_{11}$ to $R_{18}$ have the meanings given in embodiment 1;
or
b) compounds of the general formula IB;

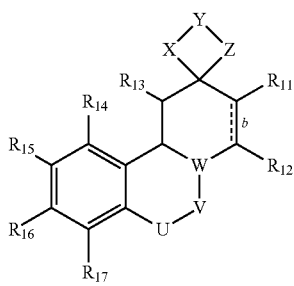

(IB)

in which:
b, V, W, X, Y, Z and $R_{11}$ to $R_{18}$ have the meanings given in embodiment 1;
U is —$CH_2$— or —O—; and
where U and V are not simultaneously —$CH_2$—,
or
c) of the general formula IC:

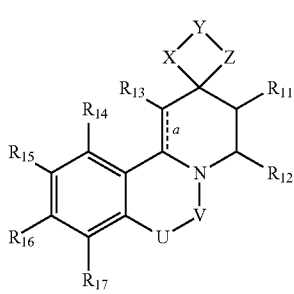

(IC)

a, X, Y, Z and $R_{11}$ to $R_{18}$ have the meanings given in embodiment 1;
U is —$CH_2$— or a chemical bond; and
V is —$CH_2$— or carbonyl;
where U and V are optionally not simultaneously —$CH_2$—.

3. A method for the in-vitro or in-vivo modulation of the cold menthol receptor TRMP8, where the receptor is brought into contact with at least one modulator which is selected from compounds of the following structure type II:

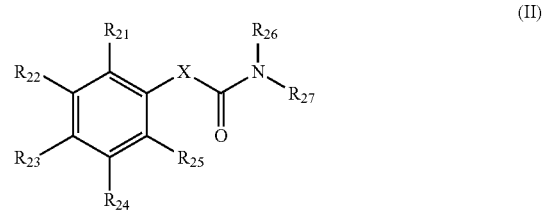

(II)

in which
$R_{21}$, $R_{22}$, $R_{23}$, $R_{24}$ and $R_{25}$ are identical or different and are selected from H;
halogen;
straight-chain or branched $C_1$-$C_6$-alkyl groups which optionally carry 1, 2, 3 or 4 identical or different substituents which are selected from $NH_2$, OH, SH, halogen or straight-chain or branched $C_1$-$C_6$-alkoxy groups;
straight-chain or branched $C_1$-$C_6$-alkoxy groups which optionally carry 1, 2, 3 or 4 identical or different substituents which are selected from $NH_2$, OH, SH, halogen or $C_1$-$C_6$-alkoxy groups;
mono- or polynuclear aryl, arylalkyl and heteroaryl groups which optionally carry 1, 2, 3 or 4 identical or different substituents which are selected from $NH_2$, OH, SH, halogen, straight-chain or branched $C_1$-$C_6$-alkyl groups and straight-chain or branched $C_1$-$C_6$-alkyloxy groups; where the heteroaryl groups have 1, 2, 3 or 4 ring heteroatoms which are identical or different and are selected from O, N and S; or
two adjacent radicals $R_{21}$, $R_{22}$, $R_{23}$, $R_{24}$ and $R_{25}$, together with the carbon atoms to which they are bonded, form a 4-, 5-, 6- or 7-membered, mono- or polyunsaturated heterocyclic ring which optionally carries 1, 2, 3, 4 or 5 identical or different substituents which are selected from straight-chain or branched $C_1$-$C_6$-alkyl groups, and which has 1, 2 or 3 ring heteroatoms which are identical or different and are selected from O, N and S;
$R_{26}$ and $R_{27}$ are identical or different and is selected from:
straight-chain or branched $C_1$-$C_6$-alkyl groups which optionally carry 1, 2, 3 or 4 identical or different substituents which are selected from $NH_2$, OH, SH, halogen or straight-chain or branched $C_1$-$C_6$-alkoxy groups;
mono- or polynuclear aryl, arylalkyl, aryloxy, heteroaryl and heteroaryloxy groups which optionally carry 1, 2, 3 or 4 identical or different substituents which are selected from $NH_2$, OH, SH, halogen, straight-chain or branched $C_1$-$C_6$-alkyl groups and straight-chain or branched $C_1$-$C_6$-alkyloxy groups; where the heteroaryl groups have 1, 2, 3 or 4 ring heteroatoms which are identical or different and are selected from O, N and S;

and $C_3$-$C_7$-cycloalkyl groups which optionally carry 1, 2, 3 or 4 identical or different substituents which are selected from $NH_2$, OH, SH, halogen, straight-chain or branched $C_1$-$C_6$-alkyl groups, or straight-chain or branched $C_1$-$C_6$-alkoxy groups; where the cycloalkyl group is optionally bonded via a $C_1$-$C_4$-alkylene group; and where optionally 1, 2 or 3 ring carbon atoms may be replaced by identical or different heteroatoms selected from O, N and S;

where in particular $R_{26}$ and $R_{27}$ are identical or different and is selected from cyclohexyl, 2-pyridyl and phenyl;

X is selected from a) C1-carbon bridges comprising up to 4 carbon atoms and of the general formula

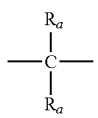

in which the radicals $R_a$, independently of one another, are H, straight-chain or branched $C_1$-$C_3$-alkyl, straight-chain or branched $C_2$-$C_3$-alkenyl or $C_2$-$C_3$-alkynyl or both $R_a$ radicals together a group of the formula

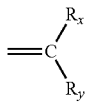

in which $R_x$ and $R_y$, independently of one another, are H, methyl or ethyl;

or b) C2-carbon bridges comprising up to 4 carbon atoms and of the general formulae (i) or (ii)

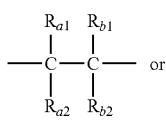

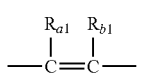

in which the radicals $R_{a1}$, $R_{a2}$, $R_{b1}$ and $R_{b2}$, independently of one another, are H, methyl, ethyl, ethenyl, or ethynyl, or one or two geminal radical pairs $R_{a1}$/$R_{a2}$ or $R_{b1}$/$R_{b2}$, independently of one another, are a group of the formula $=CH_2$;

where optionally in formula (ii) the radicals $R_{a1}$ and $R_{b1}$ are not simultaneously H or c) C3 carbon bridges comprising up to 4 carbon atoms and selected from 1,3-propylene, 1,3-propenylene or 1,3-propynylene bridges which optionally carry a side group selected from —$CH_3$ or =$CH_2$;

or d) linear 1,4-linked C4 carbon bridges which optionally has a C—C double bond or two conjugated C—C double bonds or one two C—C triple bonds;

and also salts of these compounds, in particular acid addition salts with inorganic or in particular organic, mono- or in particular polybasic carboxylic acids;

and optionally in stereoisomerically pure form or as a mixture of stereoisomers.

4. Method according to embodiment 3, where, in the compound of the formula (II), X is not a methylene or linear 1,4-butylene bridge.

5. Method according to embodiment 3 or 4, wherein, in the compounds of the formula II,
$R_{21}$, $R_{24}$ and $R_{25}$ are H and
$R_{22}$ and $R_{23}$, together with the carbon atoms to which they are bonded, form a methylenedioxy group.

6. Method according to embodiment 3, 4 or 5, in which, in the compounds of the formula II, the radicals $R_{26}$ and $R_{27}$, independently of one another, are an in each case mononuclear aryl or heteroaryl radical or a $C_3$-$C_7$-cycloalkyl radical.

7. Method for the in-vitro or in-vivo modulation of the cold menthol receptor TRMP8, where the receptor is brought into contact with at least one modulator which is selected from compounds of the following structure type III:

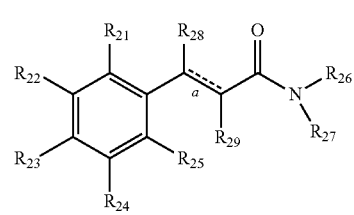

in which the bond a represents a C—C single bond or a C—C double bond;

$R_{21}$, $R_{22}$, $R_{23}$, $R_{24}$ and $R_{25}$ are identical or different and are selected from H;

halogen;

straight-chain or branched $C_1$-$C_6$-alkyl groups which optionally carry 1, 2, 3 or 4 identical or different substituents which are selected from $NH_2$, OH, SH, halogen or straight-chain or branched $C_1$-$C_6$-alkoxy groups;

straight-chain or branched $C_1$-$C_6$-alkoxy groups which optionally carry 1, 2, 3 or 4 identical or different substituents which are selected from $NH_2$, OH, SH, halogen or $C_1$-$C_6$-alkoxy groups;

mono- or polynuclear aryl, arylalkyl and heteroaryl groups which optionally carry 1, 2, 3 or 4 identical or different substituents which are selected from $NH_2$, OH, SH, halogen, straight-chain or branched $C_1$-$C_6$-alkyl groups and straight-chain or branched $C_1$-$C_6$-alkyloxy groups; where the heteroaryl groups have 1, 2, 3 or 4 ring heteroatoms which are identical or different and are selected from O, N and S; or two adjacent radicals $R_{21}$, $R_{22}$, $R_{23}$, $R_{24}$ and $R_{25}$, together with the carbon atoms to which they are bonded, form a 4-, 5-, 6- or 7-membered, mono- or polyunsaturated heterocyclic ring which optionally carries 1, 2, 3, 4 or 5 identical or different substituents which are selected from straight-chain or branched $C_1$-$C_6$-alkyl groups, and which has 1, 2 or 3 ring heteroatoms which are identical or different and are selected from O, N and S;

$R_{26}$ and $R_{27}$ are identical or different and is selected from:

straight-chain or branched $C_1$-$C_6$-alkyl groups which optionally carry 1, 2, 3 or 4 identical or different substituents which are selected from $NH_2$, OH, SH, halogen or straight-chain or branched $C_1$-$C_6$-alkoxy groups;

mono- or polynuclear aryl, arylalkyl, aryloxy, heteroaryl and heteroaryloxy groups which optionally carry 1, 2, 3 or 4 identical or different substituents which are selected from $NH_2$, OH, SH, halogen, straight-chain or branched $C_1$-$C_6$-alkyl groups and straight-chain or branched $C_1$-$C_6$-alkoxy groups; where the heteroaryl groups have 1, 2, 3 or 4 ring heteroatoms which are identical or different and are selected from O, N and S;

and $C_3$-$C_7$-cycloalkyl groups which optionally carry 1, 2, 3 or 4 identical or different substituents which are selected from $NH_2$, OH, SH, halogen, straight-chain or branched $C_1$-$C_6$-alkyl groups, or straight-chain or branched $C_1$-$C_6$-alkoxy groups; where the cycloalkyl group is optionally bonded via a $C_1$-$C_4$-alkylene group; and where optionally 1, 2 or 3 ring carbon atoms may be replaced by identical or different heteroatoms selected from O, N and S; where in particular $R_{26}$ and $R_{27}$ are identical or different and is selected from cyclohexyl, 2-pyridyl and phenyl;

and $R_{28}$ and $R_{29}$ are identical or different and are selected from H and straight-chain or branched alkyl, such as $C_1$-$C_8$-alkyl, straight-chain or branched alkenyl, such as $C_2$-$C_8$-alkenyl, straight-chain or branched alkynyl, such as $C_2$-$C_8$-alkynyl, cycloalkyl, such as $C_3$-$C_{12}$-cycloalkyl or cycloalkenyl, such as $C_5$-$C_8$-cycloalkenyl, where the carbon chain, or the carbon ring of these radicals is optionally interrupted by one or more, such as e.g. 1, 2, 3 or 4, in particular 1 or 2, heteroatoms (in the chain or in the ring), selected from O, S and N (or —NH—), in particular O, or carries one or more, such as, in particular, 1, 2 or 3, heteroatom-containing substituents, such as e.g. —COOH, —COO-alkyl, —OH, —SH, —CN, amino, nitro, as defined herein, where the sum of the carbon atoms in the radicals $R_{28}$ and $R_{29}$ together is at least 3;

and also salts of these compounds, in particular acid addition salts with inorganic or in particular organic, mono- or in particular polybasic carboxylic acids;

and optionally in stereoisomerically pure form or as a mixture of stereoisomers.

8. Method according to any one of the preceding embodiments, where the receptor is brought into contact with at least one compound which, in a cellular activity test using cells which recombinantly express the human TRPM8 receptor, modulates the permeability of these cells for $Ca^{2+}$ ions.

9. Method according to any one of the preceding embodiments, where the modulating compound has an agonistic or antagonistic effect on the cellular $Ca^{2+}$ ion permeability.

10. Method according to any one of the preceding embodiments, where the modulating compound is a TRPM8 receptor agonist.

11. Use of a compound according to the definition in any one of embodiments 1 to 7 for inducing a sensation of coldness in humans and/or animals, in particular for non-therapeutic purposes.

12. Use of a compound according to the definition in any one of embodiments 1 to 7 as active constituent of a pharmaceutical composition.

13. Use of a compound according to the definition in any one of embodiments 1 to 7 for the treatment of prostate carcinomas, for the treatment of bladder weakness or in pain therapy.

14. Use of a compound according to the definition in any one of embodiments 1 to 7 for inducing a sensation of coldness through a packaging.

15. Use of a compound according to the definition in any one of embodiments 1 to 7 for inducing a sensation of coldness through a textile.

16. Use according to embodiment 11, where a composition is used comprising one or more of the compounds according to the definitions from any one of embodiments 1 to 7 in a concentration of from 0.1 ppm to 10% by weight, based on the total weight of the composition, for achieving a cooling effect on skin or mucosa which, compared with the cooling effect of a composition of identical composition in which merely the compound or the compounds according to the definitions from any one of embodiments 1 to 7 are exchanged for menthanecarboxylic acid N-ethylamide in identical concentration, is extended by at least 10 minutes.

17. Substance according to the definition according to any one of embodiments 1 to 7 for use as mediator of the TRMP8 receptor.

18. Composition comprising at least one compound according to any one of embodiments 1 to 7.

19. Composition according to embodiment 18, selected from
   a) pharmaceutical compositions, such as antitumor agents, agents for the treatment of diseases of the bladder, painkillers;
   b) foods, such as ice cream, mousse, cream, beverages, confectionery,
   c) mouthcare compositions, such as toothpaste, mouthwash, chewing gum,
   d) bodycare compositions, such as skincare or haircare compositions, such as suncream, sunburn cream, lotions, shampoos, plasters,
   e) foams and gels.

20. Composition according to embodiment 19, comprising
   a) one or more further substances with a physiological cooling effect, where the further substance or one, several or all of the further substances (i) cause a gustatory effect or (ii) do not cause a gustatory effect, and/or
   b) one or more aroma substances without a physiological cooling effect and/or
   c) one or more trigeminally or mouth-washing effective substances without a physiological cooling effect and/or
   d) (iii) one or (iv) several compounds which, in the case of (iv), independently of one another or together, additionally cause a taste-modulating effect and/or a trigeminal and/or mouth-washing stimulus.

21. Product comprising at least one compound according to the definition according to any one of embodiments 1 to 7, selected from
   a) textile products,
   b) packaging materials,
   c) tobacco products;
   d) remedies;
   e) hygiene products, or
   f) freshening wipes.

22. Substance according to the definition according to any one of embodiments 1 to 7
23. Substance according to embodiment 22, selected from compounds according to tables 1 or 2 A to D.
24. Composition according to any one of embodiments 17 to 20 for preventing, controlling or alleviating symptoms of coughing, sneezing, inflammation, throat pain or hoarseness.
25. Method, use, substance, product or composition according to one of embodiments 2 or 8 to 24, where, instead of a compound of the formula IC, a compound of the formula IC' is present,

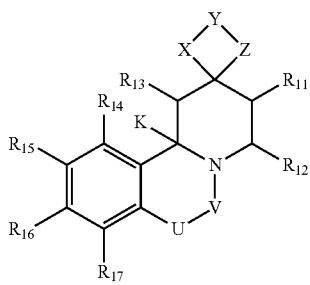

(IC')

in which
U, V, X, Y, Z and $R_{11}$ to $R_{18}$ have the meanings given in embodiment 2; and
K is a radical of the formula

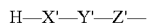

H—X'—Y'—Z'— in which
X', Y' and Z', independently of one another, have the meanings given for X, Y and Z;
and also salts of these compounds, in particular acid addition salts with inorganic or in particular organic, mono- or in particular polybasic carboxylic acids; and optionally isomers or stereoisomers thereof, in each case in pure form or as a mixture of isomers and/or stereoisomers.

For example, here, U is a chemical bond and V is carbonyl. For example, Y and Y' are identical or different, e.g. identical $C_1$-$C_8$-alkylene groups. For example, X, Z, X' and Z' are identical or different, e.g. identical, and are —O— or —S—. $R_{13}$ to $R_{17}$ are for example, independently of one another, H or —COOH, —COO-alkyl, —OH, —SH, —CN, amino, —NO$_2$, alkyl, or alkenyl groups, such as in particular H. $R_{11}$ and $R_{12}$ form, for example together with the carbon atoms to which they are bonded, a 4-, 5-, 6- or 7-membered, saturated or mono- or polyunsaturated, carbocyclic ring.

26. Method, use, substance, product or composition according to any one of embodiments 2 or 8 to 24, where, instead of a compound of the formula IB, a compound of the formula IB' is present,

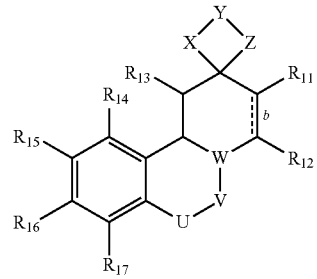

(IB')

in which:
b, U, V, X, Y, Z and $R_{11}$ to $R_{18}$ have the meanings given in embodiment 2; and W is a carboxylate radical, in particular a radical of the formula

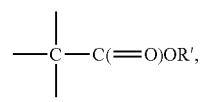

—C—C(=O)OR', where R' is alkyl, such as e.g. $C_1$-$C_6$-alkyl;
and also salts of these compounds, in particular acid addition salts with inorganic or in particular organic, mono- or in particular polybasic carboxylic acids; and optionally isomers or stereoisomers thereof, in each case in pure form or as a mixture of isomers and/or stereoisomers.

Here, U is e.g. —O—. V is for example carbonyl. Z and X are different or in particular identical and are e.g. —O— or —S—. Y is for example $C_1$-$C_8$-alkylene. $R_{13}$ to $R_{17}$ are for example, independently of one another, H or —COOH, —COO-alkyl, —OH, —SH, —CN, amino, —NO$_2$, alkyl, or alkenyl groups, such as in particular H. $R_{11}$ and $R_{12}$ form, for example together with the carbon atoms to which they are bonded, a 4-, 5-, 6- or 7-membered, saturated or mono- or polyunsaturated, carbocyclic ring.

27. Method, use, substance, product or composition according to any one of embodiments 2 or 8 to 24, where, instead of a compound of the formula IA, a compound of the formula IA' is present,

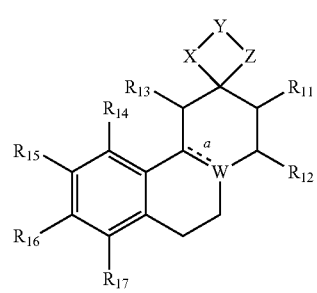

(IA')

in which X, Y, Z and $R_{11}$ to $R_{18}$ have the meanings given in embodiment 1; with the proviso that W is a carbon atom and a is optionally a double bond;
and also salts of these compounds, in particular acid addition salts with inorganic or in particular organic, mono- or in particular polybasic carboxylic acids; and optionally isomers or stereoisomers thereof, in each case in pure form or as a mixture of isomers and/or stereoisomers;

Z and X are different or in particular identical and are e.g. —O— or —S—. Y is for example $C_1$-$C_8$-alkylene. $R_{13}$ to $R_{17}$ are for example, independently of one another, H or —COOH, —COO-alkyl, —OH, —SH, —CN, amino, —$NO_2$, alkyl, or alkenyl groups, such as in particular H. $R_{11}$ and $R_{12}$ form, for example together with the carbon atoms to which they are bonded, a 4-, 5-, 6- or 7-membered, saturated or mono- or polyunsaturated, carbocyclic ring.

3. Further Embodiments of the Methods, Uses and Active Ingredients According to the Invention The following specific embodiments of active ingredients according to the invention apply correspondingly both for the active ingredients per se and also their applications according to the invention, such as e.g. in the agents, methods and uses claimed according to the invention.

3.1 Compounds of the Formula I (Structure Type I)

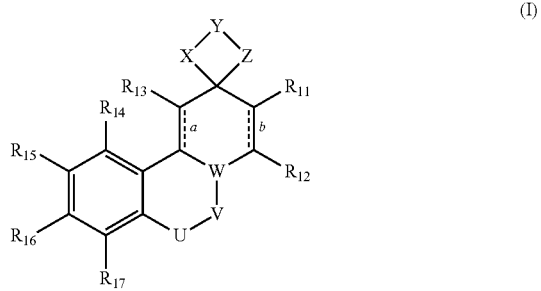
(I)

selected from compounds of the following groups (1) to (55):

(1) compounds of the formula I in which $R_{13}$ to $R_{17}$, independently of one another, is H, straight-chain or branched $C_1$-$C_6$-alkyl groups, in particular H;

(2) compounds of the formula I, in which $R_{11}$ and $R_{12}$, together with the carbon atoms to which they are bonded, form a 5- or 6-membered, saturated or monounsaturated carbo- or heterocyclic, in particular carbocyclic, ring which optionally carries 1, 2 or 3 identical or different substituents which are selected from straight-chain or branched $C_1$-$C_6$-alkyl groups, and oxo groups (=O); and the ring heteroatoms are O atoms;

(3) compounds of the formula I in which $R_{11}$ and $R_{12}$, together with the carbon atoms to which they are bonded, form a 5- or 6-membered, monounsaturated, carbo- or heterocyclic ring which optionally carries 1, 2 or 3 identical or different substituents which are selected from straight-chain $C_1$-$C_4$-alkyl groups, and carries an oxo group (=O); and the ring heteroatom is a O atom;

(4) compounds of the formula I in which $R_{11}$ and $R_{12}$ together form bridging groups selected from
—C(=O)—O—C*H($CH_3$)— in both stereoisomeric forms
—C(=O)—$CH_2$—C($CH_3$)$_2$—$CH_2$—
—C(=O)—$CH_2$—$CH_2$—$CH_2$—
where the keto group is bonded to the molecule via the $R_{12}$ or in particular via the $R_{11}$ position.

(5) compounds of the formula I in which X and Z are identical or different and are selected from —NR— in which R is H or $C_1$-$C_6$-alkyl, —S—, —S(=O)—, or —S(=O)$_2$— groups;

(6) compounds of the formula I in which X and Z are identical and are in each case —S—;

(7) compounds of the formula I in which X and Z are different and are selected from —S(=O)— or —S(=O)$_2$— groups;

(8) compounds of the formula I in which Y is selected from straight-chain $C_2$- or $C_3$-alkylene groups, in particular —$CH_2$—$CH_2$— or —$CH_2$—$CH_2$—$CH_2$—, (9) compounds of the formula I, in which X—Y—Z, together with the carbon atom to which they are bonded, form a keto group;

(10) combinations of the embodiments: (1)+(2), (1)+(3), (1)+(4)

(11) combinations of the embodiments: (1)+(5), (1)+(6), (1)+(7)

(12) combinations of the embodiments: (1)+(8),

(13) combinations of the embodiments: (1)+(9),

(14) combinations of the embodiments: (10)+(5), (10)+(6), (10)+(7)

(15) combinations of the embodiments: (10)+(8)

(16) combinations of the embodiments: (10)+(9)

(17) combinations of the embodiments: (14)+(8)

(18) combinations of the embodiments: (11)+(8)

(19) compounds of the formula I, in which a is a C—C double bond

(20) compounds of the formula I, in which b is a C—C single bond

(21) compounds of the formula I, in which a and b are a C—C double bond

(22) compounds of the formula I, in which a and b are a C—C single bond

(23) compounds of the formula I, in which W is CH

(24) compounds of the formula I, in which V is carbonyl

(25) compounds of the formula I, in which U is a chemical single bond

(26) compounds of the formula I, in which U is —O—

(27) combinations of the embodiments: (1)+(19), (1)+(20), (1)+(21), (1)+(22),

(28) combinations of the embodiments: (1)+(23), (1)+(24), (1)+(25), (1)+(26)

(29) combinations of the embodiments: (10)+(19), (10)+(20), (10)+(21), (10)+(22),

(30) combinations of the embodiments: (10)+(23), (10)+(24), (10)+(25), (10)+(26)

(31) combinations of the embodiments: (11)+(19), (11)+(20), (11)+(21), (11)+(22),

(32) combinations of the embodiments: (11)+(23), (11)+(24), (11)+(25), (11)+(26)

(33) combinations of the embodiments: (12)+(19), (12)+(20), (12)+(21), (12)+(22),

(34) combinations of the embodiments: (12)+(23), (12)+(24), (12)+(25), (12)+(26)

(35) combinations of the embodiments: (13)+(19), (13)+(20), (13)+(21), (13)+(22),

(36) combinations of the embodiments: (13)+(23), (13)+(24), (13)+(25), (13)+(26)

(37) combinations of the embodiments: (27)+(23), (27)+(24), (37)+(25), (27)+(26)

(38) combinations of the embodiments: (14)+(19), (14)+(20), (14)+(21), (14)+(22),

(39) combinations of the embodiments: (14)+(23), (14)+(24), (14)+(25), (14)+(26)

(40) combinations of the embodiments: (15)+(19), (15)+(20), (15)+(21), (15)+(22),
(41) combinations of the embodiments: (15)+(23), (15)+(24), (15)+(25), (15)+(26)
(42) combinations of the embodiments: (16)+(19), (16)+(20), (16)+(21), (16)+(22),
(43) combinations of the embodiments: (16)+(23), (16)+(24), (16)+(25), (16)+(26)
(44) combinations of the embodiments: (18)+(19), (18)+(20), (18)+(21), (18)+(22),
(45) combinations of the embodiments: (18)+(23), (18)+(24), (18)+(25), (18)+(26)
(46) combinations of the embodiments: (31)+(23), (31)+(24), (31)+(25), (31)+(26)
(47) combinations of the embodiments: (33)+(23), (33)+(24), (33)+(25), (33)+(26)
(48) combinations of the embodiments: (35)+(23), (35)+(24), (35)+(25), (35)+(26)
(49) combinations of the embodiments: (17)+(19), (17)+(20), (17)+(21), (17)+(22),
(50) combinations of the embodiments: (17)+(23), (17)+(24), (17)+(25), (17)+(26)
(51) combinations of the embodiments: (38)+(23), (38)+(24), (38)+(25), (38)+(26)
(52) combinations of the embodiments: (40)+(23), (40)+(24), (40)+(25), (40)+(26)
(53) combinations of the embodiments: (42)+(23), (42)+(24), (42)+(25), (42)+(26)
(54) combinations of the embodiments: (44)+(23), (44)+(24), (44)+(25), (44)+(26)
(55) combinations of the embodiments: (29)+(23), (29)+(24), (29)+(25), (29)+(26)

3.2 Compounds of the Formula IA

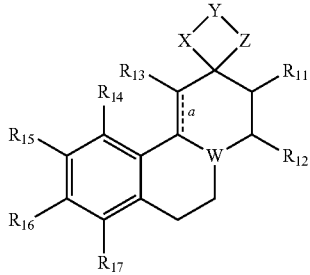

(IA)

These are selected from compounds corresponding to the groups (1) to (55) given above for formula I, insofar as permissible by the more specific meanings of formula IA.

3.3 Compounds of the General Formula IB

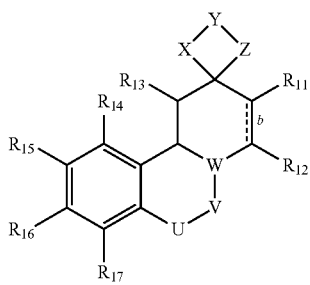

(IB)

These are selected from compounds corresponding to the groups (1) to (55) given above for formula I, insofar as permissible by the more specific meanings of formula IB.

3.4 Compounds of the formula IC

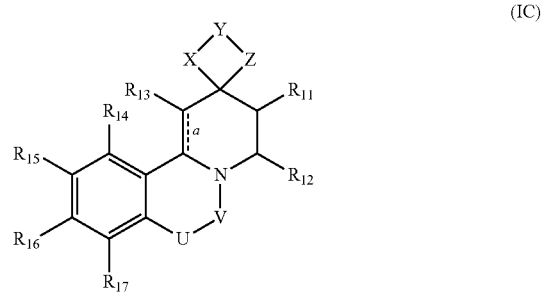

(IC)

selected from compounds corresponding to the groups (1) to (55) given above for formula I, insofar as permissible by the more specific meanings of formula IC.

3.4 Compounds of the General Formulae IA', IB' and IC'

These are selected from special compounds corresponding to the groups (1) to (55) given above for formula I, insofar as permissible by the more specific meanings of formulae IA', IB' and IC' above.

Nonlimiting examples of compounds of formula I (or of formulae IA, IB, IC, IA', IB' and IC') are summarized in table 1 below.

TABLE 1

Examples of compounds of the formula I

| No. | Formula |
|---|---|
| 1 |  |
| 2 |  |
| 3 |  |

TABLE 1-continued

Examples of compounds of the formula I

| No. | Formula |
|---|---|
| 4 | (structure) |
| 5 | (structure) |
| 6 | (structure) |
| 7 | (structure) |
| 8 | (structure) |
| 9 | (structure) |
| 10 | (structure) |
| 11 | (structure) |
| 12 | (structure) |
| 13 | (structure) |
| 14 | (structure) |
| 15 | (structure) |
| 16 | (structure) |

TABLE 1-continued

Examples of compounds of the formula I

| No. | Formula |
|-----|---------|
| 17 | |
| 18 | |
| 19 | |
| 20 | |
| 21 | |
| 22 | |
| 23 | |
| 24 | |
| 25 | |
| 26 | |
| 27 | |
| 28 | |

TABLE 1-continued

Examples of compounds of the formula I

| No. | Formula |
|---|---|
| 29 | |
| 30 | |
| 31 | |
| 32 | |
| 33 | |
| 34 | |
| 35 | |
| 36 | |

Here, X and Z are in particular: O, S, NMe, NEt, SO, $SO_2$, NPh, NiPr, NPr, $NC_4H_9$, $NC_5H_{11}$, $NC_6H_{13}$; n is here in particular 2, 3 or 4; R is in particular $C_1$-$C_6$-alkyl or phenyl.

Further examples are:

TABLE 1
(continuation)

| No. | Formula |
|---|---|
| P1 | |
| P2 | |
| P3 | |

TABLE 1-continued
| No. | Formula |
|---|---|
| P4 | 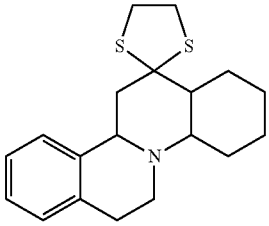 [SMILES: c1ccc2c(c1)CCN1C2CC2(SCCS2)C2CCCCC21] |
| P5 | 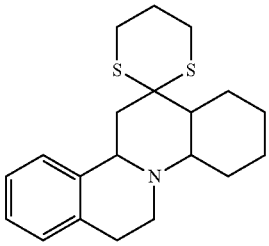 [SMILES: c1ccc2c(c1)CCN1C2CC2(SCCCS2)C2CCCCC21] |
| P6 | 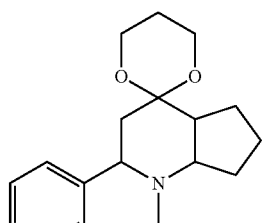 |
| P7 | 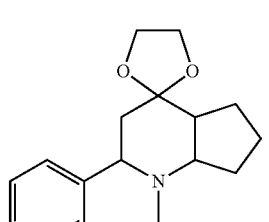 |
| P8 | 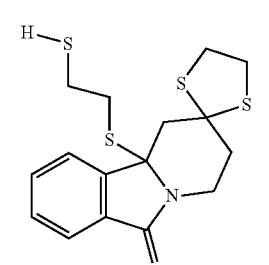 |
| P9 | 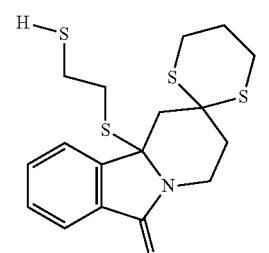 |
| P10 | 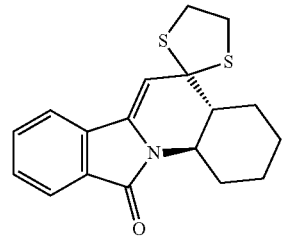 [SMILES: O=C1c2ccccc2C2=CC3(SCCS3)[C@@H]3CCCC[C@H]3N12] |
| P11 | 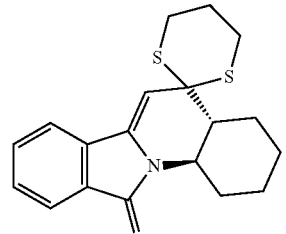 |
| P12 | 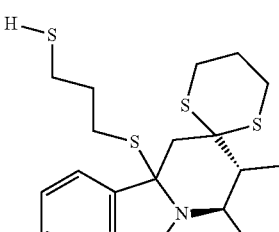 |
| P13 | 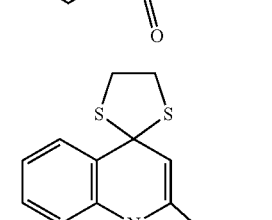 |
| P14 | 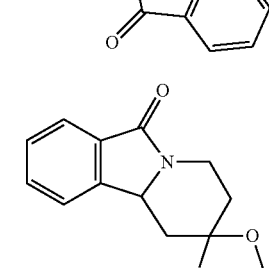 |
| P15 | 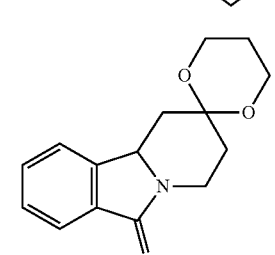 |

TABLE 1-continued

| No. | Formula |
|---|---|
| P16 | |
| P17 | |
| P18 | |
| P19 | |
| P20 | |
| P21 | |
| P22 | |
| P23 | |
| P24 | |
| P25 | |
| P26 | |

TABLE 1-continued (continuation)

| No. | Formula |
|---|---|
| P27 | |
| P28 | |
| P29 | |
| P30 | |
| P31 | |

Also provided are salts of these compounds in table 1 above, in particular acid addition salts with inorganic or in particular organic, mono- or in particular polybasic carboxylic acids; and all isomers or stereoisomers in pure form or as a mixture of isomers and/or stereoisomers.

3.6 Compounds of the General Formula II

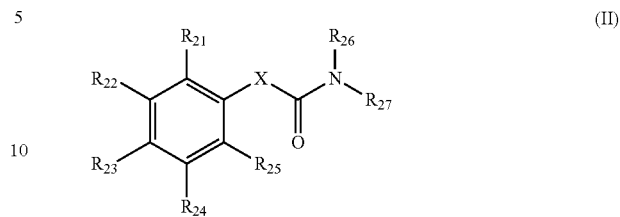

selected from compounds of the following groups (1) to (63):

(1) compounds of the formula II in which $R_{24}$ is H;
(2) compounds of the formula II in which $R_{25}$ is H or halogen;
(3) compounds of the formula II in which $R_{21}$ is H, halogen, a straight-chain or branched $C_1$-$C_6$-alkyl group which optionally carries 1, 2, 3 or 4 identical or different substituents which are selected from $NH_2$, OH, SH, halogen or straight-chain or branched $C_1$-$C_6$-alkoxy groups; or is a straight-chain or branched $C_1$-$C_6$-alkoxy group which optionally carries 1, 2, 3 or 4 identical or different substituents which are selected from $NH_2$, OH, SH, halogen or $C_1$-$C_6$-alkoxy groups;
(4) compounds of the formula II in which $R_{21}$ is H, halogen, a straight-chain or branched $C_1$-$C_6$-alkyl group; or is a straight-chain or branched $C_1$-$C_6$-alkoxy group;
(5) compounds of the formula II in which $R_{21}$ is H, methyl, ethyl, methoxy, ethoxy, or halogen, in particular H, fluorine, chlorine, bromine, methyl or methoxy;
(6) compounds of the formula II in which the radicals $R_{22}$ and $R_{23}$ are identical or different and are selected from H; halogen, straight-chain or branched $C_1$-$C_6$-alkyl groups which optionally carry 1, 2, 3 or 4 identical or different substituents which are selected from $NH_2$, OH, SH, halogen or straight-chain or branched $C_1$-$C_6$-alkoxy groups; or straight-chain or branched $C_1$-$C_6$-alkoxy groups which optionally carry 1, 2, 3 or 4 identical or different substituents which are selected from $NH_2$, OH, SH, halogen or $C_1$-$C_6$-alkoxy groups;
(7) compounds of the formula II in which the radicals $R_{22}$ and $R_{23}$ are identical or different and are selected from H, halogen, straight-chain or branched $C_1$-$C_6$-alkyl groups; or straight-chain or branched $C_1$-$C_6$-alkoxy groups;
(8) compounds of the formula II in which the radicals $R_{22}$ and $R_{23}$ are identical or different and are selected from H, halogen, methyl or methoxy
(9) compounds of the formula II in which the adjacent radicals $R_{22}$ and $R_{23}$, together with the carbon atoms to which they are bonded, form a 4-, 5-, 6- or 7-membered, mono- or polyunsaturated heterocyclic ring which optionally carries 1, 2, 3, 4 or 5 identical or different substituents which are selected from straight-chain or branched $C_1$-$C_6$-alkyl groups, and which has 1, 2 or 3 ring heteroatoms which are identical or different and are selected from O, N and S;
(10) compounds of the formula II in which the adjacent radicals $R_{22}$ and $R_{23}$, together with the carbon atoms to which they are bonded, form a 5- or 6-membered, mono-unsaturated heterocyclic ring which has 1 or 2 ring heteroatoms which are identical or different and are selected from O, N and S;

(11) compounds of the formula II in which the adjacent radicals $R_{22}$ and $R_{23}$, together form one of the groups —O—CH$_2$—O— or —O—CH$_2$—CH$_2$—O—;

(12) compounds of the formula II in which the radicals $R_{26}$ and $R_{27}$ are identical or different and are selected from straight-chain or branched $C_1$-$C_6$-alkyl groups which optionally carry 1 or 2 identical or different substituents which are selected from NH$_2$, OH, SH, halogen or straight-chain or branched $C_1$-$C_6$-alkoxy groups; mononuclear aryl, arylalkyl and heteroaryl groups which optionally carry 1 or 2 identical or different substituents which are selected from NH$_2$, OH, SH, halogen, straight-chain or branched $C_1$-$C_6$-alkyl groups and straight-chain or branched $C_1$-$C_6$-alkyloxy groups; where the heteroaryl groups have 1, 2 or 3 ring heteroatoms which are identical or different and are selected from O, N and S; and $C_3$-$C_7$-cycloalkyl groups which optionally carry 1 or 2 identical or different substituents which are selected from NH$_2$, OH, SH, halogen, straight-chain or branched $C_1$-$C_6$-alkyl groups, or straight-chain or branched $C_1$-$C_6$-alkoxy groups; where the cycloalkyl group is optionally bonded via a $C_1$-$C_4$-alkylene group and where optionally 1, 2 or 3 ring carbon atoms can be replaced by identical or different heteroatoms selected from O, N and S;

(13) compounds of the formula II in which the radicals $R_{26}$ and $R_{27}$ are identical or different and are selected from straight-chain or branched $C_1$-$C_6$-alkyl groups; mononuclear aryl, arylalkyl and heteroaryl groups which optionally carry a substituent which is selected from NH$_2$, OH, SH, halogen, straight-chain $C_1$-$C_6$-alkyl groups and straight-chain $C_1$-$C_6$-alkyloxy groups; where the heteroaryl groups have 1, 2 or 3 ring heteroatoms which are identical or different and are selected from O, N and S; and $C_3$-$C_7$-cycloalkyl groups which optionally carry 1 or 2 identical or different substituents which are selected from NH$_2$, OH, SH, halogen, straight-chain or branched $C_1$-$C_6$-alkyl groups, or straight-chain or branched $C_1$-$C_6$-alkoxy groups; where the cycloalkyl group is optionally bonded via a $C_1$-$C_4$-alkylene group; and where optionally 1 or 2 ring carbon atoms can be replaced by identical or different heteroatoms selected from O and N;

(14) compounds of the formula II in which the radicals $R_{26}$ and $R_{27}$ are identical or different and are selected from methyl, ethyl, n-prop-1-yl, n-prop-2-yl, n-butyl, sec-butyl, isobutyl, tert-butyl, n-pentyl (amyl), 2-pentyl (sec-pentyl), 3-pentyl, 2-methylbutyl, 3-methylbutyl (isopentyl or isoamyl), 3-methylbut-2-yl, 2-methylbut-2-yl; 2,2-dimethylpropyl (neopentyl);
cyclopropyl, cyclopropylmethyl, cyclopropylethyl, cyclobutyl, cyclobutylmethyl, cyclopentyl, cyclopentylmethyl, cyclohexyl, cyclohexylmethyl; cycloheptyl; benzyl; phenyl; 2-fluorophenyl, 3-fluorophenyl, 4-fluorophenyl, 2-chlorophenyl, 3-chlorophenyl, 4-chlorophenyl, 2-bromophenyl, 3-bromophenyl, 4-bromophenyl; 2-fluorobenzyl, 3-fluorobenzyl, 4-fluorobenzyl, 2-chlorobenzyl, 3-chlorobenzyl, 4-chlorobenzyl, 2-bromobenzyl, 3-bromobenzyl, 4-bromobenzyl; 2-methylphenyl, 3-methylphenyl, 4-methylphenyl, 2-methylbenzyl, 3-methylbenzyl, 4-methylbenzyl;
2-pyridyl, 3-pyridyl, 4-pyridyl, thiazolyl, oxazolyl, pyrazolyl, furanyl, morpholinyl, pyranyl,
in particular cyclohexyl, cyclopropylmethyl, phenyl, benzyl, 4-chlorophenyl, 2-methylphenyl, 2-pyridyl, 2-thiazolyl, methyl, ethyl, n-propyl, isopropyl, n-butyl, isobutyl;

(15) compounds of the formula II in which X is selected from a) C1 carbon bridges comprising 1, 2, 3 or 4 carbon atoms and of the general formula

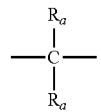

in which
one of the radicals $R_a$ is H or methyl and the other is straight-chain or branched $C_1$-$C_3$-alkyl, or are straight-chain or branched $C_2$-$C_3$-alkenyl or both $R_a$ radicals a group of the formula

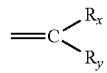

in which $R_x$ and $R_y$, independently of one another, are H, methyl or ethyl; or b) C2 carbon bridges comprising 2, 3 or 4 carbon atoms and of the general formulae

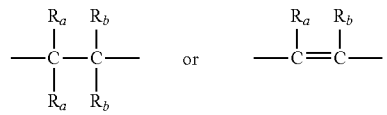

in which
the radicals $R_a$ and $R_b$, independently of one another, are H, methyl, ethyl, ethenyl, or two geminal radicals $R_a$ or $R_b$ are a group of the formula =CH$_2$;
or c) C3 carbon bridges comprising 3 or 4 carbon atoms and selected from 1,3-propylene and 1,3-propenylene bridges which optionally carry a methyl side group;
or d) linear 1,4-linked C4 carbon bridges which optionally has 1 double bond;

(16) compounds of the formula II in which X is selected from the C1-C2-, C3- and C4-bridges listed in tables 2A, 2B, 2C and 2D below.

(17) Combinations of the embodiments: (1)+(2);
(18) Combinations of the embodiments: (1)+(3), (1)+(4), (1)+(5);
(19) Combinations of the embodiments: (1)+(6), (1)+(7), (1)+(8);
(20) Combinations of the embodiments: (1)+(9), (1)+(10), (1)+(11);
(21) Combinations of the embodiments: (1)+(12), (1)+(13), (1)+(14);
(22) Combinations of the embodiments: (1)+(15), (1)+(16);
(23) Combinations of the embodiments: (17)+(3), (17)+(4), (17)+(5)
(24) Combinations of the embodiments: (17)+(6), (17)+(7), (17)+(8);
(25) Combinations of the embodiments: (17)+(9), (17)+(10), (17)+(11);
(26) Combinations of the embodiments: (17)+(12), (17)+(13), (17)+(14);
(27) Combinations of the embodiments: (17)+(15), (17)+(16);

(28) Combinations of the embodiments: (23)+(6), (23)+(7), (23)+(8);
(29) Combinations of the embodiments: (23)+(9), (23)+(10), (23)+(11);
(30) Combinations of the embodiments: (23)+(12), (23)+(13), (23)+(14);
(31) Combinations of the embodiments: (23)+(15), (23)+(16);
(32) Combinations of the embodiments: (28)+(12), (28)+(13), (28)+(14);
(33) Combinations of the embodiments: (28)+(15), (28)+(16);
(34) Combinations of the embodiments: (32)+(15), (32)+(16);
(35) Combinations of the embodiments: (29)+(12), (29)+(13), (29)+(14);
(36) Combinations of the embodiments: (29)+(15), (29)+(16);
(37) Combinations of the embodiments: (35)+(15), (35)+(16);
(38) Combinations of the embodiments: (30)+(15), (30)+(16);
(39) Combinations of the embodiments: (24)+(12), (24)+(13), (24)+(14);
(40) Combinations of the embodiments: (24)+(15), (24)+(16);
(41) Combinations of the embodiments: (39)+(15), (39)+(16);
(42) Combinations of the embodiments: (25)+(12), (25)+(13), (25)+(14);
(43) Combinations of the embodiments: (25)+(15), (25)+(16);
(44) Combinations of the embodiments: (42)+(15), (42)+(16);
(45) Combinations of the embodiments: (26)+(15), (26)+(16);
(46) Combinations of the embodiments: (18)+(6), (18)+(7), (18)+(8);
(47) Combinations of the embodiments: (18)+(9), (18)+(10), (18)+(11);
(48) Combinations of the embodiments: (18)+(12), (18)+(13), (18)+(14);
(49) Combinations of the embodiments: (18)+(15), (18)+(16);
(50) Combinations of the embodiments: (46)+(12), (46)+(13), (46)+(14);
(51) Combinations of the embodiments: (46)+(15), (46)+(16);
(52) Combinations of the embodiments: (50)+(15), (50)+(16);
(53) Combinations of the embodiments: (47)+(12), (47)+(13), (47)+(14);
(54) Combinations of the embodiments: (47)+(15), (47)+(16);
(55) Combinations of the embodiments: (53)+(15), (53)+(16);
(56) Combinations of the embodiments: (48)+(15), (48)+(16);
(57) Combinations of the embodiments: (19)+(12), (19)+(13), (19)+(14);
(58) Combinations of the embodiments: (19)+(15), (19)+(16);
(59) Combinations of the embodiments: (57)+(15), (57)+(16);
(60) Combinations of the embodiments: (20)+(12), (20)+(13), (20)+(14);
(61) Combinations of the embodiments: (20)+(15), (20)+(16);
(62) Combinations of the embodiments: (60)+(15), (60)+(16);
(63) Combinations of the embodiments: (21)+(15), (21)+(16);
(64) Compounds of the formula II, in which the radicals $R_{26}$ and $R_{27}$ are identical or different and is selected from cyclohexyl, 2-pyridyl and phenyl;
(65) Compounds of the formula II, in which the radicals $R_{26}$ and $R_{27}$, together with the N atom to which they are bonded, is —N(cyclohexyl)(2-pyridin-2yl) or —N(phenyl)$_2$.
(66) Combination of embodiment (64) with one of embodiments (1) to (63).
(67) Combination of embodiment (65) with one of embodiments (1) to (63).

Specific examples of compounds of formula 2 are summarized in table 2 (A, B, C and B) below.

TABLE 2A

| Compounds with C1 bridges |
|---|
| one carbon atom |

1

| two carbon atoms |
|---|

2

3

| three carbon atoms |
|---|

4

TABLE 2A-continued
Compounds with C1 bridges
5 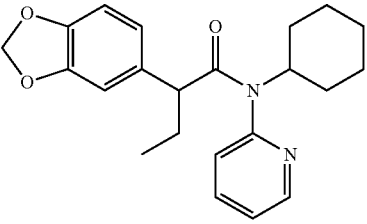 [SMILES: CCC(C(=O)N(c1ccccn1)C1CCCCC1)c1ccc2c(c1)OCO2]
6 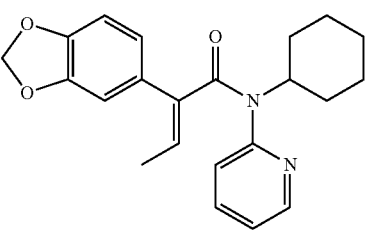 [SMILES: C/C=C(/C(=O)N(c1ccccn1)C1CCCCC1)c1ccc2c(c1)OCO2]
7 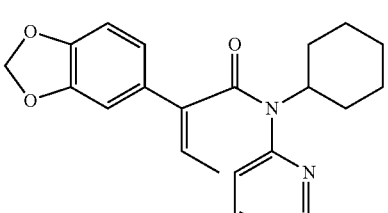
8 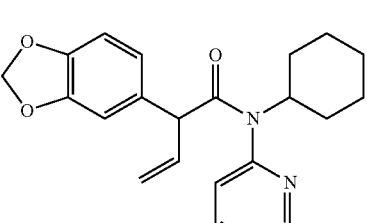
9 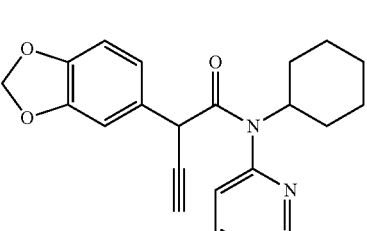
four carbon atoms
10 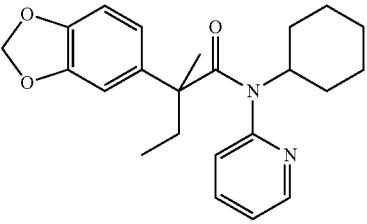 [SMILES: CCC(C)(C(=O)N(c1ccccn1)C1CCCCC1)c1ccc2c(c1)OCO2]
11 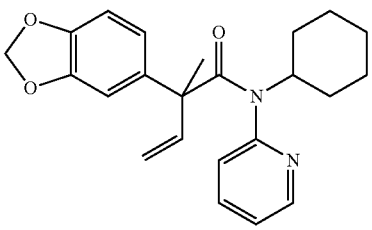 [SMILES: C=CC(C)(C(=O)N(c1ccccn1)C1CCCCC1)c1ccc2c(c1)OCO2]
12 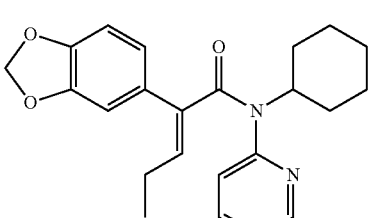
13 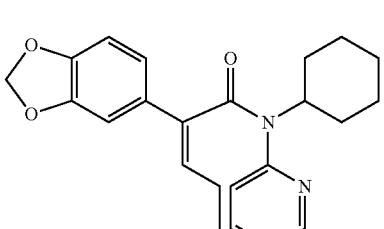
14 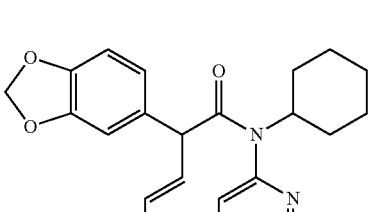
15 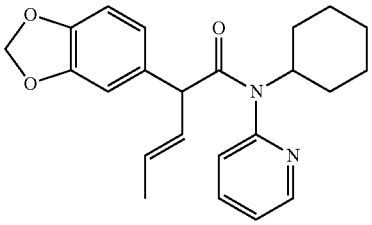 [SMILES: C/C=C/C(C(=O)N(c1ccccn1)C1CCCCC1)c1ccc2c(c1)OCO2]
16 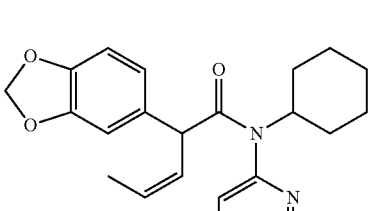

TABLE 2A-continued

Compounds with C1 bridges

17 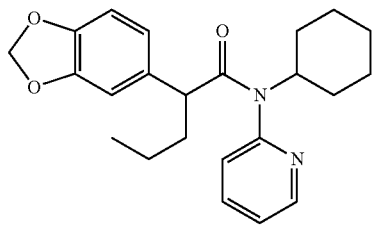 [SMILES: CCCC(C(=O)N(c1ccccn1)C1CCCCC1)c1ccc2c(c1)OCO2]

18 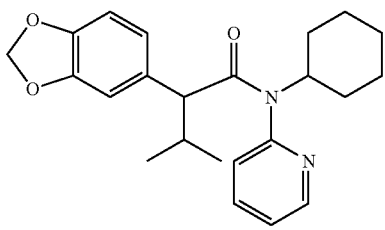 [SMILES: CC(C)C(C(=O)N(c1ccccn1)C1CCCCC1)c1ccc2c(c1)OCO2]

19 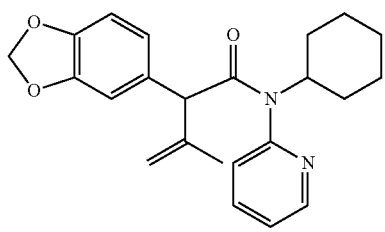 [SMILES: C=C(C)C(C(=O)N(c1ccccn1)C1CCCCC1)c1ccc2c(c1)OCO2]

20 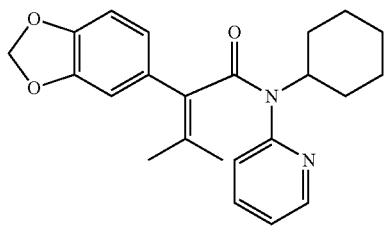 [SMILES: CC(C)=C(C(=O)N(c1ccccn1)C1CCCCC1)c1ccc2c(c1)OCO2]

21 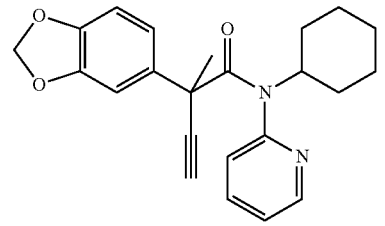 [SMILES: C#CC(C)(C(=O)N(c1ccccn1)C1CCCCC1)c1ccc2c(c1)OCO2]

22 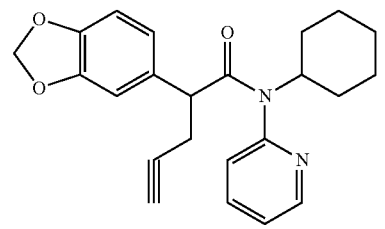 [SMILES: C#CCC(C(=O)N(c1ccccn1)C1CCCCC1)c1ccc2c(c1)OCO2]

23 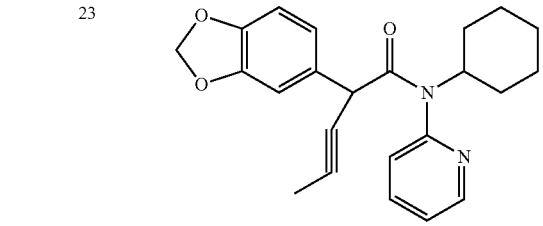

Also provided are salts of these compounds in the table above, in particular acid addition salts with inorganic or in particular organic, mono- or in particular polybasic carboxylic acids; and all isomers or stereoisomers in pure form or as a mixture of isomers and/or stereoisomers.

TABLE 2B

Compounds with C2 bridges two carbon atoms

24 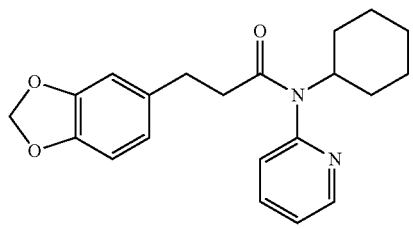 [SMILES: O=C(CCc1ccc2c(c1)OCO2)N(c1ccccn1)C1CCCCC1]

21a 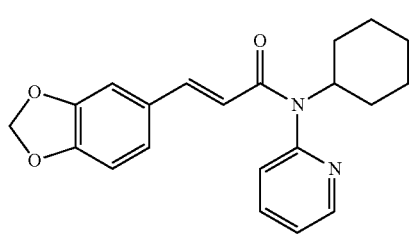 [SMILES: O=C(/C=C/c1ccc2c(c1)OCO2)N(c1ccccn1)C1CCCCC1]

26 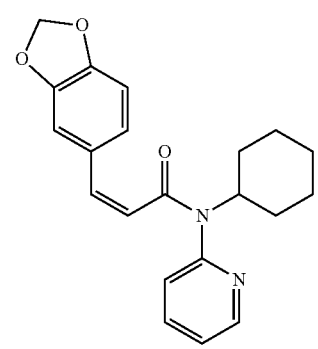 [SMILES: O=C(/C=C\c1ccc2c(c1)OCO2)N(c1ccccn1)C1CCCCC1]

three carbon atoms

27 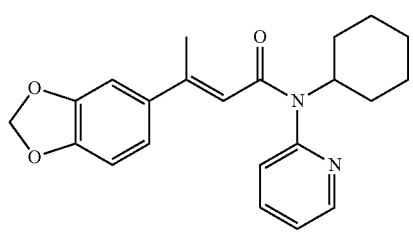 [SMILES: C/C(=C\C(=O)N(c1ccccn1)C1CCCCC1)c1ccc2c(c1)OCO2]

TABLE 2B-continued

Compounds with C2 bridges

28

29

30

31

32

33

TABLE 2B-continued

Compounds with C2 bridges

34 four carbon atoms

35

36

37

38

39

TABLE 2B-continued
Compounds with C2 bridges
40 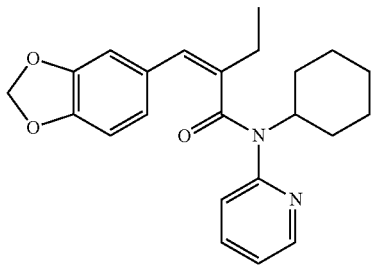 [SMILES: CC/C(=C/c1ccc2c(c1)OCO2)C(=O)N(c1ccccn1)C1CCCCC1]
41 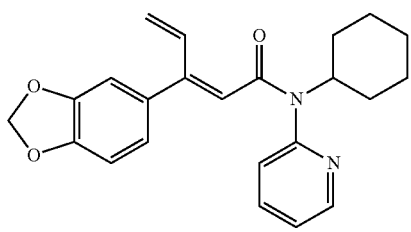 [SMILES: C=C/C(=C\C(=O)N(c1ccccn1)C1CCCCC1)c1ccc2c(c1)OCO2]
42 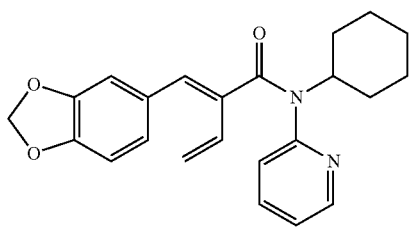 [SMILES: C=C/C(=C\c1ccc2c(c1)OCO2)C(=O)N(c1ccccn1)C1CCCCC1]
43 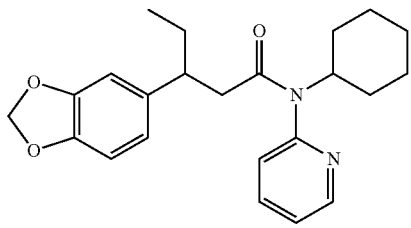 [SMILES: CCC(CC(=O)N(c1ccccn1)C1CCCCC1)c1ccc2c(c1)OCO2]
44 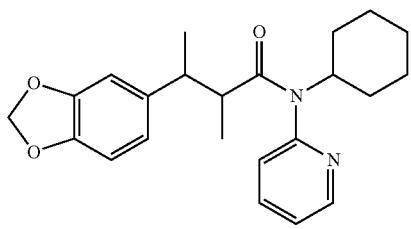 [SMILES: CC(C(=O)N(c1ccccn1)C1CCCCC1)C(C)c1ccc2c(c1)OCO2]
45 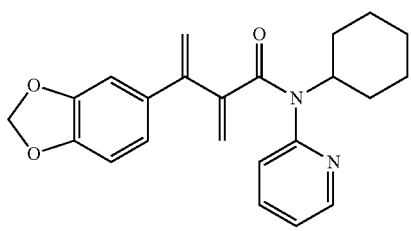 [SMILES: C=C(C(=C)c1ccc2c(c1)OCO2)C(=O)N(c1ccccn1)C1CCCCC1]
TABLE 2B-continued
Compounds with C2 bridges
46 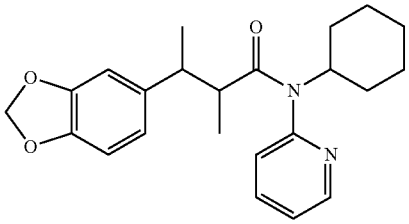 [SMILES: CC(C(=O)N(c1ccccn1)C1CCCCC1)C(C)c1ccc2c(c1)OCO2]
47 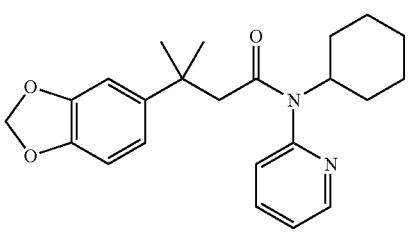 [SMILES: CC(C)(CC(=O)N(c1ccccn1)C1CCCCC1)c1ccc2c(c1)OCO2]
48 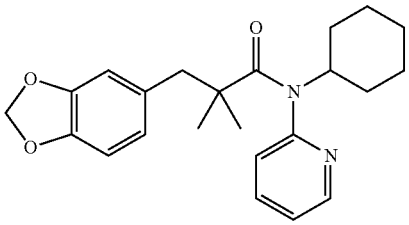 [SMILES: CC(C)(Cc1ccc2c(c1)OCO2)C(=O)N(c1ccccn1)C1CCCCC1]
four carbon atoms
49 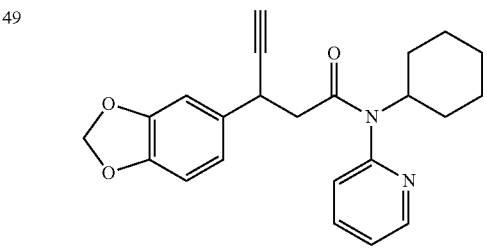
50 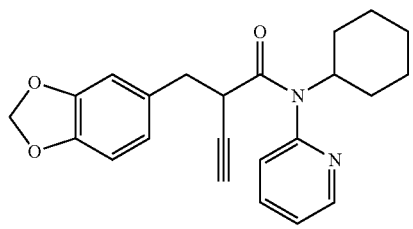 [SMILES: C#CC(Cc1ccc2c(c1)OCO2)C(=O)N(c1ccccn1)C1CCCCC1]
51 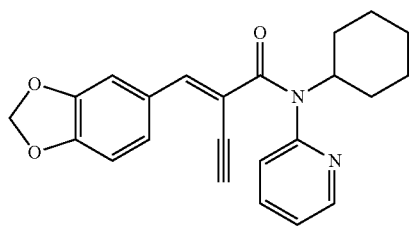 [SMILES: C#C/C(=C\c1ccc2c(c1)OCO2)C(=O)N(c1ccccn1)C1CCCCC1]

TABLE 2B-continued

Compounds with C2 bridges

52 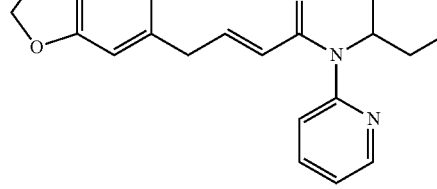

53 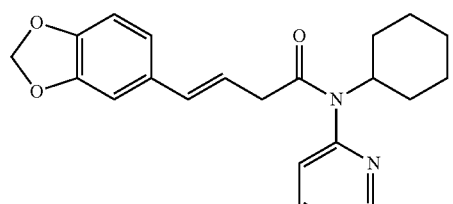

Also provided are salts of these compounds in the table above, in particular acid addition salts with inorganic or in particular organic, mono- or in particular polybasic carboxylic acids; and all isomers or stereoisomers in pure form or as a mixture of isomers and/or stereoisomers.

TABLE 2C

Compounds with C3 bridges three carbon atoms

54 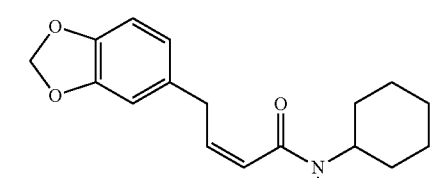

55 

56 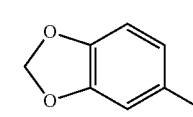

TABLE 2C-continued

Compounds with C3 bridges

57 

58 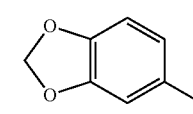

four carbon atoms

59

60

61

62

TABLE 2C-continued

Compounds with C3 bridges

| No. | Structure |
|---|---|
| 63 | (benzo[d][1,3]dioxol-5-yl)-CH2-C(CH3)=CH-C(=O)-N(cyclohexyl)(pyridin-2-yl) |
| 64 | (benzo[d][1,3]dioxol-5-yl)-CH(CH3)-CH=CH-C(=O)-N(cyclohexyl)(pyridin-2-yl) |
| 65 | (benzo[d][1,3]dioxol-5-yl)-CH=CH-CH(CH3)-C(=O)-N(cyclohexyl)(pyridin-2-yl) |
| 66 | (benzo[d][1,3]dioxol-5-yl)-CH=C(CH3)-CH2-C(=O)-N(cyclohexyl)(pyridin-2-yl) |
| 67 | (benzo[d][1,3]dioxol-5-yl)-C(CH3)=CH-CH2-C(=O)-N(cyclohexyl)(pyridin-2-yl) |
| 68 | (benzo[d][1,3]dioxol-5-yl)-CH2-CH2-CH(CH3)-C(=O)-N(cyclohexyl)(pyridin-2-yl) |
| 69 | (benzo[d][1,3]dioxol-5-yl)-CH(CH3)-CH2-CH2-C(=O)-N(cyclohexyl)(pyridin-2-yl) |
| 70 | (benzo[d][1,3]dioxol-5-yl)-CH2-CH(CH3)-CH2-C(=O)-N(cyclohexyl)(pyridin-2-yl) |
| 71 | (benzo[d][1,3]dioxol-5-yl)-C≡C-CH(CH3)-C(=O)-N(cyclohexyl)(pyridin-2-yl) |
| 72 | (benzo[d][1,3]dioxol-5-yl)-C≡C-C(=CH2)-C(=O)-N(cyclohexyl)(pyridin-2-yl) |
| 73 | (benzo[d][1,3]dioxol-5-yl)-CH(CH3)-C≡C-C(=O)-N(cyclohexyl)(pyridin-2-yl) |

TABLE 2C-continued

Compounds with C3 bridges

74 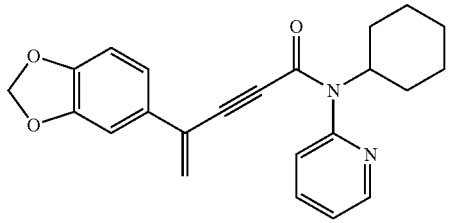 [SMILES: C=C(C#CC(=O)N(c1ccccn1)C1CCCCC1)c1ccc2c(c1)OCO2]

Also provided are salts of these compounds in the table above, in particular acid addition salts with inorganic or in particular organic, mono- or in particular polybasic carboxylic acids; and all isomers or stereoisomers in pure form or as a mixture of isomers and/or stereoisomers.

TABLE 2D

Compounds with C4 bridges
four carbon atoms

75 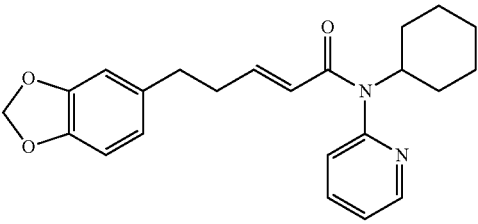 [SMILES: O=C(/C=C/CCc1ccc2c(c1)OCO2)N(c1ccccn1)C1CCCCC1]

76 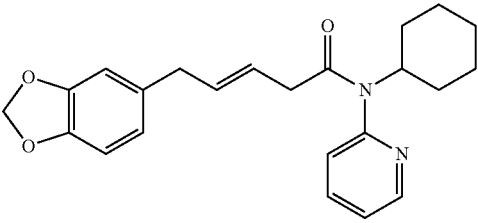 [SMILES: O=C(C/C=C/Cc1ccc2c(c1)OCO2)N(c1ccccn1)C1CCCCC1]

77 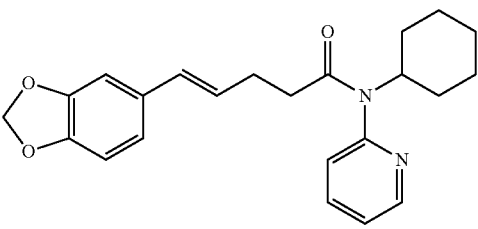 [SMILES: O=C(CC/C=C/c1ccc2c(c1)OCO2)N(c1ccccn1)C1CCCCC1]

78 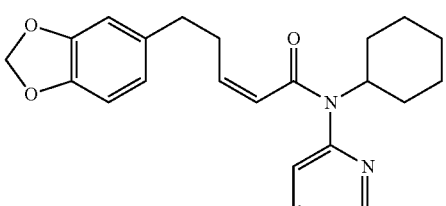

TABLE 2D-continued

Compounds with C4 bridges
four carbon atoms

79 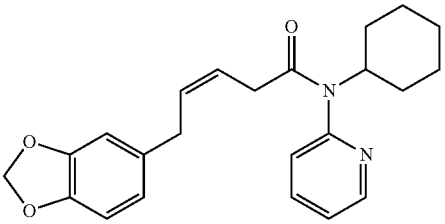 [SMILES: O=C(C/C=C\Cc1ccc2c(c1)OCO2)N(c1ccccn1)C1CCCCC1]

80 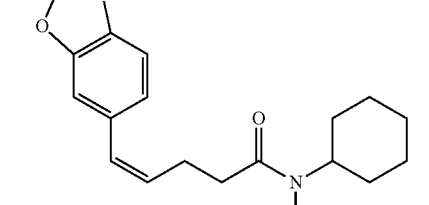

81 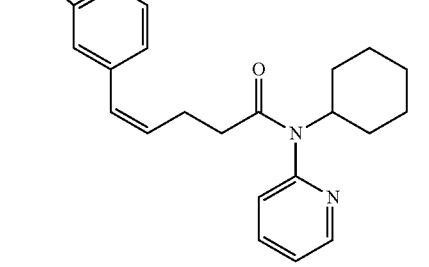

82 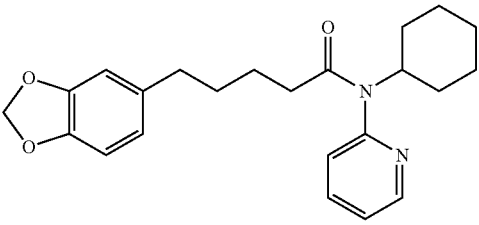 [SMILES: O=C(CCCCc1ccc2c(c1)OCO2)N(c1ccccn1)C1CCCCC1]

83 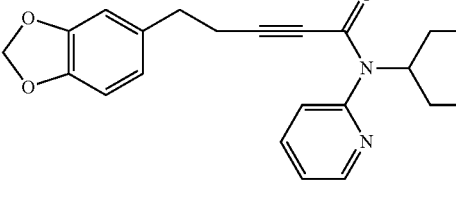

84 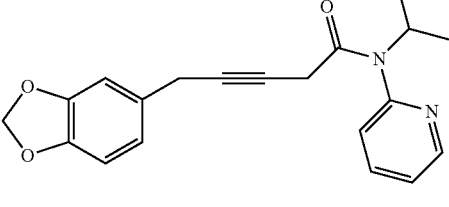

Also provided are salts of these compounds in the table above, in particular acid addition salts with inorganic or in particular organic, mono- or in particular polybasic carboxylic acids; and all isomers or stereoisomers in pure form or as a mixture of isomers and/or stereoisomers.

3.7 Compounds of the General Formula III

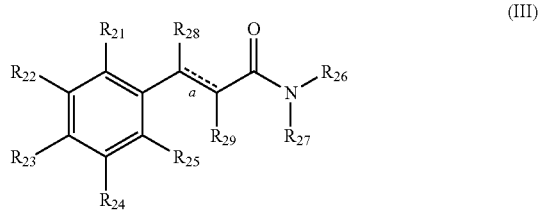

selected from compounds corresponding to the groups (1) to (67) given above for compounds of the formula II, with the proviso that X is replaced by the bridging group

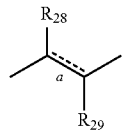

and where the groups (15) and (16) have the following meanings
(15) compounds of the formula III, in which $R_{28}$ and $R_{29}$ are identical or different and are selected from H and straight-chain or branched $C_1$-$C_8$-alkyl or straight-chain or branched $C_2$-$C_8$-alkenyl, $C_3$-$C_{12}$-cycloalkyl or $C_5$-$C_8$-cycloalkenyl, where the carbon chain, or the carbon ring of these radicals is optionally interrupted by one or two ring heteroatoms selected from O, S and N (or —NH—), in particular O, where the sum of the carbon atoms in the radicals $R_{28}$ and $R_{29}$ together is at least 3;
(16) compounds of the formula III, in which $R_{28}$ and $R_{29}$ are identical or different and are selected from H and straight-chain or branched $C_1$-$C_4$-alkyl or straight-chain or branched $C_2$-$C_4$-alkenyl, $C_3$-$C_6$-cycloalkyl or $C_5$-$C_6$-cycloalkenyl, where the carbon chain, or the carbon ring of these radicals is optionally interrupted by one or two ring heteroatoms selected from O and S, where the sum of the carbon atoms in the radicals $R_{28}$ and $R_{29}$ together is at least 3;
specific examples of compounds of the formula III are compounds according to the above table 2B, but where the C2 bridge therein is replaced by a bridge of the formula —$R_{28}$C=$CR_{29}$— according to the above definition for formula III, in particular according to above groups (15) and (16).

4. Further Embodiments of the Agents According to the Invention

4.1 General Details Regarding Fields of Application and Formulations of Active Ingredients According to the Invention The active ingredients according to the invention have a broad field of application in human cosmetics and care, in particular skincare and haircare, but can also be used pharmacologically, and also in foods and textile products, but can also be used as repellents and as a constituents of insecticidal compositions.

The compositions according to the invention may be in particular skin cosmetic, hair cosmetic, dermatological, hygiene or pharmaceutical compositions. In particular the active ingredients according to the invention, in particular active ingredients with a cooling effect, are used for skin cosmetics and/or hair cosmetics or as mouth care compositions.

The haircare or skincare preparations according to the invention are in particular in the form of an emulsion, a dispersion, a suspension, in the form of an aqueous surfactant preparation, a milk, a lotion, a cream, a balm, an ointment, a gel, granules, a powder, a stick preparation, such as e.g. a lipstick, a foam, an aerosol or a spray. Such formulations are highly suitable for topical preparations. Suitable emulsions are oil-in-water emulsions and water-in-oil emulsions or microemulsions.

As a rule, the hair cosmetic or skin cosmetic preparation is used for application to the skin (topically) or the hair. In this connection, "topical preparations" are understood as meaning preparations which are suitable for applying the active ingredients to the skin in a fine distribution, such as e.g. in a form that can be absorbed by the skin. Of suitability for this purpose are e.g. aqueous and aqueous-alcoholic solutions, sprays, foams, foam aerosols, ointments, aqueous gels, emulsions of the O/W or W/O type, microemulsions or cosmetic stick preparations.

According to one embodiment of the cosmetic composition according to the invention, it comprises a carrier. Preferred carriers are water, a gas, a water-based liquid, an oil, a gel, an emulsion or microemulsion, a dispersion or a mixture thereof. The specified carriers exhibit good skin compatibility. Of particular advantage for topical preparations are aqueous gels, emulsions or microemulsions.

The teaching according to the invention also comprises the use of the active ingredients described herein in pharmaceutical compositions for the treatment of an individual, preferably a mammal, in particular a human being, useful animal or domesticated animal. The active ingredients are administered for this in the form of pharmaceutical compositions which comprise a pharmaceutically compatible excipient with at least one active ingredient according to the invention and optionally further active ingredients. These compositions can be administered, for example, by an oral, rectal, transdermal, subcutaneous, intravenous, intramuscular or intranasal route.

Examples of suitable pharmaceutical formulations are solid medicament forms, such as (fine) powders, granules, tablets, pastilles, sachets, cachets, sugar-coated tablets, capsules such as hard and soft gelatin capsules, suppositories or vaginal medicament forms, semisolid medicament forms, such as ointments, creams, hydrogels, pastes or plasters, and also liquid medicament forms, such as solutions, emulsions, in particular oil-in-water emulsions, suspensions, for example lotions, injection and infusion preparations, eye and ear drops. Implanted release devices can also be used for administering inhibitors according to the invention. Furthermore, liposomes, microspheres or polymer matrices can also be used.

In the preparation of compositions according to the invention, active ingredients according to the invention are usually mixed or diluted with an excipient. Excipients may be solid, semisolid or liquid materials which serve as vehicle, carrier or medium for the active ingredient. The active ingredient content (of one or more simultaneously present active ingredients according to the invention) can vary here within a wide range and is, for example, in each case based on the total weight of the composition, in the ppm range from about 0.05 ppm-<0.1 ppm and 0.1 to 1000 ppm (i.e. 0.00001 to 0.1% by weight), such as e.g. 1 to 800 ppm or 100 to 500 ppm or in the range from 0.1 to 50, 1 to 30 or 2 to 10% by weight.

Suitable excipients include, for example, lactose, dextrose, sucrose, sorbitol, mannitol, starches, acacia gum, calcium phosphate, alginates, tragacanth, gelatin, calcium silicate, microcrystalline cellulose, polyvinylpyrrolidone, cellulose, water, syrup and methylcellulose. In addition, the formulations can comprise pharmaceutically acceptable carriers or customary auxiliaries, such as glidants, for example tallow, magnesium stearate and mineral oil; wetting agents; emulsifiers and suspending agents; preservatives, such as methyl and propyl hydroxybenzoates; antioxidants; antiirritant substances; chelating agents; sugar-coating auxiliaries; emulsion stabilizers, film formers; gelling agents; odor masking agents; taste correctors; resins; hydrocolloids; solvents; solubilizers; neutralizing agents; permeation accelerators; pigments; quaternary ammonium compounds; refatting and superfatting agents; ointment, cream or oil base substances; silicone derivatives; spreading auxiliaries; stabilizers; sterilants; suppository bases; tablet auxiliaries, such as binders, fillers, glidants, disintegrants or coatings; propellants; drying agents; opacifiers; thickeners; waxes; softeners; white oils. An embodiment in this respect is based on specialist knowledge, as is represented, for example, in Fiedler, H. P., Lexikon der Hilfsstoffe für Pharmazie, Kosmetik und angrenzende Gebiete [Lexicon of Auxiliaries for Pharmacy, Cosmetics and Related Fields] 4th edition, Aulendorf: ECV-Editio-Kantor-Verlag, 1996, or Hager's Handbuch der Pharmazeutischen Praxis [Handbook of Pharmaceutical Practice], Springer Verlag, Heidelberg.

Besides customary additives or auxiliaries, the compositions according to the invention can additionally comprise cosmetically and/or dermatologically and/or pharmacologically active ingredients.

Nonlimiting examples of suitable further active ingredients are:

Suitable cosmetically and/or dermatologically active ingredients are e.g. coloring active ingredients, skin and hair pigmentation agents, tinting agents, tanning agents, bleaches, keratin-hardening substances, antimicrobial active ingredients, photofilter active ingredients, repellent active ingredients, hyperemic substances, keratolytic and keratoplastic substances, antidandruff active ingredients, antiphlogistics, keratinizing substances, antioxidative active ingredients and/or active ingredients that act as free-radical scavengers, skin-moisturizing or humectant substances, refatting active ingredients, antierythimatous or antiallergic active ingredients, branched fatty acids, such as 18-methyleicosanoic acid, and mixtures thereof.

Artificially skin-tanning active ingredients which are suitable for tanning the skin without natural or artificial irradiation with UV rays; these are e.g. dihydroxyacetone, alloxan and walnut shell extract. Suitable keratin-hardening substances are as a rule active ingredients as are also used in antiperspirants, such as e.g. potassium aluminum sulfate, aluminum hydroxychloride, aluminum lactate etc.

Antimicrobial active ingredients which are used for destroying microorganisms and/or inhibiting their growth. They thus serve both as preservatives and also as deodorizing substance which reduces the formation or the intensity of body odor. These include e.g. customary preservatives known to the person skilled in the art, such as p-hydroxybenzoic esters, imidazolidinylurea, formaldehyde, sorbic acid, benzoic acid, salicylic acid etc. Such deodorizing substances are e.g. zinc ricinoleate, triclosan, undecylenic acid alkylolamides, triethyl citrate, chlorhexidine etc.

Suitable auxiliaries and additives for producing hair cosmetic or skin cosmetic preparations are familiar to the person skilled in the art and can be found in cosmetics handbooks, for example Schrader, Grundlagen und Rezepturen der Kosmetika [Fundamentals and Formulations of Cosmetics], Hüthig Verlag, Heidelberg, 1989, ISBN 3-7785-1491-1. The auxiliaries and additives are preferably cosmetically and/or pharmaceutically acceptable auxiliaries. Of pharmaceutical acceptability are the auxiliaries known for use in the field of pharmacy, food technology and related fields, in particular the auxiliaries listed in the relevant pharmacopeia (e.g. DAB, Ph. Eur., BP, NF), and also other auxiliaries whose properties do not preclude a physiological application.

Suitable auxiliaries may be: glidants, wetting agents, emulsifiers and suspending agents, preservatives, antioxidants, antiirritant substances, chelating agents, emulsion stabilizers, film formers, gel formers, odor masking agents, hydrocolloids, solvents, solubilizers, neutralizing agents, permeation accelerators, pigments, quaternary ammonium compounds, refatting and superfatting agents, ointment, cream or oil bases, silicone derivatives, stabilizers, sterilants, propellants, drying agents, opacifiers, thickeners, waxes, softeners, white oil. An embodiment in this regard is based on specialist knowledge, as represented, for example, in Fiedler, H. P. Lexikon der Hilfsstoffe fir Pharmazie, Kosmetik und angrenzende Gebiete [Lexicon of auxiliaries for pharmacy, cosmetics and related fields], 4th edition, Aulendorf: ECV-Editio-Kantor-Verlag, 1996.

Further suitable additives are selected from perfume oils, hair polymers, hair and skin conditioners, graft polymers, water-soluble or dispersible silicone-containing polymers, photoprotective agents, bleaches, care agents, colorants, tinting agents, tanning agents, dyes, consistency regulators, humectants, refatting agents, collagen, protein hydrolyzates, lipids, antioxidants, antifoams, antistats, emollients, softeners, peroxide decomposers.

Examples of suitable auxiliaries and additives are:

(1) Antioxidants selected from amino acids (e.g. glycine, histidine, tyrosine, tryptophan) and derivatives thereof, imidazoles (e.g. urocanic acid) and derivatives thereof, peptides such as D,L-carnosine, D-carnosine, L-carnosine and derivatives thereof (e.g. anserine), carotenoids, carotenes (e.g. β-carotene, lycopene) and derivatives thereof, chlorogenic acid and derivatives thereof, lipoic acid and derivatives thereof (e.g. dihydrolipoic acid), aurothioglucose, propylthiouracil and other thiols (e.g. thiorodoxin, glutathione, cystein, cystine, cystamine and the glycosyl, N-acetyl, methyl, ethyl, propyl, amyl, butyl, and lauryl, palmitoyl, oleyl, γ-linoleyl, cholesteryl and glyceryl esters thereof) and also salts thereof, dilauryl thiodipropionate, distearyl thiodipropionate, thiodipropionic acid and derivatives thereof (esters, ethers, peptides, lipids, nucleotides, nucleosides and salts), and also sulfoximine compounds (e.g. buthionine sulfoximines, homocystein sulfoximines, buthionine sulfones, penta-, hexa-, heptathionine sulfoximine), in particular in very low, tolerated doses (e.g. pmol to pmol/kg range), also (metal) chelating agents (e.g. α-hydroxyfatty acids, palmitic acid, phytic acid, lactoferrin), α-hydroxy acids (e.g. citric acid, lactic acid, malic acid), humic acid, bile acid, bile extracts, bilirubin, biliverdin, EDTA and derivatives thereof, unsaturated fatty acids and derivatives thereof (e.g. γ-linolenic acid, linoleic acid, oleic acid), folic acid and derivatives thereof, ubiquinone and ubiquinol and derivatives thereof, vitamin C and derivatives thereof (e.g. sodium ascorbate, ascorbyl palmitate, Mg ascorbyl phosphate, ascorbyl acetate), tocopherol and derivatives (e.g. vitamin E acetate, tocotrienol), vitamin A and derivatives (vitamin A palmitate, and also coniferyl benzoate of benzoin resin, rutinic acid and derivatives thereof, α-glycosylrutin, ferulic acid, furfurylidene glucitol, carnosene, butylhydroxytoluene, butylhydroxyanisol, nordihydroguaiacic acid, nordihydroguaiaretic acid, trihydroxybutyrophenone, uric acid and derivatives thereof, mannose and derivatives thereof, zinc and derivatives thereof (e.g. ZnO, $ZnSO_4$), selenium and derivatives thereof (e.g. selenmethionine), stilbenes and derivatives thereof (e.g. stilbene oxide, trans-stilbene oxide).

(2) Peroxide decomposers, i.e. compounds which are able to decompose peroxides, particularly preferably lipid peroxides. These are to be understood as meaning organic substances, such as e.g. pyridine-2-thiol-3-carboxylic acid, 2-methoxy-pyrimidinolcarboxylic acids, 2-methoxypyridinecarboxylic acids, 2-dimethylamino-pyrimidinolcarboxylic acids, 2-dimethylaminopyridinecarboxylic acids.

(3) Thickeners, such as crosslinked polyacrylic acids and derivatives thereof, polysaccharides and derivatives thereof, such as xanthan gum, agar agar, alginates or tyloses, cellulose derivatives, e.g. carboxymethylcellulose or hydroxycarboxymethylcellulose, fatty alcohols, monoglycerides and fatty acids, polyvinyl alcohol and polyvinylpyrrolidone. In particular, nonionic thickeners are used.

(4) Preservatives, which are listed below with their E number

| | | |
|---|---|---|
| E 200 | Sorbic acid | |
| E 201 | Sodium sorbate | |
| E 202 | Potassium sorbate | |
| E 203 | Calcium sorbate | |
| E 210 | Benzoic acid | |
| E 211 | Sodium benzoate | |
| E 212 | Potassium benzoate | |
| E 213 | Calcium benzoate | |
| E 214 | Ethyl p-hydroxybenzoate | |
| E 215 | Ethyl p-hydroxybenzoate Na salt | |
| E 216 | n-Propyl p-hydroxybenzoate | |
| E 217 | n-Propyl p-hydroxybenzoate Na salt | |
| E 218 | Methyl p-hydroxybenzoate | |
| E 219 | Methyl p-hydroxybenzoate Na salt | |
| E 220 | Sulfur dioxide | |
| E 221 | Sodium sulfite | |
| E 222 | Sodium hydrogensulfite | |
| E 223 | Sodium disulfite | |
| E 224 | Potassium disulfite | |
| E 226 | Calcium sulfite | |
| E 227 | Calcium hydrogensulfite | |
| E 228 | Potassium hydrogensulfite | |
| E 230 | Biphenyl (diphenyl) | |
| E 231 | Orthophenylphenol | |
| E 232 | Sodium orthophenylphenolate | |
| E 233 | Thiabendazole | |
| E 235 | Natamycin | |
| E 236 | Formic acid | |
| E 237 | Sodium formate | |
| E 238 | Calcium formate | |
| E 239 | Hexamethylenetetramine | |
| E 249 | Potassium nitrite | |
| E 250 | Sodium nitrite | |
| E 251 | Sodium nitrate | |
| E 252 | Potassium nitrate | |
| E 280 | Propionic acid | |
| E 281 | Sodium propionate | |
| E 282 | Calcium propionate | |
| E 283 | Potassium propionate | |
| E 290 | Carbon dioxide | |

Also of suitability according to the invention are preservatives or preservative auxiliaries customary in cosmetics, such as dibromodicyanobutane (2-bromo-2-bromomethylglutarodinitrile), 3-iodo-2-propynyl butylcarbamate, 2-bromo-2-nitro-propane-1,3-diol, imidazolidinylurea, 5-chloro-2-methyl-4-isothiazolin-3-one, 2-chloroacetamide, benzalkonium chloride, benzyl alcohol, formaldehyde donors.

In addition, phenyl hydroxyalkyl ethers, in particular the compound known under the name phenoxyethanol, are suitable as preservatives on account of their bactericidal and fungicidal effects on a number of microorganisms.

Other antimicrobial agents are also likewise suitable for incorporation into the preparations according to the invention. Advantageous substances are, for example, 2,4,4'-trichloro-2'-hydroxydiphenyl ether (Irgasan), 1,6-di(4-chloro-phenylbiguanido)hexane (chlorhexidine), 3,4,4'-trichlorocarbanilide, quaternary ammonium compounds, clove oil, mint oil, thyme oil, triethyl citrate, farnesol (3,7,11-trimethyl-2,6,10-dodecatrien-1-ol), and also the active ingredients and active ingredient combinations described in the patent laid-open specifications DE-37 40 186, DE-39 38 140, DE-42 04 321, DE-42 29 707, DE-43 09 372, DE-44 11 664, DE-195 41 967, DE-195 43 695, DE-195 43 696, DE-195 47 160, DE-196 02 108, DE-196 02 110, DE-196 02 111, DE-196 31 003, DE-196 31 004 and DE-196 34 019 and the patent specifications DE-42 29 737, DE-42 37 081, DE-43 24 219, DE-44 29 467, DE-44 23410 and DE-195 16 705. Sodium hydrogencarbonate can also be used advantageously. Antimicrobial polypeptides can likewise also be used.

(5) Photofilter active ingredients which absorb UV rays in the UV-B and/or UV-A region. Suitable UV filters are e.g. 2,4,6-triaryl-1,3,5-triazines in which the aryl groups can in each case carry at least one substituent which is preferably selected from hydroxy, alkoxy, specifically methoxy, alkoxycarbonyl, specifically methoxycarbonyl and ethoxycarbonyl, and mixtures thereof. Also of suitability are p-aminobenzoic acid esters, cinnamic acid esters, benzophenones, camphor derivatives, and pigments which stop UV rays, such as titanium dioxide, talc and zinc oxide.

Suitable UV filter substances are UV-A- and UV-B filter substances. Examples are:

| No. | Substance | CAS No. (=acid) |
|---|---|---|
| 1 | 4-Aminobenzoic acid | 150-13-0 |
| 2 | 3-(4'-Trimethylammonium)benzylidenebornan-2-one methylsulfate | 52793-97-2 |
| 3 | 3,3,5-Trimethylcyclohexyl salicylate (homosalate) | 118-56-9 |

| No. | Substance | CAS No. (=acid) |
|---|---|---|
| 4 | 2-Hydroxy-4-methoxybenzophenone (oxybenzone) | 131-57-7 |
| 5 | 2-Phenylbenzimidazole-5-sulfonic acid and its potassium, sodium and triethanolamine salts | 27503-81-7 |
| 6 | 3,3'-(1,4-Phenylenedimethine)bis(7,7-dimethyl-2-oxo-bicyclo[2.2.1]heptane-1-methanesulfonic acid) and its salts | 90457-82-2 |
| 7 | Polyethoxyethyl 4-bis(polyethoxy)aminobenzoate | 113010-52-9 |
| 8 | 2-Ethylhexyl 4-dimethylaminobenzoate | 21245-02-3 |
| 9 | 2-Ethylhexyl salicylate | 118-60-5 |
| 10 | 2-Isoamyl 4-methoxycinnamate | 71617-10-2 |
| 11 | 2-Ethylhexyl 4-methoxycinnamate | 5466-77-3 |
| 12 | 2-Hydroxy-4-methoxybenzophenone-5-sulfonic acid (sulisobenzone) and the sodium salt | 4065-45-6 |
| 13 | 3-(4'-Sulfobenzylidene)bornan-2-one and salts | 58030-58-6 |
| 14 | 3-Benzylidenebornan-2-one | 16087-24-8 |
| 15 | 1-(4'-Isopropylphenyl)-3-phenylpropane-1,3-dione | 63260-25-9 |
| 16 | 4-Isopropylbenzyl salicylate | 94134-93-7 |
| 17 | 3-Imidazol-4-ylacrylic acid and its ethyl ester | 104-98-3 |
| 18 | Ethyl 2-cyano-3,3-diphenylacrylate | 5232-99-5 |
| 19 | 2'-Ethylhexyl 2-cyano-3,3-diphenylacrylate | 6197-30-4 |
| 20 | Menthyl o-aminobenzoate or: 5-methyl-2-(1-methylethyl)-2-aminobenzoate | 134-09-8 |
| 21 | Glyceryl p-aminobenzoate or: 1-glyceryl 4-aminobenzoate | 136-44-7 |
| 22 | 2,2'-Dihydroxy-4-methoxybenzophenone (dioxybenzone) | 131-53-3 |
| 23 | 2-Hydroxy-4-methoxy-4-methylbenzophenone (mexenone) | 1641-17-4 |
| 24 | Triethanolamine salicylate | 2174-16-5 |
| 25 | Dimethoxyphenylglyoxalic acid or: sodium 3,4-dimethoxyphenylglyoxalate | 4732-70-1 |
| 26 | 3-(4'-Sulfobenzylidene)bornan-2-one and its salts | 56039-58-8 |
| 27 | 4-tert-Butyl-4'-methoxydibenzoylmethane | 70356-09-1 |
| 28 | 2,2',4,4'-Tetrahydroxybenzophenone | 131-55-5 |
| 29 | 2,2'-Methylenebis[6-(2H-benzotriazol-2-yl)-4-(1,1,3,3-tetramethylbutyl)phenol] | 103597-45-1 |
| 30 | 2,2'-(1,4-Phenylene)bis-1H-benzimidazole-4,6-disulfonic acid, Na salt | 180898-37-7 |
| 31 | 2,4-bis[4-(2-Ethylhexyloxy)-2-hydroxy]phenyl-6-(4-methoxyphenyl)-(1,3,5)-triazine | 187393-00-6 |
| 32 | 3-(4-Methylbenzylidene)camphor | 36861-47-9 |
| 33 | Polyethoxyethyl 4-bis(polyethoxy)paraaminobenzoate | 113010-52-9 |
| 34 | 2,4-Dihydroxybenzophenone | 131-56-6 |
| 35 | 2,2'-Dihydroxy-4,4'-dimethoxybenzophenone 5,5'-disodium sulfonate | 3121-60-6 |
| 36 | Benzoic acid, 2-[4-(diethylamino)-2-hydroxybenzoyl]-, hexyl ester | 302776-68-7 |
| 37 | 2-(2H-Benzotriazol-2-yl)-4-methyl-6-[2-methyl-3-[1,3,3,3-tetramethyl-1-[(trimethylsilyl)oxy]disiloxanyl]propyl]phenol | 155633-54-8 |
| 38 | 1,1-[(2,2'-Dimethylpropoxy)carbonyl]-4,4-diphenyl-1,3-butadiene | 363602-15-7 |

The cosmetic and dermatological preparations according to the invention can moreover advantageously comprise inorganic pigments which stop UV rays and which are based on metal oxides and/or other metal compounds which are sparingly soluble or insoluble in water, selected from the group of the oxides of zinc (ZnO), titanium (TiO$_2$), iron (e.g. Fe$_2$O$_3$), zirconium (ZrO$_2$), silicon (SiO$_2$), manganese (e.g. MnO), aluminum (Al$_2$O$_3$), cerium (e.g. Ce$_2$O$_3$), mixed oxides of the corresponding metals and also mixtures of such oxides. The inorganic pigments here may be in coated form, i.e. be surface-treated. This surface treatment can, for example, consist in providing the pigments with a thin hydrophobic layer by a method known per se, as described in DE-A-33 14 742.

(6) Repellent active ingredients, i.e. compounds which are able to keep away or drive away certain animals, in particular insects, from humans. These include, for example, 2-ethyl-1,3-hexanediol, N,N-diethyl-m-toluamide etc.

(7) Suitable hyperemic substances, which stimulate blood flow through the skin, are, for example, essential oils, such as dwarf-pine needle extract, lavender extract, rosemary extract, juniper berry extract, horse-chestnut extract, birch leaf extract, hay flower extract, ethyl acetate, camphor, menthol, peppermint oil, rosemary extract, *eucalyptus* oil etc.

(8) Suitable keratolytic and keratoplastic substances are, for example, salicylic acid, calcium thioglycolate, thioglycolic acid and its salts, sulfur etc. Suitable antidandruff active ingredients are, for example, sulfur, sulfur polyethylene glycol sorbitan monooleate, sulfur ricinol polyethoxylate, zinc pyrithione, aluminum pyrithione etc.

(9) Suitable antiphlogistics, which counteract skin irritations, are, for example, allantoin, bisabolol, dragosantol, chamomile extract, panthenol etc.

(10) Cosmetically or pharmaceutically acceptable polymers, such as cationic, amphoteric and neutral polymers.
Suitable polymers are, for example, cationic polymers with the INCI name Polyquaternium, e.g. copolymers of vinylpyrrolidone/N-vinylimidazolium salts (Luviquat FC, Luviquat HM, Luviquat MS, Luviquat Care), copolymers of N-vinylpyrrolidone/dimethylaminoethyl methacrylate, quaternized with diethyl sulfate (Luviquat PQ 11), copolymers of N-vinylcaprolactam/N-vinylpyrrolidone/N-vinylimidazolium salts (Luviquat E Hold), cationic cellulose derivatives (Polyquaternium-4 and -10), acrylamido copolymers (Polyquaternium-7) and chitosan.

Suitable cationic (quaternized) polymers are also Merquat (polymer based on dimethyldiallylammonium chloride), Gafquat (quaternary polymers which are formed by the reaction of polyvinylpyrrolidone with quaternary ammonium compounds), Polymer JR (hydroxyethylcellulose with cationic groups) and plant-based cationic polymers, e.g. guar polymers, such as the Jaguar grades from Rhodia.

Further suitable polymers are also neutral polymers, such as polyvinylpyrrolidones, copolymers of N-vinylpyrrolidone and vinyl acetate and/or vinyl propionate, polysiloxanes, polyvinylcaprolactam and other copolymers with N-vinylpyrrolidone, polyethyleneimines and salts thereof, polyvinylamines and salts thereof, cellulose derivatives, polyaspartic acid salts and derivatives thereof. These include, for example, Luviflex® Swing (partially saponified copolymer of polyvinyl acetate and polyethylene glycol, BASF).

Suitable polymers are also nonionic, water-soluble or water-dispersible polymers or oligomers, such as polyvinylcaprolactam, e.g. Luviskol® Plus (BASF), or polyvinylpyrrolidone and copolymers thereof, in particular with vinyl esters, such as vinyl acetate, e.g. Luviskol® VA 37 (BASF), polyamides, e.g. based on itaconic acid and aliphatic diamines, as are described, for example, in DE-A-43 33 238.

Suitable polymers are also amphoteric or zwitterionic polymers, such as the octylacrylamide/methyl methacrylate/tert-butylaminoethyl methacrylate-hydroxypropoyl methacrylate copolymers available under the names Amphomer (National Starch), and also zwitterionic polymers as are disclosed, for example, in the German patent applications DE39 29 973, DE 21 50 557, DE28 17 369 and DE 3708 451. Acrylamidopropyltrimethylammonium chloride/acrylic acid or methacrylic acid copolymers and the alkali metal and ammonium salts thereof are preferred zwitterionic polymers. Furthermore, suitable zwitterionic polymers are methacroylethylbetaine/methacrylate copolymers, which are commercially available under the name Amersette (AMERCHOL), and copolymers of hydroxyethyl methacrylate, methyl methacrylate, N,N-dimethylaminoethyl methacrylate and acrylic acid (Jordapon (D)).

Suitable polymers are also nonionic, siloxane-containing, water-soluble or dispersible polymers, e.g. polyethersiloxanes, such as Tegopren® (Goldschmidt) or Besi (Wacker).

Individual particular application forms of active ingredients according to the invention are described in more detail below by way of example.

4.2 Cooling Skincare and Haircare Compositions

According to one preferred embodiment, the compositions according to the invention are a cooling skincare or haircare or cleansing composition.

Preferred skin- or hair-cleansing compositions are soaps of liquid to gel-like consistency, such as transparent soaps, luxury soaps, deodorant soaps, cream soaps baby soaps, skin protection soaps, abrasive soaps and syndets, pasty soaps, soft soaps and washing pastes, peeling soaps, wet wipes, liquid washing, showering and bathing preparations, such as washing lotions, shower baths and shower gels, foam baths, oil baths and scrub preparations, shaving foams, shaving lotions and shaving creams.

According to a further preferred embodiment, the compositions according to the invention are a shower gel, a shampoo formulation or a bath preparation. Such formulations comprise at least one active ingredient according to the invention and also usually anionic surfactants as base surfactants and amphoteric and/or nonionic surfactants as cosurfactants. Further suitable active ingredients and/or auxiliaries are generally selected from lipids, perfume oils, dyes, organic acids, preservatives and antioxidants, and also thickeners/gel formers, skin conditioners and humectants.

In principle, the active ingredient content can vary over a wide range, such as e.g. 0.00001 to 50% by weight, in particular 0.001 to 10% by weight or 0.005 to 1% by weight.

i) Specific Embodiments for Compositions for Application to the Skin:

Suitable skin cosmetic compositions are, for example, face tonics, face masks, deodorants and other cosmetic lotions. Compositions for use in decorative cosmetics comprise, for example, concealing sticks, stage make-up, mascara and eyeshadows, lipsticks, kohl pencils, eyeliners, blushers, powders and eyebrow pencils.

Moreover, the dermatological compositions according to the invention can be used in nose-strips for pore cleansing, in antiacne compositions, repellents, shaving compositions, aftershave and preshave care compositions, aftersun care compositions, hair removal compositions, hair colorants, intimate care compositions, footcare compositions and also in babycare.

The skincare compositions according to the invention are in particular W/O or O/W skin creams, day and night creams, eye creams, face creams, antiwrinkle creams, sunscreen creams, moisturizing creams, bleaching creams, self-tanning creams, vitamin creams, skin lotions, care lotions and moisturizing lotions.

Skin cosmetic and dermatological compositions comprise in particular at least one active ingredient according to the invention in a fraction of from about 0.0001 to 50% by weight, such as e.g. 0.001 to 10% by weight, in particular 0.005 to 0.1% by weight, based on the total weight of the composition.

Depending on the field of application, the skin cosmetic compositions according to the invention can be applied in a form suitable for skincare, such as e.g. as cream, foam, gel, stick, mousse, milk, spray (pump spray or propellant-containing spray) or lotion.

Besides the active ingredients according to the invention and suitable carriers, the skin cosmetic preparations can also comprise further active ingredients and auxiliaries customary in skin cosmetics, as described previously. These include, preferably, emulsifiers, preservatives, perfume oils, cosmetic active ingredients, such as phytantriol, vitamin A, E and C, retinol, bisabolol, panthenol, photoprotective agents, bleaches, colorants, tinting agents, tanning agents, collagen, enzymes, protein hydrolyzates, stabilizers, pH regulators, dyes, salts, thickeners, gel formers, consistency regulators, silicones, humectants, refatting agents and further customary additives.

Preferred oil and fat components of the skin cosmetic and dermatological compositions are the aforementioned mineral and synthetic oils, such as, for example, paraffins, silicone oils and aliphatic hydrocarbons having more than 8 carbon atoms, animal and vegetable oils, such as, for example, sunflower oil, coconut oil, avocado oil, olive oil, lanolin, or waxes, fatty acids, fatty acid esters, such as, for example, triglycerides of $C_6$-$C_{30}$-fatty acids, wax esters, such as, for example, jojoba oil, fatty alcohols, vaseline, hydrogenated lanolin and acetylated lanolin, and mixtures thereof.

To establish certain properties, such as, for example, improving the feel to the touch, the spreading behavior, the water resistance and/or the binding of active ingredients and auxiliaries, such as pigments, the skin cosmetic and dermatological preparations can additionally also comprise conditioning substances based on silicone compounds. Suitable silicone compounds are, for example, polyalkylsiloxanes, polyarylsiloxanes, polyarylalkylsiloxanes, polyether siloxanes or silicone resins.

The cosmetic or dermatological preparations are produced by customary processes known to the person skilled in the art.

To produce the dermatological compositions according to the invention, the active ingredients can be mixed or diluted with a suitable auxiliary (excipient). Excipients may be solid, semisolid or liquid materials which can serve as vehicle, carrier or medium for the active ingredient. The admixing of further auxiliaries takes place if desired in the manner known to the person skilled in the art. Furthermore, the polymers and dispersions are suitable as auxiliaries in pharmacy, preferably as or in (a) coating(s) or (a) binder(s) for solid drug forms. They can also be used in creams and as tablet coatings and tablet binders.

Preferably, the cosmetic and dermatological compositions are present in the form of emulsions, in particular as water-in-oil (W/O) or oil-in-water (O/W) emulsions. However, it is also possible to choose other types of formulation, for example gels, oils, oleogels, multiple emulsions, for example in the form of W/O/W or O/W/O emulsions, anhydrous ointments or ointment bases etc. Emulsifier-free formulations such as hydrodispersions, hydrogels or a Pickering emulsion are also advantageous embodiments.

The preparation of emulsions takes place by known methods. Besides at least one active ingredient according to the invention, the emulsions generally comprise customary constituents, such as fatty alcohols, fatty acid esters and in particular fatty acid triglycerides, fatty acids, lanolin and derivatives thereof, natural or synthetic oils or waxes and emulsifiers in the presence of water. The selection of additives specific to the type of emulsion and the preparation of suitable emulsions is described, for example, in Schrader, Grundlagen und Rezepturen der Kosmetika [Fundamentals and Formulations of Cosmetics], Hüthig Buch Verlag, Heidelberg, 2nd edition, 1989, third part, to which reference is hereby expressly made.

A suitable emulsion as W/O emulsion, e.g. for a skin cream etc., generally comprises an aqueous phase which is emulsified in an oil or fatty phase by means of a suitable emulsifier system. A polyelectrolyte complex can be used for producing the aqueous phase.

Preferred fatty components which may be present in the fatty phase of the emulsions are: hydrocarbon oils, such as paraffin oil, purcellin oil, perhydrosqualene and solutions of microcrystalline waxes in these oils; animal or vegetable oils, such as sweet almond oil, avocado oil, calophylum oil, lanolin and derivatives thereof, castor oil, sesame oil, olive oil, jojoba oil, karite oil, hoplostethus oil, mineral oils whose distillation start-point under atmospheric pressure is about 250° C. and whose distillation end point is at 410° C., such as, for example, vaseline oil, esters of saturated or unsaturated fatty acids, such as alkyl myristates, e.g. isopropyl myristate, butyl myristate or cetyl myristate, hexadecyl stearate, ethyl palmitate or isopropyl palmitate, octanoic or decanoic acid triglycerides and cetyl ricinoleate.

The fatty phase can also comprise silicone oils that are soluble in other oils, such as dimethylpolysiloxane, methylphenylpolysiloxane and the silicone glycol copolymer, fatty acids and fatty alcohols.

Besides the active ingredients according to the invention, it is also possible to use waxes, such as, for example, carnauba wax, candililla wax, beeswax, microcrystalline wax, ozokerite wax and Ca, Mg and Al oleates, myristates, linoleates and stearates.

Furthermore, an emulsion according to the invention can be in the form of an O/W emulsion. One such emulsion usually comprises an oil phase, emulsifiers which stabilize the oil phase in the water phase, and an aqueous phase, which is usually present in thickened form. Suitable emulsifiers are preferably O/W emulsifiers, such as polyglycerol esters, sorbitan esters or partially esterified glycerides.

According to a further preferred embodiment, the compositions according to the invention are a shower gel, a shampoo formulation or a bathing preparation.

Such formulations comprise at least one active ingredient according to the invention and usually anionic surfactants as base surfactants and amphoteric and/or nonionic surfactants as cosurfactants. Further suitable active ingredients and/or auxiliaries are generally selected from lipids, perfume oils, dyes, organic acids, preservatives and antioxidants, and also thickeners/gel formers, skin conditioners and humectants.

These formulations comprise in particular 2 to 50% by weight, such as 5 to 40% by weight or 8 to 30% by weight, of surfactants, based on the total weight of the formulation.

In the washing, showering and bathing preparations it is possible to use all anionic, neutral, amphoteric or cationic surfactants customarily used in body cleansing compositions.

Suitable anionic surfactants are, for example, alkyl sulfates, alkyl ether sulfates, alkylsulfonates, alkylarylsulfonates, alkyl succinates, alkyl sulfosuccinates, N-alkoyl sarcosinates, acyl taurates, acyl isothionates, alkyl phosphates, alkyl ether phosphates, alkyl ether carboxylates, alpha-olefinsulfonates, in particular the alkali metal and alkaline earth metal salts, e.g. sodium, potassium, magnesium, calcium, and also ammonium and triethanolamine salts. The alkyl ether sulfates, alkyl ether phosphates and alkyl ether carboxylates can have between 1 and 10 ethylene oxide or propylene oxide units, preferably 1 to 3 ethylene oxide units, in the molecule.

These include, for example, sodium lauryl sulfate, ammonium lauryl sulfate, sodium lauryl ether sulfate, ammonium lauryl ether sulfate, sodium lauryl sarcosinate, sodium oleyl succinate, ammonium lauryl sulfosuccinate, sodium dodecylbenzenesulfonate, triethanolamine dodecylbenzenesulfonate.

Suitable amphoteric surfactants are, for example, alkylbetaines, alkylamidopropylbetaines, alkylsulfobetaines, alkyl glycinates, alkyl carboxyglycinates, alkyl amphoacetates or -propionates, alkyl amphodiacetates or -dipropionates.

For example, cocodimethylsulfopropylbetaine, laurylbetaine, cocamidopropylbetaine or sodium cocamphopropionate can be used.

Suitable nonionic surfactants are, for example, the reaction products of aliphatic alcohols or alkylphenols having 6 to 20 carbon atoms in the alkyl chain, which may be linear or branched, with ethylene oxide and/or propylene oxide. The amount of alkylene oxide is about 6 to 60 mol per mole of alcohol. Also suitable are alkylamine oxides, mono- or dialkylalkanolamides, fatty acid esters of polyethylene glycols, ethoxylated fatty acid amides, alkyl polyglycosides or sorbitan ether esters.

Moreover, the washing, showering and bathing preparations can comprise customary cationic surfactants, such as, for example, quaternary ammonium compounds, for example cetyltrimethylammonium chloride.

Furthermore, the shower gel/shampoo formulations can comprise thickeners, such as, for example, sodium chloride, PEG-55, propylene glycol oleate, PEG-120 methylglucose dioleate and others, and also preservatives, further active ingredients and auxiliaries and water.

ii) Specific Embodiments for Compositions for Application to the Hair

According to a further preferred embodiment, the compositions according to the invention are a hair treatment composition.

Hair treatment compositions according to the invention comprise in particular at least one active ingredient according to the invention in an amount in the range from about 0.0001 to 50% by weight, such as, for example, 0.001 to 10% by weight, in particular 0.005 to 0.1% by weight, based on the total weight of the composition.

Preferably, the hair treatment compositions according to the invention are in the form of a setting foam, hair mousse, hair gel, shampoo, hair spray, hair foam, end fluid, neutralizer for permanent waves, hair colorant and bleach or hot-oil treatment. Depending on the field of use, the hair cosmetic preparations can be applied as (aerosol) spray, (aerosol) foam, gel, gel spray, cream, lotion or wax. Hair sprays here comprise both aerosol sprays and also pump sprays without propellent gas. Hair foams comprise both aerosol foams and also pump foams without propellent gas. Hair sprays and hair foams comprise preferably predominantly or exclusively water-soluble or water-dispersible components. If the compounds used in the hair sprays and hair foams according to the invention are water-dispersible, they can be applied in the form of aqueous microdispersions having particle diameters of usually 1 to 350 nm, preferably 1 to 250 nm. The solids contents of these preparations here are usually in a range from about 0.5 to 20% by weight. These microdispersions generally require no emulsifiers or surfactants for their stabilization.

The hair cosmetic formulations according to the invention comprise, in a specific embodiment, a) 0.0001 to 50% by weight or 0.001 to 10, or 0.005 to 1% by weight, of at least one active ingredient according to the invention, b) 20 to 99.95% by weight of water and/or alcohol, c) 0 to 50% by weight of at least one propellent gas, d) 0 to 5% by weight of at least one emulsifier, e) 0 to 3% by weight of at least one thickener, and also up to 25% by weight of further constituents.

Alcohol is to be understood as meaning all alcohols customary in cosmetics, for example ethanol, isopropanol, n-propanol.

Also included here are all styling and conditioner polymers known in cosmetics which can be used in combination with the active ingredients according to the invention, if quite specific properties are to be established.

Suitable conventional hair cosmetic polymers are, for example, the aforementioned cationic, anionic, neutral, nonionic and amphoteric polymers, to which reference is hereby made.

To establish certain properties, the preparations can additionally also comprise conditioning substances based on silicone compounds. Suitable silicone compounds are, for example, polyalkylsiloxanes, polyarylsiloxanes, polyarylalkylsiloxanes, polyether siloxanes, silicone resins or dimethicone copolyols (CTFA) and aminofunctional silicone compounds, such as amodimethicones (CTFA).

The polymers according to the invention are suitable in particular as setting agents in hair styling preparations, in particular hair sprays (aerosol sprays and pump sprays without propellent gas) and hair foams (aerosol foams and pump foams without propellent gas).

In one preferred embodiment, spray preparations comprise a) 0.0001 to 50% by weight or 0.001 to 10, or 0.005 to 1% by weight of at least one active ingredient according to the invention, b) 20 to 99.9% by weight of water and/or alcohol, c) 0 to 70% by weight of at least one propellant, d) 0 to 20% by weight of further constituents.

Propellants are the propellants customarily used for hair sprays or aerosol foams. Preference is given to mixtures of propane/butane, pentane, dimethyl ether, 1,1-difluoroethane (HFC-152 a), carbon dioxide, nitrogen or compressed air.

A formulation for aerosol hair foams which is preferred according to the invention comprises a) 0.0001 to 50% by weight or 0.001 to 10, or 0.005 to 1% by weight, of at least one active ingredient according to the invention, b) 55 to 99.8% by weight of water and/or alcohol, c) 5 to 20% by weight of a propellant, d) 0.1 to 5% by weight of an emulsifiers, e) 0 to 10% by weight of further constituents.

Emulsifiers that can be used are all emulsifiers customarily used in hair foams. Suitable emulsifiers may be nonionic, cationic or anionic or amphoteric.

Examples of nonionic emulsifiers (INCI nomenclature) are laureths, e.g. laureth-4; ceteths, e.g. ceteth-1, polyethylene glycol cetyl ether, cetеareths, e.g. cetеareth-25, polyglycol fatty acid glycerides, hydroxylated lecithin, lactyl esters of fatty acids, alkyl polyglycosides.

Examples of cationic emulsifiers are cetyldimethyl-2-hydroxyethylammonium dihydrogenphosphate, cetyltrimonium chloride, cetyltrimmonium bromide, cocotrimonium methylsulfate, quaternium-1 to x (INCI).

Anionic emulsifiers can be selected, for example, from the group of alkyl sulfates, alkyl ether sulfates, alkylsulfonates, alkylarylsulfonates, alkylsuccinates, alkyl sulfosuccinates, N-alkoyl sarcosinates, acyl taurates, acyl isethionates, alkyl phosphates, alkyl ether phosphates, alkyl ether carboxylates, alpha-olefinsulfonates, in particular the alkali metal and alkaline earth metal salts, e.g. sodium, potassium, magnesium, calcium, and also ammonium and triethanolamine salts. The alkyl ether sulfates, alkyl ether phosphates and alkyl ether carboxylates can have between 1 and ethylene oxide or propylene oxide units, preferably 1 to 3 ethylene oxide units, in the molecule.

A preparation suitable according to the invention for styling gels can, for example, have the following composition: a) 0.0001 to 50% by weight or 0.001 to 10, or 0.005 to 1% by weight, of at least one active ingredient according to the invention, b) 80 to 99.85% by weight of water and/or alcohol, c) 0 to 3% by weight, preferably 0.05 to 2% by weight, of a gel former, d) 0 to 20% by weight of further constituents.

The use of gel formers may be advantageous in order to establish specific rheological or other application properties of the gels. Gel formers that can be used are all gel formers customary in cosmetics. These include lightly crosslinked polyacrylic acid, for example Carbomer (INCI), cellulose derivatives, e.g. hydroxypropylcellulose, hydroxyethylcellulose, cationically modified celluloses, polysaccharides, e.g. xanthan gum, caprylic/capric triglyceride, sodium acrylate copolymers, polyquaternium-32 (and) Paraffinum Liquidum (INCI), sodium acrylate copolymers (and) Paraffinum Liquidum (and) PPG-1 Trideceth-6, acrylamidopropyltrimonium chloride/acrylamide copolymers, steareth-10 allyl ether, acrylate copolymers, polyquaternium-37 (and) Paraffinum Liquidum (and) PPG-1 Trideceth-6, polyquaternium-37 (and) propylene glycol dicaprate dicaprylate (and) PPG-1 Trideceth-6, polyquaternium-7, polyquaternium-44

Specific shampoo formulations comprise a) 0.0001 to 50% by weight or 0.001 to 10, or 0.005 to 1% by weight, of at least one active ingredient according to the invention, b) 25 to 94.95% by weight of water, c) 5 to 50% by weight of surfactants, c) 0 to 5% by weight of a further conditioner, d) 0 to 10% by weight of further cosmetic constituents.

In the shampoo formulations, it is possible to use all anionic, neutral, amphoteric or cationic surfactants customarily used in shampoos.

Suitable anionic surfactants are, for example, alkyl sulfates, alkyl ether sulfates, alkylsulfonates, alkylarylsulfonates, alkyl succinates, alkyl sulfosuccinates, N-alkoyl sarcosinates, acyl taurates, acyl isothionates, alkyl phosphates, alkyl ether phosphates, alkyl ether carboxylates, alpha-olefinsulfonates, in particular the alkali metal and alkaline earth metal salts, e.g. sodium, potassium, magnesium, calcium, and also ammonium and triethanolamine salts. The alkyl ether sulfates, alkyl ether phosphates and alkyl ether carboxylates can have between 1 and 10 ethylene oxide or propylene oxide units, preferably 1 to 3 ethylene oxide units, in the molecule.

Of suitability are, for example, sodium lauryl sulfate, ammonium lauryl sulfate, sodium lauryl ether sulfate, ammonium lauryl ether sulfate, sodium lauroyl sarcosinate, sodium oleyl succinate, ammonium lauryl sulfosuccinate, sodium dodecylbenzenesulfonate, triethanolamine dodecylbenzenesulfonate.

Suitable amphoteric surfactants are, for example, alkylbetaines, alkylamidopropylbetaines, alkylsulfobetaines, alkyl glycinates, alkyl carboxyglycinates, alkyl amphoacetates or -propionates, alkyl amphodiacetates or -dipropionates.

For example, cocodimethylsulfopropylbetaine, laurylbetaine, cocamidopropylbetaine or sodium cocamphopropionate can be used.

Suitable nonionic surfactants are, for example, the reaction products of aliphatic alcohols or alkylphenols having 6 to 20 carbon atoms in the alkyl chain, which may be linear or branched, with ethylene oxide and/or propylene oxide. The amount of alkylene oxide is about 6 to 60 mol per mole of alcohol. Also of suitability are alkylamine oxides, mono- or dialkylalkanolamides, fatty acid esters of polyethylene glycols, alkyl polyglycosides or sorbitan ether esters.

Moreover, the shampoo formulations can comprise customary cationic surfactants, such as, for example, quaternary ammonium compounds, for example cetyltrimethylammonium chloride.

In order to achieve certain effects, customary conditioners can be used in combination with the active ingredients according to the invention in the shampoo formulations.

These include, for example, the aforementioned cationic polymers with the INCI name Polyquaternium, in particular copolymers of vinylpyrrolidone/N-vinylimidazolium salts (Luviquat FC, Luviquat HM, Luviquat MS, Luviquat Care), copolymers of N-vinyl-pyrrolidone/dimethylaminoethyl methacrylate, quaternized with diethyl sulfate (Luviquat D PQ 11), copolymers of N-vinylcaprolactam/N-vinylpyrrolidone/N-vinylimidazolium salts (Luviquat D Hold), cationic cellulose derivatives (Polyquaternium-4 and -10), acrylamide copolymers (Polyquaternium-7). In addition, it is possible to use protein hydrolysates, and also conditioning substances based on silicone compounds, for example polyalkylsiloxanes, polyarylsiloxanes, polyarylalkylsiloxanes, polyether siloxanes or silicone resins. Further suitable silicone compounds are dimethicone copolyols (CTFA) and aminofunctional silicone compounds such as amodimethicones (CTFA). In addition, cationic guar derivatives, such as guar hydroxypropyltrimonium chloride (INCI), can be used.

4.3 Cooling Mouthcare Compositions

Mouthcare compositions according to the invention can be formulated in a manner known per se, e.g. as toothpaste, tooth gel, or aqueous or aqueous-alcoholic mouthcare compositions (mouthwashes).

Mouthcare compositions according to the invention comprise, based on the weight of the composition, 0.00001 to 50% by weight, 0.0001 to 10% by weight, 0.001 to 5% by weight, 0.005 to 1% by weight or 0.1 to 20% by weight, 0.5 to 15% by weight or 1 to 5% by weight, of the total amount of at least one active ingredient according to the invention.

Moreover, the mouthcare compositions, in particular toothpastes, can also comprise abrasives, such as silicon oxide hydrate, dicalcium phosphate dihydrate, calcium carbonate, sodium hydrogencarbonate, calcium pyrophosphate and aluminum oxide. For example, it is also possible to use a mixture of precipitated silicon with a propensity towards viscousness and scouring precipitated silicon [Handbook of Pharmaceutical Excipients, The Pharmaceutical Society of Great Britain, 1 Lambeth High Street, London SE 1 7JN, England, pages 253-256]. The first-mentioned is used on account of its thixotropic properties, the second on account of its better effectiveness in eliminating the substances adhering to the dental surfaces. The use of these products ensures a low scouring effect since, they are amorphous solids of average hardness which are simultaneously entirely compatible with the fluoride used as mineralizing agent, since they do not comprise any lime salts which would bring about their insolubility and reduce their bioavailability.

The formulation of the mouthcare compositions according to the invention, such as, for example, toothpaste, can also comprise suitable additives and vehicles in order to improve their properties and to facilitate production. These are selected, for example, from binders, thickeners, fragrances, dyes, preservatives, wetting agents or humectants, surfactants, lubricants, opacifiers, remineralizing substances, surfactants, buffers, alcohols, vitamins, water, additional active ingredients and mixtures thereof.

As binder, it is possible to use any agent normally used in the production of this type of formulation, e.g. tragacanth gum. The binder may be present in the formulation in an amount of 0.5-1.5% by weight of the total amount.

Organic thickeners may also be incorporated in the mouthcare composition, such as sodium carboxymethylcellulose, cellulose ether, xanthan gum, carrageenans, sodium alginate and carbopols. It is also possible to use inorganic thickeners, such as silicon oxide thickeners, sodium aluminum silicates and clays, for providing the appropriate rheology. The thickener may be present in the formulation in an amount of 0.5-5% by weight of the total amount.

The toothpaste can be aromatized by adding a suitable customary fragrance, e.g. a peppermint aroma. Essential oils including inter alia clove oil, cinnamon oil, peppermint oil and spearmint oil are likewise suitable. The fragrance may be present in the formulation in an amount of 0.5-15% by weight of the total amount.

As dye, any of the dyes customarily used in the production of toothpaste can be used, for example brilliant blue FCF, C.42090 [KIRSCH PHARMA]. The dye may be present in the formulation in an amount of 0.001-0.005% by weight of the total amount.

The preservative may be any customary agent, such as, for example, a derivative or benzoic acid, e.g. p-hydroxymethyl benzoate. The preservative may be present in the formulation in an amount of 0.1-0.3% by weight of the total amount.

As sweetener, it is possible to use, e.g. sodium saccharin or cyclamic acid and derivatives thereof, e.g. sodium cyclamate. The sweetener may be present in the formulation in an amount of 0.08-0.15% by weight of the total amount.

The wetting agent or humectant used to prevent the toothpaste from drying out and hardening is in particular selected from glycerol, sorbitol, propylene glycol, xylitol and liquid polyethylene glycols, in particular a mixture of sorbitol, glycerol and xylitol, e.g. in an amount of 1-60% by weight of the total amount.

The lubricant may be any of the agents customarily used in the formulation of a toothpaste, e.g. dimethicone (polymer of dimethylpolysiloxane), which is a surface-active agent which contributes to imparting good rheological properties to the toothpaste according to the invention. The lubricant may be present in the formulation in an amount of 0.25 to 0.75% by weight of the total amount.

The opacifier used may be any of the agents customarily used, e.g. titanium dioxide. The opacifier may be present in the formulation in an amount of 0.05 to 1% by weight of the total amount.

The remineralizing agent used is a fluoride source, e.g. sodium fluoride, tin(II) fluoride and sodium monofluorophosphate, since in this way 100% of an active fluoride as agent for remineralizing the white lesions caused by the organic acids which are a consequence of bacterial metabolism. The remineralizing agent may be present in the formulation in an amount of 0.2 to 0.4% by weight of the total amount.

Typically, furthermore customary constituents may be present, such as anionic surfactants, such as e.g. sodium lauryl sulfate, sodium N-laurylsarcosinate, sodium lauryl sulfoacetate and sodium alkyl glyceryl ether sulfonate. The surfactant may be present in the formulation in an amount of 0.05 to 5% by weight of the total amount.

If desired, the toothpaste proposed by the invention can also comprise a vitamin which is selected from the group formed by vitamin A, vitamin B5, vitamin C and vitamin E, and mixtures thereof. If used, each vitamin may be present in the formulation in an amount of 0.1 to 5% by weight of the total amount. These vitamins can be used as such, in the form of provitamins or in the form of acceptable pharmaceutical salts. Vitamin A, which is usually used in the form of its palmitate salt, promotes the epithelization of the oral mucosa and protects the gingiva. Vitamin B5, more specifically D-panthenol, has a pain-alleviating, healing and anti-inflammatory effect, protects the epithelial mucosa, promotes the epithelization of injuries and smoothes scars; it is suitable for the treatment of injuries which arise as a result of dental extractions, gingivitis, stomatitis, pain after inserting dental prostheses, ulcers, traumatic damage to the mucosa, chronic and declining aphthae. Vitamin C regenerates the epithelium of oral mucosa, promotes the synthesis of collagen and the immune system (inflammatory mechanism) and increases the ability of the phagocytes to protect against bacteria. Vitamin E, which is normally used in the form of its acetate salt, has a pain-alleviating and anti-inflammatory effect, protects the oral mucosa against the over-oxidation of fat as a consequence of the formation of free radicals and against contaminating substances in the environment (ozone, cigarette smoke etc.) and favors the healing of injuries. As a result of adding one or some of these vitamins, the invention offers a toothpaste which, besides the aforementioned properties, also has anti-inflammatory features and pain-alleviating effects which increase the ability of the membranes to protect the oral mucosa and reduce the index of dental film formation and dental tartar formation and also that of bacterial contamination.

Additional active ingredients are, for example, antimicrobial and plaque-penetrating agents, such as beta-naphthol, thymol, chlorothymol and hexylresorcinol; or germicidal compounds, such as quaternary ammonium compounds; tartar control agents, such as tetrasodium pyrophosphate, GANTREZ-Polymer® S-70, sodium tripolyphosphate and zinc citrate; peroxide compounds, such as hydrogen peroxide and inorganic peroxides.

Optionally, a buffer can also be used which is present in concentrations suitable for maintaining a pH of about 6-8, such as e.g. alkali metal phosphate buffer. In addition, the presence of potassium ions exerts an effect alleviating oversensitivity.

Water or alcohol may be present in an amount of 1 to 20% by weight of the total amount of the composition.

In combination with the alcohol or instead of the alcohol, it is also possible to use glycol compounds, such as glycerol, sorbitol or propylene glycol.

The mouthcare composition according to the invention can be prepared easily by mixing suitable amounts of the different constituents in a reactor equipped e.g. with stirring paddles.

4.4. Cooling Plasters

In principle, the active ingredient content can vary over a wide range, such as e.g. 0.00001 to 50% by weight, in particular 0.001 to 10% by weight or 0.005 to 1% by weight.

Plasters according to the invention can be constructed in any desired manner, for example by the matrix system, the membrane system or the nonwoven system (Drug Dev. Ind. Pharm. 14 (1988), 183-209; Drug Dev. Ind. Pharm. 13 (1987), 589-651; Drugs of Today 23 (1987), 625-646).

The matrix system consists in the simplest manner of 3 parts: the flexible protective film, the adhesive matrix comprising the active ingredient and a peelable film. If a nonadhesive matrix is used, an edge zone of the protective film must be provided with adhesive to adhere to the skin.

By contrast, a membrane system has at least 5 parts: a flexible protective film, a reservoir with dissolved or suspended active ingredient, a membrane for controlling the release of active ingredient, an adhesive layer applied to the membrane and a peelable film.

In the nonwoven system, the layer comprising the active ingredient consists of an absorbent nonwoven or porous polymer which is impregnated with an active ingredient solution or suspension. This layer, which is firmly bonded to the protective film, is covered by a peelable film. The edge of the protective film is provided with adhesive for application to the skin.

In principle, all active ingredients according to the invention can be formulated in this way.

The auxiliaries to be used are those customary for producing plasters. Besides the adhesive agent, generally a polymer with a glass transition temperature between −70 and −10, in particular −55 and −25° C., and also a carrier film which is coated with this adhesive agent, and the active ingredient, emulsifiers, thickeners and also substances which are intended to influence the release of the active ingredient, and other auxiliaries are often added.

The adhesive polymers with the aforementioned low glass transition temperatures are known, for example from the U.S. Pat. Nos. 2,973,282 and 3,307,544. The self-adhesive bands and films should stick to human skin upon mere contact, although the cohesion of the adhesive layer and its adhesion to the carrier film should be greater than the adhesion to the skin, so that it can be removed again largely without leaving a residue. These are generally copolymers based on acrylic and methacrylic acid esters of alcohols having 2 to 12, in particular 4 to 8, carbon atoms, which can comprise numerous other comonomers in copolymerized form, for example (meth)acrylic acid, (meth)acrylonitrile, (meth)acrylamide, N-tert-butyl(meth)acrylamide, vinyl esters such as vinyl acetate, vinyl propionate or vinyl butyrate, other vinyl compounds such as styrene, also butadiene. Particular preference is given to butyl acrylate and 2-ethylhexyl acrylate. The polymers can be crosslinked by adding small amounts of comonomers having 2 or more copolymerizable double bonds, i.e. for example of diacrylates, such as butanediol diacrylate, or divinyl compounds, such as divinyl-benzene, or by adding other crosslinking agents, e.g. melamine-formaldehyde resins. Adhesive polymers which can be used are also polyisobutylenes and polyvinyl ethers of varying molecular weight.

The particle size of the dispersions should be between 50 and 500 nm, in particular between 50 and 200 nm. The particle size and the degree of crosslinking can be adjusted in a known manner depending on the polymerization conditions and the comonomers. Smaller particle sizes and an increased degree of crosslinking can bring about an increase in the release of active ingredient.

Matrix plasters can be produced in the customary manner by dissolving or finely dispersing the active ingredient in a suitable polymer solution and then drawing out this active-ingredient-containing self-adhesive mass by means of roller or knife-coating methods to give the film. In some cases, it is expedient to dissolve or very finely disperse the active ingredient, prior to adding it to the polymer solution, in an organic solvent, e.g. ethanol or acetone. Better distribution of the active ingredient in the polymer can thereby be achieved.

The plasters can also be produced in accordance with the German patent application P 38 07 283.1 by incorporating the active ingredient in finely powdered form (particle size below 200, in particular below 50 µm) into the aqueous latex dispersion, or dispersing or dissolving it in an aqueous emulsifier solution and mixing this mixture into the aqueous latex dispersion at a temperature from 10 to 80, in particular 30 to 70° C. In addition, the salt of an active ingredient in aqueous solution can also be mixed with the polymer dispersion at a pH at which the active ingredient is predominantly present in the water-soluble ionized form. By shifting the pH, the active ingredient is then converted to the uncharged water-insoluble form and simultaneously emulsified into the dispersion.

Expediently, the active ingredient is introduced as initial charge, the emulsifier and water are added and the mixture is then mixed with the polymer dispersion. The active-ingredient-containing dispersion obtained in this way is optionally provided with further auxiliaries and, as mentioned, is drawn out to give a film in a manner known per se on a protective film and dried. The drying temperature here can be between room temperature and 100° C., an optimum between desired rapid drying and bubble formation in the film, which is to be avoided, and also thermal stressing of the active ingredient generally being 35 to 45° C.

This process has the great advantage of avoiding organic solvents. However, in principle, all other customary production processes for matrix plasters are also suitable.

The resulting films have thicknesses of 10 to 800, preferably 50 to 300 µm. The film can be produced continuously or discontinuously. The coating process can be repeated several times until the film has achieved the desired thickness. The adhesive polymer layer comprises the active ingredient in a concentration in the range from 1 to 40, in particular 5 to 25% by weight. The same concentration also applies for the reservoir liquid in the membrane system and for the active ingredient solution or dispersion with which, in the nonwoven system, the nonwoven or the porous polymer is impregnated.

The emulsifiers used both for the active ingredients and also the polymers are the surfactants customary for this purpose, such as the sodium salt of relatively long-chain fatty acids and the sulfuric acid half-ester of an (optionally oxyethylated) fatty alcohol as examples of anionic surfactants, and polyoxyethylated alkylphenols and relatively long-chain fatty alcohols (e.g. hexadecan-(1)-ol) and glycerol fatty acid partial esters as examples of nonionic surfactants and coemulsifiers.

The desired viscosity of the ready-to-draw-out mass can be adjusted e.g. with polyacrylic acids or cellulose derivatives.

Additional crosslinking agents, which improve the cohesion and thus the adhesion properties of the films, that can be used are e.g. melamine-formaldehyde resins.

For the purposes of improving the release of active ingredient, source substances such as polyvinylpyrrolidone, cellulose derivatives or polyacrylates are effective since the film can increasingly absorb water and, as a result, the resistance to diffusion drops. The release of the active ingredients can be further improved by adding hydrophilic plasticizers such as glycerol, 1,2-propanediol or polyethylene glycols and lipophilic plasticizers such as triacetin, dibutyl phthalate or isopropyl myristate.

Matrix plasters usually produce an active ingredient release of the first order. The use of fillers which adsorb the active ingredient, such as Aerosil, microcrystalline cellulose or lactose, results in approximately a release of zero order.

The protective film onto which the active-ingredient-containing self-adhesive mass is dried is expediently virtually impermeable both for the active ingredient and for water vapor. It can, for example, consist of an aluminum-plastic composite film, a metalized plastic film, a plastic film which is provided with a barrier layer of e.g. polyvinylidene chloride facing the active ingredient side, or of a simple plastic film, e.g. polyester film.

The plasters according to the invention which are constructed by the membrane system are likewise produced in the customary manner (e.g. EP 0 186 071 A2, U.S. Pat. No. 4,262,003).

The plasters constructed by the nonwoven system are produced by impregnating nonwovens or porous polymers attached to the protective film with a solution or dispersion of the active ingredient in a hydrophilic or lipophilic solvent or solvent mixture. The impermeable peelable film is then applied.

4.5 Cooling Foods

Cooling foods according to the invention may be present (at ambient temperature) in solid, liquid, semisolid, pasty, creamy or foamed form. Besides conventional food constituents, they comprise at least an effective (i.e. cooling) amount of at least one active ingredient according to the invention.

Typical constituents here are fats, carbohydrates, proteins, ballast substances, water, alcohol and the like.

The protein fraction can be e.g. 0 to 50% by weight, based on the total weight of the food;
the fat fraction can be e.g. 0 to 50% by weight, based on the total weight of the food;
the carbohydrate fraction can be e.g. 0 to 90% by weight, based on the total weight of the food;
the ballast fraction can be e.g. 0 to 90% by weight, based on the total weight of the food;
the water fraction can be e.g. 0 to 95% by weight, based on the total weight of the food;
the alcohol fraction can be e.g. 0 to 15% by weight, based on the total weight of the food;
the fraction of active ingredients according to the invention can be e.g. in the range from 0.0001 to 50, 0.001 to 20, 0.005 to 1, or 0.01 to 10, in particular 0.1 to 10 or 1 to 5% by weight, based on the total weight of the food.

Examples of carbohydrates are e.g. mono- and disaccharides, glucose, galactose, mannose, lactose, maltose and sucrose; fructose and mannose; polysaccharides such as e.g. starches, maltodextrins, flour.

The term "ballast substance" refers to soluble, insoluble, fermentable, nonfermentable or any desired combination of such ballast substances. The ballast substance may be e.g. soya fibers, pectin, certain resistant starches, oligofructose, inulins, oat fibers, pea fibers, guar gum, acacia gum, modified cellulose.

The fat constituent may be any desired liquid or fat which is known to be suitable for use in foods. Typical fats are inter alia milk fat, safflower oil, canola oil, egg yolk lipid, olive oil, cottonseed oil, coconut oil, palm oil, palm kernel oil, soybean oil, sunflower oil, fish oil and fractions of all of the above oils which are derived therefrom, such as palmolein, medium-chain triglycerides (MCT), and fatty acid esters, where the fatty acids are e.g. arachidonic acid, linoleic acid, palmitic acid, stearic acid, docosahexaenoic acid, eicosapentaenoic acid, linolenic acid, oleic acid, lauric acid, capric acid, caprylic acid, caproic acid. Forms of various oils with a high oleic acid content are also considered suitable for the present use, such as sunflower oil with a high oleic acid content and safflower oil with a high oleic acid content.

The protein may be any desired protein and/or amino acid mixture which is known to be suitable for use in foods. Typical proteins are animal proteins, vegetable proteins such as soybean protein, milk protein such as low-fat milk protein, whey protein and casein, and amino acids (or salts thereof), such as isoleucine, phenylalanine, leucine, lysine, methionine, threonine, tryptophan, arginine, glutamine, taurine, valine. Preferred protein sources are whey protein, sodium caseinate or calcium caseinate, which is optionally admixed with amino acids. For some applications, a preferred protein source is hydrolyzed protein (protein hydrolysate), which is optionally admixed with amino acids.

The protein hydrolysate may be any desired suitable protein hydrolysate which is used in a food, such as soya protein hydrolysate, casein hydrolysate, whey protein hydrolysate, other animal and vegetable protein hydrolysates and mixtures thereof. The protein hydrolysate of the composition according to the invention is preferably a soya protein hydrolysate, whey protein hydrolysate or a casein protein hydrolysate which comprises short peptides and amino acids and is optionally admixed with additional amino acids. In one preferred embodiment, the protein hydrolysate suitable according to the invention comprises a high fraction of free amino acids (e.g. more than 40%) and low molecular weight peptide fragments.

The hydrolyzed protein of the composition according to the invention is also preferably admixed with various free amino acids in order to provide a nutritionally balanced amino acid content. Examples of such free amino acids are, inter alia, L-tryptophan, L-methionine, L-cysteine, L-tyrosine and L-arginine.

The foods according to the invention optionally also comprise vitamins and minerals. The person skilled in the art is aware that minimum requirements for certain vitamins and minerals have been imposed which are necessary for normal physiological function. Moreover, the person skilled in the art is aware that appropriate additional amounts of vitamin and mineral constituents have to be added to the foods in order to compensate for certain losses during the processing and storage of such compositions. The composition according to the invention optionally comprises nutritionally significant amounts of vitamins and minerals.

Examples of minerals, vitamins and other nutrients which are optionally present in the composition according to the invention are, inter alia, vitamin A, vitamin $B_6$, vitamin $B_{12}$, vitamin E, vitamin K, vitamin C, vitamin D, inositol, taurine, folic acid, thiamine, riboflavin, niacin, biotin, pantothenic acid, choline, calcium, phosphorus, iodine, iron, magnesium, copper, zinc, manganese, chloride, potassium, sodium, beta-carotene, nucleotides, selenium, chromium, molybdenum and L-carnitine. Minerals are usually added in salt form.

The composition according to the invention also usually optionally comprises emulsifiers and/or stabilizers such as lecithin (e.g. from egg or soya), modified lecithin (e.g. enzymatic or acetylated), carrageenan, xanthan gum, mono- and diglycerides, guar gum, carboxymethylcellulose, stearoyl lactylates, succinylated monoglycerides, sucrose esters of fatty acids, diacetyltartaric acid esters of monoglycerides, polyglycerol esters of fatty acids or any desired mixtures thereof.

The composition according to the invention comprises, if desired, one or more natural or artificial taste carriers for improving the palatability. It is possible to use any taste carriers used in the sector, such as strawberry, cherry, chocolate, orange, coconut, vanilla; spices such as nutmeg and cinnamon; or citric acid. In some cases where natural taste carriers, such as coconut pieces, are used, the constituent contributes to the overall nutritional value profile of the composition, i.e. it contributes to the quality and quantity of the fat, protein and/or carbohydrate constituent.

If desired, the composition according to the invention also comprises various other constituents which contribute to the nutritional value profile of the composition and/or can impart desired taste properties, such as taste enhancing or mouth feel.

Constituents of this type are, inter alia, peanuts, raisins, cheese powder, vinegar, salt, sodium bicarbonate. In the case of bars, the composition is usually provided with a chocolate coating or an aromatized coating (e.g. chocolate, vanilla, strawberry etc.).

If desired, the composition according to the invention also comprises natural or synthetic dyes in order to improve the aesthetic appeal.

The compositions according to the invention may be present in several physical forms, e.g. as liquid enteral foods or beverages for adults or children, in a semisolid form such as blancmange, cream, mousse, or a solid form, such as a cereal bar or biscuit.

The composition according to the invention can be produced by known standard methods in food technology, for example by analogous methods to those described in the following documents: U.S. Pat. Nos. 4,670,268; 4,497,800; 4,900,566; 5,104,677; 5,389,395; and 5,223,285; chocolate, cocoa and confectionery: Science and Technology, $3^{rd}$ edition, Bernard W. Minifie, Van Nostrand Reinhold, New York, 1989, pp. 502-506; to the entire contents of which reference is made.

In the case of cereal bars and biscuits, it is usually desired to bake the composition after physical shaping.

If desired, the composition according to the invention can be sterilized by known methods, for example by heat treatment such as autoclaving or sterilizing or irradiation, or be produced and packaged using sterile processes.

The composition according to the invention can be packaged in any type of container or packaging which is known to be suitable for storing foods, such as paper, glass, coated cardboard, plastic or coated metal cans.

The composition according to the invention can be nutritionally balanced. The term "nutritionally balanced" is understood as meaning that the composition contains appropriate nutrients to maintain a healthy human life over extended periods of time.

4.6. Textile Products Finished with Active Ingredients According to the Invention In principle, the active ingredient content can vary over a wide range, such as e.g. 0.00001 to 50% by weight, in particular 0.001 to 10% by weight or 0.005 to 1% by weight.

The finishing of textiles with active ingredients according to the invention is of interest in many respects.

Thus, the finishing of textiles with cooling compounds is used in particular wherever items of clothing can come into direct contact with the skin, such that the active ingredient can develop its effects, e.g. locally or systemically, through transdermal transfer. In recent times, textiles have been reported which are finished with so-called wellness additives, i.e. substances which promote wellbeing (R. Breier "Megatrend Wellness—Innovative Ideen für die Textilausrüstung", 31. Aachener Textiltage November 2004).

An insecticidal finishing in turn is of interest with regard to material protection, e.g. finishing of the textile to prevent it being eaten by moths etc., but in particular also to repel parasitic insects, such as flies.

A fundamental problem in the finishing of textiles with active ingredients is the binding of the active ingredient to the textile carrier which, on the one hand, must ensure a permanency of the finishing and, on the other hand, must be selected such that the active ingredient does not lose its effect. In this regard, various approaches have been proposed in the prior art.

Thus, e.g. cyclodextrins have been proposed for the binding of active ingredients to textiles (see, for example, DE-A-19810951 and EP-A-0 392 608). Cyclodextrins are cyclic oligosaccharides which are formed by enzymatic degradation of starch. The most common cyclodextrins are α-, β- and γ-cyclodextrins, which consist of six, seven or eight, respectively, α-1,4-linked glucose units. A characteristic property of the cyclodextrin molecules is their ring structure with largely invariable dimensions. The internal diameter of the rings is about 570 µm for α-cyclodextrin, about 780 µm for β-cyclodextrin and about 950 µm for γ-cyclodextrin. On account of their structure, cyclodextrins are in the position of being able to incorporate guest molecules, in particular hydrophobic guest molecules, in changing amounts up to saturation.

EP-A-1710345 describes the finishing of textiles with fragrances and other low molecular weight organic active ingredients via an amylose-containing substance with an amylose content of at least 30% are bonded to the textile.

As a consequence of the amylose fractions in the amylose-containing substance, the active ingredient is bonded to the textile and released in a controlled manner, such that the effect is maintained over a long period. It is assumed that the active ingredient is reversibly bonded as in the case of cyclodextrins in the cavities formed by the helical conformation of the amylose in the sense of an inclusion compound, as a result of which, on the one hand, fixing of the active ingredient to the surface of the textile carrier is achieved and, on the other hand, controlled release is possible.

Of suitability for the finishing according to the invention of textiles are, besides amylose, in principle all substances, in particular amylose-containing starches, i.e. native starches, modified starches and starch derivatives, the amylose content of which is at least 30% by weight and in particular at least 40% by weight. The starch may be native, e.g. corn starch, wheat starch, potato starch, sorghum starch, rice starch or maranta starch, be obtained by partial digestion of native starch or be chemically modified. Pure amylose as such, e.g. enzymatically obtained amylose, e.g. amylose obtained from sucrose, is also suitable. Also of suitability are mixtures of amylose and starch if the total content of amylose is at least 30% by weight, based on the total weight of the mixture. It goes without saying that here and hereinbelow all data in % by weight which refer to amylose or amylose-containing substances in mixtures of amylose and starch are always based on the total weight of amylose+starch, unless expressly stated otherwise.

Of particular suitability according to the invention are amylose-containing substances, in particular amylose and amylose-containing starches and also amylose/starch mixtures whose amylose content is at least 40% by weight and in particular at least 45% by weight, based on the total weight of the substance. As a rule, the amylose content will not exceed 90% by weight and in particular 80% by weight. Substances of this type are known and commercially available. For example, amylose-containing starches are sold by Cerestar under the trade name Amylogel® and National Starch under the trade names HYLON® V and VII.

To achieve the binding of the active ingredient(s) and the textile, the textile can be treated with the amylose-containing substance usually in an amount of at least 0.5% by weight, preferably at least 1% by weight and in particular at least 2% by weight, in each case based on the weight of the textile. As a rule, the amylose-containing substance will be used in an amount of not more than 25% by weight, often not more than 20% by weight and in particular not more than 15% by weight, based on the weight of the textile, so as not to adversely affect the tactile properties of the textile.

Firstly, the textile material is finished with the amylose-containing substance as such and then the textile finished in this way is treated with a suitable preparation of the active ingredient. As a result, the amylose-containing substance located on the textile material is loaded with the active ingredient.

However, it is also possible to use the amylose-containing substance together with an active ingredient in order to finish the textile. Here, the active ingredient and the amylose-containing substance can be applied both as a mixture of separate components and in the already prepared form of the amylase-active ingredient complex.

As a rule, the active ingredient will be used in an amount which suffices for the desired effect. The upper limit is determined by the maximum absorption capacity of the amylose units of the amylose-containing substance used and will generally not exceed 20% by weight and often 10% by weight, based on the amylose content of the substance. If desired, the active ingredient is generally used in an amount of from 0.00001 to 15% by weight, 0.0001 to 10% by weight, 0.001 to 5% by weight, 0.005 to 1% by weight or 0.1 to 10% by weight or 0.5 to 5% by weight, based on the amylose content of the amylose-containing substance.

For the textile finishing, it is also possible to use combinations of active ingredients according to the invention with other active ingredients known per se and suitable for the finishing of textiles.

Suitable further active ingredients are in principle all organic compounds and mixtures of organic compounds which are known as active ingredients and which induce a physiological effect in living organisms such as humans and animals, including microorganisms. Mention may be made of those active ingredients which are known to be able to form inclusion compounds with cyclodextrins. Of particular suitability are active ingredients which have hydrocarbon groups and in particular aliphatic, cycloaliphatic and/or aromatic structures. The molecular weight of the active ingredients is typically below 1000 daltons and often in the range from 100 to 600 daltons. Moreover suitable are inorganic compounds such as hydrogen peroxide, which as are known can be bonded into cyclodextrins (see in this regard F. Vögtle, Supramolekulare Chemie [Supramolecular Chemistry], $2^{nd}$ edition, B. G. Teubner, Stuttgart 1992, Cyclodextrins and literature cited therein).

The further active ingredients include in particular pharmaceutical active ingredients and active ingredients which promote the wellbeing of living organisms, in particular of humans, and which are generally also referred to as "wellness additives". In contrast to pharmaceutical active ingredients, the wellness additives do not necessarily have to have a therapeutic effect. Rather, the effect promoting wellbeing can be based on a large number of factors such as care, stimulating, cosmetic or other effects. Similarly of suitability are organic active ingredients which are effective against parasitic organisms. These include, for example, active ingredients which are effective against funghi and/or microorganisms, e.g. fungicides and bactericides, or which are effective against animal pests such as slugs and snails, worms, mites, insects and/or rodents, e.g. nematicides, molluscicides, insecticides, acaricides, rodenticides and repellent active ingredients, and also furthermore active ingredients to combat weeds, i.e. herbicides, or fragrances.

Preferred pharmaceutical active ingredients are those which are known to be able to be absorbed by the skin. These include, for example, ibuprofen, fluorbiprofen, acetylsalicylic acid, acetamidophen, apomorphine, butylated hydroxytoluene, chamazulene, guaiazulene, chlorthalidone, cholecalciferol, dicumarol, digoxin, diphenylhydantoin, furosemide, hydroflumethiazide, indomethacin, iproniazid phosphate, nitroglycerol, nicotin, nicotinamide, oubain, oxprenolol, papaverine alkaloids such as papaverine, laudanosine, ethaverine and narcotin, and also berberine, also retionol, trans-retinoleic acid, pretinol, spironolactone, sulpiride, theophylline, theobromine, corticosteroids and derivatives such as testosterone, 17-methyltestosterone, cortisone, corticosterone, dexamethasone, triamcinolone, methylprednisolone, fludrocortisone, fluocortolone, prednisone, prednisolone, progesterone, including estrogens and gestagens such as estradiol, estriol, ethynylestradiol 3-methyl ether, norethisterone and ethisterone, and also phenethylamine and derivatives such as tyramine, adrenalin, noradrenalin and dopamine.

Examples of active ingredients suitable according to the invention with an effect against parasitic organisms are the nematicides, bactericides, fungicides, insecticides, insect repellants, acaricides and molluscicides specified under www.reith-pfister.de/w.list.html and also under wwvw.hcl-rss.demon.co.uk/class_pesticides.html.

Examples of bactericidal and fungicidal substances comprise:
antibiotics, e.g. cycloheximide, griseofulvin, kasugamycin, natamycin, polyoxin, streptomycin, penicillin or gentamycin;
organic compounds and complexes of biocidal metals, e.g. complexes of silver, copper, tin and/or zinc, such as bis(tributyltin) oxide, copper, zinc and tin naphthenates, oxine-copper such as Cu-8, tris-N-(cyclohexyldiazeniumdi-oxy)aluminum, N-(cyclohexyldiazeniumdioxy)tributyltin, bis-N-(cyclohexyl-diazeniumdioxy) copper;
quaternary ammonium salts, e.g. benzyl-$C_8$-$C_{18}$-alkyldimethylammonium halides, in particular chlorides (benzalkonium chlorides);
aliphatic nitrogen fungicides and bactericides such as cymoxanil, dodine, dodicine, guazidines, iminoctadine, dodemorph, fenpropimorph, fenpropidin, tridemorph,
substances with peroxide groups such as hydrogen peroxide, and organic peroxides such as dibenzoyl peroxide;
organic chlorine compounds, such as e.g. chlorhexidine;
triazole fungicides such as azaconazole, cyproconazole, diclobutrazole, difenoconazole, diniconazole, epoxiconazole, fenbuconazole, fluquinconazole, flusilazole, flutriafol, hexaconazole, metconazole, propiconazole, tetraconazole, tebuconazole and triticonazole;
strobilurins such as dimoxystrobin, fluoxastrobin, kresoxim-methyl, metominostrobin, orysastrobin, picoxystrobin, pyraclostrobin and trifloxystrobin
sulfonamides such as tolylfluanid and diclofluanid;
iodine compounds such as diiodomethyl-p-tolylsulfone, napcocides 3-iodo-2-propynyl alcohol, 4-chlorophenyl-3-iodopropargylformal, 3-bromo-2,3-diiodo-3-propenylethyl carbonate, 2,3,3-triiodoallyl alcohol, 3-iodo-2-propynyl n-hexylcarbamate, 3-bromo-2,3-diiodo-2-propenyl alcohol, 3-iodo-2-propynyl phenylcarbamate, 3-iodo-2-propynyl n-butylcarbamate, O-1-(6-iodo-3-oxohex-5-ynyl) phenylcarbamate, O-1-(6-iodo-3-oxohex-5-ynyl) butylcarbamate;
isothiazolinones such as N-methylisothiazolin-3-one, 5-chloro-N-methylisothiazolin-3-one, 4,5-dichloro-N-octylisothiazolin-3-one, 1,2-benzisothiazol-3(2H)one, 4,5-trimethylisothiazol-3-one and N-octylisothiazolin-3-one.

Examples of insecticides and acaricides are
organophosphates such as acephate, azamethiphos, azinphos-methyl, chlorpyrifos, chlorpyriphos-methyl, chlorfenvinphos, diazinon, dichlorvos, dicrotophos, dimethoate, disulfoton, ethion, fenitrothion, fenthion, isoxathion, malathion, methamidophos, methidathion, methyl-parathion, mevinphos, monocrotophos, oxydemeton-methyl, paraoxon, parathion, phenthoate, phosalone, phosmet, phosphamidon, phorate, phoxim, pirimiphos-methyl, profenofos, prothiofos, sulprophos, triazophos, trichlorfon;

in particular pyrethroids such as acrinatrin, allethrin, bioallethrin, barthrin, bifenthrin, bioethanomethrin, cyclethrin, cycloprothrin, cyfluthrin, beta-cyfluthrin, cyhalothrin, gamma-cyhalothrin, lambda-cyhalothrin, cypermethrin, α-cypermethrin, β-cypermethrin, λ-cypermethrin, zeta-cypermethrin, cyphenothrin, deltamethrin, dimefluthrin, dimethrin, empenthrin, fenfluthrin, fenprithrin, fenpropathrin, fenvalerat, esfenvalerat, flucythrinate, fluvinate, tau-fluvinate, furethrin, permethrin, biopermethrin, trans-permethrin, phenothrin, prallethrin, profluthrin, pyresmethrin, resmethrin, bioresmethrin, cismethrin, tefluthrin, terallethrin, tetramethrin, tralomethrin, transfluthrin, etofenprox, flufenprox, halfenprox, protrifenbute and silafulfen.

pyrrole and pyrazole insecticides such as acetoprole, ethiprole, fipronil, tebufenpyrad, tolfenpyrad, chlorfenapyr and vaniliprole.

Examples of repellent active ingredients are in particular anthraquinone, acridine bases, copper naphthenate, butopyronoxyl, dibutyl phthalate, dimethyl phthalate, dimethyl carbate, ethohexadiol, hexamide, methoquin-butyl, N-methylneodecanamide, camphor, bergamot oil, pyrethrum, clove oil, geranium oil, thyme oil and in particular diethyl m-toluamide and 2-(2-hydroxyethyl)-1-methylpropyl 1-piperidinecarboxylate (picardin).

Examples of wellness additives are in particular the substances and substance mixtures listed below, e.g.

fats, preferably of vegetable origin, e.g. lecithins, vegetable oils such as jojoba oil, teatree oil, clove oil, evening primrose oil, almond oil, coconut oil, avocado oil, soybean oil and the like, fatty acids, e.g. ω-6-fatty acids, linolenic acid, linoleic acid, waxes of animal or vegetable origin such as beeswax, candelilla wax, shea butter, shorea butter, mango seed butter, japan wax and the like, vitamins, in particular fat-soluble vitamins, e.g. tocopherols, vitamin E, vitamin A and the like, corticosteroids such as cortisone, corticosterone, dexamethasone, triamcinolone, methylprednisolone, fludrocortisone, fluocortolone, prednisone, prednisolone, progesterone, amino acids, e.g. arginine, methionine, plant extracts such as algae extract, horse-chestnut extract, mango extract and the like.

To improve the washing permanency of the finishing according to the invention, it has proven useful if the amylose-containing substance is fixed to the textile using a binder. Suitable binders are firstly film-forming, water-insoluble polymers and, secondly, low molecular weight reactive substances which polymerize upon heating. As a rule, the binder will be used in an amount such that the weight ratio of amylose-containing substance to water-insoluble polymer is in the range from 1:1 to 100:1, preferably in the range from 1.5:1 to 50:1 and in particular in the range from 2:1 to 20:1.

As a rule, the film-forming polymers are used in the form of an aqueous dispersion of finely divided polymer particles. The particle size is of minor importance for the success according to the invention. However, it is usually below 5 µm (weight-average) and is generally 50 nm to 2 µm.

The film-forming polymer can in particular have a glass transition temperature $T_G$ in the range from −40 to 100° C., preferably −30 to +60° C., in particular −20 to +40° C. If the polymeric binder comprises a plurality of polymer components, at least the main constituent should have a glass transition temperature within this range. In particular, the glass transition temperature of the main constituent is in the range from −30° C. to +60° C. and particularly preferably in the range from −20° C. to +40° C. Preferably, all of the polymeric constituents have a glass transition temperature within these ranges. The stated glass transition temperatures refer here to the "midpoint temperature" determined in accordance with ASTM-D 3418-82 by means of DSC. In the case of crosslinkable binders, the glass transition temperature refers to the uncrosslinked state.

Examples of suitable film-forming polymers are based on the following polymer classes:

(1) polyurethane resins
(2) acrylate resins (straight acrylates: copolymers of alkyl acrylates and alkyl methacrylates);
(3) styrene acrylates (copolymers of styrene and alkyl acrylates);
(4) styrene/butadiene copolymers;
(5) polyvinyl esters, in particular polyvinyl acetates and copolymers of vinyl acetate with vinyl propionate;
(6) vinyl ester-olefin copolymers, e.g. vinyl acetate/ethylene copolymers;
(7) vinyl ester-acrylate copolymers, e.g. vinyl acetate/alkyl acrylate copolymers, and vinyl acetate/alkyl acrylate/ethylene terpolymers;

Such polymers are known and commercially available, e.g. polymers from classes (2) to (7) in the form of aqueous dispersions under the names ACRONAL, STYROFAN, BUTOFAN (BASF-AG), MOWILITH, MOWIPLUS, APPRETAN (Clariant), VINNAPAS, VINNOL (WACKER). Aqueous polyurethane dispersions (1) suitable for the method according to the invention are, in particular, those which are used for the coating of textiles (see e.g. J. Hemmrich, Int. Text. Bull. 39, 1993, No. 2, pp. 53-56; "Wässrige Polyurethan-Beschichtungssysteme" [Aqueous polyurethane coating systems] Chemiefasern/Textilind. [Chemistry Fibers/Textile Ind] 39 91 (1989) T149, T150; W. Schröer, Textilveredelung [Textile finishing] 22, 1987, pp. 459-467). Aqueous polyurethane dispersions are commercially available, e.g. under the trade names Alberdingk® from Alberdingk, Impranil® from BAYER AG, Permutex® from Stahl, Waalwijk, the Netherlands, from BASF SE or can be prepared by known processes, as are described, for example, in "Herstellverfahren für Polyurethane" [Preparation processes for polyurethanes] in Houben-Weyl, "Methoden der organischen Chemie", [Methods of organic chemistry], Volume E 20/Makromolekulare Stoffe [Macromolecular substances], p. 1587, D. Dietrich et al., Angew. Chem. 82 (1970), p. 53 ff., Angew. Makrom. Chem. 76, 1972, 85 ff. and Angew. Makrom. Chem. 98, 1981, 133-165, Progress in Organic Coatings, 9, 1981, pp. 281-240, and Römpp Chemielexikon [Chemistry lexicon], $9^{th}$ edition, volume 5, p. 3575.

The film-forming polymers can be self-crosslinking, i.e. the polymers have functional groups (crosslinkable groups) which, upon drying the composition, optionally upon heating, react with one another, with the functional groups of the amylose or with a low molecular weight crosslinker with bond formation.

Examples of crosslinkable functional groups comprise aliphatically bonded OH groups, NH—$CH_2$—OH groups, carboxylate groups, anhydride groups, capped isocyanate groups and amino groups. A polymer will often be used that also has free OH groups as reactive groups. As a rule, the fraction of the reactive functional groups is 0.1 to 3 mol/kg of polymer. The crosslinking can be effected within the polymer by the reaction of complementary-reactive functional groups. Preferably, the crosslinking of the polymer is effected by adding a crosslinker which has reactive groups which are complementary to the functional groups of the crosslinker with regard to their reactivity. Suitable pairs of functional groups which have a complementary reactivity are known to the person skilled in the art. Examples of such pairs are OH/COOH, OH/NCO, $NH_2$/COOH, $NH_2$/NCO and $M^{2+}$/COOH, where $M^{2+}$ is a divalent metal ion such as $Zn^{2+}$ $Ca^{2+}$, or $Mg^{2+}$. Examples of suitable crosslinkers are the diols or polyols specified below for the polyurethanes; primary or secondary diamines, preferably primary diamines, e.g. alkylenediamines, such as hexamethylenediamine, diethylenetriamine, triethylenetetramine, tetraethylenepentamine, N,N-bis[(aminopropyl)amino]ethane, 3,6-dioxaoctanediamine, 3,7-dioxanonanediamine, 3,6,9-trioxaundecanediamine or Jeffamines, (4,4'-diaminodicyclohexyl)methane, (4,4'-diamino-3,3-dimethyldicyclohexyl)methane; amino alcohols, such as ethanolamine, hydroxypropylamine; ethoxylated di- and oligoamines; dihydrazides of aliphatic or aromatic dicarboxylic acids, such as adipic dihydrazide; dialdehydes, such as glyoxal; partially or completely O-methylated melamines, and also compounds or oligomers which, on average, have two or more, preferably three or more, isocyanate groups or reversibly e.g. hydrogensulfite blocked isocyanate groups. In this case, the quantitative ratio of crosslinker to polymeric binder is such that the molar ratio of the reactive groups in the polymeric binder (total amount of the reactive groups in the polymers) to the reactive groups in the crosslinker is generally in the range from 1:10 to 10:1 and preferably in the range from 3:1 to 1:3. Usually, the weight ratio of polymeric binder (calculated as solid) to crosslinker is in the range from 100:1 to 1:1 and in particular in the range from 50:1 to 5:1.

As an alternative to fixing the amylose-containing substance with water-insoluble polymers, the amylose or the amylose-containing substance can also be fixed to the textile material with reactive compounds which have at least one group which is reactive towards the OH groups of the amylose, and at least one further functional group which is reactive towards the functional groups on the fibers of the textile material, e.g. OH groups, $NH_2$ groups or COOH groups. The reactive compounds include the aforementioned crosslinkers, and also the substances proposed in DE-A 40 378 for the fixing of cyclodextrins, e.g. N-hydroxymethyl and N-alkoxymethyl derivatives of urea or urea-like compounds, such as dimethylolurea (bis(hydroxymethyl)urea, di(methoxymethyl)urea, dimethylolalkanediol diurethanes, such as N,N-dimethylolethyleneurea (N,N-bis(hydroxymethyl)imidazolin-2-one), N,N-dimethyloldihydroxyethyleneurea (N, N-bis(hydroxymethyl)-4,5-dihydroxyimidazolin-2-one), dimethylolpropyleneurea and the like. Materials of this type are commercially available in the form of aqueous formulations for the finishing of textiles, e.g. under the trade names Fixapret® and Fixapret®-eco from BASF SE. The reactive materials which can be used for fixing the amylose-containing substance to the textile material include in particular also compounds with 2, 3, 4 or more (optionally reversibly blocked) isocyanate groups, specifically the polyisocyanate prepolymers based on polyether urethanes and polyester urethanes and reversibly blocked with bisulfite or CH-acidic compounds or oximenes, e.g. butanone oxime, which are described in DE 2837851, DE 19919816 and the earlier European patent application 03015121. Products of this type are also commercially available, for example under the trade names PROTOLAN®367 and PROTOLAN®357 from Rotta GmbH, Mannheim.

To fix the amylose-containing substance, the procedure known for the fixing of cyclodextrins can also be used in an analogous way, in which the cyclodextrin or in the present case the amylose-containing substance is provided with reactive anchors, for example by reacting it with dicarboxylic acids or dicarboxylic anhydrides, such as maleic acid, fumaric acid, maleic anhydride, succinic acid, succinic anhydride or adipic acid, with diisocyanates, e.g. toluene diisocyanate, isophorone diisocyanate, tetramethylene diisocyanate or hexamethylene diisocyanate, or with aminocarboxylic acids in a manner known per se in such a way that only one of the functionalities present in these compounds reacts with the OH groups of the amylose-containing substance and the other is retained for the binding to the reactive groups of the fiber material. Reactive anchors can be generated on the amylose-containing substance also by reaction with 1,3,5-trichlorotriazine, 2,3-dichloroquinoxaline-5,6-carbanoyl chloride, and also with chlorodifluoropyrimidine.

For fixing the amylose, it is also possible to use alkoxysilanes, such as diethoxydi-methylsilane, dimethoxydimethylsilane, triethoxyphenylsilane, tetraethoxysilane, and also dimeric, trimeric and higher condensation products of these compounds.

In this way, it is possible in principle to finish all textile materials, i.e. non-made-up goods and also made-up goods. Textile materials comprise here and below wovens, weft knits, warp knits and nonwovens. The textile materials can be constructed from natural fiber yarns, synthetic fiber yarns and/or mixed yarns. Suitable fiber materials are, in principle, all of the fiber materials customarily used for producing textiles. These include cotton, wool, hemp fibers, sisal fibers, flax, ramie, polyacrylonitrile fibers, polyester fibers, polyamide fibers, viscose fibers, silk, acetate fibers, triacetate fibers, aramid fibers and the like, and also mixtures of these fiber materials.

The finishing or treatment of the textile materials with the amylose-containing substance can be carried out in a manner known per se, e.g. by means of the method described in DE-A 4035378 for the finishing of textiles with cyclodextrins.

Mention may be made, for example, of methods in which the amylose-containing substance, optionally as a complex with the active ingredient, has already been spun into the fiber, the filament and/or the yarn from which the fabric is produced.

However, the textile material will often be treated with the amylose-containing substance or a complex of amylose-containing substance and active ingredient before or after making-up. For this purpose, the textile will as a rule be treated with an aqueous liquor which comprises the amylose-containing substance and optionally the active ingredient in an adequate amount. Depending on the type of application and the desired amount in which the amylose-containing substance is to be applied, the concentration of amylose-containing substance in the liquor is in the range from 1 to 40% by weight, in particular in the range from 2 to 20% by weight and specifically in the range from 4 to 15% by weight.

The type of treatment is of minor importance and can be carried out, for example, as minimal application, e.g. by spray application, as standard application in the padder or as high-moisture application. In this process, the textile material is saturated with the aqueous liquor. Optionally, excess liquor can then be removed, e.g. by squeezing off to a liquor pick-up of about 30 to 120%.

Another option for treating the textile with amylose-containing substance or complex of amylose-containing substance and active ingredient is to prepare a liquor with water, in which the desired amount of amylose-containing substance and optionally active ingredient is present, e.g. 0.5 to 20% by weight (based on the mass of the textile to be finished). The textile material is drenched through over a certain period, e.g. 10-60 min with the treatment liquor in finishing assemblies suitable for this purpose (e.g. winch beck; roller beck; paddle; etc.) and then squeezed off and/or spun off as stated above. The liquor ratio here is usually in the range from 1:2 to 1:50 and in particular in the range from 1:3 to 1:20.

Methods of this type are known to the person skilled in the art, for example from H. K Rouette, Lexikon der Textilveredlung [Lexicon of textile finishing], Laumann-Verlag, Dülmen 1995, p. 669 ff.

As a rule, the treatment with the liquor is followed by a drying operation. The temperatures here are usually in the range from 100 to 200° C. and preferably in the range from 120 to 180° C. The drying can be carried out in the equipment customary for this purpose, in the case of made-up goods for example by dry-tumbling at the temperatures stated above. In the case of goods which are not made-up, following application, the textile material will usually be guided over one or more tenters.

If the amylose-containing substance is used together with a film-forming polymer, drying leads to a fixing of the amylose-containing substance on the textile fibers. As a rule, the drying temperature will not drop below 100 and is preferably in the range from 120 to 200° C. and in particular in the range from 140 to 180° C. In general, drying takes place over a period of from 1 to 10 min, in particular 1 to 2 min, with longer drying times likewise being suitable.

For the treatment with an aqueous liquor, it has proven advantageous if the aqueous liquor comprises, besides the amylose-containing substance and optionally the active ingredient, at least one surface-active substance (or interface-active substance) which is suitable for dispersing the amylose-containing substance and the active ingredient in the aqueous liquor. The surface-active substance is preferably an oligomeric or polymeric dispersant. The term oligomeric or polymeric dispersant comprises, in contrast to low molecular weight surface-active substances, those dispersants whose number-average molecular weight is generally at least 2000 daltons, e.g. 2000 to about 100 000 daltons and in particular is in the range from about 3000 to 70 000 daltons.

As a rule, the aqueous liquor comprises the polymeric or oligomeric dispersant in an amount of from 0.5 to 20% by weight, preferably 1 to 18% by weight and in particular 5 to 15% by weight, based on the amylose-containing substance.

Suitable oligomeric or polymeric dispersants are soluble in water and comprise both neutral and amphoteric water-soluble polymers and also cationic and anionic polymers, the latter being preferred.

Examples of neutral polymeric dispersants are polyethylene oxide, ethylene oxide/propylene oxide copolymers, preferably block copolymers, polyvinyl pyrrolidone, and copolymers of vinyl acetate with vinylpyrrolidone.

The preferred anionic oligomeric or polymeric dispersants are characterized in that they have carboxyl groups and/or sulfonic acid groups and are usually used as salts, e.g. as alkali metal salts or ammonium salts.

Preferred anionic dispersants are, for example, carboxylated derivatives of cellulose, such as carboxymethylcellulose, homopolymers of ethylenically unsaturated $C_3$-$C_8$-mono- and $C_4$-$C_8$-dicarboxylic acids, e.g. of acrylic acid, of methacrylic acid, of maleic acid, of itaconic acid, copolymers of at least two different ethylenically unsaturated $C_3$-$C_8$-mono- and $C_4$-$C_8$-dicarboxylic acids as specified above, and copolymers of at least one of the aforementioned ethylenically unsaturated $C_3$-$C_8$-mono- or $C_4$-$C_8$-dicarboxylic acid with at least one neutral comonomer. Examples of neutral comonomers are N-vinyllactams, such as N-vinylpyrrolidone, vinyl esters of aliphatic $C_2$-$C_{16}$-carboxylic acids, such as vinyl acetate, vinyl propionate, amides of the aforementioned ethylenically unsaturated carboxylic acids, such as acrylamide, methacrylamide and the like, hydroxy-$C_1$-$C_4$-alkyl (meth)acrylates, such as hydroxyethyl acrylate and methacrylate, esters of ethylenically unsaturated $C_3$-$C_8$-mono- or $C_4$-$C_8$-dicarboxylic acids with polyethers, e.g. esters of acrylic acid or of methacrylic acid with polyethylene oxides or ethylene oxide/propylene oxide block copolymers, vinylaromatics, such as styrene, and $C_2$-$C_{16}$-olefins, such as ethylene, propene, 1-hexene, 1-octene, 1-decene, 1-dodecene and the like. Preference is also given to homopolymers of ethylenically unsaturated sulfonic acids, such as styrenesulfonic acid and acrylamidopropanesulfonic acid and copolymers thereof with the aforementioned comonomers. In the copolymers, the fraction of ethylenically unsaturated acid will usually be at least 20% by weight and not exceed a value of 90% by weight and in particular 80% by weight, in each case based on the total weight of all of the monomers constituting the polymer.

Copolymers of at least one of the aforementioned acids and at least one comonomer are known for this purpose and are commercially available, for example the copolymers of acrylic acid and maleic acid as Sokalan brands from BASF AG.

Likewise preferred anionic dispersants are phenolsulfonic acid-formaldehyde condensates and naphthalenesulfonic acid-formaldehyde condensates (e.g. the Tamol and Setamol brands from BASF) and lignosulfonates.

Dispersants which can be used are also low molecular weight anionic, nonionic, cationic, ampholytic and zwitterionic surfactants. Suitable surfactants are, for example, the alkali metal, ammonium or amine salts of $C_8$-$C_{18}$-alkyl sulfates, such as sodium lauryl sulfate; $C_8$-$C_{18}$-alkylsulfonates, such as dodecylsulfonate; $C_8$-$C_{18}$-alkyl ether sulfates; and also $C_8$-$C_{18}$-alkyl ethoxylates; polyoxyethylene sorbitan esters; $C_8$-$C_{18}$-alkyl glycinates; $C_8$-$C_{18}$-alkyldimethylamine oxides; betaines etc. Preference is given to the alkyl sulfates and alkylsulfonates.

If the amylose-containing substance is not used together with a film-forming, water-insoluble polymer, the textile can be treated with the polymer in a separate working step. In particular, treatment takes place together with the amylose-containing substance. Accordingly, one particular embodiment relates to a method in which the aqueous liquor additionally comprises a dispersed, film-forming, water-insoluble polymer of the type described above. The amount of film-forming polymer is selected such that the weight ratio of amylose-containing substance to water-insoluble polymer is in the range from 1:1 to 100:1, preferably in the range from 1.5:1 to 50:1 and in particular in the range from 2:1 to 20:1.

The finishing of the textile with the active ingredient can take place in a separate operation or in one operation together with the finishing with the amylose-containing substance.

If the textile is finished with the active ingredient in a separate operation, the textile will expediently likewise be treated with an aqueous liquor of the active ingredient. For this, as a rule, the active ingredient, which is usually not soluble in water, will be emulsified or dispersed in water, optionally using suitable surface-active substances. Suitable surface-active substances are in particular the aforementioned low molecular weight surfactants and, of these, preference is given to the nonionic surfactants, in particular polyoxyethylene sorbitan esters, esters of mono- or oligosaccharides with $C_6$-$C_{18}$-fatty acids and particularly preferably $C_8$-$C_{18}$-alkyl ethoxylates, in particular those with a degree of ethoxylation in the range from 6 to 50. As a rule, the aqueous liquor comprises the active ingredient in an amount of from 0.1 to 10% by weight and in particular in an amount of from 0.2 to 5% by weight. The amount of surface-active substance is generally in the range from 0.5 to 50% by weight and in particular in the range from 3 to 30% by weight, based on the active ingredient. The active ingredient can be applied from aqueous liquor using the methods customary for this purpose, e.g. by means of a padder.

However, it is also possible to carry out the finishing with active ingredient and amylose-containing substance in one operation. The procedure here is in principle as described for the finishing with the amylose-containing substance, except the aqueous liquor of the amylose-containing substance now additionally comprises the at least one active ingredient. The active ingredient here can be added separately to the liquor or in the form of an inclusion compound, i.e. in the form of a host/guest complex with the amylose-containing substance.

The method according to the invention can be used for the finishing of any desired textiles, including wovens, knits, nonwovens and the like. The type of textile material is governed primarily by the desired intended use.

The textiles to be finished may be ready-made products such as clothing, including underwear and outer clothing, such as e.g. shirts, trousers, jackets, outdoor, trekking and military finishings, roofs, tents, nets, e.g. nets to protect against insects and curtains, hand towels and bath towels, bedding and the like.

In the same way, the finishing on the raw goods can take place in pad or roller application form.

The textiles finished with active ingredients against parasitic organisms such as insects and acaricides are suitable not only for protection of human beings, but also particularly in animal protection to protect against ticks, mites, fleas and the like.

The textile materials can be constructed from natural fiber yarns, synthetic fiber yarns and/or mixed yarns, the fabric usually having a weight per area in the range from 10 to 500 g/m$^2$, preferably 20 to 250 g/m$^2$. Suitable fiber materials are in principle all fiber materials customarily used for producing textiles. These include cotton, wool, hemp fiber, sisal fibers, flax, ramie, polyacrylonitrile fibers, polyester fibers, polyamide fibers, viscose fibers, silk, acetate fibers, triacetate fibers, aramid fibers and the like, and also mixtures of these fiber materials. Also suitable are glass fibers, and also mixtures of the aforementioned fiber materials with glass fibers, e.g. glass fiber/Kevlar mixtures.

Using an amylose-based active ingredient finishing described above, the active ingredients remain in the textiles finished therewith even after several washes. Moreover, the textiles finished in this way are characterized by a pleasant handle, which is advantageous particularly for the wear comfort of clothing produced from these textiles.

4.7 Cooling Tobacco Products

In principle, the active ingredient content can vary over a wide range, such as e.g. 0.00001 to 50% by weight, in particular 0.001 to 10% by weight or 0.005 to 1% by weight.

The active ingredients according to the invention can advantageously also be used for producing tobacco products. Examples of such tobacco products comprise cigars, cigarettes, pipe tobacco, chewing tobacco and snuff tobacco.

The production of tobacco products which are supplemented with cooling additives is known per se and described e.g. in U.S. Pat. Nos. 3,111,127, 5,752,529 and US 2005/0000529, to which reference is hereby expressly made.

4.8 Cooling Packaging Materials

The active ingredients according to the invention are also advantageously suitable for producing packaging materials.

The production here likewise takes place in a manner known per se. The active ingredients can be incorporated here into the packaging material in free or e.g. encapsulated form, or be applied to the packaging material in free or encapsulated form.

Thus, correspondingly finished plastic packaging materials can be produced according to the details in the literature for producing polymer films (e.g. Ullmann, 6th ed. 2003. Vol. 36, p. 567). The production of papers coated in a suitable manner is likewise known and described e.g. in Ullmann, Vol. 25, p. 106 ff, 6th ed, 2003.

5. Active Ingredient Combinations

Optionally, the compounds (cooling active ingredients) of the formulae I (IA, IB, IC), II and/or III according to the invention can be combined with further known active ingredients, in particular also those with a comparable effect. For example, these can be combined with known cooling compounds, such as e.g. menthol, menthone, N-ethyl-p-menthanecarboxamide (WS-3, also called menthane-3-carboxylic acid-N-ethylamide), N-2,3-trimethyl-2-isopropylbutanamide (WS-23), menthyl lactate (Frescolat® ML), menthone glycerol acetal (Frescolat® MGA), monomenthyl succinate (Physcool®), monomenthyl glutarate, O-menthylglycerol, menthyl N,N-dimethylsuccinamate.

The cooling active ingredients according to the invention can preferably be combined with the following cooling active ingredients:
menthol and menthol derivatives (e.g. L-menthol, D-menthol, racemic menthol, isomenthol, neoisomenthol, neomenthol), menthyl ethers (e.g. (L-menthoxy)-1,2-propanediol, (L-menthoxy)-2-methyl-1,2-propanediol, L-menthyl methyl ether), menthyl esters (e.g. menthyl formate, menthyl acetate, menthyl isobutyrate, menthyl lactates, L-menthyl L-lactate, L-menthyl D-lactate, menthyl (2-methoxy)acetate, menthyl (2-methoxyethoxy)acetate, menthyl pyroglutamate, menthyl carbonates (e.g. menthyl propylene glycol carbonate, menthyl ethylene glycol carbonate, menthyl glycerol carbonate or mixtures thereof), the half-esters of menthols with a dicarboxylic acid or derivatives thereof (e.g. monomenthyl succinate, monomenthyl glutarate, monomenthyl malonate, O-menthylsuccinic acid ester N,N-(dimethyl) amide, O-menthylsuccinic acid ester amide), menthanecarboxamides (e.g. menthanecarboxylic acid-N-ethylamide [WS3], Nα-(menthanecarbonyl)glycine ethyl ester [WS5], menthanecarboxylic acid-N-(4-cyanophenyl)amide, menthanecarboxylic acid-N-(alkoxyalkyl)amides), menthone and menthone derivatives (e.g. L-menthone glycerol ketal), 2,3-dimethyl-2-(2-propyl)-butanoic acid derivatives (e.g. 2,3-dimethyl-2-(2-propyl)butanoic acid-N-methylamide [WS23]), isopulegol or its esters (l-(−)-isopulegol, l-(−)-isopulegol acetate), menthane derivatives (e.g. p-menthane-3,8-diol), cubebol or synthetic or natural mixtures comprising cubebol, pyrrolidone derivatives of cycloalkyldione derivatives (e.g. 3-methyl-2(1-pyrrolidinyl)-2-cyclopenten-1-one) or tetrahydropyrimidin-2-ones (e.g. icilin or related compounds, as described in WO 2004/026840).

The cooling active ingredients according to the invention can be combined particularly preferably with the following cooling active ingredients: menthyl ethers (e.g. (L-menthoxy)-1,2-propanediol, (L-menthoxy)-2-methyl-1,2-propanediol), polar menthyl esters (e.g. menthyl lactates, L-menthyl L-lactate, L-menthyl D-lactate, menthyl (2-methoxy)acetate, menthyl (2-methoxyethoxy)acetate, menthyl pyroglutamate), menthyl carbonates (e.g. menthyl propylene glycol carbonate, menthyl ethylene glycol carbonate, menthyl glycerol carbonate), the half-esters of menthols with a dicarboxylic acid or derivatives thereof (e.g. monomenthyl succinate, monomenthyl glutarate, monomenthyl malonate, O-menthylsuccinic acid ester-N,N-(dimethyl) amide, O-menthylsuccinic acid ester amide), non-inventive menthanecarboxamides (e.g. menthanecarboxylic acid-N-ethylamide [WS3], Nα-(menthanecarbonyl)glycine ethyl ester [WS5], menthanecarboxylic acid-N-(4-cyanophenyl) amide, menthanecarboxylic acid-N-(alkoxyalkyl)amides), menthone derivatives (e.g. L-menthone glycerol ketal), 2,3-dimethyl-2-(2-propyl)butanoic acid derivatives (e.g. 2,3-dimethyl-2-(2-propyl)-butanoic acid-N-methylamide), pyrrolidone derivatives of cycloalkyldione derivatives (e.g. 3-methyl-2(1-pyrrolidinyl)-2-cyclopenten-1-one) or tetrahydropyrimidin-2-ones (e.g. icilin or related compounds, which are described in WO 2004/026840).

The statements given in the whole of sections 4 and 5 also apply to the specific applications in section 6 below, unless stated otherwise.

6. Specific Applications

The following specific section of the invention relates to the use of compounds according to the invention (TRPM8 receptor modulators) for producing a long-lasting physiological cooling effect on skin or mucosa.

Physiological cooling active ingredients are regularly used in order to bring about a cool sensory impression on the skin and/or mucosa, for example on the mucosa in the oral cavity, nasal cavity and/or throat cavity, although in fact no physical cooling, as for example upon the evaporation of solvents, takes place. Physiological cooling active ingredients which can be used are either individual components or mixtures. In this connection, it should be taken into consideration that not all compounds which influence receptors in vitro which are (also) involved in the mediation of a physiological cooling effect actually produce such an effect in vivo on the skin or on mucosa. In particular, such an effect will not always proceed in an identical way. This means, for example, that the intensity of the mediated physiological cooling effect and also the course of the intensity of the cooling effect against time cannot be deduced merely from the fact that a certain compound is an agonist of a receptor involved in the mediation of a sensation of coldness.

The best known physiologically effective cooling active ingredient is L-menthol, although this has a number of disadvantages, e.g. strong odor impression, high volatility and, at higher concentrations, a bitter and/or sharp intrinsic taste, and/or a skin-irritating effect.

Strong cooling active ingredients have therefore already been sought previously which do not have the disadvantageous properties of L-menthol. Thus, e.g. lactic acid esters of menthol(s) as in DE 2 608 226 and mixed carbonates with menthol(s) and polyols as in DE 4 226 043 and menthone ketals as in EP 0 507 190 have been described.

Menthyl monoesters of dioic acids as in U.S. Pat. Nos. 5,725,865 and 5,843,466 are interesting naturally occurring alternatives, but are unable to achieve the intensity of the cooling active ingredients described previously in sensory tests.

In J. Soc. Cosmet. Chem. 1978, 29, 185-200, the results of a study on ca. 1200 compounds were presented, in which the compounds L-menthanecarboxylic acid-N-ethylamide ("WS3") and in particular Nα-(L-menthanecarbonyl)glycine ethyl ester ("WS5") were found to be the strongest cooling active ingredients. However, coupled with a strong effect, the latter has the disadvantage of being hydrolysis-sensitive and, therefore, of forming the corresponding free acid Nα-(L-menthanecarbonyl)glycine, which itself exhibits only a very weak cooling effect. Despite the described detailed investigations, a systematic prediction relating to properties of potential cooling active ingredients, especially with regard to their bitterness and/or their other trigeminal effects, is not possible and is also not described. Thus, although many of the molecules which fall under the class of menthanecarboxamides are strongly cooling, they at the same time frequently exhibit markedly bitter notes (e.g. the menthanecarboxylic acid-N-(alkyloxyalkyl)amides according to JP 2004059474) or are additionally severely irritating (WS5: N-[[5-methyl-2-(1-methylethyl)cyclohexyl]carbonyl]glycine ethyl ester, US 2005/0222256).

Nα-(Menthanecarbonyl)alkyloxyalkylamides have been described in JP 2004059474. However, coupled with a strong cooling effect and high hydrolysis stability, these have the disadvantage of being severely bitter and can therefore not be used in foods or in cosmetic products used for facial care.

Furthermore, menthyl glyoxylates and their hydrates have been described in JP 2005343795 as cooling substances.

Overviews of the cooling active ingredients used and produced hitherto can be found in M. Erman, Perfumer & Flavorist 32(10), 20-35 (2007) and M. L. Dewis in D. J. Rowe, Chemistry and Technology of Flavors and Fragrances, Blackwell Publishing Ltd, Oxford 2005, p. 212-222.

Novel compositions are described hereinbelow which have a particular physiological cooling effect and, as a result, can be used as cooling substances (cooling active ingredients) in foods and/or treats and/or mouthcare products and/or (oral) pharmaceutical preparations and/or cosmetic preparations. The compounds and/or mixtures of compounds to be indicated should preferably exhibit the weakest possible intrinsic taste, in particular taste only a little bitter, if at all, and also be as non-irritating as possible.

The invention relates to compositions, such as e.g. an aroma mixture or foods, oral hygiene agents or pharmaceutical or cosmetic preparation used for enjoyment, comprising one, two, three or more of the compounds selected from compounds according to above tables 1 and 2A to D, where the compound or the compounds is present in a concentration of 0.05 ppm-<0.1 ppm or 0.1 ppm to 50% by weight, based on the total weight of the preparation.

In particular, in the compositions described for this specific aspect of the invention, the compounds to be used according to the invention are present in a (total) concentration of from 0.05 ppm to 50% by weight, based on the total weight of the preparation or of the composition. Here, this range is composed in particular of the following sub-ranges:

0.05 ppm-<0.1 ppm. 0.1 ppm-1000 ppm and 0.1-50% by weight. Preferred concentration ranges, based on the total weight of the preparation or of the composition, are:

0.05 ppm-10% by weight, 0.5 ppm-5% by weight, 1 ppm-2.5% by weight.

Preference is given to a composition according to the invention, in particular to one according to the specific aspect of the invention, comprising (1) one or more further substances with a physiological cooling effect, where the further substance and/or one, several or all of the further substances (i) cause a gustatory effect or (ii) do not cause a gustatory effect,
and/or
(2) one or more aroma substances without a physiological cooling effect
and/or
(3) one or more trigeminally or mouth-washing effective substances without a physiological cooling effect
and/or
(4) (iii) one or
(iv) several compounds which, in the case of (iv), independently of one another or together
additionally cause a taste-modulating effect and/or a trigeminal and/or a mouth-washing stimulus.

Such a composition also preferably comprises one or more further substances with a physiological cooling effect without a gustatory effect. This avoids, with the composition according to the invention, for example only aromas with a minty aroma character being able to be obtained.

Very particular preference is given to a composition according to the invention comprising, as constituent (2), one or more aroma substances without a physiological cooling effect and/or, as constituent (3), one or more compounds which, independently of one another or together additionally cause a taste-modulating effect and/or a trigeminal and/or a mouth-washing stimulus, where the trigeminal stimulus is preferably not a physiological cooling effect. In particular, those compositions according to the invention which simultaneously comprise the last-mentioned constituents (2) and (3) have a pleasant cooling effect and a balanced sensory profile coupled with a simultaneously high impact, i.e. a high gustatory first impression.

The specific aspect of the invention preferably also relates to compositions in particular as preparations used for food, oral hygiene or enjoyment, or pharmaceutical or cosmetic preparations which comprise an amount of a compound to be used according to the invention or of a mixture of such compounds to be used according to the invention sufficient to achieve a physiological cooling effect on the skin and/or mucosa. In particular, the used amount of this compound or of this mixture should suffice to achieve a physiological cooling effect on the mucosa in the oral cavity, nasal cavity and/or throat cavity.

In this connection, reference may be made to the fact that the terms "composition" and "preparation" can be used synonymously. However, it is preferred that a preparation must be produced by means of a working step which goes beyond the mere mixing of the individual compounds. Such a working step can serve, for example, to generate a suspension or an emulsification.

Preferred compositions according to the invention comprise customary basic substances, auxiliaries and additives for preparations used for food, oral hygiene or enjoyment, or pharmaceutical or cosmetic preparations. Preferred preparations according to the invention comprise 0.000005% by weight to 20% by weight, preferably 0.00001 to 10% by weight, particularly preferably 0.0001% by weight to 0.5% by weight, of compounds to be used according to the invention, based on the total weight of the preparation. Further constituents, in particular constituents (1) (further substances with a physiological cooling effect), (2) (aroma substances without a physiological cooling effect) and/or (3) (trigeminally or mouth-washing effective substances without a physiological cooling effect) (as described above), and also further customary basic substances, auxiliaries and additives can be present in amounts of from 0.0000001 to 99.99% by weight, preferably 10 to 80% by weight, based on the total weight of the preparation. In addition, the preparations according to the invention can comprise water in an amount up to 99.99% by weight, preferably 5 to 80% by weight, based on the total weight of the preparation.

Particular preference is given to a composition according to the invention where at least one of the compounds selected from the compounds of the above tables 1 and 2A to D.

Preferably, the compounds to be used according to the invention, or their mixtures, are used for producing a drug which serves to control or alleviate the symptoms of coughing/sneezing, oral inflammation, nasal inflammation, throat inflammation or pharyngeal inflammation, throat pain or hoarseness.

A further aspect of the specific aspect of the present invention relates to a therapeutic or non-therapeutic method for achieving a physiological cooling effect on the skin and/or mucosa, with the following step:

applying an amount of a composition according to the invention that is sufficient to achieve a physiological cooling effect on the skin and/or mucosa.

Within the context of the specific aspect of the invention, it is preferred that the composition according to the invention is an aroma mixture which comprises one or more aroma substances and/or one or more further cooling active ingredients for the aromatization of manufactured goods produced using the aroma mixture.

In preparations (aroma mixtures) which are used for aromatizations of toothpastes and dental creams, the content of the substances to be used according to the invention is 0.001 to 50% by weight; preference is given to a range from 0.005 to 5% by weight and particular preference is given to a range from 0.01 to 2% by weight. In the case of customary doses of the aromas between 0.5 and 1.5% by weight, based on the ready-to-use toothpastes and dental creams, the content of the substances to be used according to the invention is then 0.000005 to 0.75% by weight, based on the finished product; preference is accordingly given to a range from 0.000025 to 0.075% by weight, and particular preference is accordingly given to a content of from 0.00005 to 0.03% by weight.

In preparations (aroma mixtures) which are used for aromatizations of chewing gums, the content of the substances to be used according to the invention is 0.005 to 10% by weight; preference is given to a range from 0.01 to 5% by weight and particular preference is given to a range from 0.05 to 2.5% by weight. In the case of a customary dose of the aromas of 1-2% by weight, based on the ready-to-use chewing gum, the content of the substances to be used according to the invention is then 0.00005 to 0.2% by weight, based on the finished product; preference is accordingly given to a range from 0.0001 to 0.1% by weight and particular preference is accordingly given to a content of from 0.0005 to 0.05% by weight.

In preparations (aroma mixtures) which are used for aromatizations of mouthwashes and mouth rinses, the content of the substances to be used according to the invention is 0.01 to 10% by weight; preference is given to a range from 0.05 to 5% by weight and particular preference is given to a range from 0.1 to 2.5% by weight. In the case of a customary dose of the aroma of 2-4% by weight, based on the ready-to-use mouthwash concentrate, the content of the substances to be used according to the invention is then 0.0002 to 0.4% by weight, based on the finished product; preference is accordingly given to a range from 0.001 to 0.2% by weight and particular preference is accordingly given to a content of from 0.002 to 0.1% by weight. In ready-to-use mouthwashes and mouth rinses, in the case of a customary dose of the aroma mixture of 0.1-0.3% by weight, the content of the substances to be used according to the invention is then 0.00001 to 0.03% by weight, based on the finished product; preference is accordingly given to a range from 0.00005 to 0.015% by weight and particular preference is accordingly given to a content of from 0.0001 to 0.0075% by weight.

Suitable aroma substances are either complex natural raw materials such as extracts obtained from plants and essential oils, or fractions and single substances obtained therefrom, or are single aroma substances obtained synthetically or by biotechnological means.

Examples of natural raw materials are e.g.:
peppermint oils, spearmint oils, *mentha arvensis* oils, anise oils, clove oils, citrus oils, cinnamon bark oils, wintergreen oils, *cassia* oils, davana oils, spruce needle oils, *eucalyptus* oils, fennel oils, *galbanum* oils, ginger oils, chamomile oils, caraway oils, rose oils, geranium oils, sage oils, yarrow oils, star anise oils, thyme oils, juniper berry oils, rosemary oils, *angelica* root oils, and the fractions of these oils.

Examples of single aroma substances are e.g.:
anethole, menthol, menthone, isomenthone, menthyl acetate, menthofuran, menthyl methyl ether, mint lactone, eucalyptol, limonene, eugenol, pinene, sabinene hydrate, 3-octanol, carvone, gamma-octalactone, gamma-nonalactone, germacrene D, viridiflorol, 1,3E,5Z-undecatriene, isopulegol, piperitone, 2-butanone, ethyl formate, 3-octyl acetate, isoamyl isovalerate, hexanol, hexanal, cis-3-hexenol, linalool, alpha-terpineol, cis and trans carvyl acetate, p-cymene, thymol, 4,8-dimethyl-3,7-nonadien-2-one, damascenone, damascone, rose oxide, dimethyl sulfide, fenchol, acetaldehyde diethyl acetal, cis-4-heptenal, isobutyraldehyde, isovaleraldehyde, cis-jasmone, anisaldehyde, methyl salicylate, myrtenyl acetate, 8-ocimenyl acetate, 2-phenylethyl alcohol, 2-phenylethyl isobutyrate, 2-phenylethyl isovalerate, cinnamaldehyde, geraniol, nerol. In the case of chiral compounds, the specified aroma substances can be present as racemate, as individual enantiomer or as enantiomer-enriched mixtures.

In preparations used for food or enjoyment, the content of the substances to be used according to the invention is 0.000005 to 0.1% by weight; preference is given to a range from 0.00005 to 0.05% by weight and particular preference is given to a range from 0.0001 to 0.02% by weight.

In cosmetic preparations, the content of the substances to be used according to the invention is 0.001 to 10% by weight; preference is given to a range from 0.005 to 5% by weight and particular preference is given to a range from 0.01 to 2% by weight.

According to the invention, it is particularly preferred that the composition according to the invention in accordance with the specific aspect of the invention is a toothpaste.

7. Possible Routes for Preparing Compounds According to the Invention

In the section which follows, various synthesis methods are described for a representative cross section of active ingredients according to the invention.

a) General Preparation Examples for Compounds According to Formula I

The preparation of representative compounds of formula I is described in the following section.

In principle, the compounds of the formula I are accessible from the reaction of keto precursors of the formula V-I with keto-reactive compounds of the formula Y-I (see Akhrem et al., Kimiya Geteotsiklicheskikh Soedinenii, 1995, 187-194, Akhrem et al., Journal of Organic Chemistry of the USSR, 1985, 21 (6), 1227-1232)

SCHEME 1:

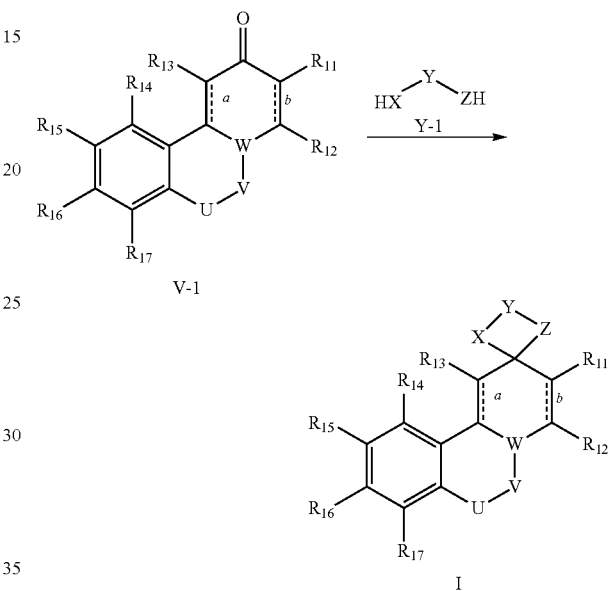

The various starting materials required for this are likewise known or are accessible by known processes.

For the preparation of compounds of the type V-I see generally: Akhrem et al. in Journal of Organic Chemistry of the USSR, 1979, 1247-1252, Akhrem et al., Izvestia Akademii Nauk SSSR Seria Himiceskaa, 1969, (10), 2338-2339, Akhrem et al., Doklady Akademii Nauk SSSR, 1972, 203 (1), 95-98.

In the sections which follow, the synthesis routes of a number of specific compound classes are shown diagrammatically. The reactions take place here using customary methods of organochemical synthesis.

Preparation Route 1-1: General Preparation of Compounds of the Formula I (Group 1)

Compounds of the formula IA

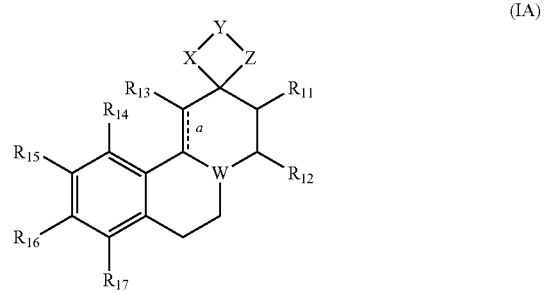

where
W=N,
a=single bond,
R$_{11}$, R$_{12}$=cycle;
R$_{13}$ to R$_{17}$=H;

The preparation takes place here according to the following scheme:

SCHEME 2:

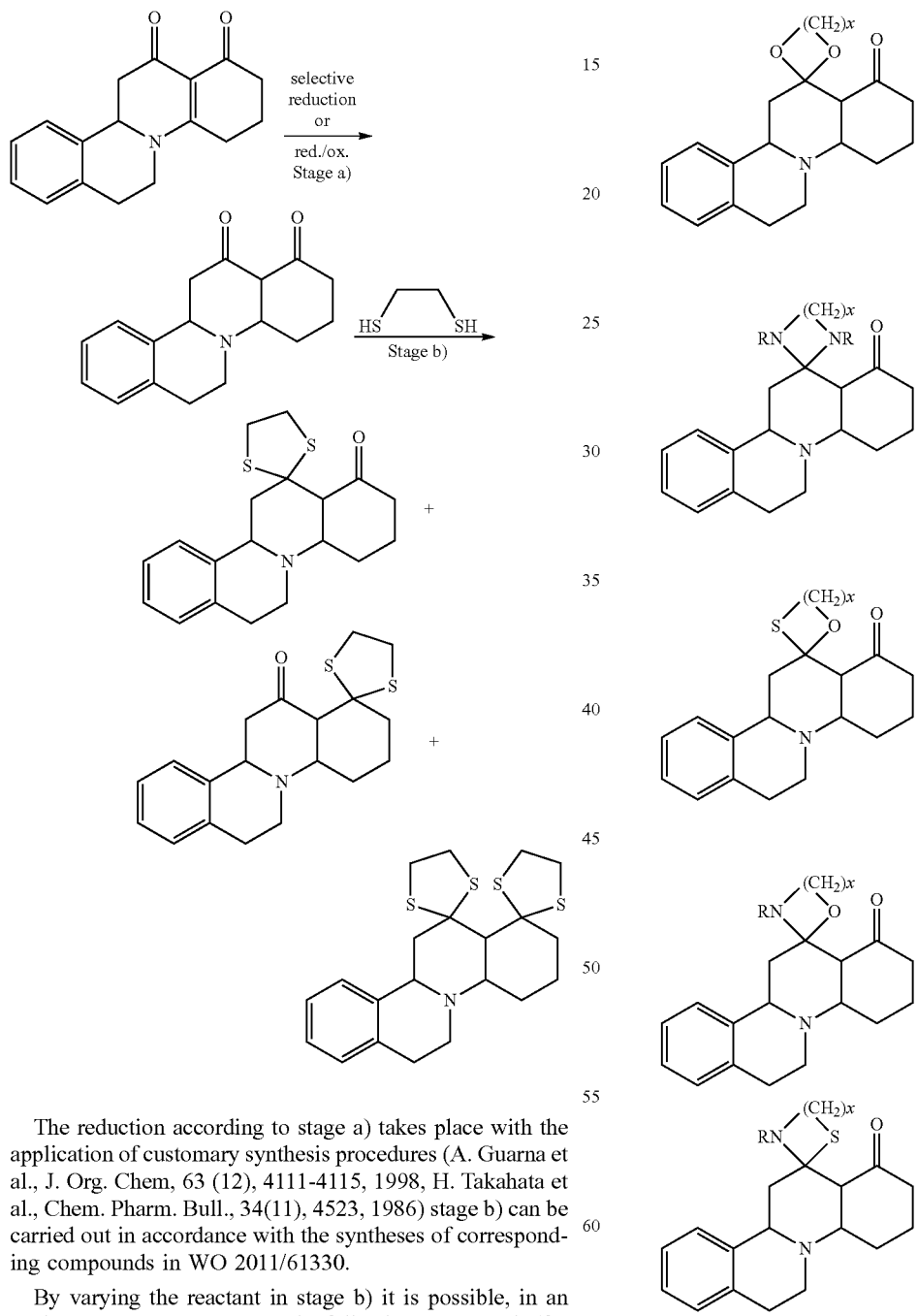

The reduction according to stage a) takes place with the application of customary synthesis procedures (A. Guarna et al., J. Org. Chem, 63 (12), 4111-4115, 1998, H. Takahata et al., Chem. Pharm. Bull., 34(11), 4523, 1986) stage b) can be carried out in accordance with the syntheses of corresponding compounds in WO 2011/61330.

By varying the reactant in stage b) it is possible, in an analogous manner, to prepare the following compounds (for an overview of this see "T. W. Greene, P. G. M. Wuts, Protective Groups in Organic Synthesis, John Wiley and Sons, Inc., 1991)

Preparation Route H1-2: General Preparation of Compounds of the Formula I (Group 2)

Compounds of the Formula IC

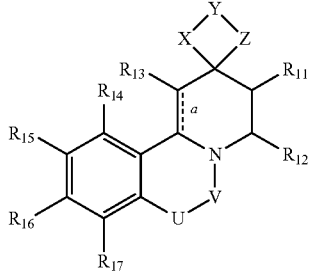
(IC)

where
U=chemical bond
a=single bond or double bond,
$R_{11}$, $R_{12}$=cycle;
$R_{13}$ to $R_{17}$=H;

The preparation takes place here according to the following scheme:

SCHEME 3:

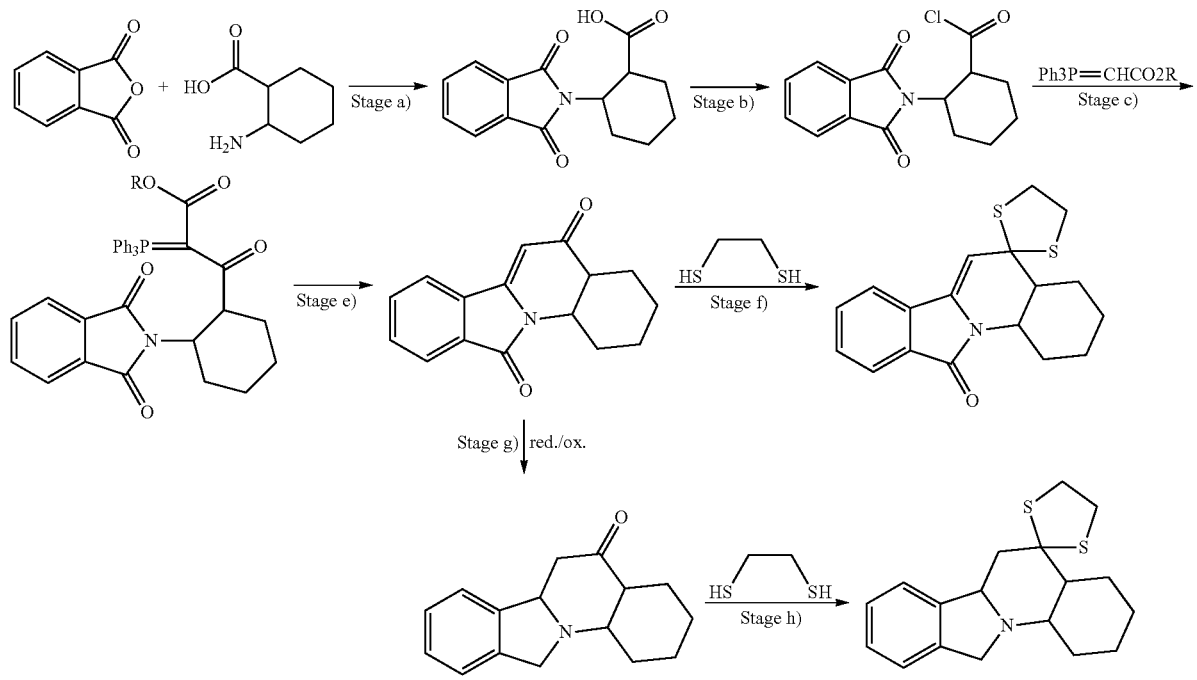

(Stage a cf. E. Guérnin et al., Eur J. Org. Chem, 3380-3391, 2007, stages b, c, e, g: cf. W. Flitsch, Liebigs Ann. Chem., 649-654, 1987) alternative reactants for stage a):

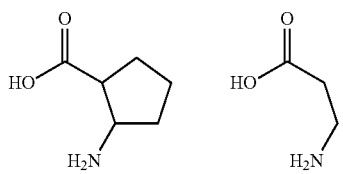

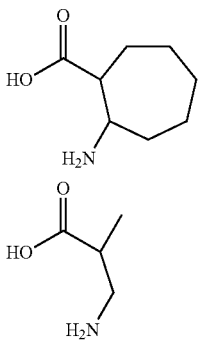

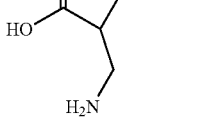

Alternative reactants to stage f) and h) analogous to scheme 2.

Preparation Route H1-3: General Preparation of Compounds of the Formula I (Group 3)

Compounds of the Formula IA

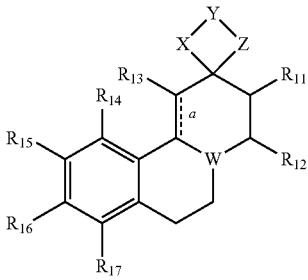
(IA)

where
W=CH
a=single bond or double bond,
$R_{11}$, $R_{12}$=cycle;
$R_{13}$ to $R_{17}$=H;

The preparation takes place here according to the following scheme:

SCHEME 4:

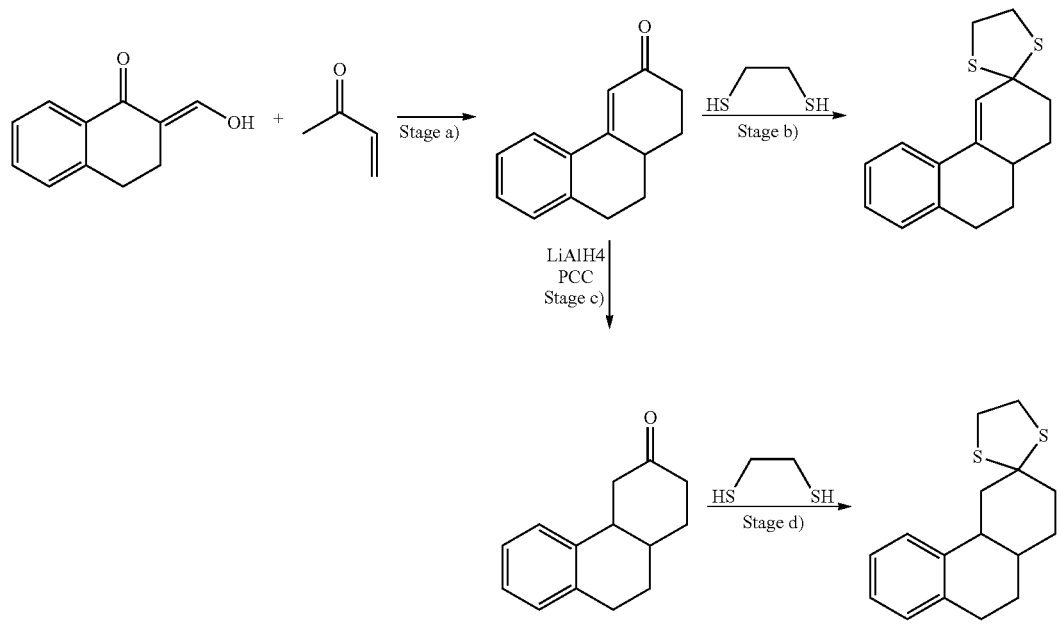

Stages a,c: see E. J. Eisenbraun et al., J. Org. Chem, 452-455, 1988. By varying the reactants of stage a) e.g. by using

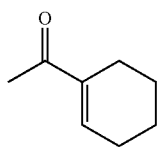

the following structures are obtained:

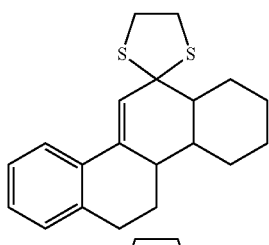

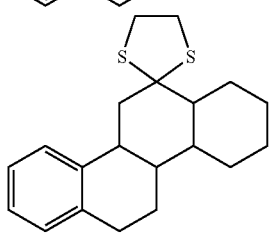

By varying the reactants of stages b) and d) analogously to scheme 2, further structural variants are obtained.

Preparation Route H1-4: General Preparation of Compounds of the Formula I (Group 4a)

Compounds of the Formula IA,

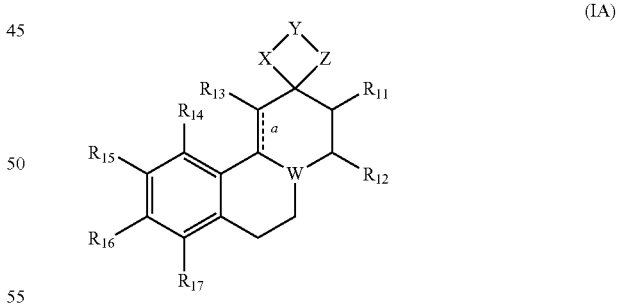

where
W=N
a=double bond or single bond
$R_{11}$, $R_{12}$=cycle;
$R_{13}$ to $R_{17}$=H;

The preparation takes place here according to the following scheme:

SCHEME 5:

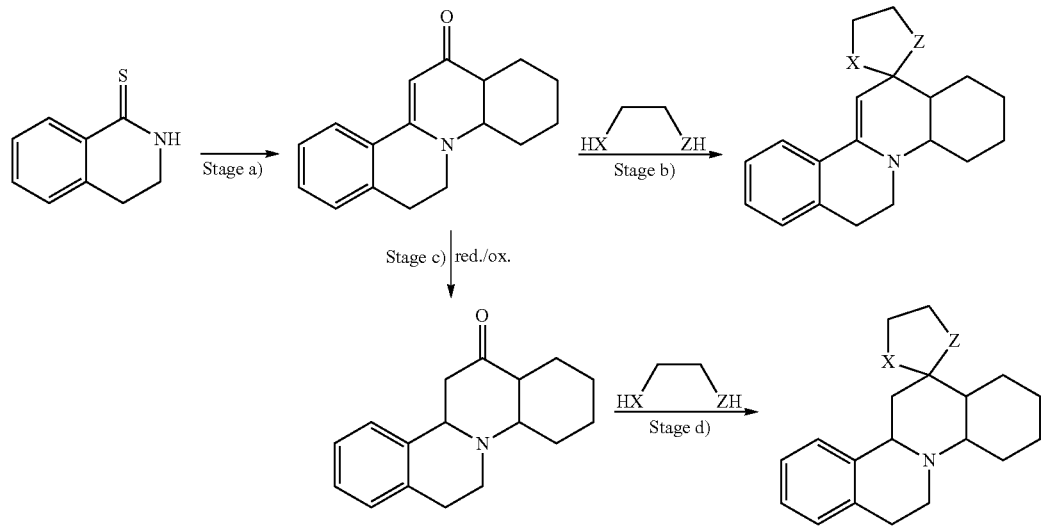

cf. S. J. Danishefsky et al., Tetrahedron Lett., 3635-3628, 1989. By varying the reactants of stages b) and d) analogously to scheme 2, further structural variants are obtained.

Preparation Route H1-5: General Preparation of Compounds of the Formula I (Group 4b)

Compounds of the Formula IC,

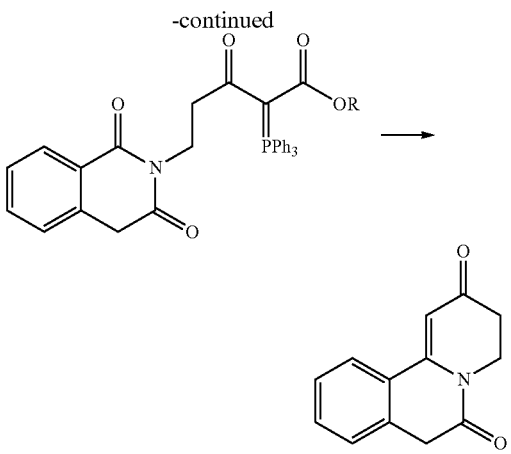

(IC)

where U=CH$_2$
V=carboxyl
a=double bond or single bond
$R_{11}$, $R_{12}$=H;
$R_{13}$ to $R_{17}$=H;

The preparation takes place here according to the following scheme: SCHEME 6:

SCHEME 6:

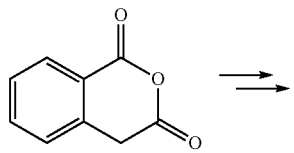

-continued

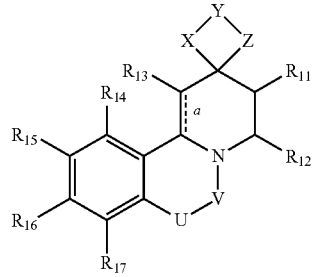

Preparation Route H1-6: General Preparation of Compounds of the Formula I (Group 5)

Compounds of the Formula IB,

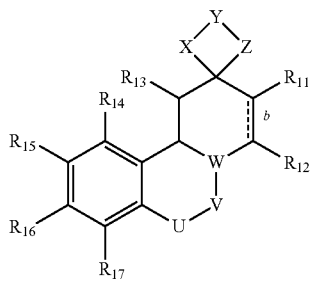

(IB)

where
W=N
b=double bond
$R_{11}$, $R_{12}$=cycle;
$R_{13}$ to $R_{17}$=H;

The preparation takes place here according to the following scheme:

SCHEME 7:

Variant 1

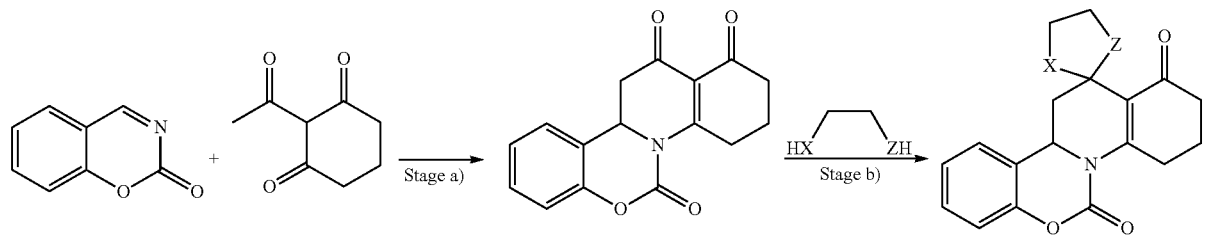

Variant 2

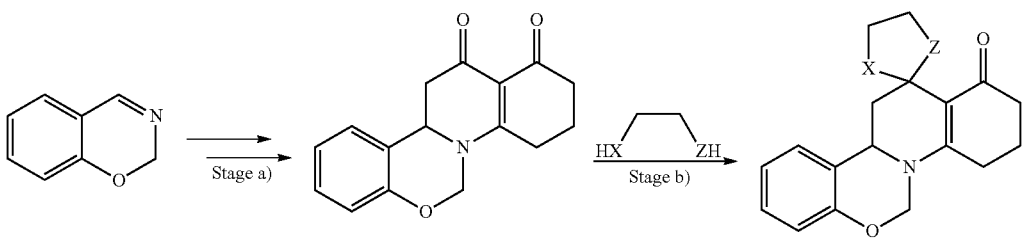

By varying the reactants of stages b) analogously to scheme 2, further structural variants are obtained.

Preparation Route H1-7: General Preparation of Compounds of the Formula I (Group 6)

Compounds of the Formula IB, (IB)

where
W=CH
b=double bond
$R_{11}$, $R_{12}$=cycle;
$R_{13}$ to $R_{17}$=H;

The preparation takes place here according to the following scheme:

SCHEME 8:

Variant A

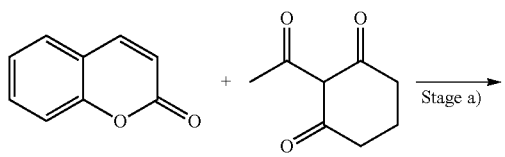

-continued

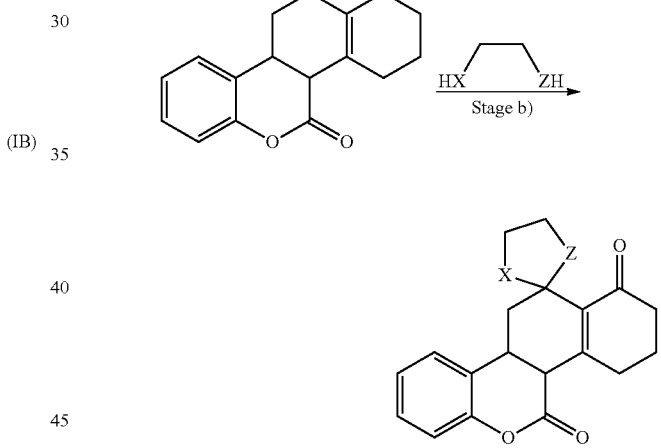

By varying the reactants from stages b) analogously to scheme 2, further structural variants are obtained.

Further nonlimiting examples of possible preparation routes of compounds according to the invention of the formulae IA, IB, IC, IA', IB' and IC' are summarized in the following schemes.

SCHEME 9:

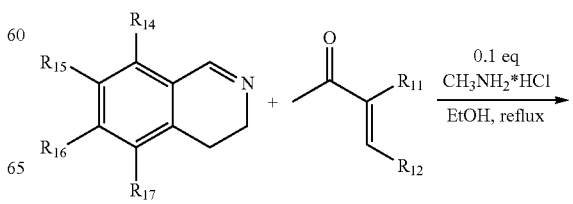

101
-continued

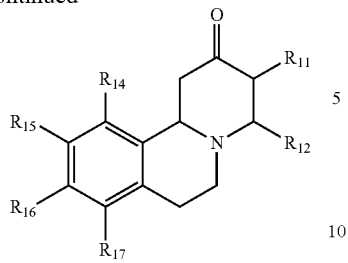

Preparation of compounds analogous to compounds of the formulae V 1, V 2
in which $R_{11}$ to $R_{17}$ can have the meanings given above.

Here, the isoquinoline, the acetylalkene (optionally in molar excess) and a suitable catalyst (e.g. methylammonium chloride) are introduced into a suitable solvent (e.g. ethanol) and stirred at a suitable temperature (e.g. reflux). When the reaction is complete, the catalyst is generally separated off by crystallization from a suitable solvent/solvent mixture (e.g. iPrOH/water). Optionally, for this, a distillative solvent change is necessary beforehand.

SCHEME 10:

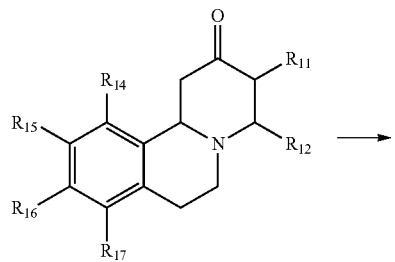

102
-continued

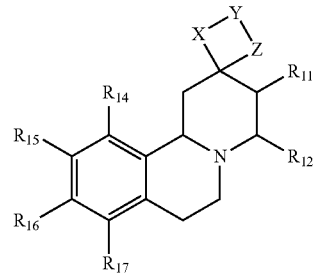

Preparation of compounds analogous to compounds of the formulae P1 to P7
in which $R_{11}$ to $R_{17}$, X, Y and Z can have the meanings given above, in particular in which X, Z=O, S and Y=—CH2-CH2-, —CH2-CH2-CH2-, CH2-C(CH3)2-CH2-

The aminoketone is firstly converted to the corresponding salt in a suitable solvent (e.g. MTBE) or solvent mixture and an excess of a suitable acid (e.g. hydrochloric acid) and then reacted with the corresponding dialcohol, dithiol or thioalcohol. As a rule, the mixture is then worked-up by aqueous extraction and the product is isolated by distillative removal of the solvent. If further purification is required, this can take place by crystallization from a suitable solvent or by chromatography.

SCHEME 11:

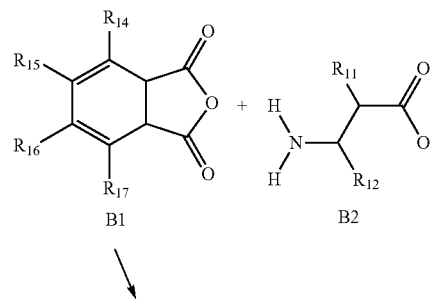

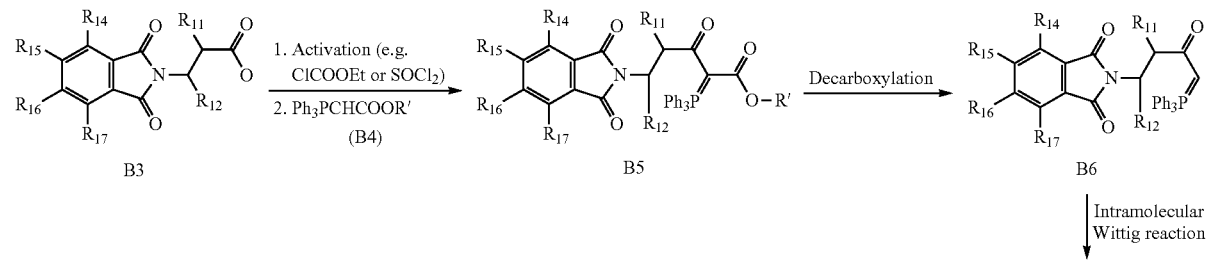

Intramolecular Wittig reaction

-continued

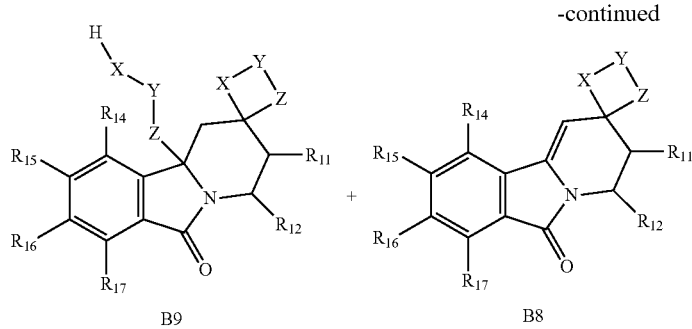

B9     B8

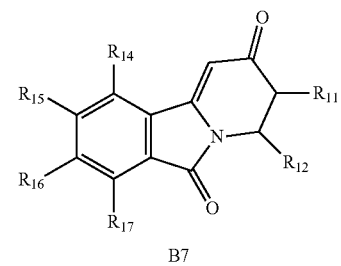

B7

Ketalization, thioketalization
1,4-Addition

Preparation of compounds analogous to compounds of the formulae V3, V4; P8, P9, P10, P11, P12 in which $R_{11}$ to $R_{17}$, X, Y and Z can have the meanings given above, and e.g. $R_{11}$, $R_{12}$=H or these two radicals, together with the carbon atoms to which they are bonded, form a carbocyclic ring having 5, 6 or 7 carbon atoms.

The synthesis of the tri- or tetracyclic analogs of the ketones V3 or V4 ideally starts from an anhydride B1 and a β-amino acid B2 which, as shown in the sterically demanding preparation example H1-20, can be reacted by stirring the two substances at a suitable temperature to give compounds of type B3. To synthesize a phosphorane B5, the acid group of a compound B3 is activated by conversion to the acid chloride or an anhydride and then reacted with a phosphorane B4 to give a compound B5. The resulting ester function is decarboxylated in the subsequent step and the released phosphorane is cyclized in a Wittig reaction to give an unsaturated ketone B6. Finally, ketalization is carried out with acid catalysis with a dithiol, diol or thioalcohol to give a compounds B8 where, depending on the reaction conditions, an addition product B9 can also be formed. If, after work-up by extraction, further purification is required, this can take place by crystallization from a suitable solvent or by chromatography.

SCHEME 12:

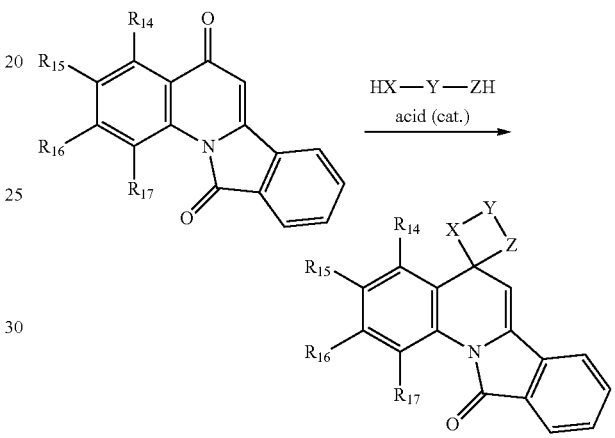

Preparation of compounds analogous to compounds of the formula P13
in which $R_{14}$ to $R_{17}$, X, Y and Z can have the meanings given above.

The ketone is admixed with an excess of dithiol, diol or thioalcohol and an acid or Lewis acid (e.g. zinc chloride) while adding a water-withdrawing agent (for example 4 Å molecular sieve, magnesium sulfate). The reaction mixture is stirred at a suitable reaction temperature and then generally worked-up by aqueous extraction. If a further purification is required, this can take place by crystallization from a suitable solvent or by chromatography.

SCHEME 13:

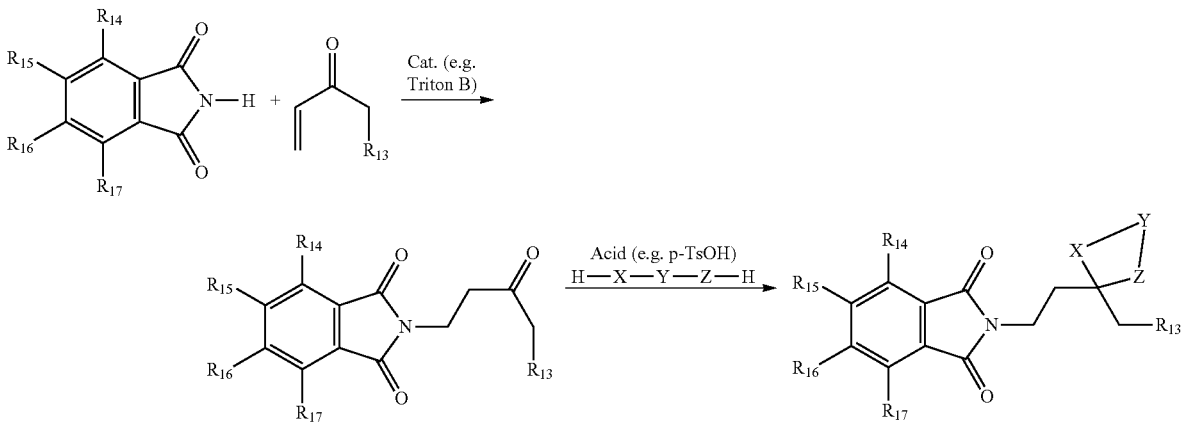

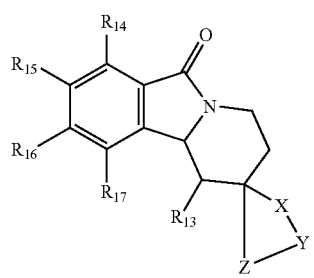
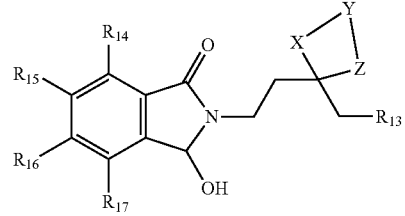

Preparation of compounds analogous to compounds of the formulae P14, P15, P16, P17
in which $R_{14}$ to $R_{17}$, X, Y and Z can have the meanings given above.

The preparation of analogs to P14 and P15 proceeds in accordance with the following literature procedures, and also the procedures given in the experimental section. (Here no longer detailed explicitly):

A. M. Islam, R. A. Raphael, *J. Chem. Soc.* 1955, 3151-3154. Bosch, Joan; Rubiralta, Mario; Moral, Montserrat; Arino, Joaquin. Journal of the Chemical Society, Perkin Transactions 1: Organic and Bio-Organic Chemistry (1972-1999) (1986), (8), 1533-9. M. Chiurato, S. Routier, Y. Troin, G. Guillaumet, Eur. J. Org. Chem 2009, 3011-3021

The O,O-acetal analogs to P14 and P15 can be converted to the corresponding thioketals as follows: the oxygen ketal is dissolved in a solvent (e.g. dichloromethane) and admixed with an excess of the dithiol or thioalcohol, and a Lewis acid (e.g. boron trifluoride-diethyl etherate). The reaction mixture is stirred at a suitable reaction temperature and then generally worked-up under neutralizing conditions in an aqueous environment. If, after removing the organic solvent, further purification of the products is required, this can take place by crystallization from a suitable solvent or by column chromatography.

SCHEME 14:

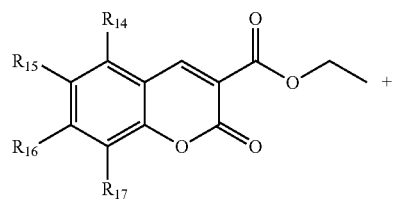

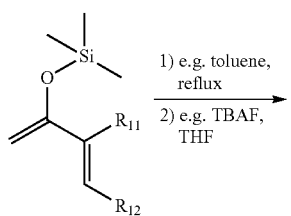

-continued

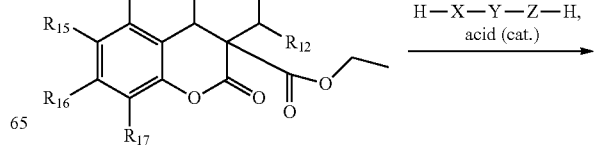

Preparation of compounds analogous to compounds of the formulae V8 and V9
in which $R_{11}$ to $R_{17}$ can have the meanings given above and e.g. $R_{11}$, $R_{12}$=H or these two radicals, together with the carbon atoms to which they are bonded, form a carbocyclic ring having 5, 6 or 7 carbon atoms.

The coumarin carboxylate and an excess of 1-cycloalk-1-enylvinyloxytrialkylsilane (e.g. the trimethylsilane compound) are dissolved in toluene or another suitable organic solvent and stirred at a suitable reaction temperature (e.g. reflux). To cleave off the trialkylsilyl group, an excess of a fluoride, e.g. tetrabutylammonium fluoride, is added and the mixture is further stirred at a suitable temperature (e.g. room temperature). (Alternatively, the acid-catalyzed cleavage of the silylenol ether to the ketone is also possible.) In this connection, it may prove to be necessary to replace the solvent used hitherto for a more suitable solvent such as THF by distillation beforehand. Alternatively, the acid-catalyzed cleavage of the silylenol ether to the ketone is also possible. When the reaction is complete, work-up is generally by means of aqueous extraction. If, after removing the organic solvent, further purification of the products is required, this can take place by crystallization from a suitable solvent or by column chromatography.

SCHEME 15:

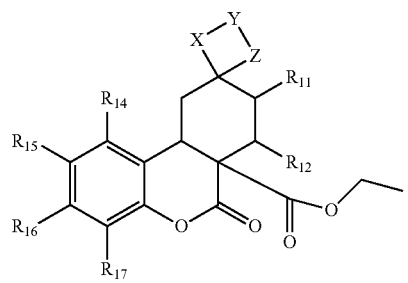

Preparation of compounds analogous to compounds of the formulae P18 to P27 in which $R_{11}$ to $R_{17}$ can have the meanings given above and e.g. $R_{11}$, $R_{12}$=H or these two radicals, together with the carbon atoms to which they are bonded, form a carbocyclic ring having 5, 6 or 7 carbon atoms.

The keto ester is admixed with an excess of dialcohol, dithiol or thioalcohol, an acidic catalyst (e.g. Amberlyst 15) and a suitable solvent (e.g. toluene) and the mixture is stirred at a suitable temperature (e.g. reflux). Optionally, it proves necessary to remove water from the reaction mixture by adding a water-withdrawing agent (e.g. 4 Å molecular sieve) or azeotropic distillation. When the reaction is complete, work-up is generally by means of aqueous extraction. If a further purification of the products is required after distillatively removing the organic solvent, this can take place by crystallization from a suitable solvent or column chromatography.

SCHEME 16:

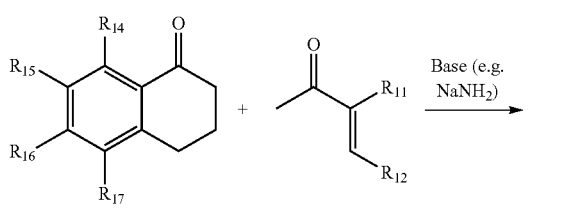

Preparation of compounds analogous to compounds of the formulae V10 and V11 in which $R_{11}$ to $R_{17}$ can have the meanings given above and e.g. $R_{11}$, $R_{12}$=H or these two radicals, together with the carbon atoms to which they are bonded, form a carbocyclic ring having 5, 6 or 7 carbon atoms.

Procedure analogous to Peak, Robinson *J. Chem. Soc.,* 1936, 759-762 or *J. Chem. Soc.,* 1937, 1581-1583.

SCHEME 17:

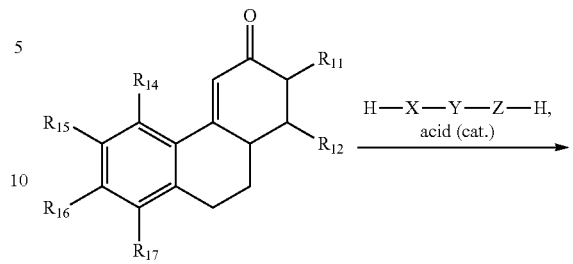

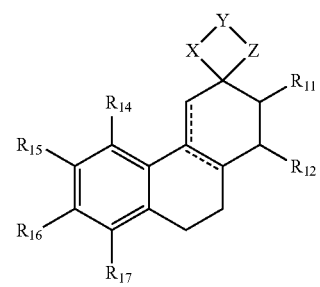

Preparation of compounds analogous to compounds of the formulae P28 to P31 where $R_{11}$ to $R_{17}$ can have the meanings given above and e.g. $R_{11}$, $R_{12}$=H or these two radicals, together with the carbon atoms to which they are bonded, form a carbocyclic ring having 5, 6 or 7 carbon atoms.

The keto ester is admixed with an excess of diol, dithiol or thioalcohol, an acidic catalyst (e.g. Amberlyst 15) and a suitable solvent (e.g. toluene) and the mixture is stirred at a suitable temperature (e.g. reflux). Optionally, it proved necessary to remove water from the reaction mixture by adding a water-withdrawing agent (e.g. 4 Å molecular sieve) or azeotropic distillation. When the reaction is complete, work-up is generally by aqueous extraction. If further purification of the products is required following distillative removal of the organic solvent, this can take place by crystallization from a suitable solvent or column chromatography.

b) General Preparation Routes for Compounds According to Formula II

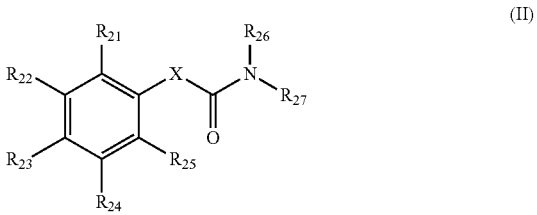

(II)

The preparation of representative compounds of the formula II is described in the following section. The various starting materials of the general formula C-II and B-II required for this are likewise known or accessible by known processes.

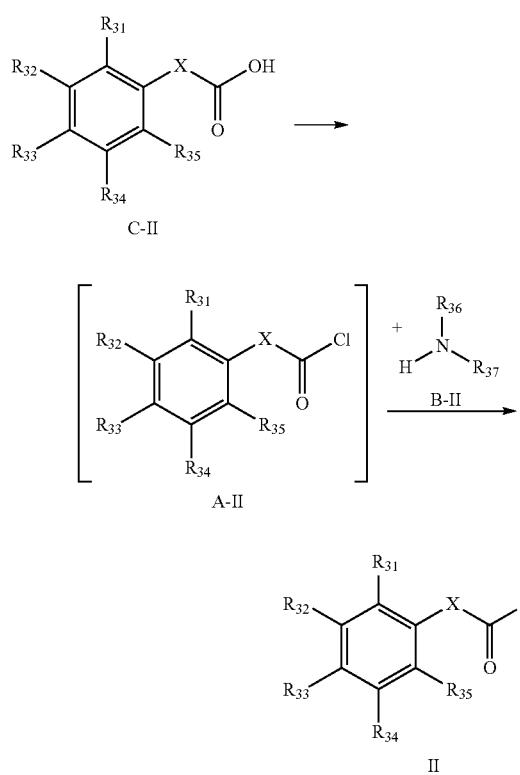

The reaction is carried out, for example, in an apolar organic solvent in the presence of an acid scavenger.

c) General Preparation Routes for Compounds According to Formula III

In the section which follows, a number of synthesis routes for compounds of the formula III according to the invention are described with reference to processes known in the literature:

Synthesis Route 1:

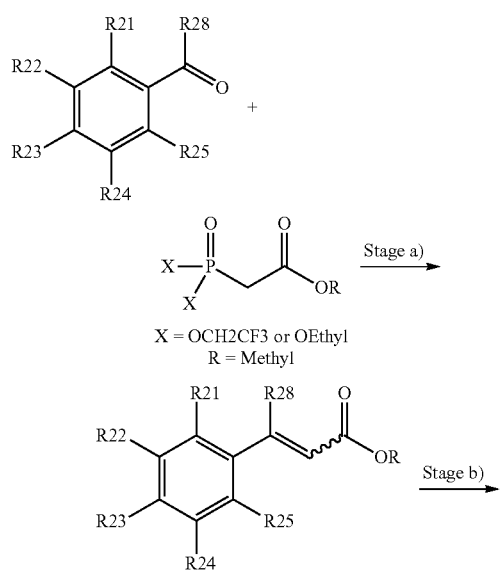

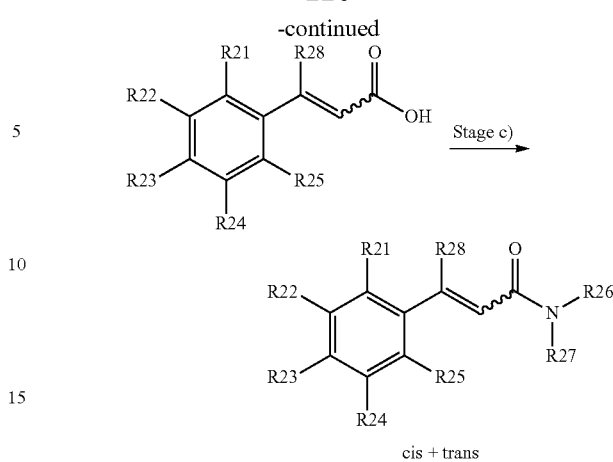

Stage a) is carried out according to the principle of a Horner-Emmons reaction by reacting the aromatic keto compound with a suitable phosphono compound (e.g. methyl P,P-bis(2,2,2-trifluoroethyl)phosphonoacetate, or dimethyl methoxycarbonyl-methanephosphonate) (cf. e.g. Sano, S. et al Chemical and Pharmaceutical Bulletin, 2002, 50, No. 5, 706-709; Duan, Z.-C., et al Journal of organic Chemistry, 2010, 75, No. 23, 8319-8321; Eguchit. et al; Tetrahedron Letters, 1992, 33, 38, 5545-5546; Sano, S. et al., Chemical and Pharmaceutical Bulletin, 2002, 50, No. 9, 1300-1302; Chintareddy et al., Journal of Organic Chemistry, 2010, 75, 21, 7166-7174; WO2004/31116; Miller, D. J. et al., Organic and Biomolecular Chemistry, 2007, 5, 20, 3287-3298; WO2009/53443; Strehlke et al., Eur. J. of Med. Chem., 1979, 14, 238-242; Tashchuk et al., Sov. Prog. Chem., 1968, 34, 11, 1148-1150; WO2005/40104; U.S. Pat. Nos. 6,110,922; 6,878,700; US2004/116518, WO2006/41404; WO2006/41405, WO2008/99415; EP 2189443; EP 2189440; WO2010/80537; US2005/26917; Luci, D. et al., Heterocycles 2004, 62, 1, 543-558; Berardi, f., et al., Bioorganic and Medical Chemistry, 2001, 9, 5, 1325-1336; Singh, C. et al., J. Med. Chem., 2008, 51, 23, 7561-7592. Gangjee, A. et al., Bioorganic and Medical Chemistry, 2006, 14, 24, 8341-8351; Sauerberg, P. et al., J. Med. Chem., 2003, 46, 23, 4883-4894) The reaction product from stage a) is saponified, converted to the acid chloride and then amidated, as described in WO 2011/61330 for structure type 3 therein.

Synthesis Route 2:

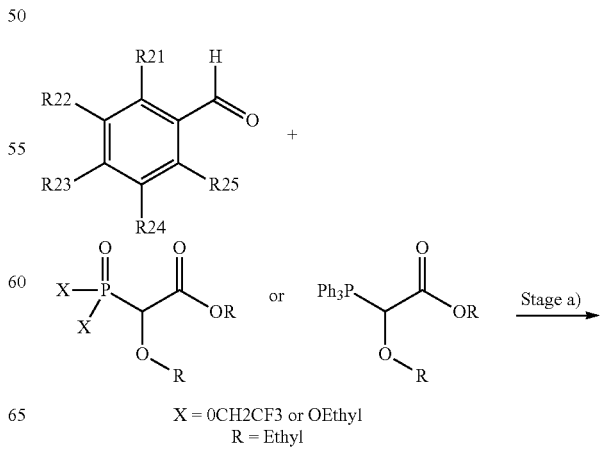

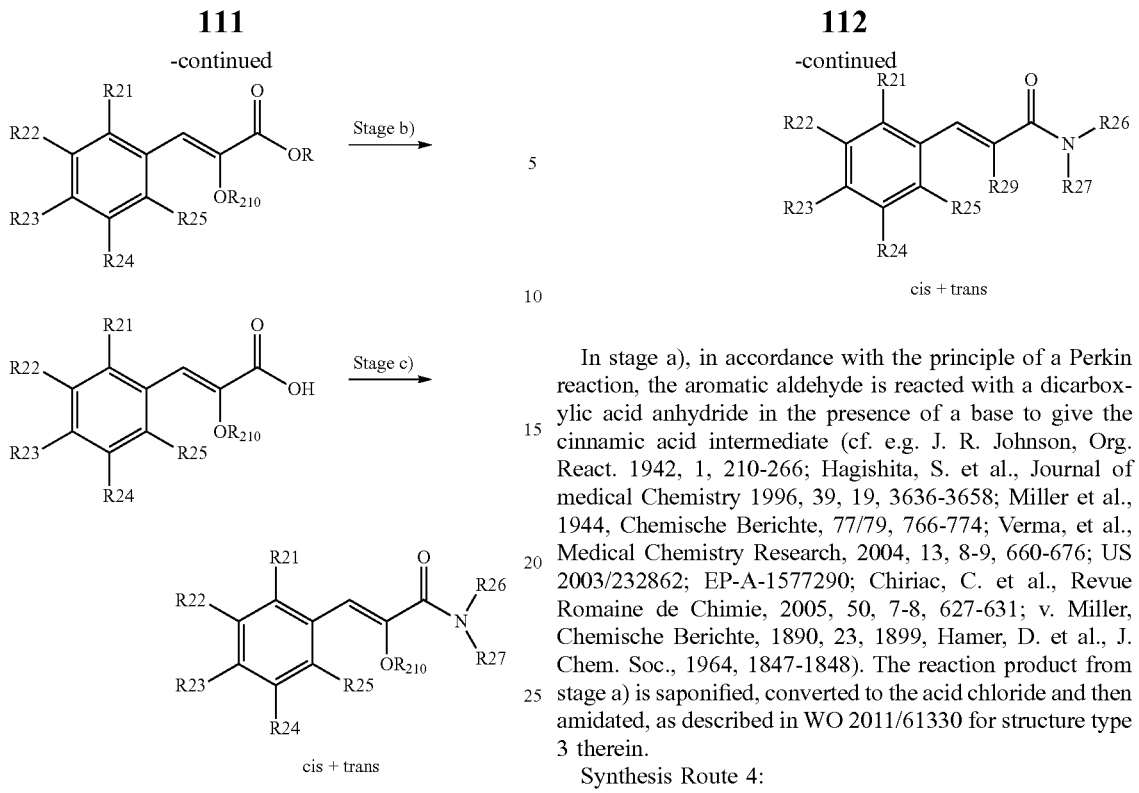

Stage a) is carried out according to the principle of a Horner-Emmons reaction by reacting the aromatic aldehyde with a suitable phosphono compound (cf. e.g. Ebdrup, S. et al, Journal of Medical Chemistry, 2003, 46, No. 8, 1306-1317; US2010/240636; WO 2008/108602; WO2004/20420; WO2004/31162; WO2004/41275; WO2009/46606; U.S. Pat. No. 6,258,850; US 2003/18207; WO2008/10238; US2010/144884; Siu, T. et al., Angewandte Chemie 2001, 113, 4849-4852). The reaction product from stage a) is saponified, converted to the acid chloride and then amidated (as described e.g. in: Fürstner, A., et al., 2006, JACS, 128, 24, 8087-8094; Fürstner, A., et al., 2005, JACS, 127, 33, 11620-11621, U.S. Pat. No. 6,362,210; Takada, K. et al., Bioorganic and Medical Chemistry Letters, 2010, 20, 4, 1330-1333; U.S. Pat. No. 3,072,649).

Synthesis Route 3:

In stage a), in accordance with the principle of a Perkin reaction, the aromatic aldehyde is reacted with a dicarboxylic acid anhydride in the presence of a base to give the cinnamic acid intermediate (cf. e.g. J. R. Johnson, Org. React. 1942, 1, 210-266; Hagishita, S. et al., Journal of medical Chemistry 1996, 39, 19, 3636-3658; Miller et al., 1944, Chemische Berichte, 77/79, 766-774; Verma, et al., Medical Chemistry Research, 2004, 13, 8-9, 660-676; US 2003/232862; EP-A-1577290; Chiriac, C. et al., Revue Romaine de Chimie, 2005, 50, 7-8, 627-631; v. Miller, Chemische Berichte, 1890, 23, 1899, Hamer, D. et al., J. Chem. Soc., 1964, 1847-1848). The reaction product from stage a) is saponified, converted to the acid chloride and then amidated, as described in WO 2011/61330 for structure type 3 therein.

Synthesis Route 4:

In stage a), in accordance with the principle of a Reformatsky reaction, the aromatic ketone is converted with bromine-substituted carboxylic acid ester in the presence of zinc into the unsaturated aromatic ester intermediate (cf. e.g. S. Reformatsky, 1887, Ber. Dtsch. Chem. Ges. 20, 1210-

1211, R. L. Shriner, 1946, Org Reaction, 1, 434-460). The reaction product from stage a) is saponified, converted to the acid chloride and then amidated, as described in WO 2011/61330 for structure type 3 therein.

Synthesis Route 5:

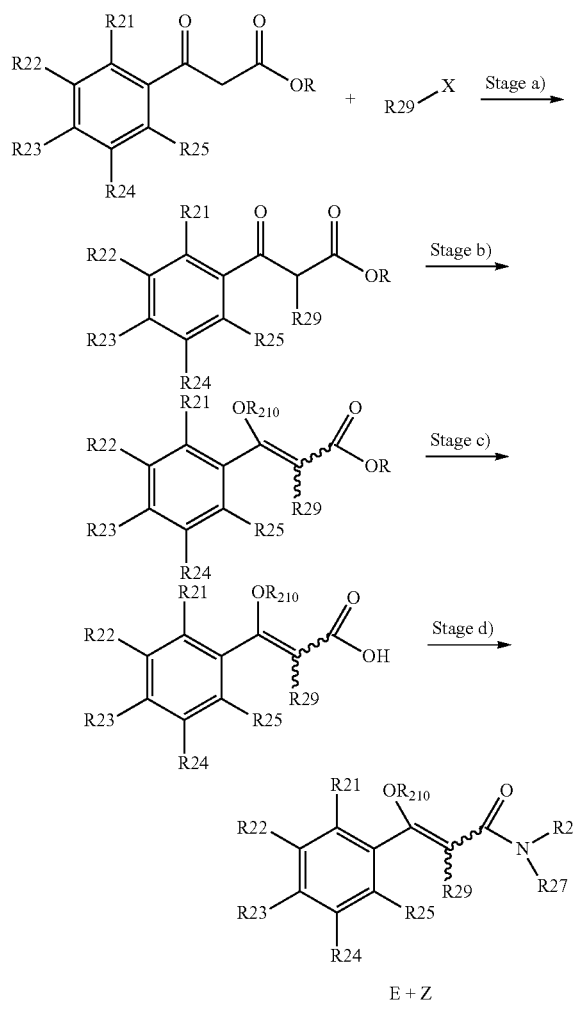

E + Z

The reaction of the aromatic β-keto carboxylic acid according to stage a) takes place in a manner known per se. It is described for various reactants in the prior art (cf. e.g. Xiao, Y., 2009 chemical communications, 3594-3596; Li, H. et al., Organic Letters 2009, 4176-4179; Chen Y.-F. et al., 2010 Advanced Synthesis and Catalysis 352, 7, 1163-1168; Wang, H. et al., Tetrahedron letters 2005, 46, 6, 963-966; Bunce, R. A., et al.; Journal of Heterocyclic Chemistry; 2007, 44; 5; 1051-1057; Gomez, V. et al., Journal of Organic Chemistry; 1994, 59, 5, 1219-1221; Okimoto, M., et al., Synlett; 2005, 16, 2507-2509; Lou, S. et al., Journal of Organic Chemistry; 2007, 72, 26; 9998-10008; Emelina, E. E. et al., Zhurnal Organicheskoi Khimii 1987, 23, 12, 2565-2570, 2263-2268; Gompper, R. et al., Chemische Berichte; 1981, 114, 8, 2866-2883; Bunce, R. et al., Journal of Organic Chemistry, 1993, 58, 25, 7143-7148; Yang, T. et al., Journal of the American Chemical Society, 2009, 131, 26, 9140-9141; Tanikaga, R. et al., Chemistry Letters, 1985), 1583-1586; Renaud, J.-L. et al., Tetrahedron, 1999, 55, 16, 5113-5128; Verhe, R. et al., Tetrahedron, 1982, 38, 24, 3649-3660; Pfleger, et al., Chemische Berichte, 1957, 90, 2404-2409; Temnikova, T. I. et al., Zhurnal Organicheskoi Khimii, 1966, 2, 7, 1168-1171, 1160-1162; Ershov, B. A. et al.; Zhurnal Organicheskoi Khimii; 1969, 5, 1378-1383, 1346-1350). Various methods for carrying out stage b) are likewise known from the prior art (cf. e.g. Gompper, R, et al., Chemische Berichte, 1981, 114, 8, 2866-2883; Arndt et al., Chemische berichte 1938, 71, 1631-1639; Claisen, Justus Liebigs Annalen der Chemie, 1917, 413, 274). Following saponification and conversion to the acid chloride, an amidation then takes place to give the end product (as described e.g. in: Fürstner, A., et al., 2006, JACS, 128, 24, 8087-8094; Fürstner, A., et al., 2005, JACS, 127, 33, 11620-11621, U.S. Pat. No. 6,362,210; Takada, K. et al., Bioorganic and Medical Chemistry Letters, 2010, 20, 4, 1330-1333; U.S. Pat. No. 3,072,649).

Synthesis Route 6:

The preparation of α,β-saturated forms of compounds of the general formula III takes place, for example, by targeted reduction of the corresponding unsaturated precursor obtained by one of synthesis routes 1 to 5 (variant a)) (cf. Desai et al., Tetrahedron Lett., 5963-5965, 2001) or by amidation of α,β-saturated carboxylic acid precursors known per se, as described e.g. in WO 2011/61330 for structure type 3 therein, and optionally in the presence of bases, such as $NEt_3$ (variante b)).

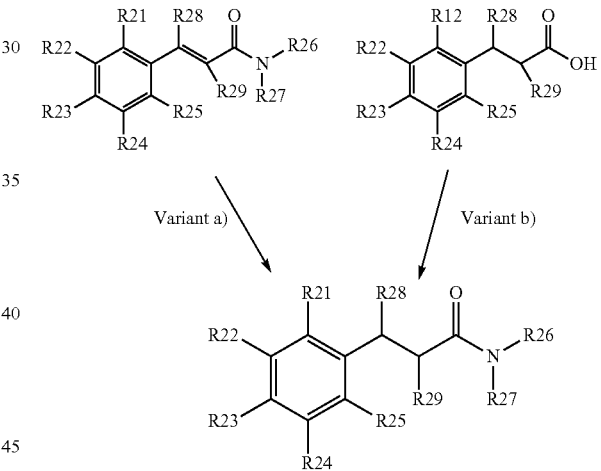

Further aspects of the present invention arise from the examples below and also from the attached patent claims.

EXPERIMENTAL SECTION

The examples below serve merely to illustrate the invention without limiting it thereto. Unless stated otherwise, all content data are based on the weight. Unless specified otherwise, customary methods known to the respective person skilled in the art in the field of organic synthesis, formulation and biochemistry are used for carrying out the following experiments.

The active ingredients of the formulae I, II and III used according to the invention are either compounds known per se or can be prepared in accordance with known synthesis methods by the person skilled in the art in the field of organic synthesis. Reference is expressly made to the disclosure of the literature references cited herein.

The invention will now be described with reference to the following nonlimiting working examples.

Reference Example 1—Cloning of Human TRPM8

The starting point for the cloning of the human TRPM8 receptor is an LnCaP cDNA library. This is, for example, commercially available (e.g. BioChain, Hayward, USA) or can be produced from the androgen-sensitive human prostate adenocarcinoma cell line LnCaP (e.g. ATCC, CRL1740 or ECACC, 89110211) using standard kits.

The coding TRPM8 sequence (WO 2010/026094; and http://www.ncbi.nm.nih.gov/entrez/viewer.fcgi?db=nuccore&id=109689694) can be PCR-amplified and cloned using standard methods. The human TRPM8 gene isolated in this way was used for producing the plasmid plnd_M8, the construction of which is illustrated by the plasmid map according to FIG. 2 of WO 2010/026094.

Alternatively to this, the TRPM8 gene can also be produced synthetically.

Reference Example 2—Generation of the HEK293 Test Cells

As test cell system, HEK293 cell line stably transfected with the human TRPM8 DNA (cf. above plasmid plnd-M8) are produced. Preference here is given to HEK293 which offers the option, via the introduced plasmid, of inducing the TRPM8 expression by means of tetracycline.

Methods for producing suitable test cell systems are known to the person skilled in the art. For example, the details of the preparation of the cells used according to the invention can be found in Behrendt H. J. et al., Br. J. Pharmacol. 141, 2004, 737-745 or the dissertation by Behrendt "Vergleichende funktionale Untersuchungen des Hitze-Capsaicin-Rezeptors (TRPV1) und des Kälte-Menthol-Rezeptors (TRPM8) in rekombinanten und nativen Zellsystemen". [Comparative functional investigations of the heat capsaicin receptor (TRPV1) and of the cold menthol receptor (TRPM8) in recombinant and native cell systems], accessible from http://www-brs.ub.ruhr-uni-bochum.de/netahtml/HSS/Diss/BehrendtHansJoerg/diss.pdf.

Reference is expressly made to the disclosure of these documents.

Reference Example 3—Assay on TRPM8 Modulators

A test comparable with the test already described in the literature by Behrendt H. J. et al., Br. J. Pharmacol. 141, 2004, 737-745 is carried out. The agonization or antagonization of the receptor can be quantified by means of a $Ca^{2+}$-sensitive dye (e.g. FURA, Fluo-4 etc.). On their own, agonists bring about an increase in the $Ca^{2+}$ signal; antagonists bring about, in the presence of e.g. menthol, a reduction in the $Ca^{2+}$ signal (in each case detected via the dye Fluo-4, which has different fluorescent properties as the result of $Ca^{2+}$).

Firstly, a fresh culture of transformed HEK cells is prepared in a manner known per se in cell culture flasks. The test cells HEK293-TRPM8 are detached from the cell culture flasks by means of trypsin and 40 000 cells/well are sown out with 100 µl of medium in 96-well plates (Greiner #655948 poly-D-lysine-coated). To induce the receptor TRPM8, tetracycline is added to the growth medium (DMEM/HG, 10% FCS tetracycline-free, 4 mM L-glutamine, 15 µg/ml blasticidin, 100 µg/ml hygromycin B, 1 µg/ml tetracycline). On the following day, the cells are loaded with Fluo-4AM dye and the test is carried out. For this, the procedure is as follows:

addition of in each case 100 µl/well of dye solution Ca-4 kit (RB 141, Molecular Devices) to in each case 100 µl of medium (DMEM/HG, 10% FCS tetracycline-free, 4 mM L-glutamine, 15 µg/ml blasticidin, 100 µg/ml hygromycin B, 1 µg/ml tetracycline)

incubation in the hatching cabinet, 30 minutes/37° C./5% $CO_2$, 30 minutes/RT preparation of the test substances (various concentrations in 200 µl of HBSS buffer), and also of positive controls (various concentrations of menthol, icilin and ionomycin in 200 µl of HBSS buffer) and negative controls (only 200 µl of HBSS buffer)

addition of the test substances in amounts of 50 µl/well and measurement of the change in fluorescence (e.g. in the assay instrument FLIPR, Molecular Devices or NovoStar, BMG) at 485 nm excitation, 520 nm emission, and evaluation of the effectiveness of the various substances/concentrations and determination of the EC50 values.

The test substances are used in the assay in triplicate in concentrations of 0.1-200 µM. Normally, the compounds are kept ready in DMSO solutions and are diluted down to a maximum DMSO concentration of 2% for the assay.

The evaluation surprisingly reveals that, according to the invention, it was possible for the first time to prepare agonists of TRPM8 which differ significantly in structural terms from agonists known hitherto, such as (−) menthol, icilin and other modulators described by Behrendt H. J. et al., in Br. J. Pharmacol. 141, 2004, 737-745 (cf. table 1 therein), and, moreover, in some cases exhibit better activities than (−) menthol, or are as comparably effective as icilin.

Some specific preparation examples of compounds of the above general formula I follow:

2. Preparation Examples

Preparation Example H1-8: Preparation of the Precursor V1 analogous to Szantay et al., *Heterocycles*, 1977, 1793

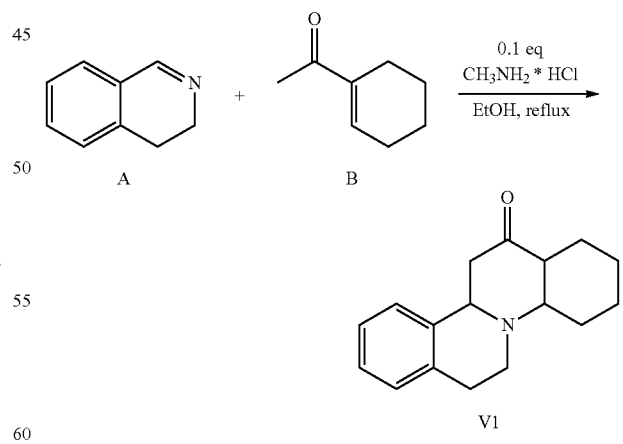

15 g (0.11 mol, 1.0 eq) of 3,4-dihydroisoquinoline (A), 28.4 g (0.23 mol, 2.0 eq) of 1-acetylcyclohexene (B), 0.77 g (0.011 mol, 0.1 eq) of methylammonium chloride and 150 ml of ethanol are combined and heated at reflux for 64 h. The reaction mixture is concentrated and the residue is admixed with 100 ml of iPrOH. The warm solution is inoculated, and 8 ml of water are added over 15 min. The mixture is cooled to 0-5° C. and filtered. The solid is washed with 20 ml of iPrOH and dried overnight in a stream of nitrogen.

Yield (V1): 15.7 g (54%) with an HPLC purity of 99 area %

CAS number product: 1424-91-5

Preparation Example H1-9: Preparation of the Precursor V2 analogous to Szantay et al., *Heterocycles,* 1977, 1793

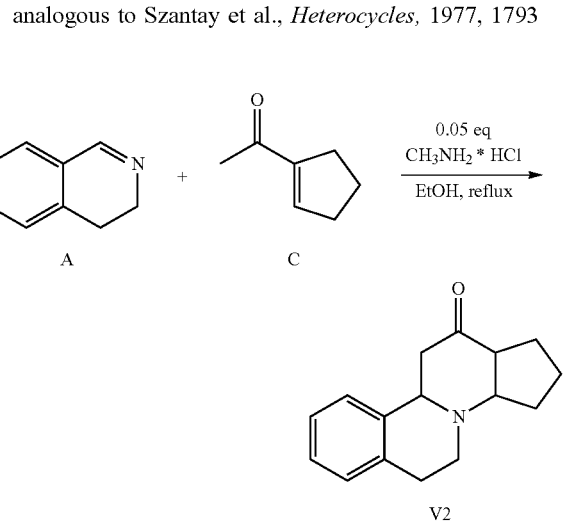

5 g (38 mmol, 1.0 eq) of 3,4-dihydroisoquinoline (A), 4.6 g (42 mmol, 1.1 eq) of 1-acetylcyclopentene (C), 0.13 g (1.9 mmol, 0.05 eq) of methylammonium chloride and 63 ml of ethanol are combined and heated under reflux for 14 days. The reaction mixture is concentrated and admixed with 60 ml of 1 N aqueous HCl and 50 ml of EtOAc. The phases are separated, the organic phase is discarded and the aqueous phase is admixed dropwise with 25% aqueous sodium hydroxide solution until a pH of 9-10 is reached. The crystallized-out solid is filtered off and washed with 100 ml of water. It is dried overnight in a stream of nitrogen and recrystallized from EtOH.

Yield (V2): 2.6 g of solid with an HPLC purity of 100 area %.

CAS No. product: 1424-86-5

Preparation Example H1-10: Preparation of Compound P1

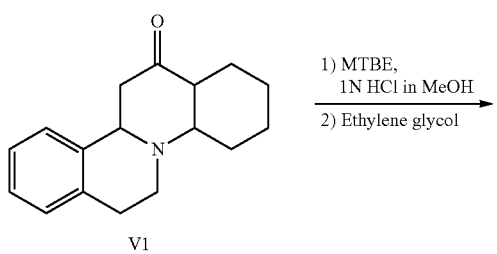

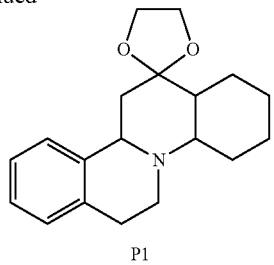

1 g (3.9 mmol, 1 eq) of ketone V1 are admixed with 5 ml of MTBE and then with 4.8 ml of 1 N HCl in methanol. The resulting solution is concentrated at low temperature and then admixed with 5 ml of ethylene glycol. Gentle distillation is again carried out and the solution is then stirred at 75° C. for 5 h. It is cooled to room temperature and the solution is admixed with 5 ml of saturated sodium carbonate solution and 10 ml of water. The organic phase is separated off and the aqueous phase is post-extracted with 5 ml of EtOAc. The combined organic phases are washed with 3×25 ml of water and then dried over sodium sulfate. The solvent is removed under reduced pressure and the residue is crystallized from petroleum ether. The crystals are filtered off with suction and dried in vacuo.

Yield (P1): 710 mg (61%) with an HPLC purity of 92.4 area %

$^1$H-NMR (CDCl$_3$): 7.2-7.0 (m, 4H); 4.13-3.90 (m, 4H); 3.69 (d, 1H); 3.42-3.33 (m, 1H); 3.08-2.94 (m, 1H); 2.83-2.70 (m, 1H); 2.43-2.15 (m, 4H); 1.90-1.59 (m, 5H); 1.40-1.13 (m, 4H) [ppm]

Preparation Example H1-11: Preparation of Compound P2

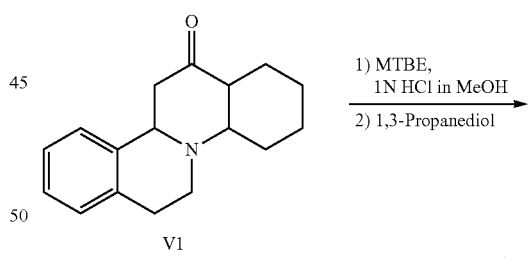

1 g (3.9 mmol, 1 eq) of ketone V1 are admixed with 5 ml of MTBE and then with 4.8 ml of 1 N HCl in methanol. The resulting solution is concentrated at low temperature and then admixed with 7.5 ml of 1,3-propanediol. Gentle distillation is again carried out and the solution is then stirred at 75° C. for 45 h. It is cooled to room temperature and the solution is admixed with 5 ml of saturated sodium carbonate solution and 10 ml of water. The organic phase is separated off and the aqueous phase is post-extracted with 5 ml of EtOAc. The combined organic phases are washed with 3×25 ml of water and then dried over sodium sulfate. The solvent is removed under reduced pressure and the residue is purified by column chromatography.

Yield (P2): 890 mg (73%) with an HPLC purity of 82.9 area % (comprises ca. 15% starting material)

$^1$H-NMR (CDCl$_3$): 7.25-6.95 (m, 4H); 4.16-4.05 (m, 2H); 3.92-3.72 (m, 2H); 3.63 (d, 1H); 3.36-3.18 (m, 2H); 3.05-2.75 (m, 2H); 2.44-2.34 (m, 1H); 2.20-1.97 (m, 3H); 1.83-1.68 (m, 2H); 1.54-1.08 (m, 8H) [ppm]

Preparation Example H1-12: Preparation of Compound P3

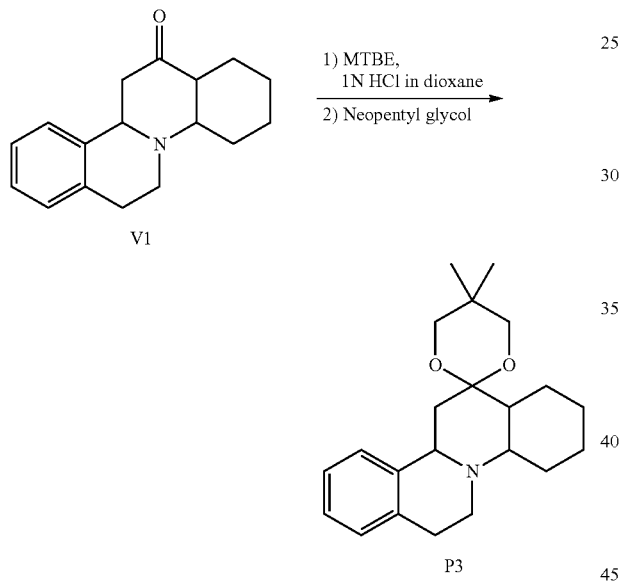

1 g (3.9 mmol, 1 eq) of ketone V1 are admixed with 2 ml of MTBE and then with 1.5 ml of 1.25 N HCl in dioxane. The resulting solution is concentrated on a rotary evaporator and then transferred to a reaction flask with 1.2 g (3 eq) of neopentyl glycol and 3 ml of DMSO. The mixture is stirred for one week at 70-75° C. For the work-up, 10 ml of saturated sodium carbonate solution, 20 ml of water and 10 ml of EtOAc are added. The organic phase is washed with 2×10 ml of water, dried over sodium sulfate and concentrated on a rotary evaporator. The residue is purified by column chromatography.

Yield (P3): 450 mg (34%) with an HPLC purity of 90.8 area %.

$^1$H-NMR (CDCl$_3$): 7.20-7.03 (m, 4H); 3.83 (tr, 2H), 3.62 (d, 1H); 3.44 (d, 1H); 3.234 (d, 2H); 3.17 (d, 1H); 3.05 (m, 1H); 2.83-2.75 (m, 1H); 2.46-2.35 (m, 2H); 2.21-2.11 (m, 2H); 1.85-1.71 (m, 2H); 1.58-1.08 (m, 6H); 1.22 (s, 3H), 0.78 (s, 3H) [ppm]

Preparation Example H1-13: Preparation of Compound P4

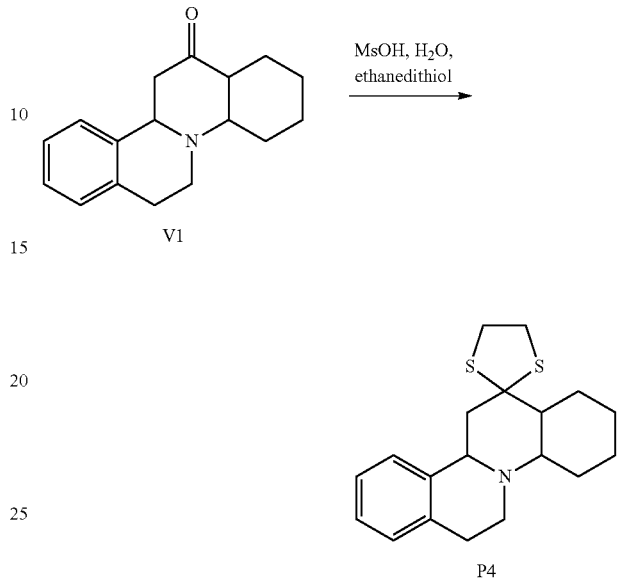

1.3 g of water are initially introduced and slowly admixed with 2.3 g (6 eq) of methanesulfonic acid. 0.55 g (1.5 eq) of ethanedithiol are added and then 1 g (3.9 mmol) of ketone V1. The reaction mixture is stirred overnight at room temperature and slowly added to a mixture of 12 ml of toluene and 5 ml of 25% NaOH. The mixture is stirred for 5 min and then the phases are separated. The organic phase is washed with 3×5 ml of water and concentrated by evaporation, and the residue is crystallized from heptane/MTBE with the addition of a few drops of iPrOH.

Yield (P4): 580 mg (45%) with an HPLC purity of 93.4 area %

$^1$H-NMR (CDCl$_3$): 7.24-6.99 (m, 4H); 3.70 (d, 1H); 3.43-3.15 (m, 5H); 3.05-2.93 (m, 1H); 2.76 (d, 2H); 2.40-2.10 (m, 5H); 1.88-1.62 (m, 3H); 1.52-1.37 (m, 1H); 1.37-1.12 (m, 3H) [ppm]

Preparation Example H1-14: Preparation of Compound P5

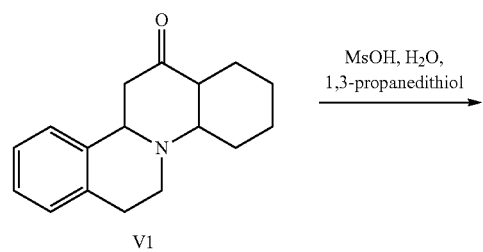

-continued

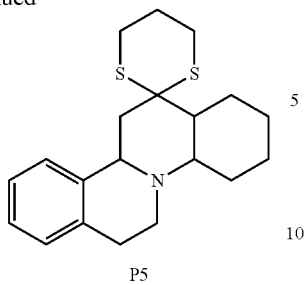

P5

1.3 g of water are initially introduced and slowly admixed with 2.3 g (6 eq) of methanesulfonic acid. 0.64 g (1.5 eq) of 1,3-propanedithiol are added and then 1 g (3.9 mmol) of ketone V1. The reaction mixture is stirred overnight at room temperature and then slowly added to a mixture of 12 ml of toluene and 5 ml of 25% NaOH. Stirring is carried out for 5 min and then the phases are separated. The organic phase is concentrated by evaporation and the residue is purified by column chromatography.

Yield (P5): 605 mg (45%) with an HPLC purity of 93.8 area %.

$^1$H-NMR (CDCl$_3$): 7.20-7.00 (m, 4H); 4.06 (d, 1H); 3.40-3.29 (m, 1H); 3.29-3.18 (m, 1H); 3.18-3.04 (m, 2H); 3.04-2.92 (m, 1H); 2.84-2.55 (m, 4H); 2.49-2.37 (m, 1H); 2.35 (d, 1H); 2.26-2.00 (m, 3H); 1.93-1.72 (m, 3H); 1.72-1.61 (m, 1H); 1.57-1.42 (m, 1H); 1.38-1.02 (m, 3H) [ppm]

Preparation Example H1-15: Preparation of Compound P6

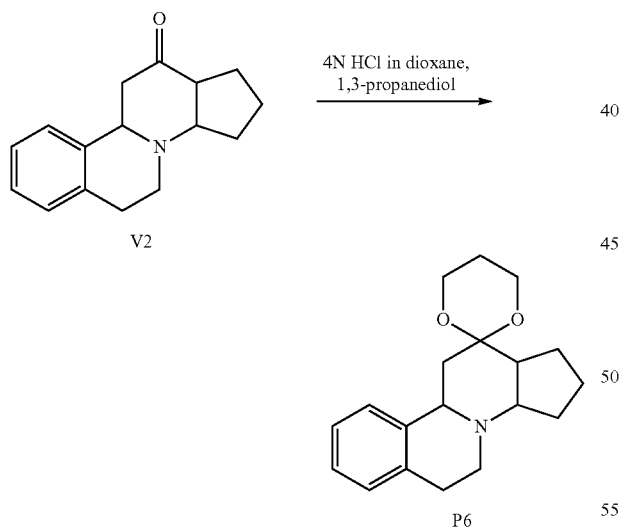

0.8 g of ketone V2 are admixed with 40 ml of 1,3-propanediol and 3 ml of 4 N HCl in dioxane and stirred at RT for 4 days. 20 ml of MTBE, 20 ml of saturated sodium hydrogencarbonate solution and 80 ml of water are added and the mixture is stirred for 5 min. The phases are separated, the aqueous phase is post-extracted 2× with in each case 20 ml of MTBE and the combined organic phases are washed 2× with in each case 40 ml of water. The MTBE phase is dried over sodium sulfate and concentrated in a rotary evaporator.

Yield (P6): 1.1 g with an HPLC purity of 95.9 area % (85:15 isomer mixture).

$^1$H-NMR (CDCl$_3$): 7.30-7.00 (m, 4H); 4.11-3.38 (m, 5H); 3.27-3.14 (m, 1H); 3.10-2.97 (m, 1H); 2.79-2.45 (m, 4H); 2.26-1.53 (m, 10H) [ppm]

Preparation Example H1-16: Preparation of Compound P7

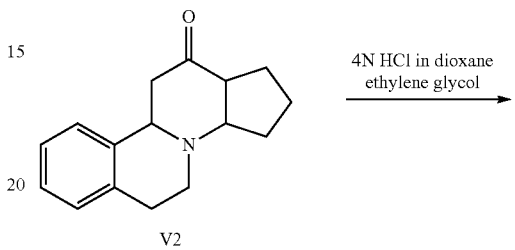

0.8 g of ketone V2 are admixed with 40 ml of ethylene glycol and 3 ml of 4 N HCl in dioxane and stirred at RT for 4 days. 20 ml of MTBE, 20 ml of saturated sodium hydrogencarbonate solution and 80 ml of water are added and the mixture is stirred for 5 min. The phases are separated, the aqueous phase is post-extracted 2× with in each case 20 ml of MTBE and the combined organic phases are washed 2× with in each case 40 ml of water. The MTBE phase is dried over sodium sulfate and concentrated in a rotary evaporator.

Yield (P7): 0.97 g with an HPLC purity of 97.2 area %.

$^1$H-NMR (CDCl$_3$): 7.26-7.00 (m, 4H); 4.11-3.92 (m, 4H); 3.58 (d, 1H); 3.28-3.18 (m, 1H); 3.10-2.95 (m, 1H); 2.78-2.72 (m, 1H); 2.68 d, 1H); 2.24 (d, 1H); 2.13 (tr, 1H); 2.07-1.52 (m, 8H) [ppm]

Preparation Example H1-17: Preparation of Compound V3

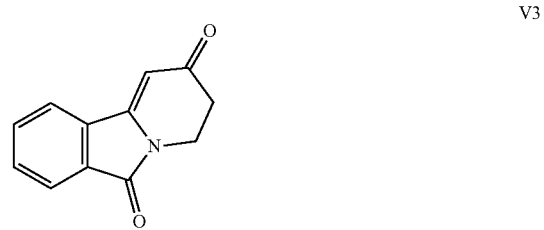 [SMILES: O=C1C=C2c3ccccc3C(=O)N2CC1]

The preparation takes place analogously to Flitsch and Pandl, *Liebigs Ann. Chem.,* 1987, 649.

CAS No. (product): 108292-84-8

Preparation Example H1-18: Preparation of Compound P8

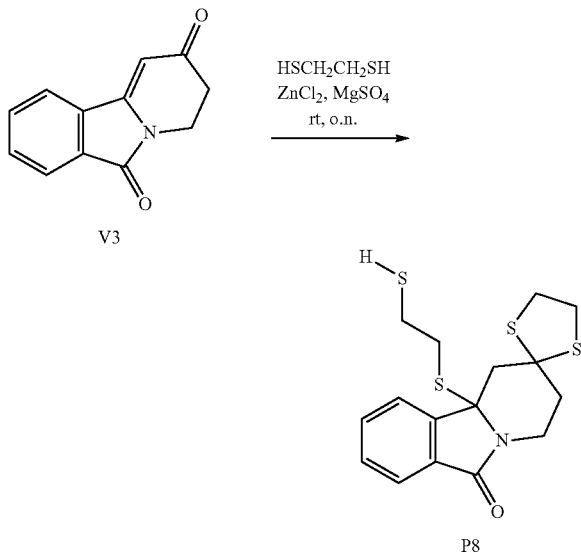

254 mg (1.28 mmol) of ketone V3 and 256 mg of magnesium sulfate are suspended in 1.3 ml (12 eq) of ethanedithiol and admixed, with stirring, with 256 mg (1.5 eq) of ZnC$_2$. Stirring is carried out for two days at room temperature and the reaction mixture is then admixed with 40 ml of dichloromethane and 40 ml of water. The aqueous phase is separated off and extracted two more times with 40 ml of dichloromethane in each case. The combined organic phases are dried over sodium sulfate and concentrated on a rotary evaporator. The crude product obtained is purified by column chromatography over silica gel with heptane/EtOAc as eluent.

Yield (P8): 334 g (71%) of viscous colorless oil with an HPLC purity of 100 area %

$^1$H-NMR (CDCl$_3$): 7.82 (d, 1H); 7.68-7.55 (m, 1H); 7.50 (tr, 1H); 4.38 (d, 1H); 3.56-3.24 (m, 5H); 2.94 (d, 1H); 2.32 (d, 1H); 2.29-1.85 (m, 6H); 1.47 (tr, 1H), [ppm]

Preparation Example H1-19: Preparation of Compound P9

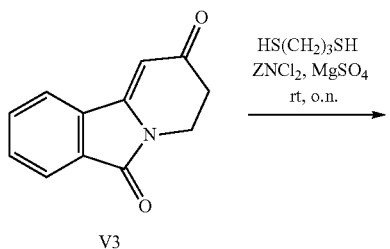

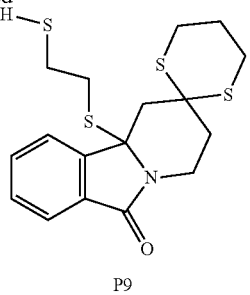

210 mg (1.05 mmol) of ketone V3 and 210 mg of magnesium sulfate are suspended in 1.3 ml (12 eq) of 1,3-propanedithiol and admixed, with stirring, with 210 mg (1.5 eq) of ZnCl$_2$. Stirring is carried out for 64 h at room temperature and the reaction mixture is then admixed with 40 ml of dichloromethane and 40 ml of water. The aqueous phase is separated off and extracted two more times with 40 ml of dichloromethane in each case. The combined organic phases are dried over sodium sulfate and concentrated on a rotary evaporator. The crude product obtained is purified by column chromatography over silica gel with heptane/EtOAc as eluent.

Yield (P9): 229 mg (55%) colorless resin with an HPLC purity of 100 area %

$^1$H-NMR (CDCl$_3$): 7.83 (d, 1H); 7.68-7.53 (m, 2H); 7.48 (tr, 1H); 4.32 (d, 1H); 3.59 (tr, 1H); 3.05-2.91 (m, 3H); 2.91-2.77 (m, 2H); 2.58 (d, 1H); 2.40-2.28 (m, 2H); 2.13-1.88 (m, 4H); 1.85-1.72 (m, 2H); 1.53-1.37 (m, 2H); 1.13 (tr, 1H) [ppm]

Preparation Example H1-20: Preparation of Compound Z1

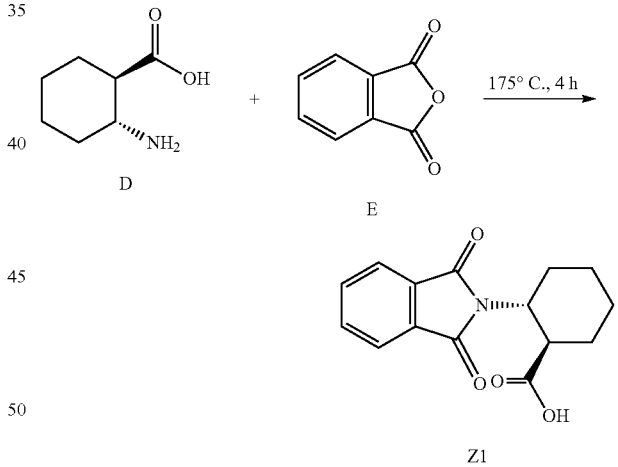

A mixture of 14.8 g (100 mmol) of phthalic anhydride (E) and 14.3 g (100 mmol) of (1R,2R)-2-aminocyclohexanecarboxylic acid (D) is heated at 175° C. for 4 h with stirring. The mixture is cooled to room temperature and the viscous oil is taken up in 400 ml of dichloromethane. The organic phase is washed with 3×60 ml of 0.1 N HCl, dried over sodium sulfate and concentrated on a rotary evaporator. The resulting viscous, pale yellow oil is stirred with 50 ml of heptane. The resulting white solid is filtered off, washed with 2×5 ml of heptane and dried in vacuo.

Yield (Z1): 27.3 g (100%) with an HPLC purity of 100%.
CAS No. (product): 755025-03-7

$^1$H-NMR (CDCl$_3$): 11.2-9.3 (br s, 1H); 7.82-7.73 (m, 2H); 7.73-7.57 (m, 2H); 4.30 (tr, 1H); 3.44 (tr, 1H); 2.20-1.99 (m, 2H); 1.99-1.28 (m, 6H) [ppm]

Preparation Example H1-20: Preparation of Compound Z2

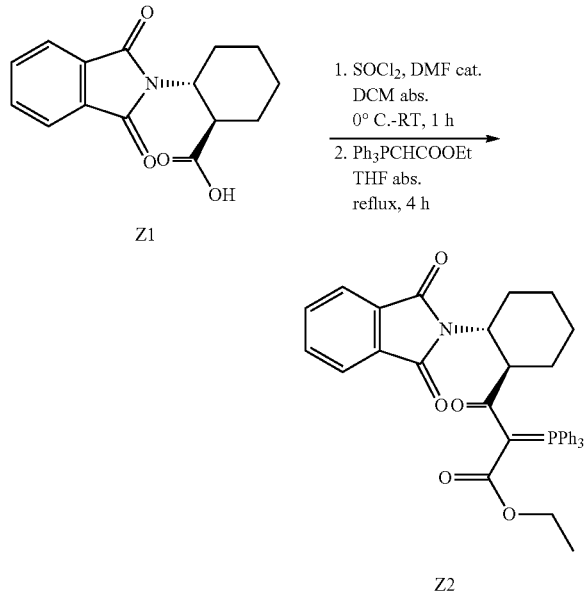

6.83 g (25 mmol) of 2-phthalimidocyclohexanecarboxylic acid (Z1) are dissolved in 250 ml of dry dichloromethane and admixed with 0.19 ml of DMF. The solution is cooled to 0° C. to −10° C. and, at this temperature, admixed with 29.7 g (250 mmol, eq) of thionyl chloride over the course of 20 min. The mixture is heated to RT, post-stirred for one hour at RT and concentrated on a rotary evaporator. The acid chloride is taken up in THF and added dropwise to a solution of 17.4 g (50 mmol, 2.0 eq) of ethyl (triphenylphosphora-nilidine)acetate in 150 ml of THF at 19-27° C. over the course of 90 min. The reaction solution is then refluxed for 8 h, during which a white solid precipitates out and the reaction solution turns deep red. The mixture is cooled to RT, the precipitated solid is filtered off via a frit and the filter cake is after-washed with THF. The combined mother liquors and washing liquors are concentrated on a rotary evaporator in order to isolate the product as red foam.

Yield (Z2): 18.8 g with an HPLC purity of 55 area %.

Preparation Example H1-22: Preparation of Compound Z3

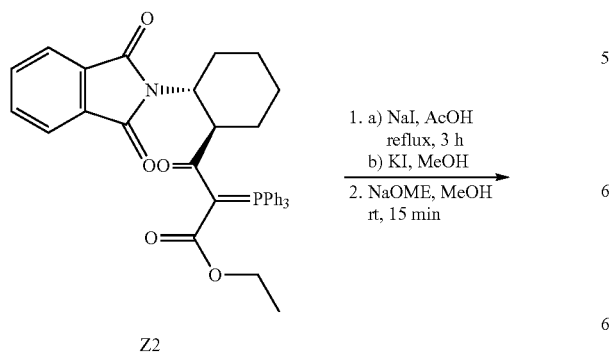

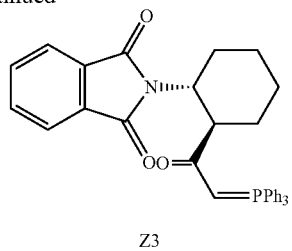

15 g (~20 mmol) of phosphorane Z2 are dissolved in 60 ml of glacial acetic acid and heated under reflux in the presence of 6 g (40 mmol, 2.0 eq) of sodium iodide for 3 h. The dark red reaction solution is concentrated on a rotary evaporator, and the red-brown residue is taken up in 40 ml of methanol and added to a solution of 12 g (72 mmol, 3.6 eq) of potassium iodide in 120 ml of water. The aqueous phase is extracted with dichloromethane (3×60 ml) and the combined organic phases are washed with water (2×100 ml) and dried over sodium sulfate. The organic solution is concentrated on a rotary evaporator to a volume of 20-40 ml and admixed with the same amount of heptane. The mixture is further concentrated in vacuo, leaving behind a brown-yellow foam.

The foam is dissolved in 40 ml of methanol and admixed, with stirring at RT via a dropping funnel, with a mixture of 16 ml of MeOH and 3.9 ml of NaOMe solution (30% in MeOH). The mixture is then stirred for 15 min at RT. The dark brown MeOH solution is poured onto 200 ml ice/water mixture, as a result of which, after vigorous stirring, a brown slime precipitates out. The aqueous solution is decanted off and the remainder is filtered. The brown residue that is formed is dissolved in dichloromethane (ca. 150 ml) and any water remains are separated off via a separating funnel. The dichloromethane phase is dried over sodium sulfate and concentrated on a rotary evaporator.

Yield (Z3): 10.02 g (94%) of brown-white foam

Preparation Example H1-23: Preparation of Compound V4

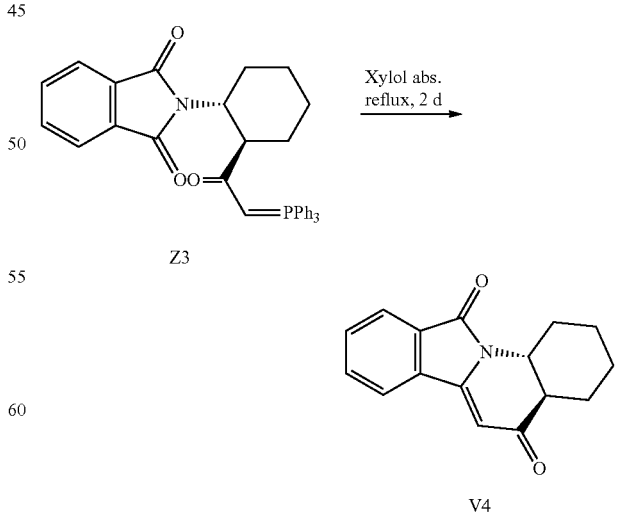

8 g (15 mmol) of phosphorane Z3 are stirred under reflux with 500 m of xylene for 2 days. The solvent is drawn off on a rotary evaporator and the remaining brown oil is passed through a column over silica gel. 1.75 g of product are isolated which are recrystallized from ethanol.

Yield (V4): 1.0 g (26%) with an HPLC purity of 92.3% and 391 mg with an HPLC purity of 63%.

$^1$H-NMR (CDCl$_3$): 7.88 (d, 1H); 7.77 (d, 1H); 7.74-7.60 (m, 2H); 6.07-5.98 (m, 1H); 4.70-4.59 (m, 1H); 2.95 (s, 1H); 2.68-2.55 (m, 1H); 1.98-1.84 (m, 1H); 1.84-1.68 (m, 1H); 1.58 (d, 1H); 1.50-1.32 (m, 3H); 1.32-1.17 (m, 1H) [ppm]

Preparation Example H1-24: Preparation of Compound P10

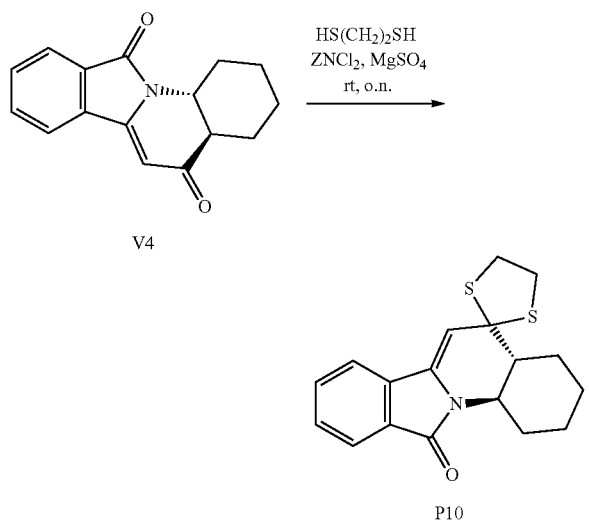

500 mg (1.97 mmol) of tetracycle V4 und 400 mg (1.7 eq) of magnesium sulfate are suspended in 2 ml (12 eq) of ethanedithiol and admixed, with stirring at RT, with 400 mg (1.5 eq) of zinc chloride. The mixture is stirred at RT for 42 h and then diluted, for work-up, with 50 ml of dichloromethane and 50 ml of water. The aqueous phase is separated off and extracted twice more with in each case 50 ml of dichloromethane (2×50 ml). The combined organic phases are dried over sodium sulfate and concentrated on a rotary evaporator. The resulting viscous yellow oil is purified by column chromatography.

Yield (P10): 683 mg of pale yellow viscous oil with an HPLC purity of 82 area %

$^1$H-NMR (CDCl$_3$): 7.80-7.73 (m, 1H); 7.62-7.39 (m, 3H), 5.90 (s, 1H); 4.39 (s, 1H); 3.51-3.35 (m, 3H); 3.35-3.21 (m, 1H); 2.20-1.05 (m, 9H) [ppm]

Preparation Example H1-25: Preparation of Compound P11 Und P12

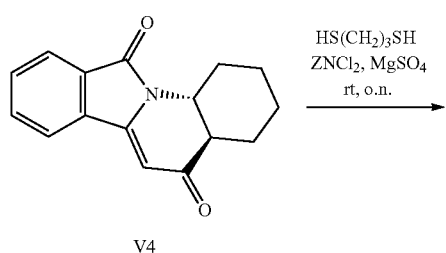

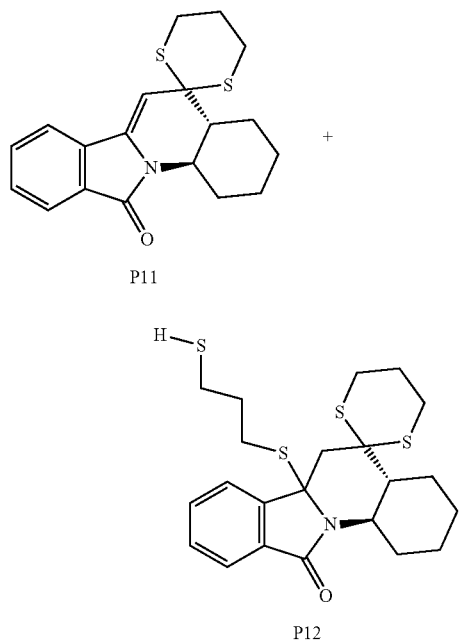

269 mg (1.06 mmol) of tetracycle V4 and 212 mg (1.7 eq) of magnesium sulfate are suspended in 1.3 ml (12 eq) of 1,3-propanedithiol and admixed, with stirring at RT, with 212 mg (1.5 eq) of zinc chloride. The mixture is stirred at RT for 64 h and then diluted, for work-up, with 50 ml of dichloromethane and 50 ml of water. The aqueous phase is separated off and extracted two more times with 50 ml of dichloromethane in each case. The combined organic phases are dried over sodium sulfate and concentrated on a rotary evaporator. The resulting yellow oil is purified by column chromatography.

Yield (P11): 63 mg (17%) of diastereomer 1

73 mg (20%) of diastereomer 2

Yield (P12): 151 mg (31%)

Diastereomer 1 of P11

$^1$H-NMR (CDCl$_3$): 7.78 (d, 1H); 7.61 (d, 1H); 7.54 (tr, 1H); 7.47 (tr, 1H); 5.79 (s, 1H); 4.64 (s, 1H); 3.06 (tr, 1H), 2.97-2.70 (m, 3H); 2.30 (d, 1H); 2.23-1.04 (m, 10H) [ppm]

Diastereomer 2 of P11

$^1$H-NMR (CDCl$_3$): 7.80 (d, 1H); 7.66 (d, 1H); 7.55 (tr, 1H); 7.47 (tr, 1H); 6.49 (s, 1H); 3.97 (tr, 1H); 3.79 (d, 1H); 3.40 (tr, 1H); 3.11 (tr, 1H); 2.97-2.89 (m, 1H); 2.84-2.74 (m, 1H); 2.44 (d, 1H); 2.22-2.15 (m, 1H); 2.03-1.17 (m, 8H) [ppm]

P12:

$^1$H-NMR (CDCl$_3$): 7.78 (d, 1H); 7.67-7.51 (m, 2H); 7.44 (tr, 1H); 4.02 (tr, 1H); 3.38 (d, 1H); 3.02 (tr, 1H); 2.93-2.70 (m, 3H); 2.70-2.57 (m, 4H); 2.57-2.46 (m, 1H); 2.44-1.18 (m, 15H); 1.12 m, 1H) [ppm]

Preparation Example H1-26: Preparation of Compound V5

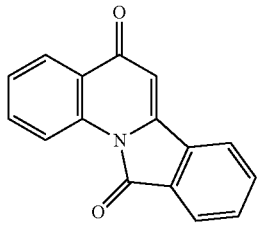

The preparation takes place analogously to *Helv. Chim Acta*, 2011, 94, 1703-1717.

Preparation Example H1-27: Preparation of Compound P13

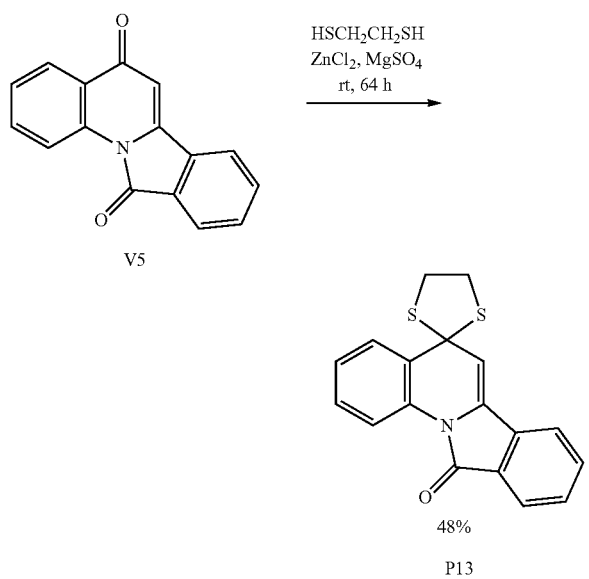

990 mg (4.0 mmol) of tetracycle V5 and 800 mg (1.7 eq) of magnesium sulfate are suspended in 4.0 ml (12 eq) of ethanedithiol and admixed, with stirring at RT, with 800 mg (1.5 eq) of zinc chloride. The mixture is stirred at RT for 64 h and then diluted, for work-up, with 80 ml of dichloromethane and 80 ml of water (product partially insoluble). The aqueous phase is separated off and the organic phase is concentrated. The residue is digested in iPrOH/water, filtered off with suction and washed with a small amount of iPrOH. It is dried in a stream of nitrogen and the residue is digested again in MeOH, filtered off with suction and dried.

Yield (P13): 880 mg (68%) of yellow solid with a content of ca. 70% (according to NMR, still comprises ca. 30% starting material)

$^1$H-NMR (DMSO-$d_6$): 8.30-8.16 (m, 1H); 8.04 (d, 1H); 8.01 (d, 1H); 7.91-7.78 (m, 1H); 7.75-7.68 (m, 1H); 7.60 (tr, 1H); 7.53-7.44 (m, 1H); 6.92 (s, 1H); 4.20-4.02 (m, 4H) [ppm]

Preparation Example H1-28: Preparation of Compound Z4

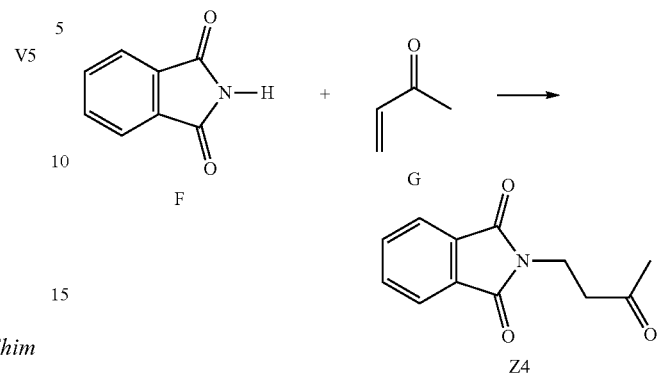

CAS: 3783-77-5

The preparation takes place according to: A. M. Islam, R. A. Raphael, *J. Chem. Soc.* 1955, 3151-3154.

Preparation Example H1-29: Preparation of Compound Z5

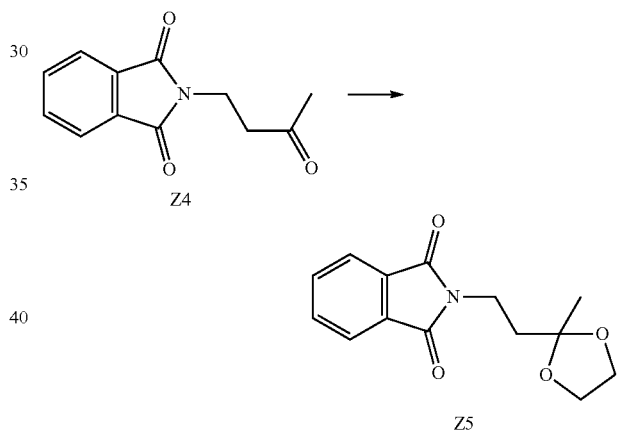

CAS: 87764-41-0

The preparation takes place in accordance with:

Bosch, Joan; Rubiralta, Mario; Moral, Montserrat; Arino, Joaquin. *Journal of the Chemical Society, Perkin Transactions 1: Organic and Bio-Organic Chemistry* (1972-1999), 1986, (8), 1533-9.

Preparation Example H1-30: Preparation of Compound P14

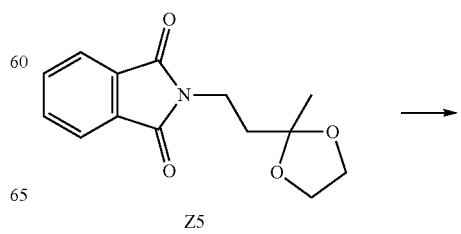

-continued

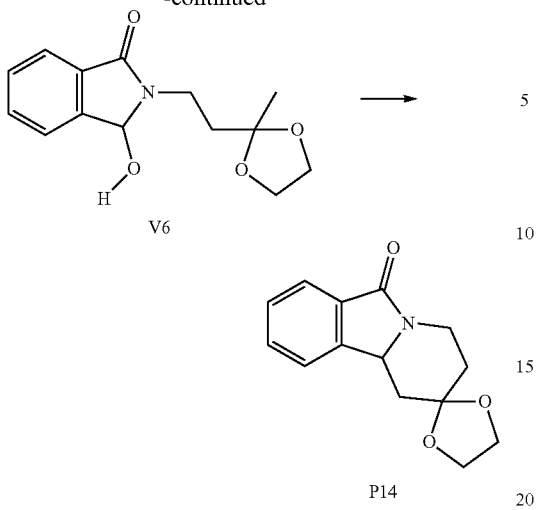

CAS (intermediate; V6): 1174751-64-4

CAS (product, P14): 817554-52-2

Prepared analogously to: M. Chiurato, S. Routier, Y. Troin, G. Guillaumet, *Eur. J. Org. Chem* 2009, 3011-3021

Preparation Example H1-31: Preparation of Compound Z6

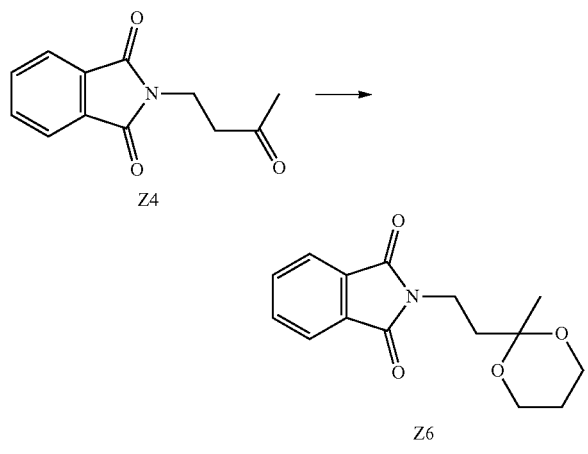

5.43 g (25 mmol) of 4-phthalimidobutan-2-one Z4 are dissolved in 150 ml of toluene, admixed with 4.28 g (56.25 mmol, 2.25 eq) of 1,3-propanediol and 0.24 g (1.25 mmol, 0.05 eq) of para-toluenesulfonic acid monohydrate and heated under reflux for 24 h on a water separator. The mixture is cooled to RT and washed with 3×30 ml of saturated sodium hydrogencarbonate solution. The combined aqueous phases are extracted once with 90 ml of EtOAc and the combined organic phases are dried over sodium sulfate and concentrated on a rotary evaporator. The colorless oil obtained is crystallized from heptane.

Yield (Z6): 7.09 g with an HPLC purity of 88 area %

$^1$H-NMR (CDCl$_3$): 7.89-7.80 (m, 2H); 7.74-7.66 (m, 2H); 3.97-3.80 (m, 6H); 2.11 (tr, 2H); 1.84-1.72 (m, 1H); 1.66-1.56 (m, 1H); 1.48 (s, 3H) [ppm]

Preparation Example H1-32: Preparation of Compound V7

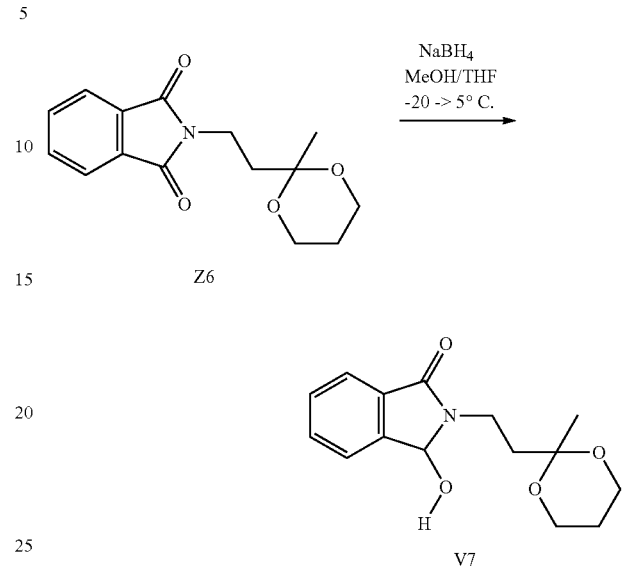

Under a nitrogen atmosphere, 3.64 g (12.5 mmol) of compound Z6 are initially introduced and dissolved in a mixture of 100 ml of MeOH and 125 ml of THF. The mixture is cooled to −15° C., and 0.71 g (18.75 mmol, 1.5 eq) of sodium borohydride are added in portions. The mixture is post-stirred for 30 min at −15° C. and then heated to 0-5° C. over the course of 1 h.

For work-up, 30 ml of water and 75 ml of sodium hydrogencarbonate solution are added and the mixture is extracted 3 times with 150 ml of dichloromethane in each case and once with 250 ml of EtOAc. The combined organic phases are dried over sodium sulfate and then concentrated on a rotary evaporator. The resulting pale red oil is purified by column chromatography.

Yield (V7): 3.20 g (87%, colorless oil);

$^1$H-NMR (CDCl$_3$): 7.66-7.55 (m, 3H); 7.52 (tr, 1H); 6.45 (d, 1H); 5.83 (d, 1H); 3.91-3.77 (m, 4H); 3.69-3.59 (m, 1H); 3.43-3.34 (m, 1H); 2.08-1.87 (m, 2H); 1.70-1.47 (m, 2H); 1.37 (s, 3H) [ppm]

Preparation Example H1-33: Preparation of Compound P15

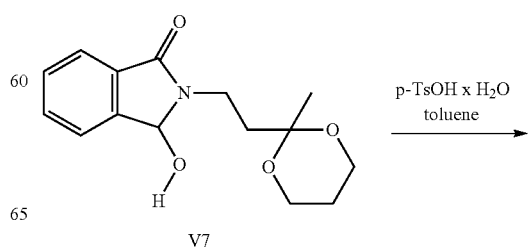

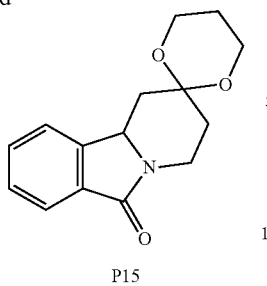

P15

2.77 g (10 mmol) of compound V7 are admixed with 200 ml of toluene and 3.57 g (15 mmol, 1.5 eq) of para-toluenesulfonic acid monohydrate and refluxed for 24 h on a water separator. The reaction mixture is cooled to RT and washed with saturated NaHCO$_3$ solution. The aqueous phase is extracted twice with 200 ml of dichloromethane in each case. The combined organic phases are dried over sodium sulfate, filtered and concentrated on a rotary evaporator. The crude product is purified by column chromatography.

Yield (P15): 321 mg (12%, pale yellow oil, product content according to $^{13}$C-NMR: 55-60%)

Preparation Example H1-34: Preparation of Compound P16

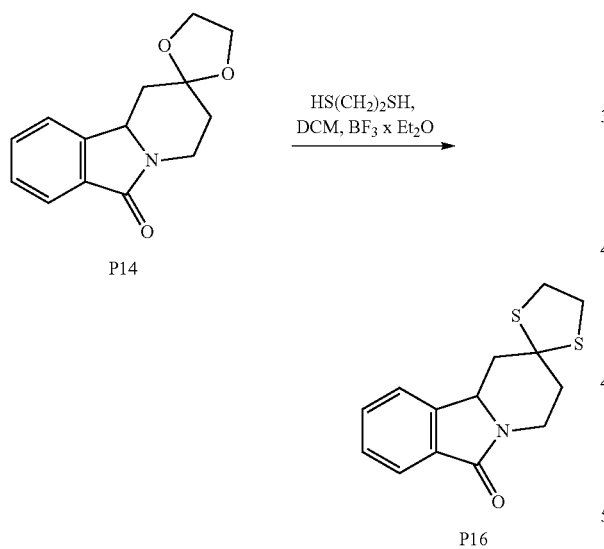

470 mg (1.92 mmol) of compound P14 are dissolved in 25 ml of dichloromethane and, at RT, slowly admixed with 0.9 g (10 mmol, 5 eq) of ethanedithiol and 1.36 g (10 mmol, eq) of boron trifluoride diethyl etherate. The mixture is stirred at RT for 18 h and then the reaction mixture is added to 25 ml of 2 N NaOH. The organic phase is separated off and the aqueous phase is extracted 3 times with 50 ml of dichloromethane in each case. The combined organic phases are dried over magnesium sulfate, and filtered and the solvent is removed under reduced pressure.

Yield (P16): 532 mg (100%)

$^1$H-NMR (CDCl$_3$): 7.89-7.24 (m, 4H); 4.59-4.44 (m, 2H); 3.51-3.32 (m, 4H); 3.25 tr, 1H); 2.70 d, 1H); 2.20 (d, 1H); 2.07-1.96 (m, 1H); 1.62 (tr, 1H) [ppm]

Preparation Example H1-35: Preparation of Compound P17

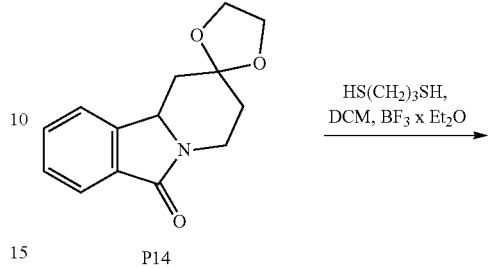

470 mg (1.92 mmol) of compound P14 are dissolved in 25 ml of DCM and, at RT, slowly admixed with 1.04 g (9.6 mmol, 5 eq) of 1,3-propanedithiol and 1.36 g (9.6 mmol, 5 eq) of boron trifluoride diethyl etherate. The mixture is stirred at RT for 18 h and then the reaction mixture is added to 25 ml of 2 N NaOH. The organic phase is separated off and then the aqueous phase is extracted 3 times with 50 ml of dichloromethane in each case. The combined organic phases are dried over magnesium sulfate and filtered, and the solvent is removed under reduced pressure.

Yield (P17): 578 mg (104%)

$^1$H-NMR (CDCl$_3$): 7.89-7.25 (m, 4H); 4.76 (d, 1H); 4.41-4.30 (m, 1H); 3.40 (tr, 1H); 3.01-2.81 (m, 5H); 2.50-2.37 (m, 1H); 2.07 (br s, 2H); 1.77 (m, 1H); 1.45 (tr, 1H) [ppm]

Preparation Example H1-36: Preparation of Compound V8

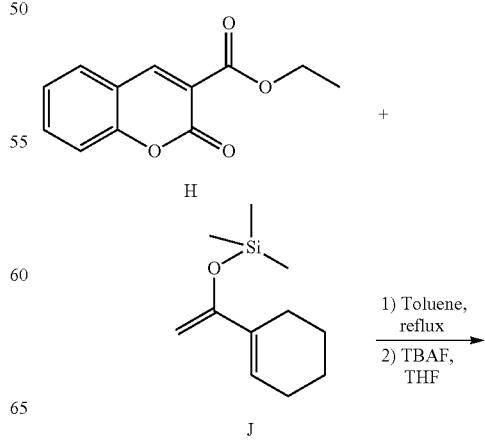

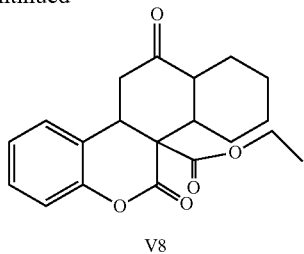

23 g (105 mmol) of ethyl 3-coumarincarboxylate (H) and 34.9 g (141 mmol, 1.34 eq) of 1-cyclohex-1-enyl-vinyloxytrimethylsilane (J) are dissolved in 438 ml of toluene and boiled at reflux for 22 h. The reaction mixture is concentrated by evaporation, admixed with 231 ml of THF and then at 16° C. with 43.2 g (1.30 eq) of tetrabutylammonium fluoride. The mixture is post-stirred at RT for 15 minutes. 500 ml of water and 250 ml of MTBE are added, the mixture is stirred thoroughly and the phases are separated. The aqueous phase is post-extracted with 100 ml of MTBE. The combined organic phases are washed with 500 ml of water and then concentrated on a rotary evaporator. The resulting oil is admixed with n-heptane, the crystal mixture obtained is stirred for 15 min and filtered with suction. The filter residue is post-washed with 50 ml of iPrOH and then dried in a stream of nitrogen.

Yield (V8): 25.5 g (71%) with an HPLC purity 97.9 area % (two diastereomers 78:18)

$^1$H-NMR (CDCl$_3$, main isomer): 7.35-7.04 (m, 4H); 4.14-3.93 (m, 2H); 3.56 (dd, 1H); 2.75-2.55 (m, 2H); 2.50-2.36 (m, 2H); 2.17-2.03 (m, 2H); 1.88-0.93 (tr, 3H) [ppm]

Preparation Example H1-37: Preparation of Compound V9

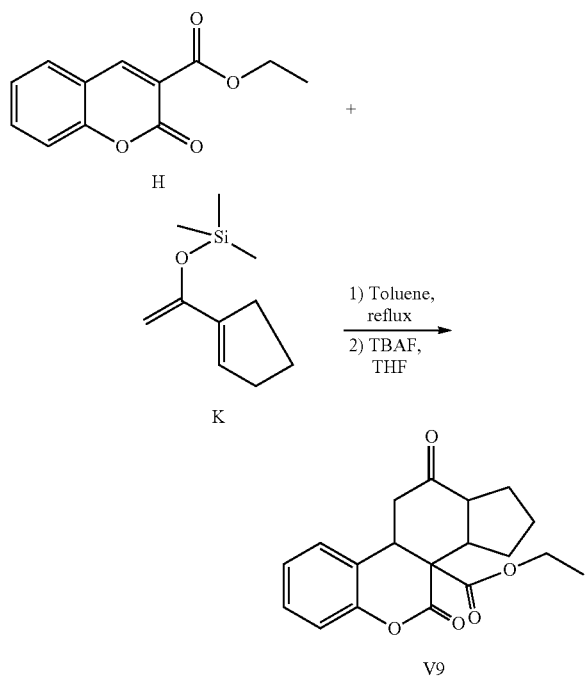

14 g (64.2 mmol) of ethyl-3-coumarincarboxylate (H) and 22.8 g (89.8 mmol, 1.40 eq) of 1-cyclopent-1-enylvinyloxy) trimethylsilane (K) are dissolved in 266 ml of toluene and boiled at reflux for 24 h. The reaction mixture is concentrated on a rotary evaporator, admixed with 140 ml of THF and, at 16° C., with 26.3 g (83.4 mmol, 1.30 eq) of tetrabutylammonium fluoride. The mixture is post-stirred for 15 minutes at RT. 304 ml of water and 152 ml of MTBE are added, the mixture is thoroughly stirred and the phases are separated. The aqueous phase is post-extracted with 61 ml of MTBE. The combined organic phases are washed with 304 ml of water and then concentrated on a rotary evaporator. The resulting oil is admixed with 31 g of isopropanol and cooled to 0° C., and the precipitated solid is filtered off with suction. The residue is washed with 10 ml of ice-cold i-PrOH and then with 10 ml of n-heptane at RT and dried in a stream of argon for two days.

Yield (V9): 7.1 g (34%) with an HPLC purity of 91.2 area %

$^1$H-NMR (CDCl$_3$, two isomers): 7.37-7.03 (m, 4H, both isomers); 4.16-3.98 (m, 2H, both isomers); 3.84 (dd, 1H, one isomer); 3.62 (dd, 1H, one isomer); 3.49-3.27 (m, 1H, one isomer); 3.05-2.89 (m, 1H, both isomers); 2.68-2.20 (m, 3H, both isomers+1H, one isomer); 1.92-1.19 (m, 5H both isomers); 1.06 (tr, 3H, one isomer); 0.98 (tr, 3H, one isomer) [ppm]

Preparation Example H1-38: Preparation of Compound P18

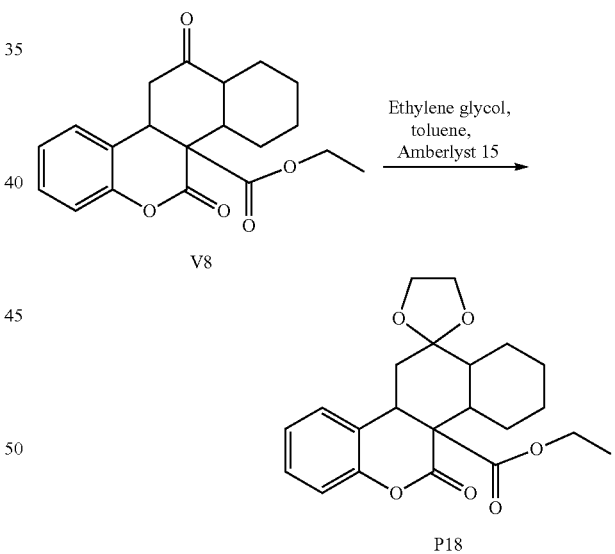

1 g (2.9 mmol) of ketoester V8 are admixed with 0.19 g (3.1 mmol, 1.05 eq) of ethylene glycol, 10 ml of toluene and 0.1 g of Amberlyst 15 and boiled at reflux overnight. The mixture is filtered, the resulting solution is concentrated by evaporation and the residue is crystallized from isopropanol in an ice bath. The mixture is filtered, and the residue is washed with a small amount of cold iPrOH and dried in a drying cabinet at 40° C.

Yield (P18): 0.54 g (48%) with an HPLC purity of 92.9 area %

$^1$H-NMR (DMSO-d$_6$): 7.35-7.25 (m, 2H); 7.17-7.05 (m, 2H); 4.06-3.83 (m, 6H); 3.46-3.33 (m, 1H); 2.23-2.12 (m,

1H); 2.04-1.94 (m, 2H); 1.87-1.75 (m, 2H); 1.75-1.65 (m, 2H); 1.41-1.00 (m, 5H); 1.80 (tr, 3H); [ppm]

Preparation Example H1-39: Preparation of Compound P19

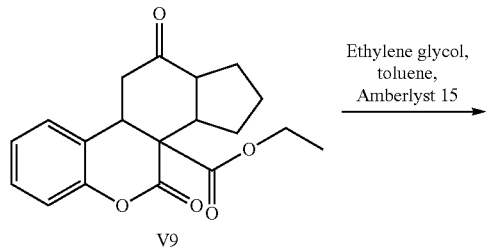

1.2 g (3.65 mmol) of ketoester V9 are admixed with 0.45 g (7.3 mmol, 2.0 eq) of ethylene glycol, 12.5 ml of toluene and 0.12 g of Amberlyst 15 and boiled at reflux overnight. 200 mg of 4 Å molecular sieve are added and the mixture is heated at reflux for a further 4 h. The mixture is filtered, and the resulting solution is washed twice with 20 ml of water in each case and concentrated on a rotary evaporator.

Yield (P19): 1.22 g (90%) with an HPLC purity of 90.2 area %

$^1$H-NMR (CDCl$_3$): 7.31-6.96 (m, 4H, both isomers); 4.11-3.84 (m, 6H, both isomers); 3.73 (dd, 1H, one isomer); 3.47 (dd, 1H, one isomer); 3.19-3.09 (m, 1H, one isomer); 2.48-2.15 (m, 2H, both isomers); 1.99-1.32 (m, 6H, both isomers+1H one isomer); 1.05 (tr, 1H, one isomer); 0.97 (m, 1H, one isomer) [ppm]

Preparation Example H1-40: Preparation of Compound P20

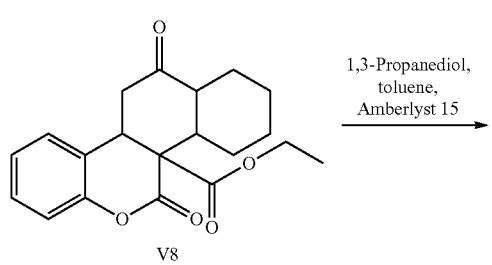

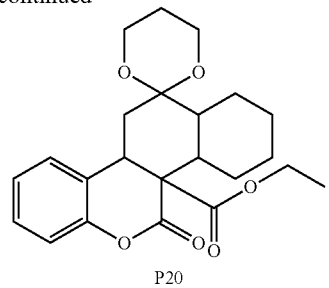

1 g (2.9 mmol) of ketoester V8 are admixed with 0.23 g (3.1 mmol, 1.05 eq) of 1,3-propanediol, 10 ml of toluene and 0.1 g of Amberlyst 15 and boiled at reflux overnight. The mixture is filtered, and the resulting solution is concentrated by evaporation and crystallized from isopropanol in an ice bath. The mixture is filtered, and the residue is washed with a small amount of cold iPrOH and dried in a drying cabinet at 40° C.

Yield (P20): 0.65 g (56%) with an HPLC purity of 73 area %

$^1$H-NMR (DMSO-d$_6$): 7.41-7.28 (m, 2H); 7.20-7.05 (m, 2H); 4.14-3.82 (m, 5H); 3.68-3.61 (d, 1H); 3.24 (d, 1H); 3.09 (m, 1H); 2.50-0.91 (m, 13H); 0.78 (tr, 1H) [ppm]

Preparation Example H1-41: Preparation of Compound P21

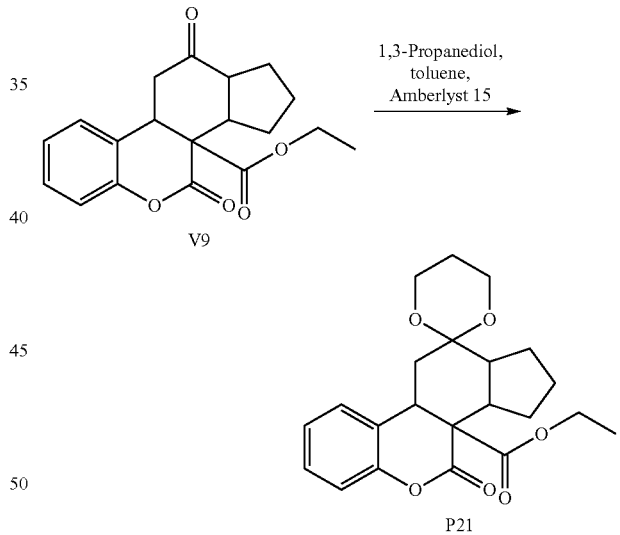

1.2 g (3.65 mmol) of ketoester V9 are admixed with 0.56 g (7.3 mmol, 2.0 eq) of 1,3-propanediol, 12.5 ml of toluene and 0.12 g of Amberlyst 15 and boiled at reflux overnight. 200 mg of 4 Å molecular sieve and a further 0.12 g of Amberlyst 15 are added and the mixture is heated at reflux for a further 88 h. It is filtered and the resulting solution is concentrated on a rotary evaporator. The residue is taken up in THF, admixed with 10 ml of 1,3-propanediol, concentrated and, after adding 0.12 g of Amberlyst 15, stirred overnight at 110° C. The mixture is cooled and admixed with 250 ml of water and 100 ml of toluene, and the organic phase is separated off and washed a further 2 times with 30 ml of water in each case. The organic phase is concentrated and purified by column chromatography.

Yield (P21): 0.40 g (28%) with an HPLC purity of 90.8 area %

$^1$H-NMR (CDCl$_3$): 7.19-6.98 (m, 4H, both isomers); 4.08-3.87 (m, 5H, both isomers); 3.81-3.72 (m, 1H, both isomers); 3.58 (dd, 1H, one isomer); 3.33 (dd, 1H, one isomer); 2.99-2.83 (m, 1H, one isomer); 2.44-1.20 (m, 11H, both isomers); 1.06 (tr, 1H, one isomer); 0.97 (m, 1H, one isomer) [ppm]

Preparation Example H1-40: Preparation of Compound P22

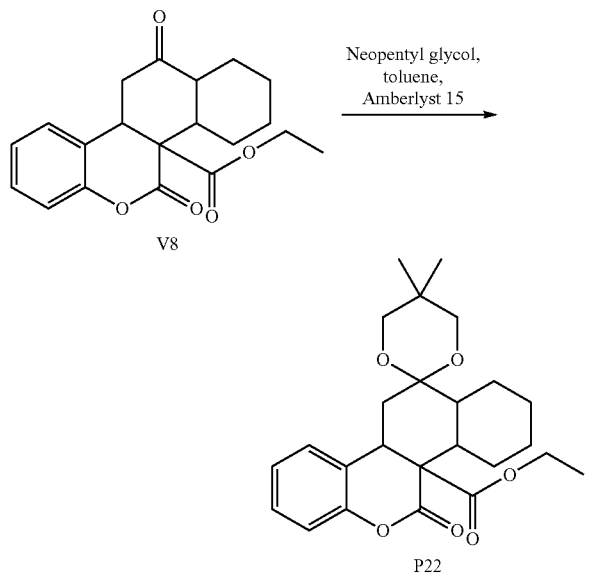

1 g (2.9 mmol) of ketoester V8 are admixed with 0.32 g (3.1 mmol, 1.05 eq) of neopentyl glycol, 10 ml of toluene and 0.1 g of Amberlyst 15 and boiled at reflux overnight. The mixture is filtered, the resulting solution is concentrated by evaporation and the residue is crystallized from isopropanol in an ice bath. The mixture is filtered, and the filter cake is washed with a small amount of cold iPrOH and dried at 40° C. in a drying cabinet.

Yield (P22): 0.78 g (62%) with an HPLC purity of 81.7 area %

$^1$H-NMR (CDCl$_3$): 7.41-7.28 (m, 2H); 7.20-7.05 (m, 2H); 4.07-3.87 (m, 3H); 3.82 (d, 1H); 3.68 (d, 1H); 2.24-1.98 (m, 3H); 1.78-1.64 (m, 3H); 1.50-1.00 (m, 8H); 0.97-0.86 (m, 1H); 0.78 (tr, 3H); 0.70 (s, 3H) [ppm]

Preparation Example H1-43: Preparation of Compound P23

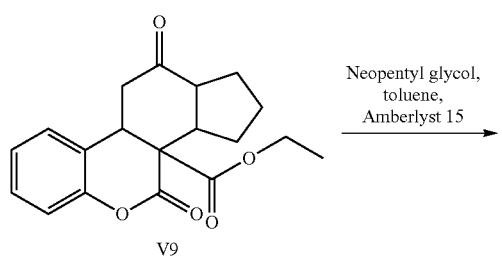

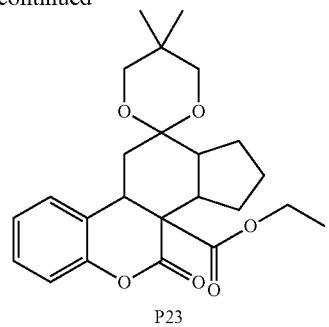

1.2 g (3.65 mmol) of ketoester V9 are admixed with 0.56 g (7.3 mmol, 2.0 eq) of neopentyl glycol, 12.5 ml of toluene and 0.12 g of Amberlyst 15 and boiled at reflux overnight. 200 mg of 4 Å molecular sieve are added and the mixture is heated at reflux for a further 4 h. The mixture is filtered and the resulting solution is concentrated on a rotary evaporator. The residue is crystallized from a small amount of MTBE/heptane mixture with a couple of drops of isopropanol in the ice bath. Filtration is carried out and the filter residue is washed with a small amount of heptane and dried in a stream of nitrogen.

Yield (P23): 1.25 g (83%) with an HPLC purity of 88.2 area % (two isomers)

$^1$H-NMR (CDCl$_3$): 7.19-6.98 (m, 4H, both isomers); 4.08-3.87 (m, 5H, both isomers); 3.81-3.72 (m, 1H, both isomers); 3.58 (dd, 1H, one isomer); 3.33 (dd, 1H, one isomer); 2.99-2.83 (m, 1H, one isomer); 2.44-1.20 (m, 11H, both isomers); 1.06 (tr, 1H, one isomer); 0.97 (m, 1H, one isomer) [ppm]

Preparation Example H1-44: Preparation of Compound P24

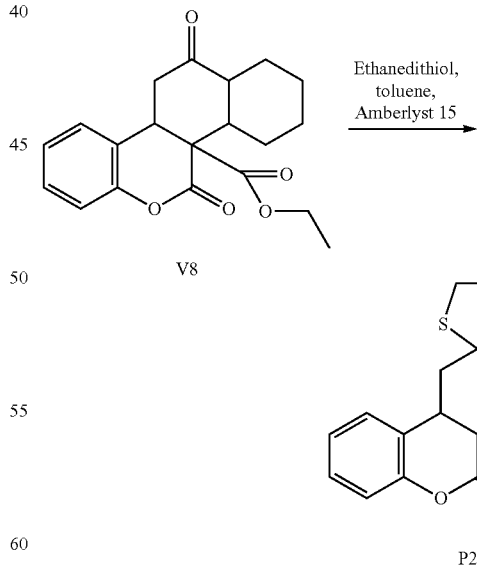

1.0 g (2.9 mmol) of ketoester V8 are admixed with 0.55 g (5.8 mmol, 2.0 eq) of ethanedithiol, 10 ml of toluene and 0.1 g of Amberlyst 15 and stirred at 60° C. for 24 h. 0.4 g of 4 Å molecular sieve are added and the mixture is stirred at 60° C. for a further hour. The mixture is filtered and the resulting solution is concentrated by evaporation. The residue is taken up in dichloromethane, and the solution is washed with water and twice with NaHCO₃ solution, and the organic phase is concentrated on a rotary evaporator.

Yield (P24): 0.94 g (77%) with an HPLC purity of 92.9 area %

¹H-NMR (CDCl₃): 7.32-6.95 (m, 4H); 4.13-3.88 (m, 4H); 3.48 (d, 1H); 3.35-3.17 (m, 4H); 2.43-2.22 (m, 3H); 2.17-2.04 (m, 2H); 1.91 (tr, 1H); 1.76 (d, 2H); 1.51-1.28 (m, 3H); 1.24-1.10 (m, 1H); 0.90 (tr, 3H) [ppm]

Preparation Example H1-45: Preparation of Compound P25

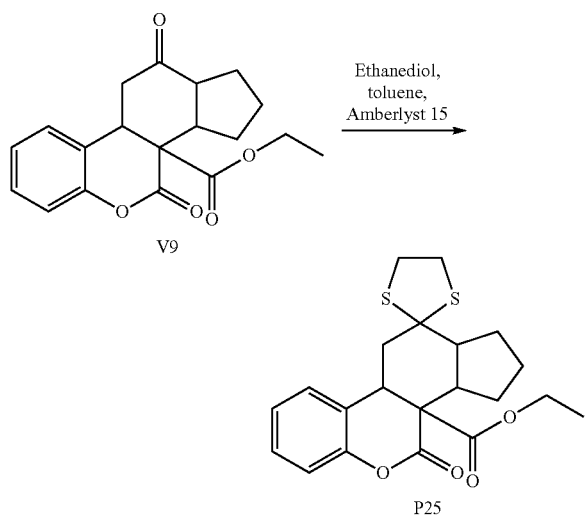

1.2 g (3.65 mmol) of ketoester V9 are admixed with 0.69 g (7.3 mmol, 2.0 eq) of ethanedithiol, 12.5 mol of toluene and 0.12 g of Amberlyst 15 and stirred overnight at 80° C. The mixture is filtered and the organic phase is washed twice with 15 ml of saturated sodium hydrogencarbonate solution in each case and once with water. The organic phase is concentrated on a rotary evaporator and the residue is purified by column chromatography.

Yield (P25): 1.20 g (81%) with an HPLC purity of 93.7 area % (two isomers)

¹H-NMR (CDCl₃): 7.30-6.96 (m, 4H); 4.10-3.95 (m, 2H); 3.76 (d, 1H, one isomer); d, 3.43 (d, 1H, one isomer); 3.40-3.06 (m, 5H); 2.72-1.38 (m, 9H); 1.05 (tr, 3H, one isomer); 0.97 (tr, 3H, one isomer) [ppm]

Preparation Example H1-46: Preparation of Compound P26

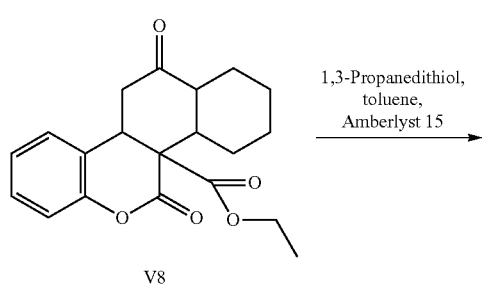

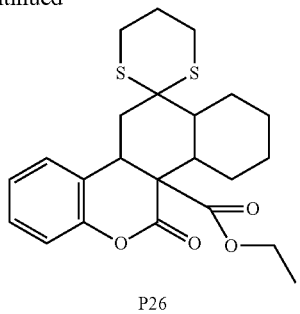

1.0 g (2.9 mmol) of ketoester V8 are admixed with 0.63 g (5.8 mmol, 2.0 eq) of 1,3-propanedithiol, 10 ml of toluene and 0.1 g of Amberlyst 15 and stirred at 60° C. for 24 h. 0.4 g of 4 Å molecular sieve are added and the mixture is stirred at 60° C. for a further hour. The mixture is filtered and the resulting solution is concentrated by evaporation. The residue is crystallized from iPrOH, and the suspension is cooled in an ice bath and filtered. The filter cake is washed with a small amount of iPrOH and dried in a vacuum drying cabinet at 40° C.

Yield (P26): 0.85 g (67%) with an HPLC purity of 98.9 area %

¹H-NMR (CDCl₃): 7.32-6.98 (m, 4H); 4.10-3.89 (m, 2H); 3.74 (d, 1H); 3.11-2.94 (m, 2H); 2.87 (d, 1H); 2.75 (d, 1H); 2.70-2.55 (m, 1H); 2.44-2.22 (m, 3H); 2.13-1.96 (m, 2H); 1.89-1.67 (m, 4H); 1.56 (q, 1H); 1.46 (d, 1H); 1.33 (q, 1H); 1.22-1.09 (m, 1H); 0.92 (tr, 3H) [ppm]

Preparation Example H1-47: Preparation of Compound P27

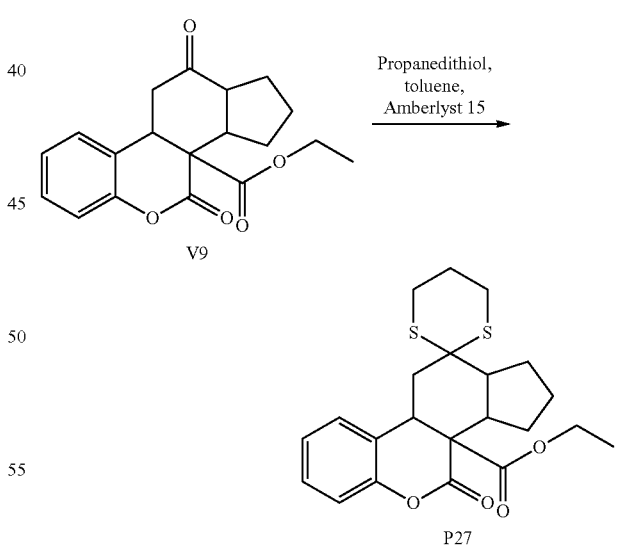

1.2 g (3.65 mmol) of ketoester V9 are admixed with 0.79 g (7.3 mmol, 2.0 eq) of 1,3-propanedithiol, 12.5 ml of toluene and 0.12 g of Amberlyst 15 and stirred at 80° C. for 20 h. The mixture is filtered and the organic phase is washed with 15 ml of saturated sodium hydrogencarbonate solution and with 10 ml of water. The organic phase is concentrated on a rotary evaporator and the residue is crystallized from MTBE/heptane with a few drops of iPrOH.

Yield (P27): 0.85 g (56%) with an HPLC purity of 100 area % (two isomers)

¹H-NMR (CDCl₃): 7.32-6.99 (m, 4H); 4.09-3.96 (m, 2H); 3.93 (d, 1H, one isomer); 3.69 (d, 1H, one isomer); 3.15-2.73 (m, 4H); 2.67-1.40 (m, 12H); 1.05 (tr, 3H, one isomer); 0.97 (tr, 3H, one isomer) [ppm]

Preparation Example H1-48: Preparation of Compound V10

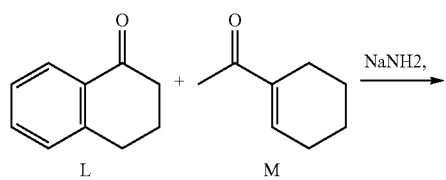

The preparation takes place analogously to: Peak, Robinson, *J. Chem. Soc.*, 1936, 759-762 or Peak, Robinson, *J. Chem. Soc.*, 1937, 1881-1583.

CAS (product): 99887-26-0

Preparation Example H1-49: Preparation of Compound V11

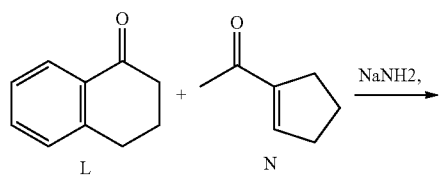

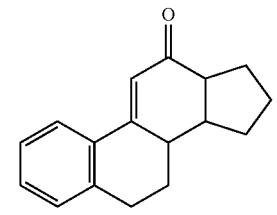

The preparation takes place analogously to: Hawthorne, Robinson, *J. Chem. Soc.*, 1936, 763.

CAS (product): 31301-53-8

Preparation Example H1-50: Preparation of Compound P28

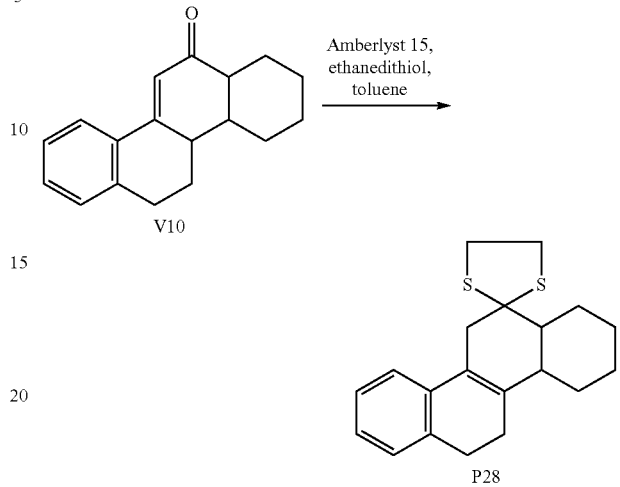

1.5 g (5.94 mmol) of ketone V10 are admixed with 0.70 g (7.43 mmol, 1.25 eq) of ethanedithiol, 10 ml of toluene and 0.3 g of Amberlyst 15 and stirred overnight at 80-100° C. The mixture is filtered and the filtrate is concentrated on a rotary evaporator. The residue is crystallized from n-heptane and dried at RT in a vacuum drying cabinet.

Yield (P28): 1.35 g (69%)

¹H-NMR (CDCl₃): 7.14-6.95 (m, 4H); 3.34-3.05 (m, 5H); 2.98 (d, 1H); 2.81-2.60 (m, 2H); 2.39-2.04 (m, 5H); 1.92-1.71 (m, 2H); 1.65 (tr, 1H); 1.32 (br s, 3H), 0.93-0.78 (m, 1H) [ppm]

Preparation Example H1-51: Preparation of Compound P9

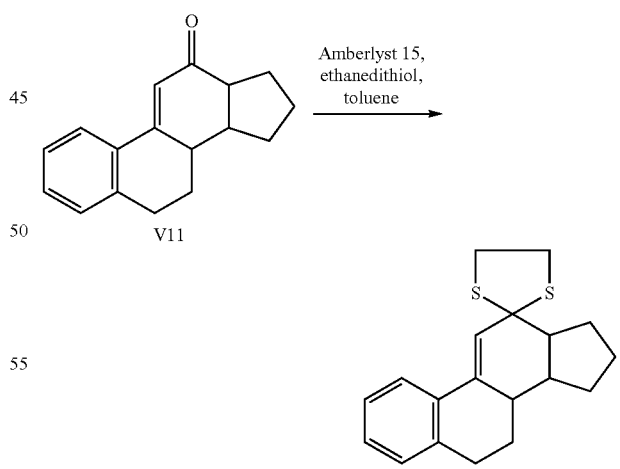

1.2 g (5.04 mmol) of ketone V11 are admixed with 0.52 g (5.54 mmol, 1.1 eq) of ethanedithiol, 15 ml of toluene and 0.2 g of Amberlyst 15 and stirred for 2 h at 80-100° C. The mixture is filtered and the filtrate is concentrated on a rotary evaporator. The residue is crystallized from n-heptane and dried at RT in a vacuum drying cabinet.

Yield (P29): 0.60 g (38%) with an HPLC purity of 88.4 area %

$^1$H-NMR (CDCl$_3$): 7.69 (d, 1H); 7.20-7.00 (m, 3H); 6.43 (s, 1H); 3.47-3.20 (m, 3H); 3.20-3.07 (m, 1H); 2.91-2.75 (m, 2H); 2.13-1.23 (m, 11H) [ppm]

Preparation Example H1-52: Preparation of Compound P30

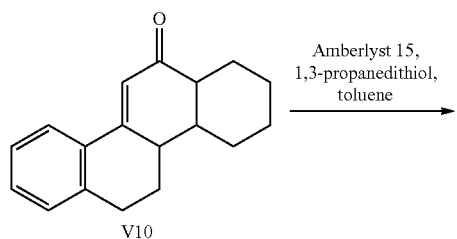

1.5 g (5.94 mmol) of ketone V10 are admixed with 0.80 g (7.43 mmol, 1.25 eq) of 1,3-propanedithiol, 10 ml of toluene and 0.3 g of Amberlyst 15 and stirred at 80-100° C. for 26 h. The mixture is filtered and the filtrate is concentrated on a rotary evaporator. The residue is crystallized from n-heptane and dried at 30° C. in a vacuum drying cabinet.

Yield: 1.06 g (52%) with an HPLC purity of 90.0 area %

$^1$H-NMR (CDCl$_3$): 7.25-7.01 (m, 4H); 3.50 (d, 1H); 3.23 (tr, 1H); 3.04-2.63 (m, 5H); 2.59 (dtr, 1H); 2.37 (d, 1H); 2.35-2.01 (m, 5H); 1.96-1.70 (m, 3H); 1.70-1.53 (m, 1H); 1.51-1.22 (m, 3H); 0.96-0.83 (m, 1H) [ppm]

Preparation Example H1-53: Preparation of Compound P31

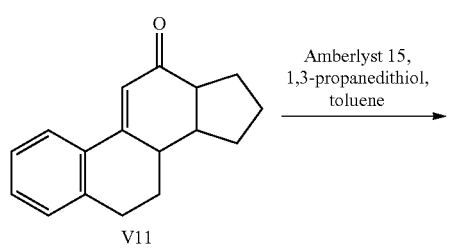

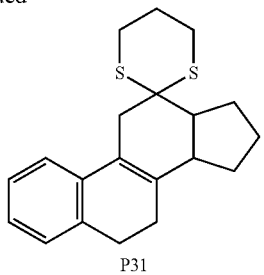

1.2 g (5.04 mmol) of ketone V11 are admixed with 0.60 g (5.54 mmol, 1.1 eq) of 1,3-propanedithiol, 15 ml of toluene and 0.2 g of Amberlyst 15 and stirred for 2 h at 80-100° C. The mixture is filtered, the filtrate is concentrated on a rotary evaporator and the residue is purified by column chromatography.

Yield: 1.08 g (65%)

$^1$H-NMR (CDCl$_3$): 7.24-7.03 (m, 4H); 3.03-2.63 (m, 8H); 2.33-2.21 (m, 1H); 2.16-1.61 (m, 7H); 1.60-1.40 (m, 2H); 1.35-1.18 (m, 2H); 0.91-0.83 (m, 1H) [ppm]

3. Formulation Examples

In the formulation examples which follow, without being limited thereto, the active ingredient ("TRPM8 agonist") used is in particular compounds according to tables 1 and 2 A to D.

a) Mouthcare

Formulation Example FM-1: Mouthwash

Suitable mouthwashes can be prepared according to the following base formulation:

| % by wt. | Ingredient type | Ingredient examples |
|---|---|---|
| 0.01-0.1% | Antibacterial agents | Beta-naphthol, thymol, chlorothymol and hexylresorcinol |
| 5-25% | Humectants | Glycerol, sorbitol, propylene glycol and polyalkylene glycol |
| 0.01-0.2% | Essential oils | Clove oil, peppermint oil and spearmint oil |
| 0-30% | Ethanol | |
| 0-5% | Polymer | Polyoxyalkylene block copolymers Mw 5000-30000 |
| 40-80% | Water | |
| 0.001-10% | TRPM8 agonist | |
| 0-10% | Further additives | |

A mouthwash of the following composition is prepared:

| Fraction | Ingredient |
|---|---|
| 177 ml | Ethanol 95% |
| 250 g | Sorbitol 70% |
| 50 ml | TRPM8 agonist as 1% solution in the ethanol |
| 0.30 g | Peppermint oil |
| 0.64 g | Methyl salicylate |
| 0.922 g | Eucalyptol |
| 0.639 g | Thymol |
| 1.50 g | Benzoic acid |

-continued

| Fraction | Ingredient |
|---|---|
| 5.00 g | Pluronic ® F127 nonionic surfactant |
| 0.60 g | Sodium saccharin |
| 0.30 g | Sodium citrate |
| 0.10 g | Citric acid |
| q.s. 1 liter | Water |

To prepare a mouthwash, the above-described components are mixed together in the stated amounts.

Formulation Example FM-2: Toothpaste

Suitable toothpastes can be prepared according to the following basic formulation:

| % by wt. | Ingredient type | Ingredient examples |
|---|---|---|
| 0.05-0.2% | Fluorides | Sodium fluoride, tin(II) fluoride, Sodium monofluorophosphate; |
| 10-55% | Humectants | Glycerol, sorbitol, propylene glycol, polyalkylene glycol |
| 0-50% | Polymers | Polyoxyalkylene block copolymers Mw 5000-30000 |
| 10-50% | Water | |
| 10-55% | Abrasives | Calcium pyrophosphate, dicalcium phosphate, silicon oxide hydrate; |
| 2-10% | Binder | Karaya gum, tragacanth USP, sodium alginate, Irish moss, methylcellulose |
| 2-8% | Surfactant | Sodium lauryl sulfate, sodium N-laurylsarcosinate, dioctyl sodium sulfosuccinate, sodium lauryl sulfoacetate |
| 0-10% | Peroxygen compound | Hydrogen peroxide, inorganic peroxides |
| 0.001-10% | TRPM8 agonist | |
| 0-10% see above | Further additives | |

Formulation Example FM-3: Chewing Gum

Suitable chewing gums can be prepared according to the following basic formulation:

| % by wt. | Ingredient |
|---|---|
| 15-25% | Chewing gum base |
| 20-30% | Glucose syrup |
| 50-60% | Icing sugar |
| 0.001-10% | TRPM8 agonist |
| 1-2% | Plasticizer (e.g. glycerol) |
| 3-6% | Water |

Instead of the glucose syrup and the icing sugar, for "sugar-free" formulations, the sugar alcohols mannitol, xylitol and sorbitol, "Palatinitol" and others, as well as artificial sweeteners, such as saccharin, cyclamate, acesulfame-K and aspartame, can also be used.

b) Bodycare

Formulation Example FK-1: Hair Tonic

| | % | Ingredient (INCI) |
|---|---|---|
| A | q.s. | Perfume oil |
| | 1.00 | PEG-40 hydrogenated castor oil |

| | % | Ingredient (INCI) |
|---|---|---|
| B | 65.0 | Alcohol |
| | 1.0 | Panthenol |
| | 0.5 | Polyquarternium-16 |
| | 0.1 | Menthol |
| | 27.4 | Aqua dem. |
| | 5.00 | Aqueous solution with ca. 0.001-10% TRPM8 agonist |

Preparation: Mix phase A. Add phase B and stir until everything has dissolved, adjust pH to pH 7.0.

Formulation Example FK-2: Hair Gel

| | % | Ingredient (INCI) |
|---|---|---|
| A | 45.00 | Carbopol 940 1% in water |
| | 0.70 | Aminomethyl propanol |
| B | 7.50 | VP/methacrylamide/vinyl imidazole copolymer |
| | 0.10 | Perfume oil |
| | 0.30 | PEG-40 hydrogenated castor oil |
| | 0.30 | Preservative |
| | 0.05 | Disodium EDTA |
| | 0.30 | Panthenol |
| | 8.00 | Alcohol |
| | 5.00 | Aqueous solution with ca. 0.001-10% TRPM8 agonist |
| | 32.75 | Aqua dem. |

Preparation: Weigh in the components of phase A and homogenize. Dissolve phase B and stir into phase A. Adjust pH to pH 6.9.

Formulation Example FK-3: Cosmetic Sunscreen Preparation

In the following formulations, a cosmetic sunscreen preparation comprising a combination of at least inorganic pigment and organic UV filter is described.

The preparation of the formulations specified below takes place in a customary manner known to the person skilled in the art.

| | | | |
|---|---|---|---|
| A | 7.50 | Uvinul MC 80 | Ethylhexyl cinnamate |
| | 2.00 | Uvinul M 40 | Benzophenone-3 |
| | 0.80 | Rylo PG 11 | Polyglyceryl dimmer soyate |
| | 1.00 | Span 60 | Sorbitan stearate |
| | 0.50 | Vitamin E acetate | Tocopheryl acetate |
| | 3.00 | Dracorin 100 SE | Glyceryl stearate, PEG-100 stearate |
| | 1.00 | Cremophor CO 410 | PEG-40-hydrogenated castor oil |
| B | 3.00 | T-Lite SF | Titanium dioxide, aluminum oxide hydrate, dimethicone/methicone copolymer |
| | 1.00 | Cetiol SB 45 | *Butyrospermum parkii* (Shea Butter) |
| | 6.50 | Finsolv TN | $C_{12-15}$-alkyl benzoate |
| C | 5.00 | Butylene glycol | Butylene glycol |
| | 0.30 | Keltrol | Xanthan gum |
| | 0.10 | Edeta BD | Disodium EDTA |
| | 0.10 | Allantoin | Allantoin |
| | 66.20 | Water dem. | Aqua dem. |
| D | 1.00 | Sepigel 305 | Polyacrylamide, $C_{13-14}$-isoparaffin, laureth-7 |
| | 0.001-10% | | TRPM8 agonist |
| | q.s. | | Preservative |

Formulation Example FK-4: Moisturizing Bodycare Cream

| | % | Ingredient (INCI) |
|---|---|---|
| A | 6.0 | PEG-7-hydrogenated castor oil |
| | 10.0 | Cetearyl ethylhexanoate |
| | 5.0 | Isopropyl myristate |
| | 7.0 | Mineral oil |
| | 0.5 | Shea Butter (*Butyrospermum parkii*) |
| | 0.5 | Aluminum stearate |
| | 0.5 | Magnesium stearate |
| | 0.2 | Bisabolol |
| | 0.7 | Quaternium-18 hectorite |
| B | 5.0 | Dipropylene glycol |
| | 0.7 | Magnesium sulfate |
| | q.s. | Preservative |
| | 62.9 | Aqua dem. |
| | q.s. | Perfume oil |
| C | 1.0 | Aqueous solution with 0.001-10% TRPM8 agonist |

Preparation: Heat phases A and B separately to ca. 80° C. Stir phase B into phase A and homogenize. Cool with stirring to ca. 40° C., add phase C and homogenize again. Allow to cool with stirring to room temperature.

Formulation Example FK-5: Care Shampoo

| | % | Ingredient (INCI) |
|---|---|---|
| A | 30.0 | Sodium laureth sulfate |
| | 6.0 | Sodium cocoamphoacetate |
| | 6.0 | Cocamidopropylbetaine |
| | 3.0 | Sodium laureth sulfate, glycol distearate, cocamide-MEA, laureth-10 |
| | 1.0 | Aqueous solution with 0.001-10% TRPM8 agonist |
| | 7.7 | Polyquaternium-44 |
| | 2.0 | Amodimethicone |
| | q.s. | Perfume oil |
| | q.s. | Preservative |
| | 1.0 | Sodium chloride |
| | 43.3 | Aqua dem. |
| B | q.s. | Citric acid |

Preparation: Mix the components of phase A and dissolve. Adjust the pH to 6-7 with citric acid.

Formulation Example FK-6: Shower Gel

| | % | Ingredients (INCI) |
|---|---|---|
| A | 40.0 | Sodium laureth sulfate |
| | 5.0 | Decyl glucoside |
| | 5.0 | Cocamidopropylbetaine |
| | 1.0 | Aqueous solution with 0.001-10% TRPM8 agonist |
| | 1.0 | Panthenol |
| | q.s. | Perfume oil |
| | q.s. | Preservative |
| | 2.0 | Sodium chloride |
| | 46.0 | Aqua dem. |
| B | q.s. | Citric acid |

Preparation: Mix the components of phase A and dissolve. Adjust the pH to 6-7 with citric acid.

Formulation Example FK-7: Shampoo

| | % | Ingredients (INCI) |
|---|---|---|
| A | 40.0 | Sodium laureth sulfate |
| | 5.0 | Sodium $C_{12-15}$-pareth-15-sulfonate |
| | 5.0 | Decyl glucoside |
| | q.s. | Perfume oil |
| | 0.1 | Phytantriol |
| | 44.6 | Aqua dem. |
| | 1.0 | Aqueous solution with 0.001-10% TRPM8 agonist |
| | 0.3 | Polyquaternium-10 |
| | 1.0 | Panthenol |
| | q.s. | Preservative |
| | 1.0 | Laureth-3 |
| | 2.0 | Sodium chloride |

Preparation: Mix the components of phase A and dissolve. Adjust the pH to 6-7 with citric acid.

Formulation Example FK-8: Foot Balm

| | % | Ingredients (INCI) |
|---|---|---|
| A | 2.0 | Ceteareth-6, stearyl alcohol |
| | 2.0 | Ceteareth-25 |
| | 5.0 | Cetearyl ethylhexanoate |
| | 4.0 | Cetyl alcohol |
| | 4.0 | Glyceryl stearate |
| | 5.0 | Mineral oil |
| | 0.2 | Menthol |
| | 0.5 | Camphor |
| B | 69.3 | Aqua dem. |
| | q.s. | Preservative |
| C | 1.0 | Bisabolol |
| | 1.0 | Tocopheryl acetate |
| D | 1.0 | Aqueous solution with 0.001-10% TRPM8 agonist |
| | 5.0 | Witch hazel extract |

Preparation: Heat the components of phases A and B separately to ca. 80° C. Stir phase B into phase A with homogenization. Cool to ca. 40° C. with stirring, add phases C and D and briefly after homogenize. Cool to room temperature with stirring.

Formulation Example FK-9: Face Cleansing Lotion—O/W Type

| | % | Ingredients (INCI) |
|---|---|---|
| A | 10.0 | Cetearyl ethylhexanoate |
| | 10.0 | Caprylic/capric triglyceride |
| | 1.5 | Cyclopentasiloxane, cyclohexasiloxane |
| | 2.0 | PEG-40-hydrogenated castor oil |
| B | 3.5 | Caprylic/capric triglyceride, sodium acrylate copolymer |
| C | 1.0 | Tocopheryl acetate |
| | 0.2 | Bisabolol |
| | q.s. | Preservative |
| | q.s. | Perfume oil |
| D | 3.0 | Polyquaternium-44 |
| | 0.5 | Cocotrimonium methosulfate |
| | 0.5 | Ceteareth-25 |
| | 2.0 | Panthenol, propylene glycol |
| | 4.0 | Propylene glycol |
| | 0.1 | Disodium EDTA |
| | 1.0 | Aqueous solution with 0.001-10% TRPM8 agonist |
| | 60.7 | Aqua dem. |

Preparation: Dissolve phase A. Stir phase B into phase A, incorporate phase C into the combined phases A and B. Dissolve phase D, stir into the combined phases A, B and C and homogenize. Afterstir for 15 min.

Formulation Example FK-10: Body Spray

| | % | Ingredients (INCI) |
|---|---|---|
| A | 3.0 | Ethylhexyl methoxycinnamate |
| | 2.0 | Diethylaminohydroxybenzoyl hexylbenzoate |
| | 1.0 | Polyquaternium-44 |
| | 3.0 | Propylene glycol |
| | 2.0 | Panthenol, propylene glycol |
| | 1.0 | Cyclopentasiloxane, cyclohexasiloxane |
| | 10.0 | Octyldodecanol |
| | 0.5 | PVP |
| | 10.0 | Caprylic/capric triglyceride |
| | 3.0 | $C_{12-15}$-alkyl benzoate |
| | 3.0 | Glycerol |
| | 1.0 | Tocopheryl acetate |
| | 0.3 | Bisabolol |
| | 1.0 | Aqueous solution with 0.001-10% TRPM8 agonist |
| | 59.2 | Alcohol |

Preparation: Weigh in the components of phase A and dissolve to give a clear solution.

Formulation Example FK-11: Skincare Gel

| | % | Ingredients (INCI) |
|---|---|---|
| A | 3.6 | PEG-40-hydrogenated castor oil |
| | 15.0 | Alcohol |
| | 0.1 | Bisabolol |
| | 0.5 | Tocopheryl acetate |
| | q.s. | Perfume oil |
| B | 3.0 | Panthenol |
| | 0.6 | Carbomer |
| | 1.0 | Aqueous solution with 0.001-10% TRPM8 agonist |
| | 75.4 | Aqua dem. |
| C | 0.8 | Triethanolamine |

Formulation Example FK-12: Aftershave Lotion

| | % | Ingredients (INCI) |
|---|---|---|
| A | 10.0 | Cetearyl ethylhexanoate |
| | 5.0 | Tocopheryl acetate |
| | 1.0 | Bisabolol |
| | 0.1 | Perfume oil |
| | 0.3 | Acrylates/$C_{10-30}$ alkyl acrylate crosspolymer |
| B | 15.0 | Alcohol |
| | 1.0 | Panthenol |
| | 3.0 | Glycerol |
| | 1.0 | Aqueous solution with 0.001-10% TRPM8 agonist |
| | 0.1 | Triethanolamine |
| | 63.5 | Aqua dem. |

Preparation: Mix the components of phase A. Dissolve phase B, incorporate into phase A and homogenize.

Formulation Example FK-13: Aftersun Lotion

| | % | Ingredients (INCI) |
|---|---|---|
| A | 0.4 | Acrylates/$C_{10-30}$-alkyl acrylate crosspolymer |
| | 15.0 | Cetearyl ethylhexanoate |
| | 0.2 | Bisabolol |
| | 1.0 | Tocopheryl acetate |
| | q.s. | Perfume oil |
| B | 1.0 | Panthenol |
| | 15.0 | Alcohol |
| | 3.0 | Glycerol |
| | 1.0 | Aqueous solution with 0.001-10% TRPM8 agonist |
| | 63.2 | Aqua dem. |
| C | 0.2 | Triethanolamine |

Preparation: Mix the components of phase A. Stir phase B into phase A with homogenization. Neutralize with phase C and homogenize again.

Formulation Example FK-14: Sunscreen Lotion

| | % | Ingredients (INCI) |
|---|---|---|
| A | 4.5 | Ethylhexyl methoxycinnamate |
| | 2.0 | Diethylaminohydroxybenzoyl hexylbenzoate |
| | 3.0 | Octocrylene |
| | 2.5 | Di-$C_{12-13}$-alkyl malate |
| | 0.5 | Tocopheryl acetate |
| | 4.0 | Polyglyceryl-3-methylglucose distearate |
| B | 3.5 | Cetearyl isononanoate |
| | 1.0 | VP/Eicosene copolymer |
| | 5.0 | Isohexadecane |
| | 2.5 | Di-$C_{12-13}$-alkyl malate |
| | 3.0 | Titanium dioxide, trimethoxycaprylylsilane |
| C | 5.0 | Glycerol |
| | 1.0 | Sodium cetearyl sulfate |
| | 0.5 | Xanthan gum |
| | 59.7 | Aqua dem. |
| D | 1.0 | Aqueous solution with 0.001-10% TRPM8 agonist |
| | 1.0 | Phenoxyethanol, methylparaben, ethylparaben, butylparaben, propylparaben, isobutylparaben |
| | 0.3 | Bisabolol |

Preparation: Heat the components of phases A and B separately to ca. 80° C. Stir phase B into phase A and homogenize. Heat phase C to ca. 80° C. and stir into the combined phases A and B with homogenization. Cool to ca. 40° C. with stirring, add phase D and homogenize again.

Formulation Example FK-15: Plaster 50 parts of active ingredient according to preparation example H 3-7 were dispersed in 100 parts of a 10% strength sodium lauryl sulfate solution with vigorous stirring and heating to 50° C. 880 parts of a 50% strength butyl acrylate dispersion were stirred into the resulting emulsion and the resulting active-ingredient-containing polymer dispersion was spread out using a suitable spreading knife on a polyester film with a thickness of 15 μm (Kalle, D-Wiesbaden) and dried at 35 to 40° C. with controlled atmospheric humidity. Depending on the knife setting, weights per area of 5 mg/cm² resulted, which could be further increased through repeated application. The self-adhesive film produced in this way and having an active ingredient content of 5% was provided with a siliconized peelable film made of polyester (Scotch Pak 75 mu m, 3M) and cut to the desired dimensions.

The quantitative data refer in each case to parts by weight.

c) Foods

Formulation Example FN-1: Blancmange

Formulation (for 100 ml)

| Ingredient | Amount |
| --- | --- |
| Fat-free dried milk | 10.715 g |
| Sucrose | 5 g |
| Novelose starch, National Starch | 7 g |
| Vegetable oil mixture | 2.2 g |
| Carrageenan | 0.016 g |
| Vanilla flavoring | 0.5 g |
| Sodium stearoyl-2-lactylate | 0.095 g |
| Yellow dye | 0.189 g |
| Magnesium phosphate | 0.165 g |
| Vitamin premix | 1.84 g |
| Trace element premix | 0.015 g |
| TRPM8 agonist | 0.5 g |
| Water | 81.94 g |

Preparation:

Heat nine tenths of the water to 43.3° C. Dissolve low-fat milk powder in the water. Heat oil to 60° C. and add carrageenan and oil-soluble vitamins to the oil. Mix oil into the product. Add the other constituents apart from the modified starch, vanilla flavoring and vitamin premix. Homogenize the mixture. Slowly add starch. Add active ingredient, vitamins and flavoring. Standardize solids content. Heat in sterile units and package in cans.

d) Formulation Example FT-1: Textile Finishing with Active Ingredients According to the Invention Firstly, an aqueous slurry of amylase-containing starch is prepared by admixing 570 g of deionized water with 10 g of a standard commercial preservative. 20 g of carboxymethylcellulose were dissolved therein, then 400 g of an amylase-containing starch with an amylase content of 50% by weight were added and a slurry was prepared with stirring.

Aqueous liquors with amylase-containing starch were then prepared by one of the two following methods:

Method 1: The respective slurry is adjusted to a starch content of 5 or 15% by weight by dilution with water.

Method 2: The respective slurry is firstly diluted to a starch content of 5 or 15% by weight with water and then admixed with 30 g/l of a 30% strength by weight aqueous polyurethane dispersion (nonionogenic).

The finishing of a fabric with amylase-containing starch and active ingredient according to the invention then takes place:

Cotton fabric sample with a weight per area of 124 g/m² is treated with one of the above-prepared liquors using a padder up to a liquor absorption of 80% by weight, based on the weight of the fabric. Drying is then carried out for 2 min at 120° C.

The fabric samples finished in this way are then treated with an aqueous active ingredient formulation by padding an aqueous emulsion/suspension of an active ingredient according to the invention with an active ingredient content of from 1 to 7% by weight onto the fabric sample up to a liquor absorption of 79-80% by weight. The fabric samples treated in this way are then dried in a domestic dryer to a residual moisture of 15%.

The active-ingredient-loaded fabric produced in this way can then be further investigated, such as e.g. as to their cooling effect upon skin contact or their repellent effect on insects.

Further Formulation Examples

Example S-1—Preparation of Aromas with Cooling Effect of the *Eucalyptus* Menthol Type Using the Cooling Substances According to the Invention The following were mixed (all data, unless noted otherwise, in % by weight):

| Component | |
| --- | --- |
| Anethol | 10 |
| Peppermint oil *Mentha piperita* Willamette type | 20 |
| Peppermint oil *Mentha arvensis*, rectified | 20 |
| l-Menthyl lactate | 1 |
| 2-Hydroxyethyl menthyl carbonate | 2 |
| 2-Hydroxypropyl menthyl carbonate | 2 |
| 1,8-Cineol (Eucalyptol) | 5 |
| l-Menthol | 39.4 |
| TRPM8 Agonist | 0.6 |
| Total | 100 |

The aromas obtained in this way were incorporated into a standard toothpaste mass based on silica in a concentration of 1.2% by weight.

Example S-2—Preparation of Aromas with Cooling Effect of the Spearmint Type Using the Cooling Substances According to the Invention The following were mixed (all data, unless noted otherwise, in % by weight):

| Component | |
| --- | --- |
| Menthol | 29.25 |
| Carvone | 20 |
| Spearmint oil, native type | 20 |
| Anethol | 5 |
| Peppermint oil *Mentha arvensis* rectified | 10 |
| Peppermint oil *Mentha piperita* Willamette type | 15 |
| TRPM8 Agonist | 0.75 |
| Total | 100 |

The aromas obtained were incorporated with a concentration of 1.2% into a toothpaste mass which consists to a fraction of 65% of sodium bicarbonate.

Example S-3—Preparation of Aromas with Cooling Effect and a Spicy-Aromatic Taste Impression Using the Cooling Substances According to the Invention The following were mixed (all data, unless noted otherwise, in % by weight):

| Component | |
|---|---|
| l-Menthol | 29.2 |
| Peppermint oil *Mentha arvensis*, rectified | 25 |
| Peppermint oil *Mentha piperita* Willamette type | 15 |
| Anethol | 10 |
| Spearmint oil, native | 10 |
| Cinnamaldehyde | 5 |
| Eugenol | 5 |
| TRPM8 Agonist | 0.8 |
| Total | 100 |

The aromas obtained in this way were each incorporated into a standard toothpaste mass based on silica in a concentration of 1.2% by weight.

Example S-4—Preparation of Aromas with Cooling Effect and Wintergreen Taste Using the Cooling Substances According to the Invention The following were mixed (all data, unless noted otherwise, in % by weight):

| Component | |
|---|---|
| Anethol | 10 |
| Peppermint oil *Mentha arvensis* | 12 |
| Peppermint oil *Mentha piperita* Willamette type | 12 |
| Methyl salicylate | 25 |
| l-Menthol | 40.5 |
| Compounds of the formula . . . | 0.5 |
| Total | 100 |

The aromas obtained in this way were incorporated into a standard toothpaste mass based on silica in a concentration of 1.2% by weight.

Example S-5—Preparation of Aromas with Cooling Effect and Peppermint Taste Using the Cooling Substances According to the Invention The following were mixed (all data, unless noted otherwise, in % by weight):

| Component | |
|---|---|
| Peppermint oil *Mentha arvensis* | 59 |
| l-Menthone | 20 |
| l-Menthol | 20 |
| TRPM8 Agonist | 1 |
| Total | 100 |

The aromas obtained in this way were each incorporated into a sugar-free standard chewing gum mass in a concentration of 1.5% by weight.

Example S-6—Preparation of Aromas with Cooling Effect and Spearmint Taste Using the Cooling Substances According to the Invention The following were mixed (all data, unless noted otherwise, in % by weight):

| Component | |
|---|---|
| Peppermint oil *Mentha piperita*, Madras type | 50 |
| Eucalyptol | 20 |
| l-Menthol | 13.5 |
| l-Menthone | 10 |
| Spearmint oil, Midwest Scotch type | 5 |
| TRPM8 Agonist | 1.5 |
| Total | 100 |

The aromas obtained in this way were each incorporated into a sugar-free standard chewing gum mass in a concentration of 1.5% by weight.

Example S-7—Preparation of Aromas with Cooling Effect and an Aromatic-Spicy Cinnamon Taste Using the Cooling Substances According to the Invention The following were mixed (all data, unless noted otherwise, in % by weight):

| Component | |
|---|---|
| Menthyl methyl ether | 3 |
| Cinnamaldehyde | 10 |
| Anethol | 10 |
| Eugenol | 2 |
| Peppermint oil *Mentha piperita*, Madras type | 10 |
| Peppermint oil *mentha arvensis* | 10 |
| Spearmint oil, Midwest Scotch type | 10 |
| l-Menthol | 40 |
| 2-Hydroxyethyl menthyl carbonate | 2 |
| 2-Hydroxypropyl menthyl carbonate | 2 |
| TRPM8 Agonist | |
| Total | 100 |

The aromas obtained in this way were each incorporated into a sugar-free standard chewing gum mass in a concentration of 1.5% by weight.

Example S-8—Preparation of Mouthwash Aromas with Cooling Effect Using the Cooling Substances According to the Invention The following were mixed (all data, unless noted otherwise, in % by weight):

| Component | |
|---|---|
| Anethol | 30 |
| Eucalyptol | 25 |
| l-Menthol | 44.4 |
| TRPM8 Agonist | 0.6 |
| Total | 100 |

The aromas were each incorporated with a concentration of 0.15% by weight into a ready-to-use mouthwash, and/or with a concentration of 3% by weight into a mouthwash concentrate.

Example S-9—Toothpaste ('Silica Opaque')

All data, unless noted otherwise, in % by weight.

| Constituent | |
| --- | --- |
| Deionized water | 26.53 |
| Sorbitol 70% | 45 |
| Solbrol M Na salt | 0.15 |
| Trisodium phosphate | 0.1 |
| Saccharin | 0.2 |
| Sodium monofluorophosphate | 1.12 |
| PEG 1500 | 5 |
| Sident 9 (abrasive silica) | 10 |
| Sident 22 S (thickening silica) | 8 |
| Sodium carboxymethylcellulose | 0.9 |
| Titanium(IV) oxide | 0.5 |
| Sodium lauryl sulfate (SLS) | 1.5 |
| Pellitorine solution PLM (comprising 10% Pellitorine) | — |
| Aroma, *eucalyptus* menthol type (example S-1) | 1 |

Example S-10—Toothpaste (Calcium Carbonate Base)

All data, unless noted otherwise, in % by weight.

| Constituent | |
| --- | --- |
| Deionized water | 27.5 |
| Saccharin | 0.2 |
| Solbrol M sodium salt | 0.2 |
| Sodium monofluorophosphate | 0.8 |
| Sorbitol 70% | 29 |
| Calcium carbonate | 35 |
| Sident 22 S (thickening silica) | 2.5 |
| Sodium carboxymethylcellulose | 1.3 |
| Titanium dioxide | 0.5 |
| Sodium lauryl sulfate | 2 |
| Pellitorine solution PLM (comprising 10% Pellitorine) | — |
| Aroma, *eucalyptus* menthol type (example S-1) | 1 |

Example S-20—Sugar-Free Chewing Gum

All data, unless noted otherwise, in % by weight.

| Constituent | 1 |
| --- | --- |
| Gum base (chewing gum base) | 30 |
| Sorbitol, powdered | 40 |
| Isomalt, powdered | 9.5 |
| Xylitol | 2 |
| Mannitol D | 3 |
| Aspartame | 0.1 |
| Acesulfame K | 0.1 |
| EmulgumTM (soya lecithin with high content of phospholipids) | 0.3 |
| Sorbitol (70% in water) | 13 |
| 1,2-Propylene glycol | — |
| Glycerol | 1 |
| Pellitorine solution PLM (comprising 10% pellitorine) | — |
| *Eucalyptus* aroma, peppermint type (example S-5) | 1 |

Example S-22—Sugar-Free Chewing Gums

The chewing gum base K1 consisted of 2.0% butyl rubber (isobutene-isoprene copolymer, MW=400 000, 6.0% polyisobutene (MW=43 800), 43.5% polyvinyl acetate (MW=12 000), 31.5% polyvinyl acetate (MW=47 000), 6.75% triacetin and 10.25% calcium carbonate. The preparation of the chewing gum base K1 and of the chewing gums can take place analogously to U.S. Pat. No. 5,601,858.

All data, unless noted otherwise, in % by weight.

| Constituent | |
| --- | --- |
| Chewing gum base K1 | 26 |
| Triacetin | 0.25 |
| Lecithin | 0.5 |
| Sorbitol, crystalline | Ad 100 |
| Mannitol | 15.3 |
| Glycerol | 12.1 |
| Saccharin Na | 0.17 |
| Encapsulated aspartame | 1.08 |
| Amorphous silica | 1 |
| Cottonseed oil | 0.5 |
| Polyoxyethylene sorbitan monolaurate (E-432) | 1 |
| encapsulated l-carvone (loading: 30%) | — |
| l-Menthyl l-lactate | — |
| Aroma, spearmint type (example S-6) | 1 |

Example S-26—Bonbons ('Hardboiled Candy')

All data, unless noted otherwise, in % by weight.

| Constituent | |
| --- | --- |
| Water | 2.75 |
| Sugar | 60.1 |
| Glucose syrup | 36.9 |
| Maltose | — |
| Palm kernel oil | — |
| Citric acid | — |
| *Ginseng* extract | — |
| Blue dye | — |
| Aroma, spearmint type (example S-2) | 0.25 |

Example S-27—Instant Beverage Powder

All data, unless noted otherwise, in % by weight.

| Constituent | |
| --- | --- |
| Sugar (sucrose) | Ad 100 |
| Citric acid | 11.58 |
| Trisodium citrate | 0.7 |
| Tricalcium phosphate | 0.6 |
| Vitamin C | 0.66 |
| Grindsted ® JU 543 Stabilizer System (Danisco) | 0.9 |
| Saccharin | 0.561 |
| Lemon aroma, spray-dried | 1.75 |
| Orange aroma, spray-dried | |
| Aroma, *eucalyptus* menthol type (example S-1), spray-dried on maltodextrin (DE 15-19) and gum arabic, aroma loading 40% | 1.75 |

45 g of this instant beverage powder were dissolved in each case in 1000 ml with stirring. The beverages obtained had a refreshing, cooling taste of citrus, cinnamon and mint.

Example S-31—Preparation of an Extrudate for Providing Beverage Mixtures with a Cooling Effect All data, unless noted otherwise, in % by weight.

| Constituent | |
|---|---|
| Glucose syrup, spray-dried (DE value: 31-34) [Glucidex IT33W (Roquette)] | 62.0 |
| Maltodextrin (DE value: 17-20), Cerestar | 28.4 |
| Emulsifier Monomuls, emulsifier based on hydrogenated palm oil; melting point: 64° C. (Grünau) | 1.8 |
| Dextrose monohydrate (DE value: 99.5), Cerestar | 1.8 |
| Water | 2.0 |
| Orange-vanilla aroma | 3.2 |
| Aroma, *eucalyptus* menthol type (example S-1) | 0.8 |

Preparation Note (See Also WO 03/092412):

All constituents were mixed and conveyed by means of single-point dosing to a twin-screw extruder. The extrusion temperatures were between 100 and 120° C., the specific energy input was 0.2 kWh/kg. The strands emerging from the die plate (of the extruder) provided with 1 mm bores were cut directly after leaving the dies to particles with a diameter ca. 1 mm by means of rotating knives.

Example S-32—Preparation of Fluidized-Bed Granules for Providing Beverage Mixtures with a Cooling Effect In a granulation apparatus of the type shown in EP 163 836 (having the following features: diameter of inflow plate: 225 mm, spray die: two-substance die; sieving discharge: zigzag siever; filter: internal hose filter), a solution consisting of 44% by weight of water, 8% by weight of lemon aroma, 3% by weight of aroma *eucalyptus* menthol type (see example S-1), 13% by weight of gum arabic and 32% by weight of hydrolyzed starch (maltodextrin DE 15-19) and also some green dye is granulated. The solution is sprayed into the fluidized-bed granulator at a temperature of 32° C. To fluidize the bed content, nitrogen is blown in an amount of 140 kg/h. The inlet temperature of the fluidizing gas is 140° C. The temperature of the waste gas is 76° C. As sieving gas nitrogen is likewise introduced in an amount of 15 kg/h at a temperature of 50° C. The content of the fluidized bed is ca. 500 g. The granulation output is ca. 2.5 kg per hour. Free-flowing granules with an average particle diameter of 360 micrometers are obtained. The granules are round and have a smooth surface. On account of the constant pressure loss of the filter and of the likewise constant bed content, steady-state conditions with regard to the granulation process are assumed.

Example S-33—Preparation of Teabags with Rooibos and/or Black Tea and Extrudates from Example S-31 or Granules from Example S-32 for Providing Tea Beverages with a Cooling Effect In each case 800 g of red bush tea (Rooibos tea) were mixed once with 33 g of the extrudates from example S-31 and once with 30 g of granules from application example 32, portioned and then filled into teabags.

In each case 800 g of black tea (leaf grade Fannings) were mixed once with 33 g of the extrudates from example S-31 and once with 30 g of granules from example S-32, portioned and then filled into teabags.

Test Example 1—Evaluation of the Course Over Time of the Cooling Intensities of the Compounds to be Used According to the Invention The cooling substances to be used according to the invention were incorporated into toothpaste according to the following table.

TABLE

| | |
|---|---|
| Deionized water | 27.52 |
| Sorbitol 700/0 | 45 |
| Solbrol M Na salt | 0.15 |
| Trisodium phosphate | 0.1 |
| Saccharin | 0.2 |
| Sodium monofluorophosphate | 1.12 |
| PEG 1500 | 5 |
| Sident 9 (abrasive silica) | 10 |
| Sident 22 S (thickening silica) | 8 |
| Sodium carboxymethylcellulose | 0.9 |
| Titanium(IV) oxide | 0.5 |
| Sodium lauryl sulfate (SLS) | 1.5 |
| Respective cooling substance | 0.01 |
| Total | 100 |

All data in % by weight

The sensory properties of the resulting toothpaste were evaluated by a trained panel (of 6 people). For this, the teeth were cleaned using the toothpaste containing the compounds according to the invention firstly for 30 sec, then the toothpaste foam was spat out and the mouth was rinsed once with water. The subjects assessed the intensity of the sensation of coldness on a scale from 0 (no sensation of coldness) to 9 (extremely strong sensation of coldness). The assessment of the sensation of coldness was carried out in each case after 30 sec, 1, 5, 10, 20, 30, 45 and 60 min.

As compounds according to the invention from structure classes 1, 2 and 3, the compounds were tested.

For comparison, toothpastes with identical composition were tested which comprised, as conventional cooling substance, menthane-3-carboxylic-acid-N-ethylamide ("WS 3", see also U.S. Pat. No. 4,150,052).

Reference is expressly made to the disclosure of the documents cited herein.

The invention claimed is:

1. A method for the in-vitro or in-vivo modulation of the cold menthol receptor TRPM8, where the receptor is brought into contact with a substance selected from compounds P1 to P31:

| No. | Formula |
|---|---|
| P1 | |

| No. | Formula |
|-----|---------|
| P2  | 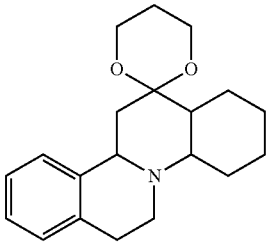 [SMILES: c1ccc2c(c1)CCN1C2CC2(OCCCO2)C2CCCCC21] |
| P3  | 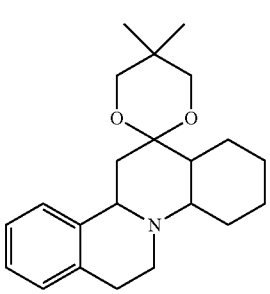 [SMILES: CC1(C)COC2(CC3c4ccccc4CCN3C3CCCCC32)OC1] |
| P4  | 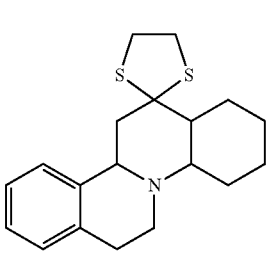 [SMILES: c1ccc2c(c1)CCN1C2CC2(SCCS2)C2CCCCC21] |
| P5  | 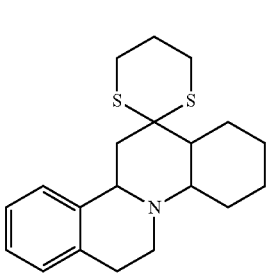 [SMILES: c1ccc2c(c1)CCN1C2CC2(SCCCS2)C2CCCCC21] |
| P6  | 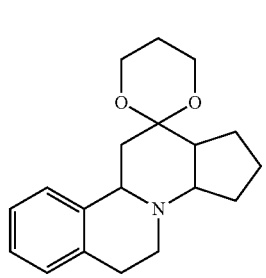 [SMILES: c1ccc2c(c1)CCN1C2CC2(OCCCO2)C2CCCC21] |
| P7  | 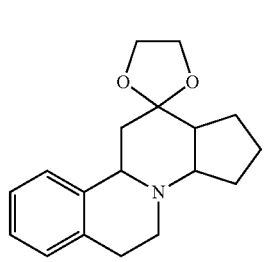 [SMILES: c1ccc2c(c1)CCN1C2CC2(OCCO2)C2CCCC21] |
| No. | Formula |
|-----|---------|
| P8  | 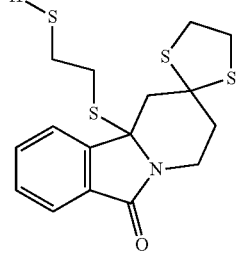 |
| P9  | 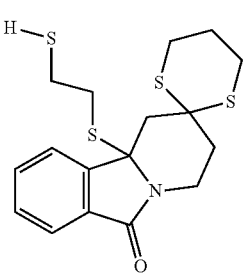 [SMILES: O=C1c2ccccc2C2(SCCS)CC3(CCN12)SCCCS3] |
| P10 | 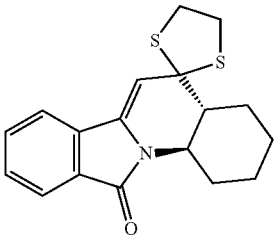 [SMILES: O=C1c2ccccc2C2=CC3(SCCS3)[C@@H]3CCCC[C@H]3N12] |
| P11 | 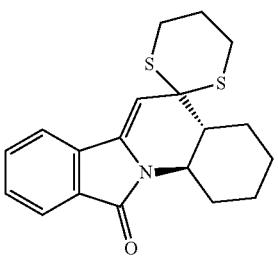 [SMILES: O=C1c2ccccc2C2=CC3(SCCCS3)[C@@H]3CCCC[C@H]3N12] |
| P12 | 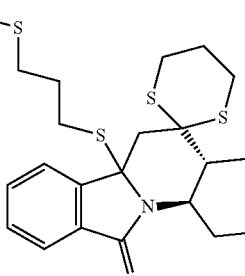 |
| P13 | 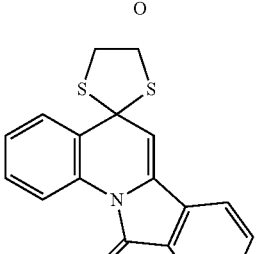 |

| No. | Formula |
|---|---|
| P14 | 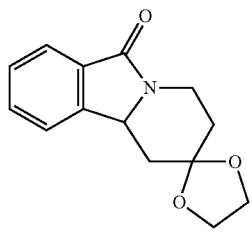 [SMILES: O=C1c2ccccc2C2CC3(CCN12)OCCO3] |
| P15 | 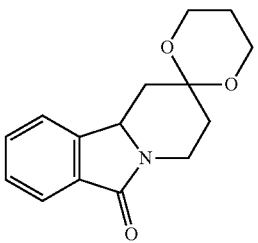 [SMILES: O=C1c2ccccc2C2CC3(CCN12)OCCCO3] |
| P16 | 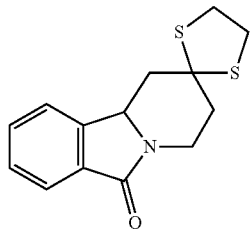 [SMILES: O=C1c2ccccc2C2CC3(CCN12)SCCS3] |
| P17 | 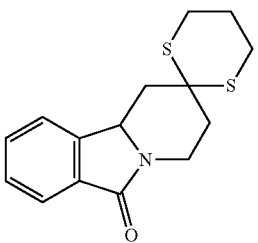 [SMILES: O=C1c2ccccc2C2CC3(CCN12)SCCCS3] |
| P18 | 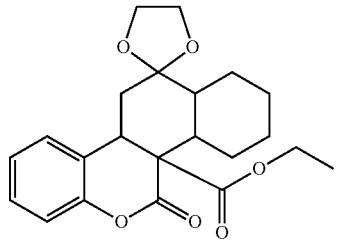 [SMILES: CCOC(=O)C12C(=O)Oc3ccccc3C1CC1(OCCO1)C1CCCCC12] |
| P19 | 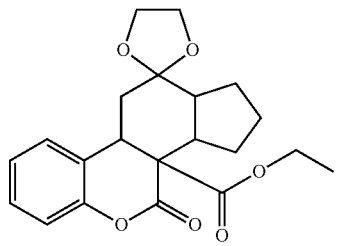 [SMILES: CCOC(=O)C12C(=O)Oc3ccccc3C1CC1(OCCO1)C1CCCC12] |
| No. | Formula |
|---|---|
| P20 | 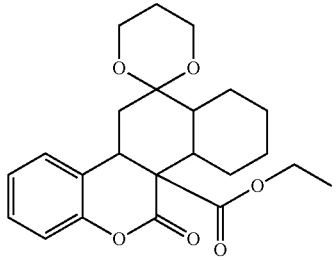 [SMILES: CCOC(=O)C12C(=O)Oc3ccccc3C1CC1(OCCCO1)C1CCCCC12] |
| P21 | 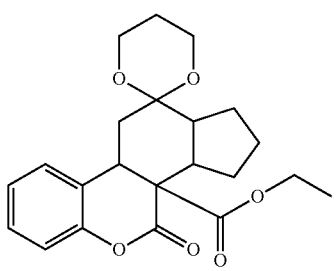 [SMILES: CCOC(=O)C12C(=O)Oc3ccccc3C1CC1(OCCCO1)C1CCCC12] |
| P22 | 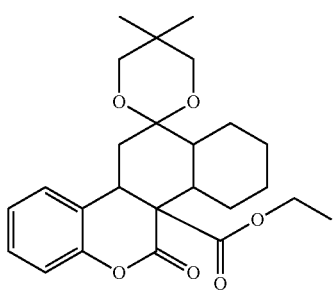 [SMILES: CCOC(=O)C12C(=O)Oc3ccccc3C1CC1(OCC(C)(C)CO1)C1CCCCC12] |
| P23 | 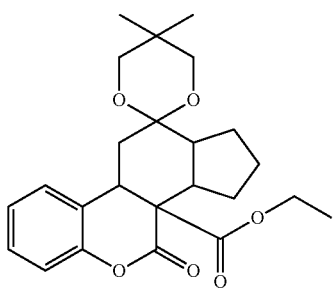 [SMILES: CCOC(=O)C12C(=O)Oc3ccccc3C1CC1(OCC(C)(C)CO1)C1CCCC12] |
| P24 | 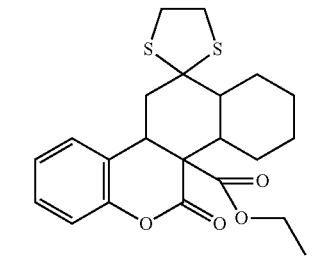 [SMILES: CCOC(=O)C12C(=O)Oc3ccccc3C1CC1(SCCS1)C1CCCCC12] |

-continued

| No. | Formula |
|---|---|
| P25 | |
| P26 | |
| P27 | |
| P28 | |
| P29 | |
| P30 | |

-continued

| No. | Formula |
|---|---|
| P31 | |

2. A method for the in-vitro or in-vivo modulation of the cold menthol receptor TRPM8, where the receptor is brought into contact with a composition comprising a substance selected from compounds P1 to P31:

| No. | Formula |
|---|---|
| P1 | |
| P2 | |
| P3 | |
| P4 | |

-continued
| No. | Formula |
|---|---|
| P5 | 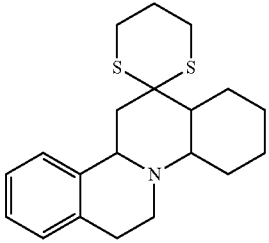 [SMILES: c1ccc2c(c1)CCN1C2CC2(SCCCS2)C2CCCCC21] |
| P6 | 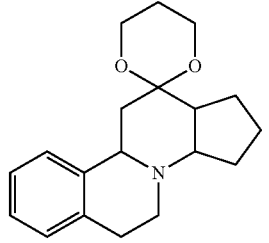 [SMILES: c1ccc2c(c1)CCN1C2CC2(OCCCO2)C2CCCC21] |
| P7 | 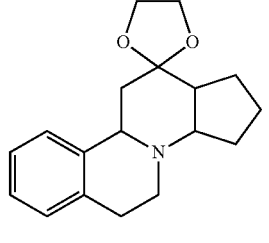 [SMILES: c1ccc2c(c1)CCN1C2CC2(OCCO2)C2CCCC21] |
| P8 | 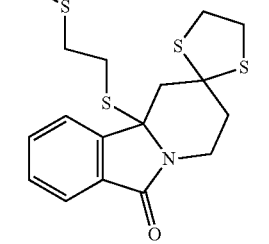 |
| P9 | 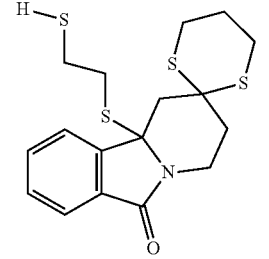 [SMILES: O=C1c2ccccc2C2(SCCS)CC3(CCN12)SCCCS3] |
| P10 | 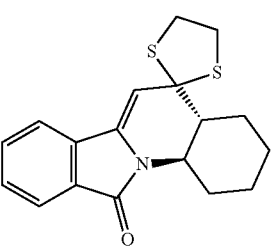 [SMILES: O=C1c2ccccc2C2=CC3(SCCS3)[C@@H]3CCCC[C@H]3N12] |
-continued
| No. | Formula |
|---|---|
| P11 | 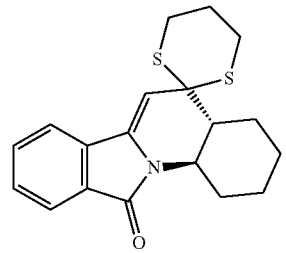 [SMILES: O=C1c2ccccc2C2=CC3(SCCCS3)[C@@H]3CCCC[C@H]3N12] |
| P12 | 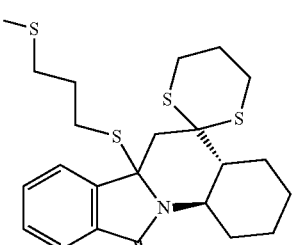 |
| P13 | 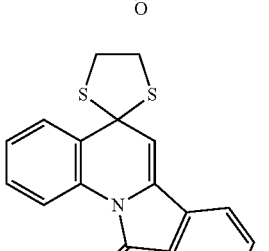 |
| P14 | 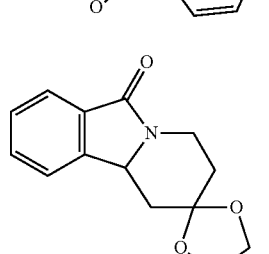 |
| P15 | 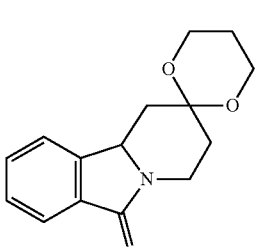 |
| P16 | 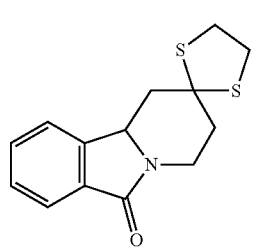 [SMILES: O=C1c2ccccc2C2CC3(CCN12)SCCS3] |

| No. | Formula |
|---|---|
| P17 | 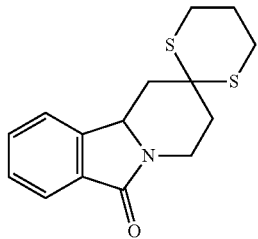 [SMILES: O=C1c2ccccc2C2CC3(CCN12)SCCCS3] |
| P18 | 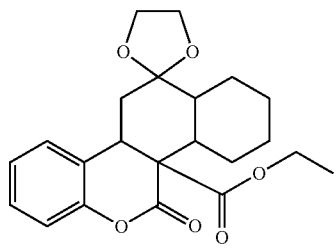 [SMILES: CCOC(=O)C12C(=O)Oc3ccccc3C1CC1(OCCO1)C1CCCCC12] |
| P19 | 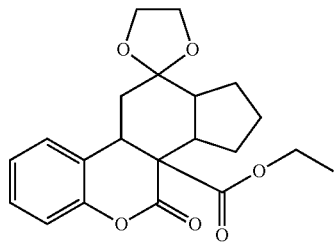 [SMILES: CCOC(=O)C12C(=O)Oc3ccccc3C1CC1(OCCO1)C1CCCC12] |
| P20 | 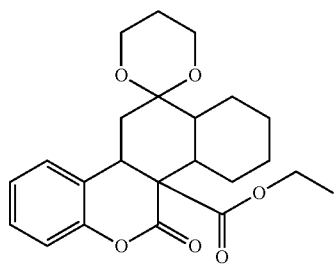 [SMILES: CCOC(=O)C12C(=O)Oc3ccccc3C1CC1(OCCCO1)C1CCCCC12] |
| P21 | 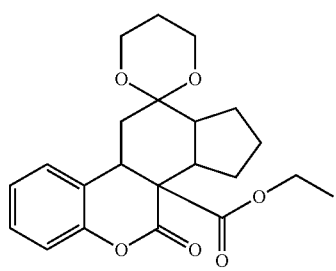 [SMILES: CCOC(=O)C12C(=O)Oc3ccccc3C1CC1(OCCCO1)C1CCCC12] |
| No. | Formula |
|---|---|
| P22 | 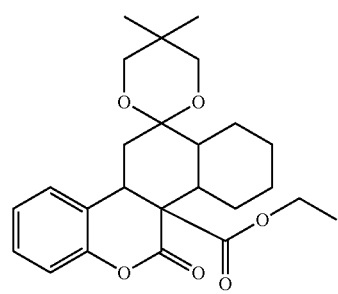 [SMILES: CCOC(=O)C12C(=O)Oc3ccccc3C1CC1(OCC(C)(C)CO1)C1CCCCC12] |
| P23 | 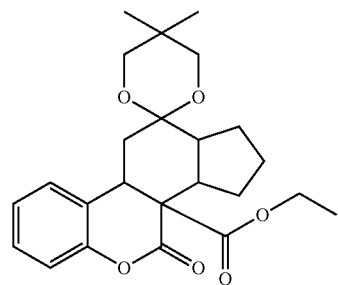 [SMILES: CCOC(=O)C12C(=O)Oc3ccccc3C1CC1(OCC(C)(C)CO1)C1CCCC12] |
| P24 | 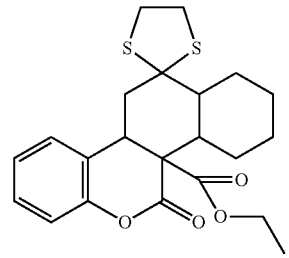 [SMILES: CCOC(=O)C12C(=O)Oc3ccccc3C1CC1(SCCS1)C1CCCCC12] |
| P25 | 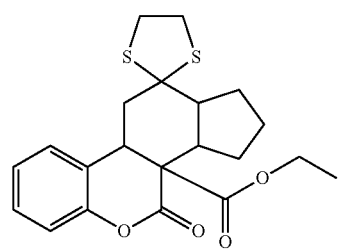 [SMILES: CCOC(=O)C12C(=O)Oc3ccccc3C1CC1(SCCS1)C1CCCC12] |
| P26 | 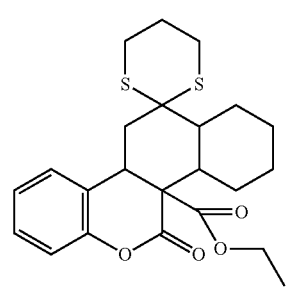 [SMILES: CCOC(=O)C12C(=O)Oc3ccccc3C1CC1(SCCCS1)C1CCCCC12] |

| No. | Formula |
|---|---|
| P27 | 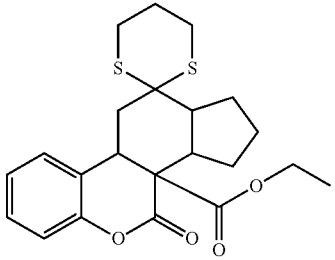 [SMILES: CCOC(=O)C12C(=O)Oc3ccccc3C1CC1(SCCCS1)C1CCCC12] |
| P28 | 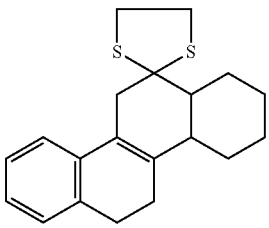 [SMILES: c1ccc2c(c1)CCC1=C2CC2(SCCS2)C2CCCCC12] |
| P29 | 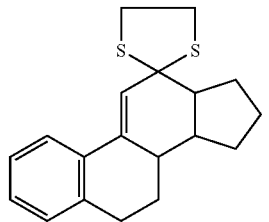 [SMILES: C1=C2c3ccccc3CCC2C2CCCC2C12SCCS2] |
| P30 | 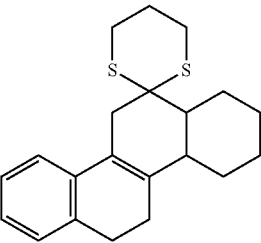 [SMILES: c1ccc2c(c1)CCC1=C2CC2(SCCCS2)C2CCCCC12] |
| P31 | 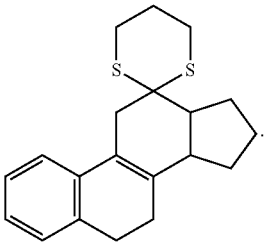 [SMILES: c1ccc2c(c1)CCC1=C2CC2(SCCCS2)C2CCCC12] |

3. The method according to claim 1, wherein the substance is selected from compounds P1 to P13.

4. The method according to claim 1, wherein the substance is selected from compounds P14 to P31.

5. The method according to claim 1, wherein the substance is selected from compounds P20 to P31.

6. The method according to claim 1, wherein the substance is selected from compounds P25 to P31.

7. The method according to claim 1, wherein the substance is selected from compounds P14 to P19.

8. The method according to claim 1, wherein the substance is selected from compounds P1 to P7.

* * * * *